United States Patent
Ambavaram et al.

(10) Patent No.: US 10,450,580 B2
(45) Date of Patent: Oct. 22, 2019

(54) TRANSCRIPTIONAL REGULATION FOR IMPROVED PLANT PRODUCTIVITY

(71) Applicant: Yield10 Bioscience, Inc., Woburn, MA (US)

(72) Inventors: Madana M.R. Ambavaram, Norwood, MA (US); Mariya Somleva, Cambridge, MA (US)

(73) Assignee: Yield10 Bioscience, Inc., Woburn, MA (US)

( * ) Notice: Subject to any disclaimer, the term of this patent is extended or adjusted under 35 U.S.C. 154(b) by 0 days.

(21) Appl. No.: 15/897,958

(22) Filed: Feb. 15, 2018

(65) Prior Publication Data

US 2018/0340183 A1    Nov. 29, 2018

Related U.S. Application Data

(63) Continuation of application No. 14/653,431, filed as application No. PCT/US2013/076308 on Dec. 18, 2013, now abandoned.

(60) Provisional application No. 61/738,675, filed on Dec. 18, 2012.

(51) Int. Cl.
  *C12N 15/82* (2006.01)
  *C07K 14/415* (2006.01)

(52) U.S. Cl.
  CPC ........ *C12N 15/8261* (2013.01); *C07K 14/415* (2013.01); *C12N 15/8241* (2013.01); *C12N 15/8245* (2013.01); *C12N 15/8251* (2013.01); *C12N 15/8271* (2013.01); *C12N 15/8273* (2013.01); *Y02A 40/146* (2018.01)

(58) Field of Classification Search
  None
  See application file for complete search history.

(56) References Cited

U.S. PATENT DOCUMENTS

| | | | |
|---|---|---|---|
| 6,706,866 | B1 | 3/2004 | Thomashow et al. |
| 7,663,025 | B2 | 2/2010 | Heard et al. |
| 8,110,723 | B2 | 2/2012 | Bloksberg et al. |
| 2005/0086718 | A1* | 4/2005 | Heard .................. C07K 14/415 800/298 |
| 2007/0022495 | A1 | 1/2007 | Reuber et al. |
| 2008/0072340 | A1 | 3/2008 | Troukhan et al. |
| 2009/0094717 | A1* | 4/2009 | Troukhan .............. C07K 14/415 800/290 |
| 2011/0167514 | A1 | 7/2011 | Brover et al. |
| 2012/0005773 | A1 | 1/2012 | Aasen et al. |

FOREIGN PATENT DOCUMENTS

| | | |
|---|---|---|
| WO | WO-2005/112608 A2 | 12/2005 |
| WO | WO-2014/093614 A1 | 6/2014 |

OTHER PUBLICATIONS

Abate et al., "Separation and structural characterization of cyclic and open chain oligomers produced in the partial pyrolysis of microbial poly (hydroxybutyrates)," Macromolecules, 28(23): 7911-7916 (1995).

Dietz et al., "AP2/EREBP transcription factors are part of gene regulatory networks and integrate metabolic, hormonal and environmental signs in stress acclimation and retrograde signalling," Protoplasma, 245(1-4): 3-14 (2010).

International Search Report and Written Opinion for International Application No. PCT/US2013/076308 dated May 23, 2014.

Invitation to Pay Additional Fees for PCT/US2013/076308, "Transcriptional Regulation for Improved Plant Productivity;" dated Mar. 27, 2014. (4614.1011-001).

Jaglo et al., "Components of the Arabidopsis C-Repeat/Dehydration-Responsive Element Binding Factor Cold-Response Pathway are Conserved in *Brassica napus* and Other Plant Species," Plant Physiology, 127: 910-917 (Nov. 2001).

Mizoi et al., "AP2/ERF family transcription factors in plant abiotic stress responses," Biochim Biophys Acta., 1819(2): 86-96 (2012).

Nakano et al., "Genome-Wide Analysis of the ERF Gene Family in Arabidopsis and Rice," Plant Physiologym, 140: 411-432 (Feb. 2006).

Notification of Transmittal of the International Search Report and the Written Opinion of the International Search Authority for PCT/US2013/076308, "Transcriptional Regulation for Improved Plant Productivity;" dated Jun. 4, 2014. (4614.1011-001).

Ohto et al., "Control of seed mass by APETALA2," PNAS, 102(8): 3123-3128 (2005).

Saibo et al., "Transcription factors and regulation of photosynthetic and related metabolism under environmental stresses," Annals of Botany, 103(4): 609-623 (2009).

Zhang et al., "Overexpression of the Soybean GmERF3 Gene, a AP2/ERF Type Transcription Factor for Increase Tolerances to Salt, Drought, and Diseases in Transgenic Tobacco," J Exp Biol, 60(13): 3781-3796 (2009).

Zhang et al., "Progresses on Plant AP2/ERF Transcription Factors," Hereditas, 34(7): 835-847 (2012).

* cited by examiner

*Primary Examiner* — Ashley K Buran
(74) *Attorney, Agent, or Firm* — Pearne & Gordon LLP

(57) ABSTRACT

Methods comprising DNA constructs and polynucleotides of functional transcription factors for improving photosynthetic capacity, biomass and/or grain yield and stress tolerance in various crop and model plants, dicots and monocots with the $C_3$ or $C_4$ photosynthetic pathways are described herein.

14 Claims, 22 Drawing Sheets

Specification includes a Sequence Listing.

TRANSCRIPTIONAL REGULATION FOR IMPROVED PLANT PRODUCTIVITY

RELATED APPLICATIONS

This application is a continuation of U.S. application Ser. No. 14/653,431, filed Jun. 18, 2015, which is the U.S. National Stage of International Application No. PCT/US2013/076308, filed on Dec. 18, 2013, published in English, which claims the benefit of U.S. Provisional Application No. 61/738,675, filed on Dec. 18, 2012.

GOVERNMENT SUPPORT

This invention was made with government support under Award Number DE-EE0004943 awarded by Department of Energy. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

File name: MBQ-01102_SEQUENCELISTING.txt; created Feb. 15, 2018; 163 KB in size.

BACKGROUND OF THE INVENTION

The increasing size of the global population, the increasing standard of living in emerging nations such as China and the use of renewable resources such as plants to produce biofuels and bio-based chemicals has placed additional pressure on agriculture. These factors together with the limited availability of additional arable land and water resources means that crop productivity or yield is the key to feeding these demands. Agriculture needs to deliver greater output with reduced inputs. In addition to traditional and marker assisted breeding programs there is an increased need for the identification and application of novel genes which can broadly impact crop yield as well as reduce the impact of environmental stress conditions such as drought, frost, heat and salinity and require fewer chemical inputs such as fertilizer, herbicides, pesticides and fungicides. For example, the 2010 worldwide biofuel production (mainly supplied by bioethanol derived from plant carbohydrate sources, such as starch, sugar from maize, sugarcane and biodiesel from plant oil (from palm and soybean)) reached 28 billion gallons of output providing roughly 2.7% of the world's fuels for road transport. One of the keys to achieving higher yield is to enhance the photosynthetic capacity of plants such that more carbon dioxide is fixed per plant together with up-regulating key metabolic pathways leading to increased levels of storage carbohydrates such as starch and sucrose or lipids such as fatty acids and triglycerides (oils) in plant tissues. In the case of biomass crops used for forage or energy production, increasing the total biomass per plant is also a highly desirable outcome. In many cases efforts to increase storage carbohydrates or oil in plants have been focused on genetic modification using genes encoding individual enzymes in specific metabolic pathways i.e. "single enzyme" or metabolic pathway approaches.

Transcription factors (TFs) are considered potential alternatives to "single enzyme" approaches for the manipulation of plant metabolism (Grotewold, 2008, *Curr. Opin. Biotechnol.* 19: 138-144). They are critical regulators of differential gene expression during plant growth, development and environmental stress responses. Transcription factors either directly interact with genes involved in key biological processes or interact with the regulation of other TFs that then bind to target genes thus achieving high levels of specificity and control. The resulting outcome is a multilayered regulatory network that affects multiple genes and leads to, for example, fine-tuned changes in the flux of key metabolites through interconnected or competing metabolic pathways (Ambavaram et al., 2011, *Plant Physiol.* 155: 916-931). There is limited information on transcription factors directly involved in the regulation of photosynthesis-related genes in plants, improvement of photosynthetic parameters has been reported in transgenic crop and model plants overexpressing members of the AP2/EREB, bZIP, NF-X1, NF-Y(HAP), and MYB families of TFs (Saibo et al., 2009, *Ann. Bot.-London* 103: 609-623). Most of these TFs are stress-induced and confer tolerance to an array of abiotic stress factors, such as drought, salinity, high or low temperatures, and photoinhibition (Hussain et al., 2011, *Biotechnology Prog.* 27: 297-306, see also WO 2005/112608 A2 and U.S. Pat. No. 6,835,540 B2 to Broun). Only a few TFs, such as Dof1 and MNF from maize are associated with expression of genes involved in $C_4$ photosynthesis (Weissmann & Brutnell, 2012, *Curr. Opin. Biotechnol.* 23: 298-304; Yanagisawa, 2000, *Plant J.* 21: 281-288). Increased growth of different vegetative and/or floral organs resulting in improved biomass production have been reported in plants overexpressing TFs, such as ARGOS, AINTEGUMENTA, NAC1, ATAF2, MEGAINTEGUMENTA, and ANGUSTIFOLIA (Rojas et al., 2010, *GM Crops* 1: 137-142 and references therein; see also WO 2011/109661 A1, WO 2010/129501, WO 2009/040665 A2, WO 02/079403 A2 and U.S. Pat. No. 7,598,429 B2 to Heard et al. and U.S. Pat. No. 7,592,507 B2 to Beekman et al.). Modifications of plant metabolic pathways by altering the expression of transcription factors regulating genes in the biosynthesis of lignin (US 2012/0117691 A1 to Wang et al.) and secondary metabolites (U.S. Pat. No. 6,835,540 B2 to Broun) have also been reported.

Thus, a need exists for identification of transcription factors whose increased or modified expression not only results in increased levels of the light harvesting pigments used in photosynthesis and improved photosynthetic capacity of the plants but which also up-regulate key metabolic pathways resulting in one or more additional desirable effects selected from the group comprising: increased levels of starch, glucose or sucrose (non-structural carbohydrates) in plant tissues; increased levels of fatty acids; increased production of biomass and/or grain yield; and enhanced stress tolerance. It is also desirable to be able to identify suitable variants of such transcription factors in a wide range of crop species and to be able to engineer these genes in a wide range of crops including dicots and monocots with $C_3$ or $C_4$ photosynthetic pathways.

Specific crops of interest for practicing this invention include: switchgrass, *Miscathus, Medicago*, sweet sorghum, grain sorghum, sugarcane, energy cane, elephant grass, maize, wheat, barley, oats, rice, soybean, oil palm, safflower, sesame, flax, cotton, sunflower, *Camelina, Brassica napus, Brassica carinata, Brassica juncea*, pearl millet, foxtail millet, other grain, oilseed, vegetable, forage, woody and biomass crops.

SUMMARY OF THE INVENTION

This invention is generally in the area of novel genes and methods for increasing plant crop yield using those novel genes. Described herein is the use of novel transcription factors that when overexpressed in a plants of interest affect the regulation of multiple biological pathways in the crop resulting in, for example, higher levels of photosynthetic pigments in green tissue, increased photosynthetic efficiency, increased content of non-structural carbohydrates (starch, sucrose, glucose) and fatty acids in leaf tissues, increased biomass yield and improved stress tolerance.

Screening of a number of transcription factor candidates has resulted in the identification of novel transcription factors that when expressed from a heterologous promoter in transgenic plants results in plants having increased expression of these transcription factors. The increased expression levels can be up to 1.2 fold 1.3 fold, 1.5 fold, 2 fold, 3 fold, 4 fold, 5 fold, 6 fold, 7 fold, 8 fold, a 9 fold or greater than 10 fold the level of background expression found in a wild-type plant (e.g., non-transgenic plant, test plant or control plant). As a result of the increased expression of these transcription factors a number of beneficial traits are achieved including but not limited to: increased levels of photosynthetic pigments; increased photosynthetic capacity; increased levels of non-structural carbohydrates, including starch, sucrose and glucose in plant tissues; increased levels of fatty acids in plant tissues; increased biomass growth rate and yield; and improved stress tolerance in comparison to wild-type plants. Methods for identifying transcription factors and producing the transgenic plants are also described herein. The transcription factor genes, their homologs and/or orthologs and the methods described herein for increasing their expression or for expressing them in heterologous hosts can achieve yield improvements in a wide range of crop plants.

A higher photosynthesis rate in plants transformed with the transcription factors of the invention and their homologs and/or orthologs combined with elevated levels of photosynthetic pigments achieved by the methods described lead to increased accumulation of products of the central carbon metabolism, such as starch, soluble sugars and fatty acids as well as improved biomass and grain production. It is also likely that plants with elevated levels of expression of these transcription factors will also be useful for increasing the production of other products produced in plants by genetic engineering including for example, storage starches. The overall potential impact of increasing the expression of these transcription factors in plants is illustrated in FIG. 1. Improved stress tolerance mediated by the transcription factors of the invention, produce transgenic plants with better agronomic performance under abiotic and biotic stress conditions than non-transformed controls or test plants (also referred to as wild type). In another related aspect, a quick and reliable method for testing the stress response of large populations of transgenic and wild type plants (e.g., crops) is also described. Also described herein are novel gene sequences, polypeptides encoded by them, gene constructs and methods for their use to produce transgenic plants, plant products, crops and seeds.

These transgenic plants, portions of transgenic plants, transgenic crops and transgenic seeds generated by the introduction of or increased expression of the functional transcription factors and their homologs, orthologs and function fragments identified herein have improved photosynthetic capacity, improved biomass production, and/or improved grain yield and stress tolerances compared to wild-type plants.

This invention relates to the identification of transcription factor genes which when expressed to higher levels than is found in wild type plants or expressed in heterologous plants results in one or more desirable traits selected from: higher levels of photosynthetic pigments; higher photosynthetic activity; higher levels of starch and/or sucrose and/or glucose; higher yield of biomass; and improved stress tolerances.

In one aspect of the invention, genes encoding transcription factors belonging to the APETALA2 (AP2)/ETHYLENE RESPONSE FACTOR (ERF) family (e.g., SEQ. ID NO: 1 and 2) and transcription factors from the Nuclear-Factor Y (NF-YB) family (e.g., SEQ ID NO: 3) and their homologues and orthologs from other plant species are described as well as methods of producing transgenic plants overexpressing these transcription factors genes in a wide range of plants to achieve one or more traits selected from: higher levels of photosynthetic pigments; higher photosynthetic activity; higher levels of starch and/or sucrose and/or glucose; higher yield, and improved stress tolerance.

Host plants include but are not limited to food crops, forage crops, bioenergy and biomass crops, perennial and annual plant species. Examples of specific crops of interest for practicing this invention include: switchgrass, *Miscathus, Medicago*, sweet sorghum, grain sorghum, sugarcane, energy cane, elephant grass, maize, wheat, barley, oats, rice, soybean, oil palm, safflower, sesame, flax, cotton, sunflower, *Camelina, Brassica napus, Brassica carinata, Brassica juncea*, pearl millet, foxtail millet, other grain, oilseed, vegetable, forage, woody and biomass crops.

In a first aspect, a transgenic plant, or a portion of a plant, or a plant material, or a plant seed, or a plant cell comprising one or more nucleotide sequences encoding one or more AP2/ERF and/or NF-YB transcription factors, wherein the AP2/ERF transcription factor is encoded by the nucleotide sequence of SEQ ID NO: 1 or 2 and the NF-YB transcription factor is encoded by the nucleotide sequence of SEQ ID NO: 3 and the increased expression of one or more transcription factors is increased resulting in one or more traits selected from: higher levels of photosynthetic pigments; higher photosynthetic activity; higher levels of starch and/or sucrose and/or glucose; higher yield; and improved stress tolerance in the transgenic plant, portion of a plant, plant material, plant seed, or plant cell is described. The increased expression of the transcription factors can be measured in a number of ways including a fold increase over the wild type plant such as 1.5 fold, 2 fold, 3 fold, 4 fold, 5 fold 6 fold 7 fold 8 fold greater than 9 fold higher than the expression of the same gene in a wild type plant. In some cases the increased expression results from the expression of the transcription factor gene through genetic manipulation to express the transcription factor in a heterologous plant host. An example of this particular embodiment would be expressing one of the genes, including homolog or orthologs, isolated from switchgrass in a plant selected from *Miscathus, Medicago*, sweet sorghum, grain sorghum, sugarcane, energy cane, elephant grass, maize, wheat, barley, oats, rice, soybean, oil palm, safflower, sesame, flax, cotton, sunflower, *Camelina, Brassica napus, Brassica carinata, Brassica juncea*, pearl millet, foxtail millet, other grain, oilseed, vegetable, forage, woody and biomass crops.

In a first embodiment of the first aspect, the expression of the one or more transcription factors increases the level of photosynthetic pigments including chlorophyll and/or carotenoids. The improvement is compared to a non-transgenic plant and such improvement can be measured in a variety of ways, including a fold increase or percent increase, such as 10%, 20%, 50% or 75%.

In a second embodiment of the first aspect, as compared to the wild type plant, the increased expression of the one or more transcription factors improves the rate of photosynthesis in the plant. The improvement is compared to a non-transgenic plant and such improvement can be measured in a variety of ways, including a fold increase or percent increase, such as 10%, 20%, 30%, 40%, 50% or higher.

In a third embodiment of the first aspect, as compared to the wild type plant, the increased expression of one or more transcription results in increased levels of starch and/or sucrose and/or glucose in the plant tissue. The increase in levels of starch and/or sucrose and/or glucose in the plant tissue alone or in combination can be measured as a % of dry weight of the plant tissue analyzed for example 2%, 3%, 4%, 5%, 10%, 15%, 20% of the dry weight of the plant tissue.

In a fourth embodiment as compared to the wild type plant, the expression of the one or more transcription factors results in plants with higher biomass yields. The improvement is compared to a non-transgenic plant and such improvement can be measured in a variety of ways, percent increase such as 10%, 20%, 50% or greater than 50% increase in the dry weight of the plant as compared to a wild type plant.

In a fifth embodiment as compared to the wild type plant, the expression of one or more transcription factors improves tolerance to one or more abiotic stress factors selected from excess or deficiency of water and/or light, high or low temperature, and high salinity. The improvement is compared to a non-transgenic plant and such improvement can be measured in a variety of ways, including a fold increase or percent increase, such as 10%, 20%, 50% or 75%.

In a second embodiment of the first aspect or of the first embodiment, the transcription factor is encoded by an ortholog, homolog, or functional fragment of SEQ ID NO: 1, 2, or 3. In a third embodiment of the first aspect or other embodiment, a promoter is operably linked to one or more nucleotide sequence of SEQ ID NO: 1, 2, or 3 in a plant transformation vector.

In a third embodiment of the first aspect or other embodiment, the plant has increased starch content, soluble sugar content, grain yield, plant size, organ size, leaf size, and/or stem size when compared to a non-transgenic plant.

In a fourth embodiment of the first aspect or other embodiment, the expression of one or more transcription factors increases the production of food crops, feed crops, or crops used in the production of fuels or industrial products, when compared to a non-transgenic plant.

In a second aspect, an isolated nucleotide sequence comprising a nucleic acid sequence encoding an AP2/ERF or an NF-YB transcription factor; wherein the transcription factor is functional in a plant, selected from the group consisting of SEQ ID NO: 1, 2, and 3; and expression of the transcription factor result in higher levels of starch and/or sucrose and/or glucose in the plant.

In a first embodiment of the second aspect, the expression resulting in higher levels of one or more of starch, sucrose and glucose and higher biomass, or higher levels of one or more of starch, sucrose and glucose with no significant increase in biomass.

In a second embodiment of the second aspect or of the first embodiment of the second aspect, the nucleic acid sequence further comprises at least 60%, 65%, 70%, 75%, 80%, 85%, 90%, 95%, or 99% sequence identity to SEQ ID NO:1, 2, or 3.

In a third embodiment of the second aspect or the embodiments, the plant further comprises a temporal promoter for expression of all transcription factors such that the gene is overexpressed one the plant is fully grown and the accumulation of storage materials in the seed is initiated. Methods of screening for plants with this outcome are also contemplated. Alternatively, other select promoters for desirable expression of the transcription factors are contemplated.

In a fourth embodiment of the second aspect or of the embodiments, the expression of the transcription factor increases photosynthetic activity, carbon flow and/or total content of photosynthetic pigments when compared to a non-transgenic plant.

In a fifth embodiment of the second aspect or of any of the other embodiments, the nucleic acid sequence encoding a polypeptide of SEQ ID NO: 4, 5, or 6.

In a third aspect, a transcription factor, comprising an AP2/ERF or a NF-YB transcription factor polypeptide selected from SEQ ID NO: 4, 5, and 6; wherein the transcription factor is functional in a plant and the expression of the transcription factor increases a carbon flow in the transgenic plant is described.

In a first embodiment of the third aspect, the transcriptional factor is functional in a $C_3$ or $C_4$ dicotyledonous plant, a $C_3$ or $C_4$ monocotyledonous plant, In a second embodiment of the third aspect or of any of the other embodiments, the polypeptide sequence further comprises at least 60%, 65%, 70%, 75%, 80%, 85%, 90%, 95%, or 99% sequence identity to SEQ ID NO: 4, 5, or 6.

In a third embodiment of the third aspect or of any of the other embodiments, the increased carbon flow is due to increased biomass yield, or increased starch, glucose or sucrose in plant tissues when compared to a non-transgenic plant.

In a fourth embodiment of the third aspect or of any of the other embodiments, expression the transcription factor increases photosynthetic activity, carbon flow and/or total content of photosynthetic pigments when compared to a non-transgenic plant.

In a fourth aspect, a biobased transgenic plant product obtained from the transgenic plant of the first aspect and any of the embodiment described having a 100% biobased carbon flow is described. In certain embodiments of this fourth aspect, the product is an article having a biobased content of at least 50%, at least 60%, at least 70%, at least 75%, at least 80%, at least 85%, 90% or 95%.

In a fifth aspect, a method of producing a transgenic plant, comprising coexpressing one or more AP2/ERF and a NF-YB transcription factor, wherein the AP2/ERF transcription factor is encoded by the nucleotide sequence of SEQ ID NOs: 1 or 2 and the NF-YB transcription factor is encoded by the nucleotide sequence of SEQ ID NO: 3 is described.

In a sixth aspect, a method for testing the response of plants to different abiotic stress factors in tissue culture for identification of plants with increased tolerance to the stress factors, comprising comparing a test plant with the transgenic plant of claim 1 under one or more conditions that cause stress including adverse changes in water, light, temperature, and salinity is described.

In a seventh aspect methods for transformation comprising incorporating into the genome of a plant with one or more vectors comprising the nucleotide sequences described herein are described.

In an eighth aspect or of any of the embodiments of the first aspect, the transgenic plant of the first aspect has an increased photochemical quantum yield than the yield of a non-transgenic plant.

In a ninth aspect or of any of the embodiments of the first aspect, the transgenic plant of the first aspect has a starch content (e.g., yield) increased by at least 2 fold greater than the corresponding starch content of a non-transgenic plant.

In a tenth aspect or of any of the embodiments of the first aspect, the transgenic plant of the first aspect has a starch content of at least 2 fold greater to about 4.3 greater than the content of a non-transgenic plant.

In an eleventh aspect or of any of the embodiments of the first aspect, the transgenic plant of the first aspect has a chlorophyll content that is greater than the content of a non-transgenic plant or has a chlorophyll content that is at least 1.1 greater to about 2.5-fold greater than the content of a non-transgenic plant.

In a twelfth aspect or of any of the embodiments of the first aspect, the transgenic plant of the first aspect has a sucrose content that is higher than the content of a non-transgenic plant or a sucrose content that is at least two fold greater to about 4.3 fold greater than the content of a non-transgenic plant.

In a thirteenth aspect or of any of the embodiments of the first aspect, the transgenic plant of the first aspect has an electron transport rate above the rate of a non-transgenic plant.

In a further embodiment of any of the aspects, the plant is selected from switchgrass, Miscathus, Medicago, sweet sorghum, grain sorghum, sugarcane, energy cane, elephant grass, maize, wheat, barley, oats, rice, soybean, oil palm, safflower, sesame, flax, cotton, sunflower, Camelina, Brassica napus, Brassica carinata, Brassica juncea, pearl millet, foxtail millet, other grain, oilseed, vegetable, forage, industrial, woody and biomass crops.

In a further embodiment, transgenic plants of the previous embodiments can be screened to identify plants where the overall biomass yield is similar to the wild type plant but the levels of one or more traits selected from: increased concentration of photosynthetic pigments; increased photosynthesis efficiency; increased levels of starch and/or sucrose and/or glucose; increased levels of fatty acids and increased stress tolerance higher than the levels in the wild-type plants. For example a transgenic plant with a biomass yield similar to a wild type plant but with a cumulative level of starch plus glucose plus sucrose 1.5 fold, 2 fold, 5 fold, 10 fold or more higher can be identified.

In a further embodiment, a screening method for identifying specific genes or combinations of genes which can be used to achieve some of the individual trait improvements is described herein.

In certain embodiments, methods related to upregulation of the central carbon metabolism by PvSTR1, PvSTIF1 and PvBMY1 leading to increased photosynthetic pigments and activity and elevated levels of starch, soluble sugars and fatty acids as well as improved stress tolerance and productivity of plants and plant products are described. These methods include the incorporation of one or more of the transcription factors described by SEQ. ID NOs: 1, 2 and 3 and homologs, orthologs and functional fragments thereof. For example, the transgenic plant can comprise SEQ ID NO: 1, SEQ ID NO: 2 or SEQ ID: NO:3, or a homolog, ortholog or functional fragment thereof or any combination of two or more of SEQ ID NO: 1, SEQ ID NO: 2 and SEQ ID: NO:3, including their homologs, othologs or functional fragments thereof (e.g., SEQ ID NO:1 and SEQ ID NO:2; SEQ ID NO: 1 and SEQ ID NO: 3; homolog of SEQ ID NO: 1 and SEQ ID NO: 2; homolog of SEQ ID NO: 1 and a homolog of SEQ.2; etc.).

In a fourteenth aspect of the invention, a transgenic plant, or a portion of a plant, or a plant material, or a plant seed, or a plant cell comprising one or more nucleotide sequences encoding a family of AP2/ERF or NF-YB transcription factor, wherein the AP2/ERF transcription factor is encoded by the nucleotide sequence of SEQ ID NO:1 or 2 and the NF-YB transcription factor is encoded by the nucleotide sequence of SEQ ID NO:3; wherein the expression of the one or more transcription factors increases carbon flow in the transgenic plant, portion of a plant, plant material, plant seed, or plant cell is described. In a first embodiment of the fourteenth aspect, the expression of the one or more transcription factors improves tolerance to one or more abiotic stress factors selected from excess or deficiency of water and/or light, from high or low temperature, and high salinity. In a second embodiment of the fourteenth aspect or of the first embodiment of the aspect, the transcription factor is encoded by an ortholog, homolog, or functional fragment encoded by SEQ ID NO: 1, 2, or 3. In a third embodiment of the fourteenth aspect or of any of the embodiments of the aspect, the transgenic plant, portion of a plant or plant material, plant seed or plant cell, further comprises a vector containing a promoter operably linked to one or more nucleotide sequence of SEQ ID NO: 1, 2, or 3. In a fourth embodiment of the fourteenth aspect or of any of the embodiments of the aspect the plant is selected from a crop plant, a model plant, a monocotyledonous plant, a dicotyledonous plant, a plant with C3 photosynthesis, a plant with C4 photosynthesis, an annual plant, a perennial plant, a switchgrass plant, a maize plant, or a sugarcane plant. In a fifth embodiment of the fourteenth aspect or of any of the embodiments of the aspect the annual or perennial plant is a bioenergy or biomass plant. In a sixth embodiment of the fourteenth aspect or of any of the embodiments of the aspect expression of one or more transcription factors increases photosynthetic activity, carbon flow and/or total content of photosynthetic pigments. In a seventh embodiment of the fourteenth aspect or of any of the embodiments of the aspect the increased carbon flow results in increased biomass yield when compared to a non-transgenic plant. In an eighth embodiment of the fourteenth aspect or of any of the embodiments of the aspect, wherein the plant has an increase of one or more of the following: starch content, soluble sugars content, grain yield, plant size, organ size, leaf size, and/or stem size when compared to a non-transgenic plant. In a ninth embodiment of the fourteenth aspect or of any of the embodiments of the aspect the expression of one or more transcription factors leads to increases in the production of food crops, feed crops, or crops for the production of fuels or industrial products, when compared to a non-transgenic plant.

In a fifteenth aspect of the invention, an isolated nucleotide sequence comprising a nucleic acid sequence encoding an AP2/ERF or an NF-YB transcription factor; wherein the transcription factor selected from the group consisting of SEQ ID NOs: 1, 2, and 3 is functional in a plant; and expression of the transcription factor increases carbon flow in the transgenic plant is described. In a first embodiment of the fifteenth aspect, the plant is selected from the group consisting of a C3 or C4 dicotyledonous plant, a C3 or C4 monocotyledonous plant, grass, a switchgrass plant, a maize plant, or a sugarcane plant. In a second embodiment of the fifteenth aspect or of any of the embodiments of the aspect, the nucleic acid sequence further comprises at least 60%, 65%, 70%, 75%, 80%, 85%, 90%, 95%, or 99% sequence identity to SEQ ID NO: 1, 2, or 3. In a third embodiment of the fifteenth aspect or of any of the embodiments of the aspect, the increased biomass yield is due to increased carbon flow when compared to a non-transgenic plant. In a fourth embodiment of the fifteenth aspect or of any of the embodiments of the aspect, expression of the transcription factor increases photosynthetic activity, carbon flow and/or total content of photosynthetic pigments when compared to a non-transgenic plant. In a fifth embodiment of the fifteenth aspect or of any of the embodiments of the aspect, the nucleic acid sequence encodes a polypeptide of SEQ ID NOs: 4, 5, or 6. In a sixth embodiment of the fifteenth aspect or of any of the embodiments of the aspect, the increased carbon flow increases the starch, sucrose and glucose levels in a transgenic plant without the same corresponding increase in biomass yield.

In a sixteenth aspect, a transcription factor, comprising an AP2/ERF or a NF-YB transcription factor polypeptide selected from SEQ ID NOs: 4, 5, and 6; wherein the transcription factor is functional in a plant and the expression of the transcription factor increases a carbon flow in the transgenic plant is described. In a first embodiment of the sixteenth aspect, the plant is selected from the group consisting of a C3 or C4 dicotyledonous plant, a C3 or C4 monocotyledonous plant, grass, or a switchgrass plant, a maize plant, or a sugarcane plant. In a second embodiment of the sixteenth aspect or of the first embodiment of the aspect, the polypeptide sequence further comprises at least 60%, 65%, 70%, 75%, 80%, 85%, 90%, 95%, or 99% sequence identity to SEQ ID NO:4, 5, or 6. In a third embodiment of the sixteenth aspect or of the first or second embodiment of the aspect, the increased biomass yield is due to increased carbon flow when compared to a non-transgenic plant. In a fourth embodiment of the sixteenth aspect or of the first, second or third embodiment of the aspect, expression of the transcription factor increases photosynthetic activity, carbon flow and/or total content of photosynthetic pigments when compared to a non-transgenic plant.

In a seventeenth aspect, a method for manufacturing a transgenic seed for producing a crop of transgenic plants with an enhanced trait resulting from the expression of one or more transcription factors or homologs, orthologs or functional fragments thereof, encoded by the nucleotide sequence of SEQ ID NO: 1, 2 or 3, comprising: a) screening a population of plants transformed with transcription factor(s) for the enhanced trait; b) selecting from the population one or more plants that exhibit the trait; and c) collecting seed from the selected plant is described. In a first embodiment of the seventeenth aspect, the seed is maize seed or sorghum seed and the enhanced trait is seed carbon content.

In an eighteen aspect, a method of producing a transgenic plant, comprising coexpressing one or more AP2/ERF and NF-YB transcription factors in a plant, wherein the AP2/ERF transcription factor is encoded by the nucleotide sequence of SEQ ID NO:1 or 2 and the NF-YB transcription factor is encoded by the nucleotide sequence of SEQ ID NO:3 is described.

In a nineteenth aspect, a method for testing the response of a plant to different stress factors in tissue culture for identification of plants with increased tolerance to the stress factors, comprising comparing a test plant with the transgenic plant of the fourteen aspect under one or more conditions that cause stress including changes in water, light, temperature, and salinity is described. In an embodiment of the seventeenth, eighteen or nineteen aspect, further comprising introducing into a plant one or more vectors comprising the nucleotide sequences of the invention.

In any of the aspects or embodiments described above, the photochemical quantum yield of the plant is at least 2-fold greater than the yield of a corresponding non-transgenic plant. In any of the aspects or embodiments described above, the plant has a starch yield increased by at least 2-fold the content of a corresponding non-transgenic plant. In any of the aspects or embodiments described above, the plant has a starch yield increased by at least 2-fold to about a 4.5-fold content of a corresponding non-transgenic plant. In any of the aspects or embodiments described above, the plant has a chlorophyll content that is 1.5 times greater than the content of a corresponding non-transgenic plant. In any of the aspects or embodiments described above, the plant has a chlorophyll content that is at least 1.5 fold greater to about 2.5 fold greater than the content of a corresponding non-transgenic plant. In any of the aspects or embodiments described above, the plant has a sucrose content that is at least 1.5 fold greater than the content of a corresponding non-transgenic plant. In any of the aspects or embodiments described above, the plant has a sucrose content that is at least two fold greater to about 4.3 fold greater than the content of a corresponding non-transgenic plant. In any of the aspects or embodiments described above, the plant has a plant grown rate increased by at least 10% above the rate of a corresponding non-transgenic plant. In any of the aspects or embodiments described above, the plant is switchgrass, maize, or sugar cane.

In a twentieth aspect, a method for enhancing a trait in a transgenic plant relative to a control non-transgenic plant, comprising: (a) increasing expression of at least one nucleic acid sequence encoding a transcription factor from AP2/ERF and NF-YB families, selected from the nucleic acid sequence of SEQ ID NO: 1, SEQ ID NO: 2, and SEQ ID NO: 3, or an ortholog, homolog or functional fragment thereof; and (b) selecting for a transgenic plant having an enhanced trait relative to a control plant is described. In a first embodiment of the twentieth aspect, the trait is selected from one or more of the following: carbon flow, primary metabolites, tolerance to one or more abiotic stress factors, and one or more photosynthetic pigments.

In a twenty-first aspect, a transgenic plant having a trait modification relative to a corresponding non-transgenic plant, comprising one or more nucleotide sequences encoding a AP2/ERF or NF-YB transcription factors, wherein the AP2/ERF transcription factor is encoded by the nucleotide sequence of SEQ ID NO:1 or 2 and the NF-YB transcription factor is encoded by the nucleotide sequence of SEQ ID NO:3 or a ortholog, homolog, or functional fragment thereof, wherein the trait modification is selected from one or more of the following: carbon flow, levels of photosynthetic pigments; photosynthetic capacity; levels of starch, sucrose and glucose in plant tissues, levels of fatty acids in plant tissues; biomass growth rate and yield; and stress tolerance is described. In a first embodiment of the twenty-first aspect, the trait modification is a greater than 3 fold yield of starch or soluble sugars and the increase in biomass production is less than 1.5 fold.

In a twenty-second aspect, a transgenic maize plant having an increased non-structural carbohydrate content comprising, a) introducing into a plant cell one or more nucleotides encoding AP2/ERF and/or NF-YB transcription factor, wherein the AP2/ERF transcription factor is encoded by the nucleotide sequence of SEQ ID NO: 1 or 2 and the NF-YB transcription factor is encoded by the nucleotide sequence of SEQ ID NO:3 or a ortholog, homolog, or functional fragment thereof, and b) producing a transgenic plant from the plant cell having an increased non-structural carbohydrate content compared to a corresponding non-transgenic plant is described. In a first embodiment of the aspect a seed or plant tissue is obtained by the transgenic maize or sorghum plant.

In a twenty-third aspect, a method of identifying a drought and salinity resistant transgenic plant having one or more nucleotides encoding an AP2/ERF and/or NF-YB transcription factor, wherein the AP2/ERF transcription factor is encoded by the nucleotide sequence of SEQ ID NO:1 or 2 and the NF-YB transcription factor is encoded by the nucleotide sequence of SEQ ID NO:3 or a ortholog, homolog, or functional fragment thereof comprising, (a) growing a population of transgenic and wild-type plants under conditions of drought and salinity stress; (b) selecting a transgenic plant that exhibits tolerance to drought and salinity, thereby identifying a transgenic plant that comprises a genotype associated with tolerance to drought and salinity is described.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4A-C shows the multiple sequence alignment for the conserved domains of PvSTR1 (FIG. 4A), PvSTIF1 (FIG. 4B) and PvBMY1 (FIG. 4C) in switchgrass (*Panicum virgatum* L.) and other plant species. The alignments of the DNA-binding domain sequences (AP2/ERF for STIF1 and STR1 and NFYB-HAP3 for BMY1) obtained using clustal W program (Thompson et al., 1994, *Nucleic Acids Res.* 11: 4673-4680) are shown in the boxes.

DETAILED DESCRIPTION OF THE INVENTION

Figure 1:
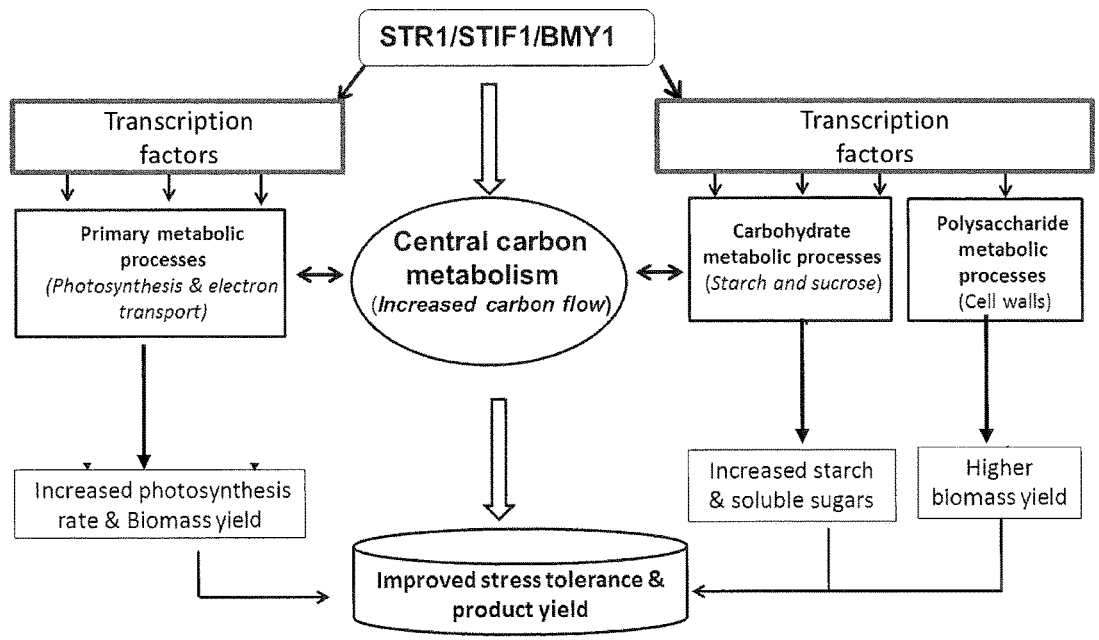
FIG. 1 graphically illustrates the transcriptional regulatory network model of the switchgrass transcription factors PvSTR1, PvSTIF1 and PvBMY1 and their association to improved plant productivity and stress tolerance. The thick arrows illustrate the observed increased carbon flow directly regulated by the transcription factors, whereas the small arrows indicate the interactions with downstream TFs for regulation of key genes in major metabolic pathways.

A description of example embodiments of the invention follows.

I. Definitions

Unless otherwise indicated, the disclosure encompasses all conventional techniques of plant transformation, plant breeding, microbiology, cell biology and recombinant DNA, which are within the skill of the art. See, e.g., Sambrook and Russell, *Molecular Cloning: A Laboratory Manual*, 3rd edition, 2001; *Current Protocols in Molecular Biology*, F. M. Ausubel et al. eds., 1987; *Plant Breeding: Principles and Prospects*, M. D. Hayward et al., 1993; *Current Protocols in Protein Science*, Coligan et al., eds., 1995, (John Wiley & Sons, Inc.); the series *Methods in Enzymology* (Academic Press, Inc.): *PCR 2: A Practical Approach*, M. J. MacPherson, B. D. Hames and G. R. Taylor eds., 1995.

Unless otherwise noted, technical terms are used according to conventional usage. Definitions of common terms in molecular biology may be found in Lewin, *Genes VII*, 2001

(Oxford University Press), *The Encyclopedia of Molecular Biology*, Kendrew et al., eds., 1999 (Wiley-Interscience) and *Molecular Biology and Biotechnology, a Comprehensive Desk Reference*, Robert A. Meyers, ed., 1995 (VCH Publishers, Inc), *Current Protocols In Molecular Biology*, F. M. Ausubel et al., eds., 1987 (Green Publishing), Sambrook and Russell, *Molecular Cloning: A Laboratory Manual*, 3rd edition, 2001.

A number of terms used herein are defined and clarified in the following section.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, "transformed" and "transfected" encompass the introduction of a nucleic acid (e.g., a vector) into a cell by a number of techniques known in the art.

"Plasmids" are designated by a lower case "p" preceded and/or followed by capital letters and/or numbers.

The term "plant" is used in its broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that is largely differentiated into a structure that is present at any stage of a plant's development. Such structures include, but are not limited to, a fruit, shoot, stem, leaf, flower petal, etc.

The term "plant tissue" includes differentiated and undifferentiated tissues of plants including those present in roots, shoots, leaves, inflorescences, anthers, pollen, ovaries, seeds and tumors, as well as cells in culture (e.g., single cells, protoplasts, embryos, callus, etc.). Plant tissue may be in planta, in organ culture, tissue culture, or cell culture.

The term "plant part" as used herein refers to a plant structure, a plant organ, or a plant tissue.

A "non-naturally occurring plant" refers to a plant that does not occur in nature without human intervention. Non-naturally occurring plants include transgenic plants, plants created through genetic engineering and plants produced by non-transgenic means such as traditional or market assisted plant breeding.

The term "plant cell" refers to a structural and physiological unit of a plant, comprising a protoplast and a cell wall. The plant cell may be in the form of an isolated single cell or a cultured cell, or as a part of a higher organized unit such as, for example, a plant tissue, a plant organ, or a whole plant.

The term "plant cell culture" refers to cultures of plant units such as, for example, protoplasts, cells and cell clusters in a liquid medium or on a solid medium, cells in plant tissues and organs, microspores and pollen, pollen tubes, anthers, ovules, embryo sacs, zygotes and embryos at various stages of development.

The term "plant material" refers to leaves, stems, roots, inflorescences and flowers or flower parts, fruits, pollen, anthers, egg cells, zygotes, seeds, cuttings, cell or tissue cultures, or any other part or product of a plant.

A "plant organ" refers to a distinct and visibly structured and differentiated part of a plant, such as a root, stem, leaf, flower bud, inflorescence, spikelet, floret, seed or embryo.

The term "non-transgenic plant" refers to a plant that has not been genetically engineered with heterologous nucleic acids. These non-transgenic plants can be the test or control plant when comparisons are made, including wild-type plants.

A "corresponding non-transgenic plant" refers to the plant prior to the introduction of heterologous nucleic acids. This plant can be the test plant or control plant, including wild type plants.

A "trait" refers to morphological, physiological, biochemical and physical characteristics or other distinguishing feature of a plant or a plant part or a cell or plant material.

The term "trait modification" refers to a detectable change in a characteristic of a plant or a plant part or a plant cell induced by the expression of a polynucleotide or a polypeptide of the invention compared to a plant not expressing them, such as a wild type plant. Some trait modifications can be evaluated quantitatively, such as content of different metabolites, proteins, pigments, lignin, vitamins, starch, sucrose, glucose, fatty acids and other storage compounds, seed size and number, organ size and weight, total plant biomass and yield of genetically engineered products.

Trait modifications of further interest include those to seed (such as embryo or endosperm), fruit, root, flower, leaf, stem, shoot, seedling or the like, including: enhanced tolerance to environmental conditions including freezing, chilling, heat, drought, water saturation, radiation and ozone; improved growth under poor photoconditions (e.g., low light and/or short day length), or changes in expression levels of genes of interest. Other phenotype that can be modified relate to the production of plant metabolites, such as variations in the production of photosynthetic pigments, enhanced or compositionally altered protein or oil production (especially in seeds), or modified sugar (insoluble or soluble) and/or starch composition. Physical plant characteristics that can be modified include cell development (such as the number of trichomes), fruit and seed size and number, yields and size of plant parts such as stems, leaves and roots, the stability of the seeds during storage, characteristics of the seed pod (e.g., susceptibility to shattering), root hair length and quantity, internode distances, or the quality of seed coat. Plant growth characteristics that can be modified include growth rate, germination rate of seeds, vigor of plants and seedlings, leaf and flower senescence, male sterility, apomixis, flowering time, flower abscission, rate of nitrogen uptake, biomass or transpiration characteristics, as well as plant architecture characteristics such as apical dominance, branching patterns, number of organs, organ identity, organ shape or size.

As used herein "abiotic stress" includes but is not limited to stress caused by any one of the following: drought, salinity, extremes or atypical temperature, chemical toxicity and oxidative variation. The ability to improve plant tolerance to abiotic stress would be of great economic advantage to farmers worldwide and would allow for the cultivation of crops during adverse conditions and in territories where cultivation of crops may not otherwise be possible.

Methods and Transgenic Plants, Plant Tissue, Seed and Plant Cell of the Invention Described herein are methods of producing a transgenic plant, plant tissue, seed, or plant cell, wherein said plant, plant tissue, seed or plant cell comprises incorporated in the genome of said plant, plant tissue, seed, or plant cell: a polynucleotide encoding a plant transcription factor together with sequences to enable its increased expression or regulatory sequences inserted to increase the expression of a heterologous plant transcription factor.

It was found that incorporation of transcription factors encoded by the nucleotides SEQ ID NOs: 1, 2, and 3 modified expression of certain genes in a transgenic plant and increased the carbon flow of the transgenic plant without the corresponding increase in biomass. For example, increases in the levels of non-structural carbohydrates such as starch, sucrose and glucose levels in a transgenic plant are found to be greater than 2 fold increase but without an increase in the biomass or an insignificant increase in the biomass compared to the increases in the non-structural carbohydrates.

II. Transcriptional Regulation of Gene Expression in Plants

Transcription factors (TFs) are known to be involved in various biological processes, acting as activators or repressors of other genes or gene families, suggesting the function of various transcriptional regulatory mechanisms in regulating downstream signal transduction pathways. The regulatory logic that drives any plant response is governed by the combination of signaling regulators, TFs, their binding site in the regulatory regions of target genes (cis-regulatory elements; CREs) and other regulatory molecules (e.g., chromatin modifiers and small RNAs), as well as protein and RNA degradation machinery (Krishnan & Pereira, 2008, Brief Funct Genomic. Proteomic. 7: 264-74). TFs control the expression of many target genes through specific binding of the TF to the corresponding CRE in the promoters of respective target genes. For example, recent reports suggest that the maize Dof1 and MNF factors bind to the promoter of PEPC, an enzyme in the $C_4$ cycle of photosynthesis (reviewed in Weissmann & Brutnell, 2012, Current Opinion Biotech. 23: 298-304). Several TFs are known to be induced by stress, acting as activators or repressors, suggesting the function of various transcriptional regulatory mechanisms in regulating specific biological processes and or pathways.

Identification and Mapping Regulatory Domains of TFs:

Targeted gene regulation via designed transcription factors has great potential for precise phenotypic modification and acceleration of novel crop trait development. Over the past few years many transcription factors have been shown to contain regulatory domains, which can increase or decrease their transcriptional and/or DNA-binding activity. The mechanisms by which this regulation takes place frequently involve phosphorylation, dimer formation or interaction with negative or positive cofactors (Facchinetti et al., 1997, Biochem. J. 324: 729-736). Nevertheless, different organisms have evolved with diverse temporal and spatial regulation of transcription. In general, the temporal and spatial regulations are mediated by different classes of DNA binding transcriptional activator proteins. Unlike DNA binding domains, the transcription activation domains (TAD) have less primary amino acid sequence similarity. The TADs have been classified into acidic, glutamine-rich, proline-rich and serine/threonine-rich. We have identified putative transcription activation domains of the transcription factors of the invention based on the bioinformatics analysis.

Spatio-temporal Gene Expression Through Novel Cis-regulatory Elements:

Spatio-temporal gene expression is the activation of genes within specific tissues of an organism at specific times during development. Plant promoters have attracted increasing attention because of their irreplaceable role in modulating the spatio-temporal expression of genes interacting with transcription factors (TFs). The control of gene expression is largely determined by cis-regulatory modules localized in the promoter sequence of regulated genes and their cognate transcription factors. While there has been a substantial progress in dissecting and predicting cis-regulatory activity, our understanding of how information from multiple enhancer elements converge to regulate a gene's expression remains elusive. Constitutive promoters are widely used to functionally characterize plant genes in transgenic plants but their lack of specificity and poor control over protein expression can be a major disadvantage. On the other hand, promoters that provide precise regulation of temporal or spatial transgene expression facilitate such studies by targeting overexpression or knockdown of target genes to specific tissues and/or at particular developmental stages. Promoter-based transgenic technologies have already been applied to a great effect in wheat, where a heat-inducible promoter in transgenic plants effectively controlled the spatio-temporal expression of a transgene (Freeman et al., 2011, Plant Biotech. J. 9: 788-796). A modular synthetic promoter for the spatio-temporal control of transgene expression in stomata has been reported by fusing a guard cell-specific element from the promoter of the potato phosphoenolpyruvate carboxylase (PEPC) gene with the ethanol-inducible gene switch AlcR/alcA (Xiong et al., 2009, J. Exp. Bot. 60: 4129-4136). Recently, a chimeric inducible system was developed, which combined the cellular specificity of the AtMYB60 minimal promoter with the positive responsiveness to dehydration and ABA of the rd29A promoter (Rusconi et al., 2013, J. Exp. Bot. 64: 3361-3371). Remarkably, the synthetic module specifically up-regulated gene expression in guard cells of Arabidopsis, tobacco, and tomato in response to dehydration or ABA. Likewise, promoter cloning and subsequent manipulation of spatio-temporal gene expression together with transcription activation domains from the switchgrass transcription factors described in the presented invention offers a significant promise in genetically engineering novel adaptive traits in biomass and bioenergy crops.

IV. Plant Transformation Technologies

The transcription factor genes of this invention can be introduced into the genome of any plant by any of the methods for nuclear transformation known in the art. Methods for transformation of a range of plants useful for practicing the current invention are described in the examples herein. Any other genes of interest can be introduced into the genome and/or plastome of any plant by any of the methods for nuclear and plastid transformation known in the art. Other genes of interest can include herbicide resistance genes, pest resistance genes, fungal resistance genes, genes for enhancing oil yield or genes for novel metabolic pathways enabling the production of non-plant products to be made by the plant. The product of any transgene can be targeted to one or more of the plant cell organelles using any of the targeting sequences and methods known in the art.

A. Genetic Constructs for Transformation

DNA constructs useful in the methods described herein include transformation vectors capable of introducing transgenes into plants. As used herein, "transgenic" refers to an organism in which a nucleic acid fragment containing a heterologous nucleotide sequence has been introduced. The transgenes in the transgenic organism are preferably stable and inheritable. The heterologous nucleic acid fragment may or may not be integrated into the host genome.

Several plant transformation vector options are available, including those described in Gene Transfer to Plants, 1995, Potrykus et al., eds., Springer-Verlag Berlin Heidelberg N.Y., Transgenic Plants: A Production System for Industrial and *Pharmaceutical Proteins,* 1996, Owen et al., eds., John Wiley & Sons Ltd. England, and *Methods in Plant Molecular Biology: A Laboratory Course Manual,* 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts.

Engineered minichromosomes can also be used to express one or more genes in plant cells. Cloned telomeric repeats introduced into cells may truncate the distal portion of a chromosome by the formation of a new telomere at the integration site. Using this method, a vector for gene transfer can be prepared by trimming off the arms of a natural plant chromosome and adding an insertion site for large inserts (Yu et al., 2006, *Proc. Natl. Acad. Sci. USA* 103: 17331-17336; Yu et al., 2007, *Proc. Natl. Acad. Sci. USA* 104: 8924-8929).

An alternative approach to chromosome engineering in plants involves in vivo assembly of autonomous plant minichromosomes (Carlson et al., 2007, *PLoS Genet* 3: 1965-74). Plant cells can be transformed with centromeric sequences and screened for plants that have assembled autonomous chromosomes de novo. Useful constructs combine a selectable marker gene with genomic DNA fragments containing centromeric satellite and retroelement sequences and/or other repeats.

Another approach useful to the described invention is Engineered Trait Loci ("ETL") technology (U.S. Pat. No. 6,077,697; US 2006/0143732). This system targets DNA to a heterochromatic region of plant chromosomes, such as the pericentric heterochromatin, in the short arm of acrocentric chromosomes. Targeting sequences may include ribosomal DNA (rDNA) or lambda phage DNA. The pericentric rDNA region supports stable insertion, low recombination, and high levels of gene expression. This technology is also useful for stacking of multiple traits in a plant (US 2006/0246586).

Zinc-finger nucleases (ZFNs) are also useful for practicing the invention in that they allow double strand DNA cleavage at specific sites in plant chromosomes such that targeted gene insertion or deletion can be performed (Shukla et al., 2009, *Nature* 459: 437-441; Townsend et al., 2009, *Nature* 459: 442-445). This approach may be particularly useful for the present invention which can involve transcription factor genes which are naturally present in the genome of the plant of interest. In this case the ZFNs can be used to change the sequences regulating the expression of the TF of interest to increase the expression or alter the timing of expression beyond that found in a non-engineered or wild type plant.

A transgene may be constructed to encode a multifunctional transcription factor combining different domains of the transcription factors identified herein as useful for practicing the claimed invention through gene fusion techniques in which the coding sequences of different domains of the different genes are fused with or without linker sequences to obtain a single gene encoding a single protein with the activities of the individual genes. Such synthetic fusion gene/TF combinations can be further optimized using molecular evolution technologies.

B. Tissue Culture-Based Methods for Nuclear Transformation

Transformation protocols as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, *Plant Cell Rep.* 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

C. In Planta Transformation Methods

Procedures for in planta transformation can be simple. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, *The Plant* 16: 735-743), transformation of germinating seeds (Feldmann & Marks, 1987, *Mol. Gen. Genet.* 208: 1-9), floral dip (Clough and Bent, 1998, *Plant J.* 16: 735-743), and floral spray (Chung et al., 2000, *Transgenic Res.* 9: 471-476). Other plants that have successfully been transformed by in planta methods include rapeseed and radish (vacuum infiltration, Ian and Hong, 2001, *Transgenic Res.,* 10: 363-371; Desfeux et al., 2000, *Plant Physiol.* 123: 895-904), *Medicago truncatula* (vacuum infiltration, Trieu et al., 2000, *Plant* 22: 531-541), camelina (floral dip, WO/2009/117555 to Nguyen et al.), and wheat (floral dip, Zale et al., 2009, *Plant Cell Rep.* 28: 903-913). In planta methods have also been used for transformation of germ cells in maize (pollen, Wang et al. 2001, *Acta Botanica Sin.,* 43, 275-279; Zhang et al., 2005, *Euphytica,* 144, 11-22; pistils, Chumakov et al. 2006, *Russian J. Genetics,* 42, 893-897; Mamontova et al. 2010, *Russian J. Genetics,* 46, 501-504) and Sorghum (pollen, Wang et al. 2007, *Biotechnol. Appl. Biochem.,* 48, 79-83)

D. Transformation of Plants with Genes of Interest

Transgenic plants can be produced using conventional techniques to express any genes of interest in plants or plant cells (*Methods in Molecular Biology,* 2005, vol. 286, Transgenic Plants: Methods and Protocols, Pena L., ed., Humana Press, Inc. Totowa, N.J.). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed.

Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole plants. Detailed description of transformation techniques are within the knowledge of those skilled in the art.

1. Genes for Transcription Factors

Crop improvement using transcription factors (TFs) is a promising approach as they are likely to regulate a wide range of target genes whose products contribute to plant agronomic performance under normal and stress conditions. TF-mediated improvement of stress tolerance has been reported in diverse crop species, both dicots and monocots (Hussain et al., 2011, *Biotechnology Prog.* 27: 297-306). The first efforts included overexpression of the AP2/ERF factors CBF1, DREB1A and CBF4 that resulted in drought/salt/cold tolerance in *Arabidopsis* (Jaglo-Ottosen et al., 1998, *Science* 280: 104-106). Since then, the orthologous genes of CBF/DREB have been identified in many crop plants and functional tests revealed conservation of function (reviewed in Xu et al., 2011. *J. Int. Plant Biol.* 53: 570-585). It has also been shown that ectopic overexpression of these TF genes caused, in addition to increased stress tolerance, some specific phenotypic changes—dark-green, dwarfed plants with higher levels of soluble sugars and proline have been obtained. More recent evidence suggested the role of an AP2 family protein SHINE/WAX INDUCER 1 (SHN) as a global level regulator of cell wall biosynthesis which could be economically valuable for biofuel production from lignocellulosic crops (Ambavaram et al., 2011, *Plant Physiol.* 155: 916-931).

In studies with model plants, it has been shown that transcription factors belonging to the AP2/ERF, NF-Y, bZIP, MYB, Zinc-finger and NAC families confer tolerance to both biotic and abiotic stresses. Comparative genomics has also been used to find genes with conserved functions between model plants (mainly Arabidopis) and crop plants, such as rice and maize demonstrating the utility of using the dicot-monocot models together. For example, expression of an *Arabidopsis* AP2/ERF-like transcription factor in rice resulted in an increase in leaf biomass and bundle sheath cells that probably contributed to the enhanced photosynthetic assimilation and efficiency (Karaba et al., 2009, *Proc. Natl. Acad. Sci. USA* 104: 15270-15275).

2. Reporter Genes and Selectable Marker Genes

Reporter genes or selectable marker genes may be included in an expression cassette as described in US Patent Applications 20100229256 and 20120060413 incorporated by reference herein. An expression cassette including a promoter sequence operably linked to a heterologous nucleotide sequence of interest can be used to transform any plant by any of the methods described above. Useful selectable marker genes and methods of selection transgenic lines for a range of different crop species are described in the examples herein.

E. Transgene Expression in Plants

Plant promoters can be selected to control the expression of the transgene in different plant tissues or organelles for all of which methods are known to those skilled in the art (Gasser & Fraley, 1989, *Science* 244: 1293-1299). In one embodiment, promoters are selected from those of eukaryotic or synthetic origin that are known to yield high levels of expression in plant and algae. In a preferred embodiment, promoters are selected from those that are known to provide high levels of expression in monocots.

1. Inducible Promoters

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize 1n2-2 promoter, which is activated by benzenesulfonamide herbicide safeners, the maize GST promoter, which is activated by hydrophobic electrophlic compounds that are used as pre-emergent herbicides, and the tobacco PR-1 promoter which is activated by salicylic acid. Other chemical-regulated promoters include steroid-responsive promoters [see, for example, the glucocorticoid-inducible promoter (Schena et al., 1991, *Proc. Natl. Acad. Sci. USA* 88: 10421-10425; McNellis et al., 1998, *Plant J.* 14:247-257) and tetracycline-inducible and tetracycline-repressible promoters (see, for example, Gatz et al., 1991, *Mol. Gen. Genet.* 227: 229-237; U.S. Pat. Nos. 5,814,618 and 5,789,156, herein incorporated by reference in their entirety).

A three-component osmotically inducible expression system suitable for plant metabolic engineering has recently been reported (Feng et al., 2011, *PLoS ONE* 6: 1-9).

2. Constitutive Promoters

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

3. Weak Promoters

Where low level expression is desired, weak promoters may be used. Generally, the term "weak promoter" is intended to describe a promoter that drives expression of a coding sequence at a low level. Where a promoter is expressed at unacceptably high levels, portions of the promoter sequence can be deleted or modified to decrease expression levels. Such weak constitutive promoters include, for example, the core promoter of the Rsyn7 promoter (WO 99/43838 and U.S. Pat. No. 6,072,050).

4. Tissue Specific Promoters

"Tissue-preferred" promoters can be used to target gene expression within a particular tissue. Compared to chemically inducible systems, developmentally and spatially regulated stimuli are less dependent on penetration of external factors into plant sells. Tissue-preferred promoters include those described by Van Ex et al., 2009, *Plant Cell Rep.* 28: 1509-1520; Yamamoto et al., 1997, *Plant J.* 12: 255-265; Kawamata et al., 1997, *Plant Cell Physiol.* 38: 792-803; Hansen et al., 1997, *Mol. Gen. Genet.* 254: 337-343; Russell et al., 199), *Transgenic Res.* 6: 157-168; Rinehart et al., 1996, *Plant Physiol.* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Differ.* 20: 181-196, Orozco et al., 1993, *Plant Mol. Biol.* 23: 1129-1138; Matsuoka et al., 1993, *Proc. Natl. Acad. Sci.*

USA 90: 9586-9590, and Guevara-Garcia et al., 1993, *Plant J.* 4: 495-505. Such promoters can be modified, if necessary, for weak expression.

4.i. Seed/Embryo Specific Promoters

"Seed-preferred" promoters include both "seed-specific" promoters (those promoters active during seed development such as promoters of seed storage proteins) as well as "seed-germinating" promoters (those promoters active during seed germination). See Thompson et al., 1989, *BioEssays* 10: 108-113, herein incorporated by reference. Such seed-preferred promoters include, but are not limited to, Cim1 (cytokinin-induced message), cZ19B1 (maize 19 kDa zein), milps (myo-inositol-1-phosphate synthase), and celA (cellulose synthase). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1. The stage specific developmental promoter of the late embryogenesis abundant protein gene LEA has successfully been used to drive a recombination system for excision-mediated expression of a lethal gene at late embryogenesis stages in the seed terminator technology (U.S. Pat. No. 5,723,765 to Oliver et al).

4.ii. Leaf Specific Promoters

Leaf-specific promoters are known in the art. See, for example, WO/2011/041499 and U.S. Patent No 2011/0179511 A1 to Thilmony et al.; Yamamoto et al., 1997, *Plant J.* 12: 255-265; Kwon et al., 1994, *Plant Physiol.* 105: 357-367; Yamamoto et al., 1994, *Plant Cell Physiol.* 35: 773-778; Gotor et al., 1993, *Plant* 3: 509-518; Orozco et al., 1993, *Plant Mol. Biol.* 23: 1129-1138, and Matsuoka et al., 1993, *Proc. Natl. Acad. Sci. USA* 90: 9586-9590.

4.iii. Temporal Specific Promoters

Also contemplated are temporal promoters that can be utilized during the developmental time frame, for example, switched on after plant reaches maturity in leaf to enhance carbon flow.

4iv. Anther/Pollen Specific Promoters

Numerous genes specifically expressed in anthers and/or pollen have been identified and their functions in pollen development and fertility have been characterized. The specificity of these genes has been found to be regulated mainly by their promoters at the transcription level (Ariizumi et al., 2002, *Plant Cell Rep.* 21: 90-96 and references therein). A large number of anther- and/or pollen-specific promoters and their key cis-elements from different plant species have been isolated and functionally analyzed.

4.v. Floral Specific Promoters

Floral-preferred promoters include, but are not limited to, CHS (Liu et al., 2011, *Plant Cell Rep.* 30: 2187-2194), OsMADS45 (Bai et al., 2008, *Transgenic Res.* 17: 1035-1043), PSC (Liu et al., 2008, *Plant Cell Rep.* 27: 995-1004), LEAFY, AGAMOUS, and AP1 (Van Ex et al., 2009, *Plant Cell Rep.* 28: 1509-1520), AP1 (Verweire et al., 2007, *Plant Physiol.* 145: 1220-1231), PtAGIP (Yang et al., 2011, *Plant Mol. Biol. Rep.* 29: 162-170), Lem1 (Somleva & Blechl, 2005, *Cereal Res. Comm.* 33: 665-671; Skadsen et al., 2002, *Plant Mol. Biol.* 45: 545-555), Lem2 (Abebe et al., 2005, *Plant Biotechnol. J.* 4: 35-44), AGL6 and AGL13 (Schauer et al., 2009, *Plant* 59: 987-1000).

4.vi. Combinations of Promoters

Certain embodiments use transgenic plants or plant cells having multi-gene expression constructs harboring more than one promoter. The promoters can be the same or different.

Any of the described promoters can be used to control the expression of one or more of the transcription factor genes of the invention, their homologs and/or orthologs as well as any other genes of interest in a defined spatiotemporal manner.

F. Requirements for Construction of Plant Expression Cassettes

Nucleic acid sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra. The following is a description of various components of typical expression cassettes.

1. Transcriptional Terminators

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

2. Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adh1 gene have been shown to enhance expression, particularly in monocotyledonous cells. In addition, a number of non-translated leader sequences derived from viruses are also known to enhance expression, and these are particularly effective in dicotyledonous cells.

G. Coding Sequence Optimization

The coding sequence of the selected gene may be genetically engineered by altering the coding sequence for optimal expression in the crop species of interest. Methods for modifying coding sequences to achieve optimal expression in a particular crop species are well known (Perlak et al., 1991, *Proc. Natl. Acad. Sci. USA* 88: 3324 and Koziel et al., 1993, *Biotechnology* 11: 194-200).

H. Construction of Plant Transformation Vectors

Numerous vectors available for plant transformation are known to those of ordinary skill in the plant transformation arts. The genes pertinent to this disclosure can be used in conjunction with any such vectors. The choice of vector depends upon the selected transformation technique and the target species.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof (See, for example, U.S. Pat. No. 5,639, 949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non *Agrobacterium* transformation include pCIB3064, pSOG 19, and pSOG35. (See, for example, U.S. Pat. No. 5,639,949).

I. Transformation and Selection of Cultures and Plants

Plant cultures can be transformed and selected using one or more of the methods described above which are well known to those skilled in the art. In switchgrass, selection occurs by incubating the cultures on a callus growth medium containing bialaphos. In an alternative embodiment, selection can occur in the presence of hygromycin. Resistant calluses are then cultured on a regeneration medium (Somleva, 2006, *Agrobacterium Protocols*, Wang K., ed., Vol. 2, pp 65-74, Humana Press; Somleva et al., 2002, *Crop Sci.* 42: 2080-2087) containing the preferred selection agent. Examples of specific selectable markers and transgenic plant selection methods for a number of crop species are described in the examples herein.

EXAMPLES

Example 1. Identification and Functional Characterization of Candidate Transcription Factor Genes Potentially Involved in Photosynthesis and Biomass Related Traits The following approaches were used to identify and annotate potential switchgrass transcription factors (TFs):

A. Gene Prediction Based on Systems Biology Approach

A rice regulatory association network that has been developed based on genome wide expression profiles (Ambavaram et al., 2011, *Plant Physiol.* 155: 916-931) was used to identify switchgrass orthologs of TFs with predicted function in the regulation of genes involved in photosynthesis and biomass related traits. Publicly available databases were used to perform BlastN and BlastP reciprocal searches between the genomes of rice (a $C_3$ monocot; http://rice-.plantbiology.msu.edu), maize (a monocot possessing the NADP-ME subtype of $C_4$ photosynthesis; found at world wide web maizesequence.org and switchgrass an NAD-ME $C_4$ monocot at phytozome.net/search.php?show=blast&org=Org_Pvirgatum to identify candidate genes for functional validation and experimental analysis. Comparisons of gene ontology (GO) terms from the molecular function category revealed the most obvious functions of DNA binding and transcriptional regulatory activity of the identified TFs.

Based on genome-wide orthologous prediction, candidate genes were retrieved from the corresponding websites and their percentage of identity was evaluated (Table 1).

TABLE 1

Candidate transcription factor genes.

| Rice gene | Maize gene | Switchgrass ortholog | % identity | E-value |
| --- | --- | --- | --- | --- |
| LOC_Os02g10480 | GRMZM2G138349 | Pavirv00027905m | 87.75 | 1e-86 |
| LOC_Os07g41580 | GRMZM2G384528 | Pavirv00029298m | 94.83 | 4e-58 |
| LOC_Os02g52670 | GRMZM2G103085 | Pavirv00031839m | 78.00 | 3e-11 |
| LOC_Os09g11480 | EU942421 | Pavirv00046166m | 75.44 | 2e-13 |
| LOC_Os03g09170 | GRMZM2G113060 | Pavirv00021049m | 61.11 | 3e-37 |
| LOC_Os02g32140 | GRMZM2G016434 | Pavirv00013751m | 97.26 | 8e-27 |
| LOC_Os09g29960 | GRMZM2G089850 | Pavirv00059600m | 94.59 | 3e-17 |
| LOC_Os11g06770 | GRMZM2G544539 | Pavirv00009307m | 91.94 | 1e-19 |
| LOC_Os04g52090 | GRMZM2G068967 | Pavirv00015875m | 98.31 | 2e-21 |
| LOC_Os04g55520 | GRMZM2G119865 | Pavirv00033364m | 66.67 | 4e-18 |

B. Functional Annotation of Select Switchgrass TFs

According to the plant transcription factor database (see world wide web at planttfdb.cbi.edu.cn) and switchgrass genome (world wide web at phytozome.net), SEQ ID NO: 1 (Pavirv00046166m) and SEQ ID NO: 2 (Pavirv00013751m) are switchgrass transcription factors belonging to the APETALA2 (AP2)/ETHYLENE RESPONSE FACTOR (ERF) family and SEQ ID NO: 3 (Pavirv00029298m) is a switchgrass transcription factor from the Nuclear-Factor Y (NF-YB) family. The analysis of their protein sequences using a database of protein domains, families and functional sites (world wide web at expacy.org) revealed the characteristic AP2 domain (SEQ ID NO: 4 and SEQ ID NO: 5, underlined) and NFYA-HAP2 motif (SEQ ID NO: 6, underlined), respectively. Comparisons of gene ontology terms for the switchgrass genes SEQ ID NO: 1 and SEQ ID NO: 2 revealed the 'transcription factor' activity (GO: 0003700), whereas SEQ ID NO: 3 belongs to the MNFs based on its sequence-specific transcription regulator activity (GO: 00030528). According to the TF-function association network, these switchgrass orthologous TF genes may be associated with functions in "primary" carbon metabolism and several "cellular metabolic" processes.

C. Expression Analysis of Novel Transcription Factors in Switchgrass.

For validation of the bioinformatics findings, the tissue specific expression of the candidate TF genes (Table 1) in switchgrass was analyzed by RT-PCR. Total RNA was isolated from root (R), culm (C), leaf sheath (LS), young leaf (YL), mature leaf (ML), and panicle (P) tissues of wild type plants. After DNase treatment and column purification, total RNA (200 ng per reaction) was subjected to reverse transcription and PCR in a one-step RT-PCR assay (Qiagen) with gene-specific primers.

Figure 2:
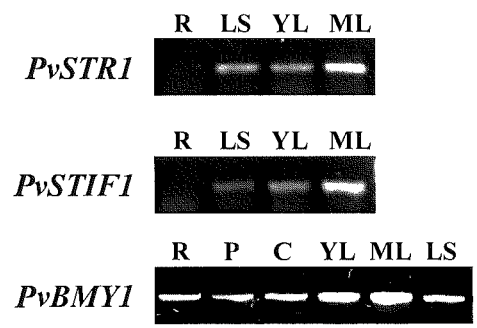
FIG. 2 illustrates the tissue specific expression pattern of the transcription factor genes PvSTR1, PvSTIF1 and PvBMY1 in wild type switchgrass analyzed by RT-PCR. Total RNA was isolated from roots (R), young leaves (YL), culms (C), mature leaves (ML), leaf sheaths (LS), and/or panicles (P) of wild-type plants and subjected to reverse transcription and PCR using One Step RT-PCR Kit (Qiagen) and primers specific for the coding regions of the TF genes.

The results revealed the differences in the expression levels of the candidate TF genes (listed in Table 1) in young and mature leaves, roots, and stem tissues (culm, leaf sheath and panicle). Based on their expression patterns we identified three genes which were highly expressed in mature leaf and these, three genes (SEQ ID NO: 1, SEQ ID NO: 2, and SEQ ID NO: 3) were selected for overexpression and functional analysis in switchgrass. The highest transcript accumulation for these three genes was observed in mature leaves (FIG. 2). No expression of the selected AP2/ERF transcription factors (SEQ ID NO: 1 and SEQ ID NO: 2) was detected in roots under the experimental conditions, while transcripts of the switchgrass NF-Y gene (SEQ ID NO: 3) were present at different levels in all tissues analyzed (FIG. 2).

Based on the effects of these TFs on plant metabolism and phenotype (see Example 5), the genes and the encoded polypeptides were designated as PvSTR1 (STarch Regulator 1; SEQ ID NO: 1 and SEQ ID NO: 4), PvSTIF1 (STress Inducible Factor 1; SEQ ID NO: 2 and SEQ ID NO: 5), and PvBMY1 (BioMass Yield 1, SEQ ID NO: 3 and SEQ ID NO: 6).

D. Identification of Homologous Genes of PvSTR1, PvSTIF1 and PvBMY1 Transcription Factors:

The sequence homology search was performed by comparing the deduced amino acid sequences of PvSTR1, PvSTIF1 and PvBMY1 to a translated non-redundant nucleotide database found on the world wide web at blast.ncbi.nlm.nih.gov and phytozome.net using tBLASTN and to a protein database using BLASTP. Transcription factor genes that are homologous to the transcription factors of the invention will typically have a polypeptide sequence of their conserved domain or the entire coding region 80% or more identical to the SEQ ID NOS: 4-6. As used herein, a "homolog" means a protein that performs the same biological function as another protein including these identified by sequence identity search. In silico analysis resulted in the identification of several homologs of each of the three transcription factors of the invention indicated as PvSTR2-5 (SEQ ID NOS: 7-10), PvSTIF2-4 (SEQ ID NOs: 11-13), and PvBMY2-6 (SEQ ID NOs: 14-18) for the homologs of PvSTR1, PvSTIF1 and PvBMY1, respectively.

Figure 3:
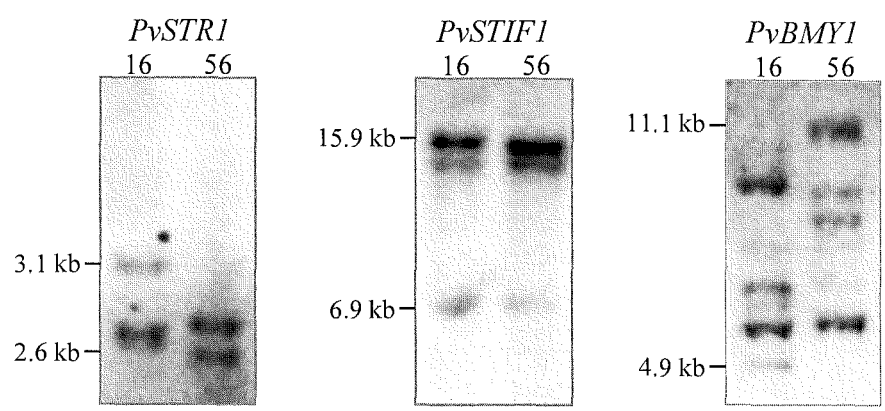
FIG. 3 demonstrates the presence of genes homologous to the transcription factor genes PvSTR1, PvSTIF1 and PvBMY1 in the switchgrass genome as detected by Southern blot hybridization. Genomic DNA isolation, digestion with EcoRI and hybridization with probes specific for the coding regions of the transcription factor genes was performed as described previously (Somleva et al., 2008, *Plant Biotechnol J*, 6: 663-678). 16 and 56, Alamo genotypes (our designation).

The copy number of each of the TF genes in the switchgrass genome was also determined by Southern blot hybridizations. Two genotypes from the switchgrass cultivar Alamo—56 and 16 (our designation) were studied. Callus cultures from these genotypes were used in all the experiments on switchgrass transformation (as described in Example 3). The results revealed the presence of the same number of homologs of PvSTR1, PvSTIF1 and PvBMY1 in the two genotypes analyzed (FIG. 3).

Based on the existing sequential similarity, including the presence of identical DNA-binding domains, overexpression of the identified homologous genes PvSTR2-5, PvSTIF2-4, and PvBMY2-6 can readily be tested for trait modifications similar to the ones induced by PvSTR1, PvSTIF1 and PvBMY1.

E. Identification of Orthologous Genes of PvSTR1, PvSTIF1 and PvBMY1 Transcription Factors:

"Orthologs" and "paralogs" refer to polynucleotide and polypeptide sequences which are homologous to the claimed sequences. These genes are related because they originate from a common ancestral gene and potentially retain a similar function in the course of evolution. Orthologs are structurally related genes in different species that are derived by speciation, while paralogs are structurally related genes in the same species that are derived by genetic duplication. Orthologous genes are identified based upon percentage similarity or identity of the complete sequence or of a conserved domain. Closely related transcription factors can share about 70%, 75%, or about 80% or more amino acid sequence identity. Sequences with sufficient similarity may also bind to the same DNA binding sites of transcriptional regulatory elements.

Figure 4B:
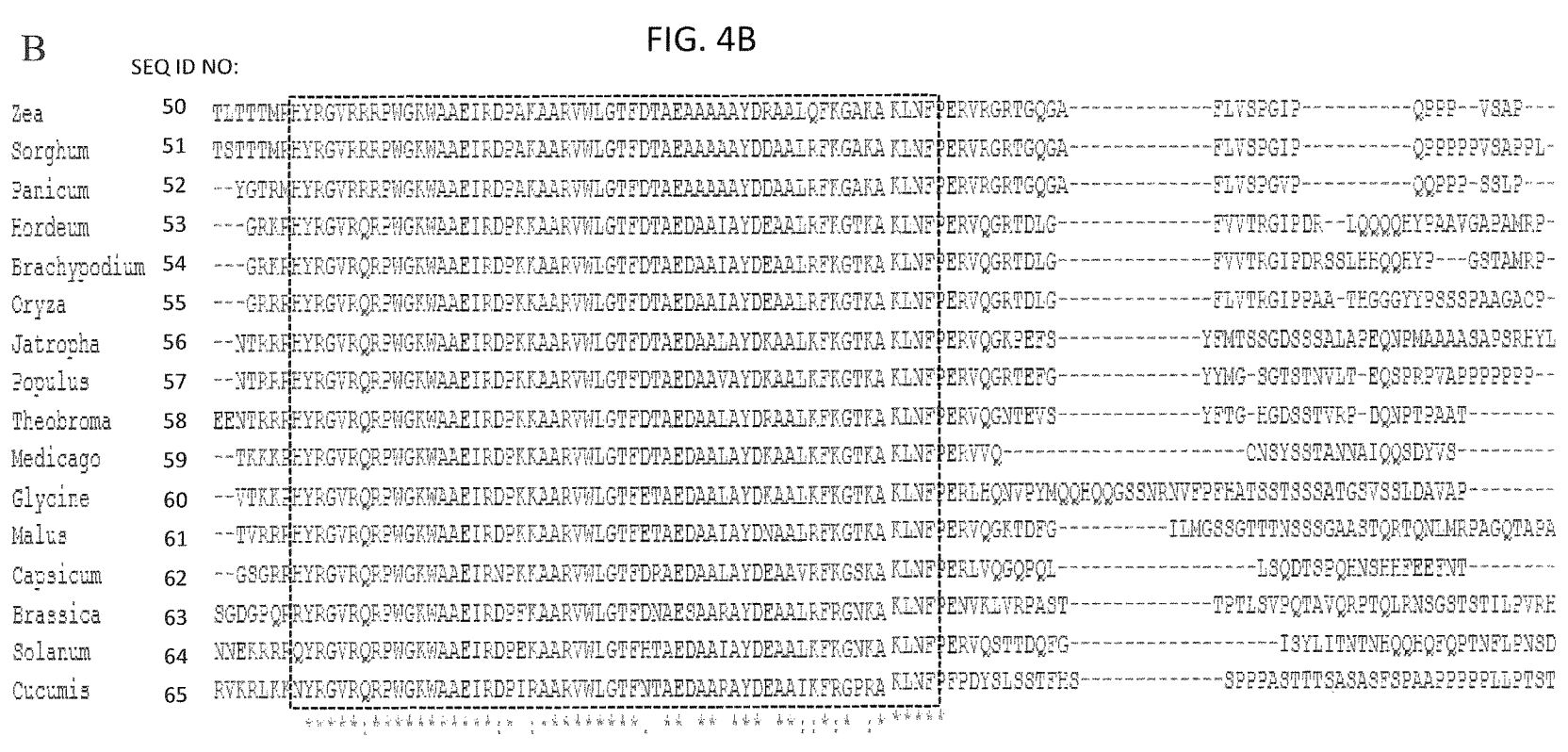
Figure 4C:
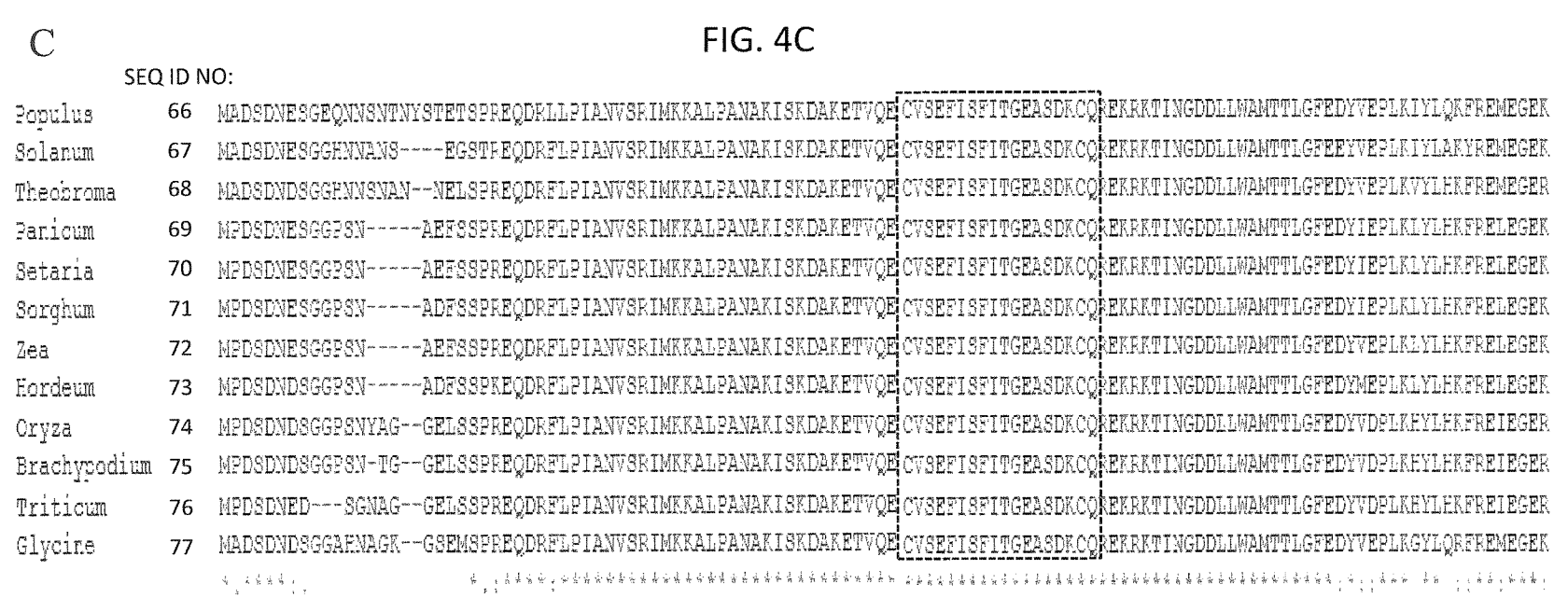
Figure 5A:
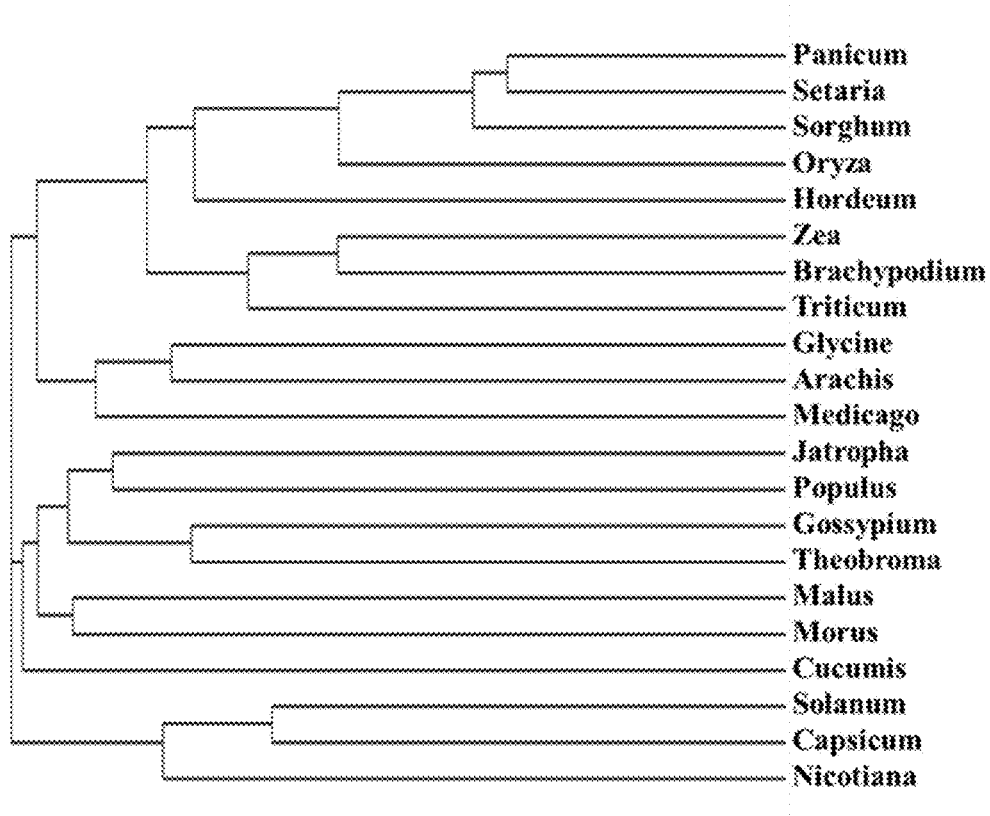
FIG. 5 illustrates the possible phylogenetic relationships among the higher plant taxa, including monocotyledonous and dicotyledonous species, based on the conservative domains of PvSTR1 (A), PvSTIF1 (B) and PvBMY1 (C).
Figure 5B:
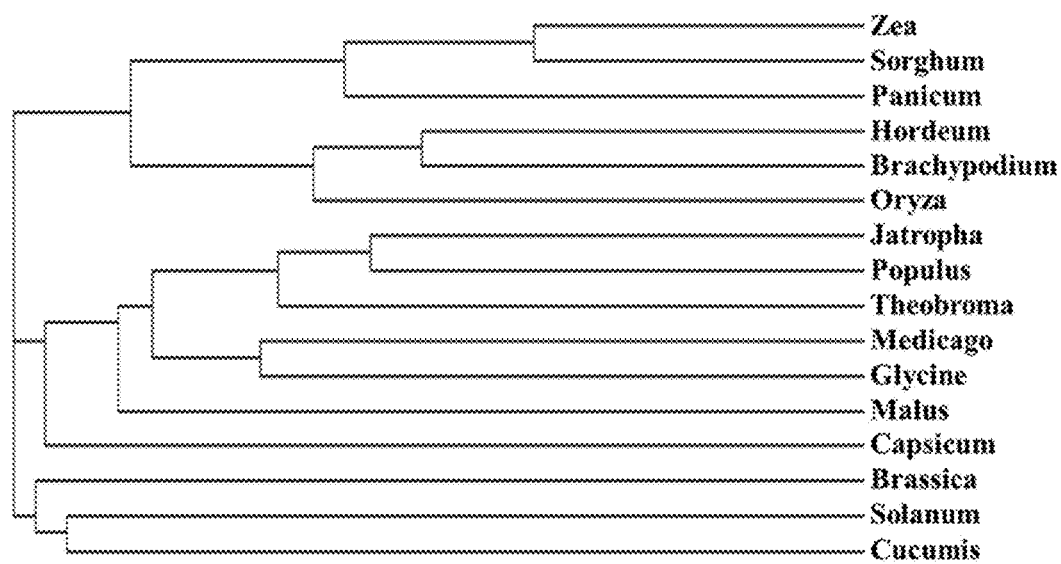
Figure 5C:
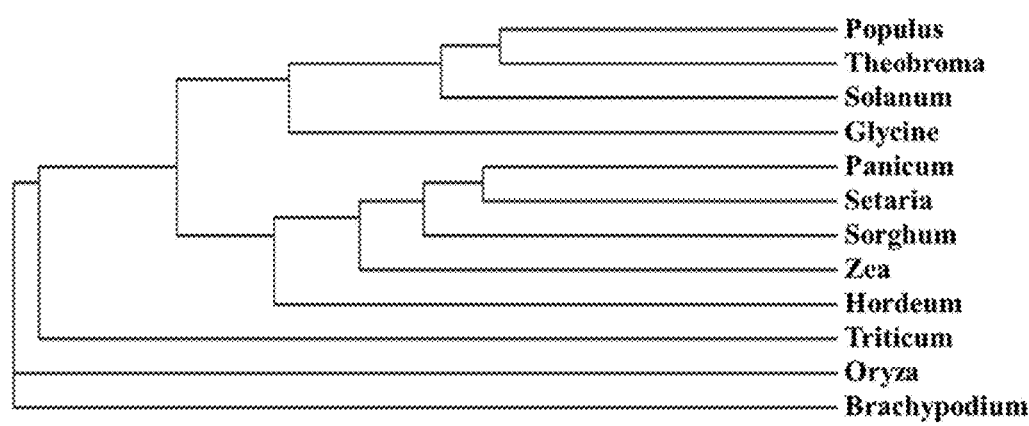

Orthologs of the switchgrass transcription factor genes PvSTR1, PvSTIF1 and PvBMY1 were identified using methods well known in the art. Orthologous polypeptide sequences from different plant species with more than 75%, 80%, 85%, greater than 90% identity of the conserved binding domains are shown in FIG. 4. The phylogenetic relationships were also estimated based on the conserved domain sequences of PvSTR1, PvSTIF1 and PvBMY1 (FIG. 5).

Example 2. Design and Construction of Transformation Vectors for Overexpression of Transcription Factor Genes in Switchgrass All gene constructs were made using widely available genetic components and standard molecular biology techniques. Each of the genes was cloned in an individual expression cassette and 2-5 cassettes were assembled in one vector for plant transformation.

Figure 6A:
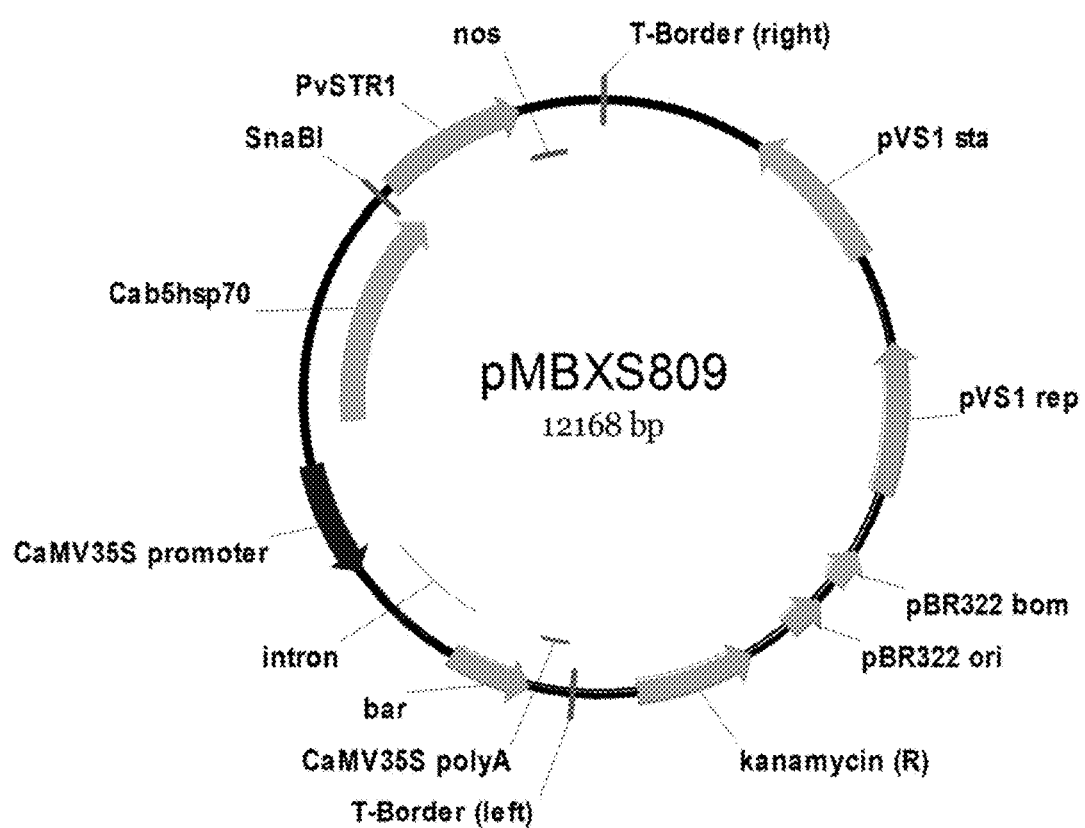
FIG. 6 shows the vectors pMBXS809 (A), pMBXS810 (B) and pMBXS855 (C) harboring the TF genes and the marker gene bar.
Figure 6B:
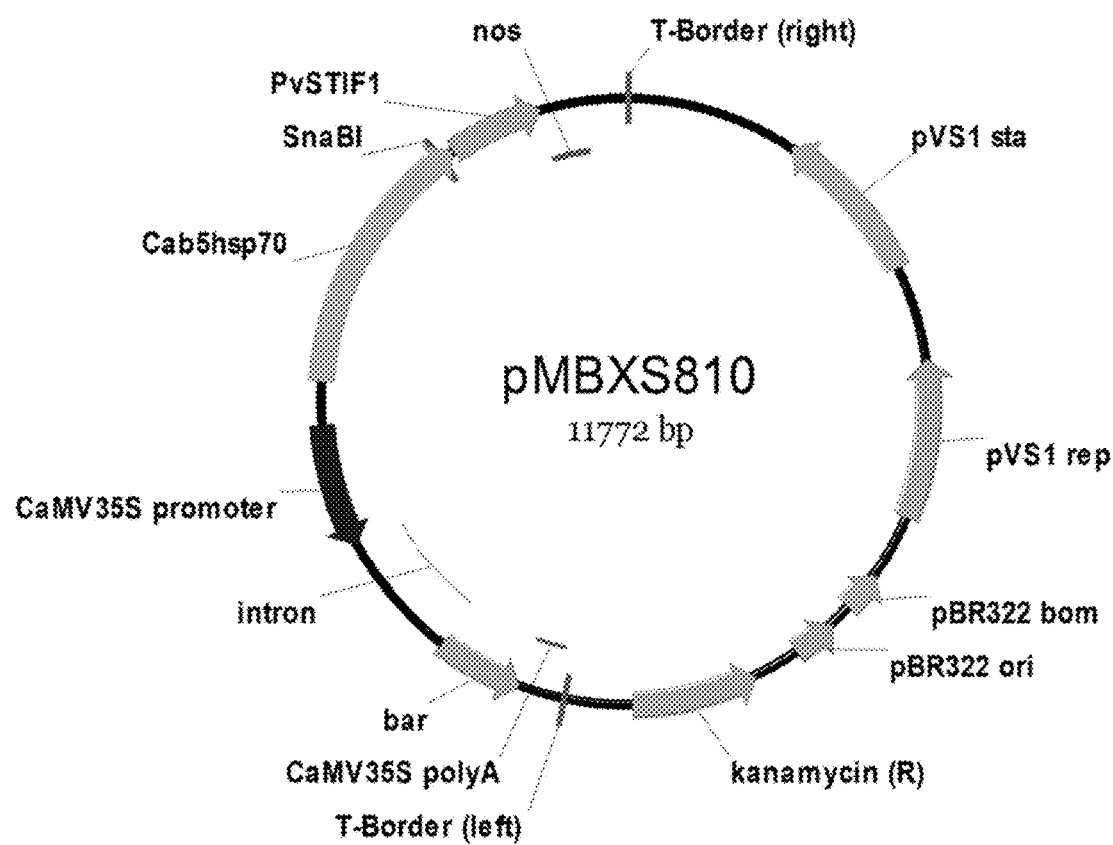
Figure 6C:
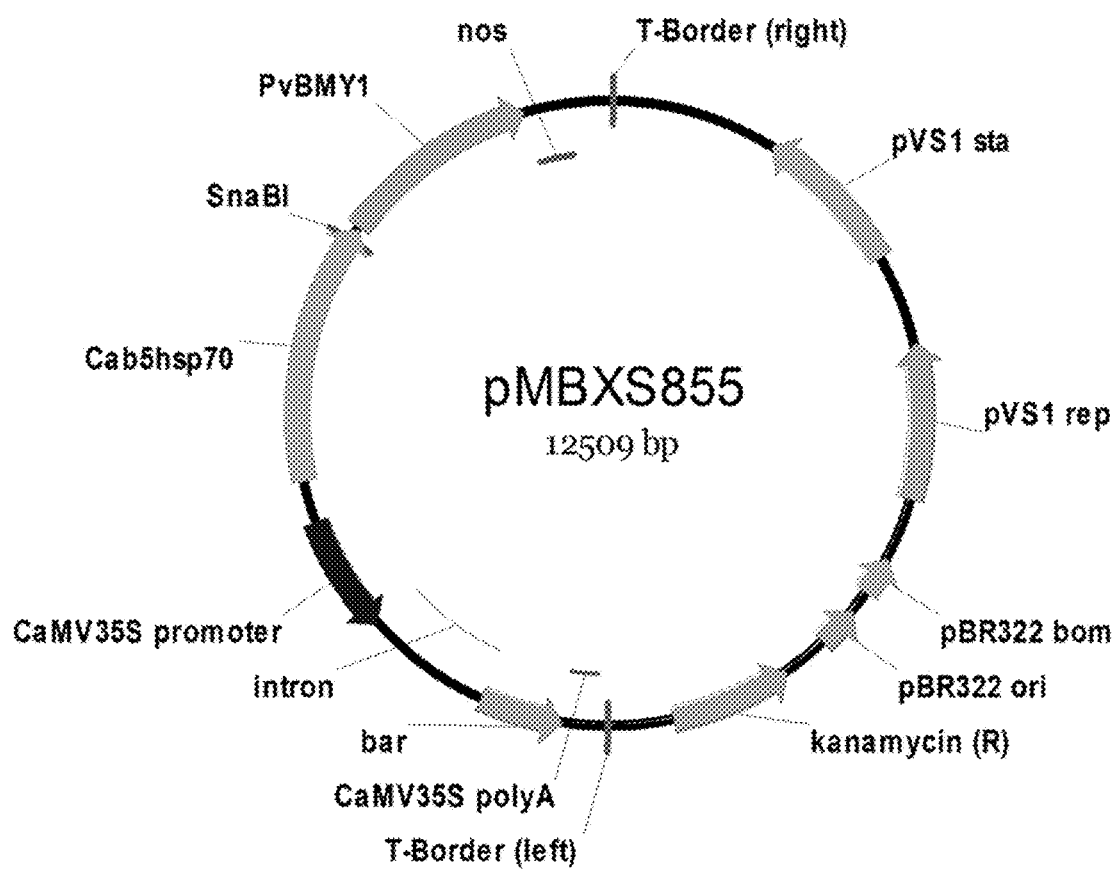
Figure 7A:
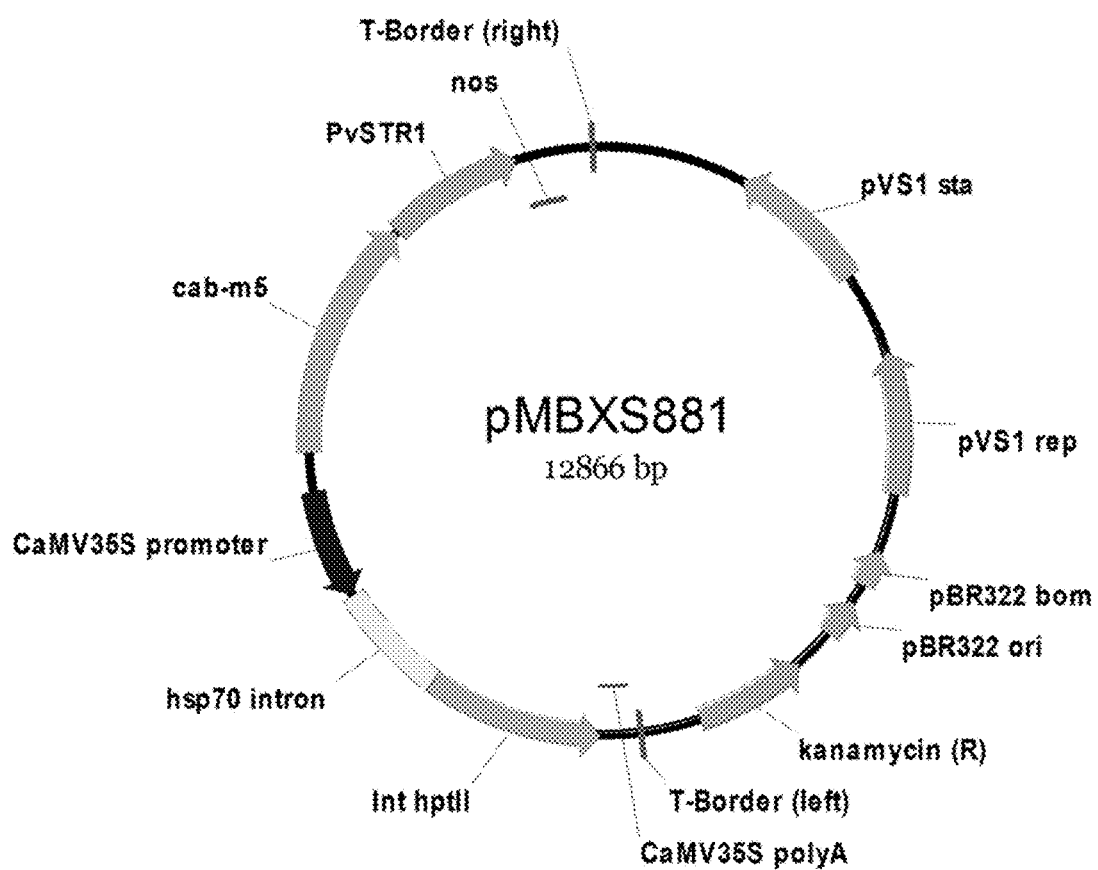
FIG. 7 depicts the vectors pMBXS881 (A), pMBXS882 (B) and pMBXS883 (C) harboring the TF genes and the marker gene hptII.
Figure 7B:
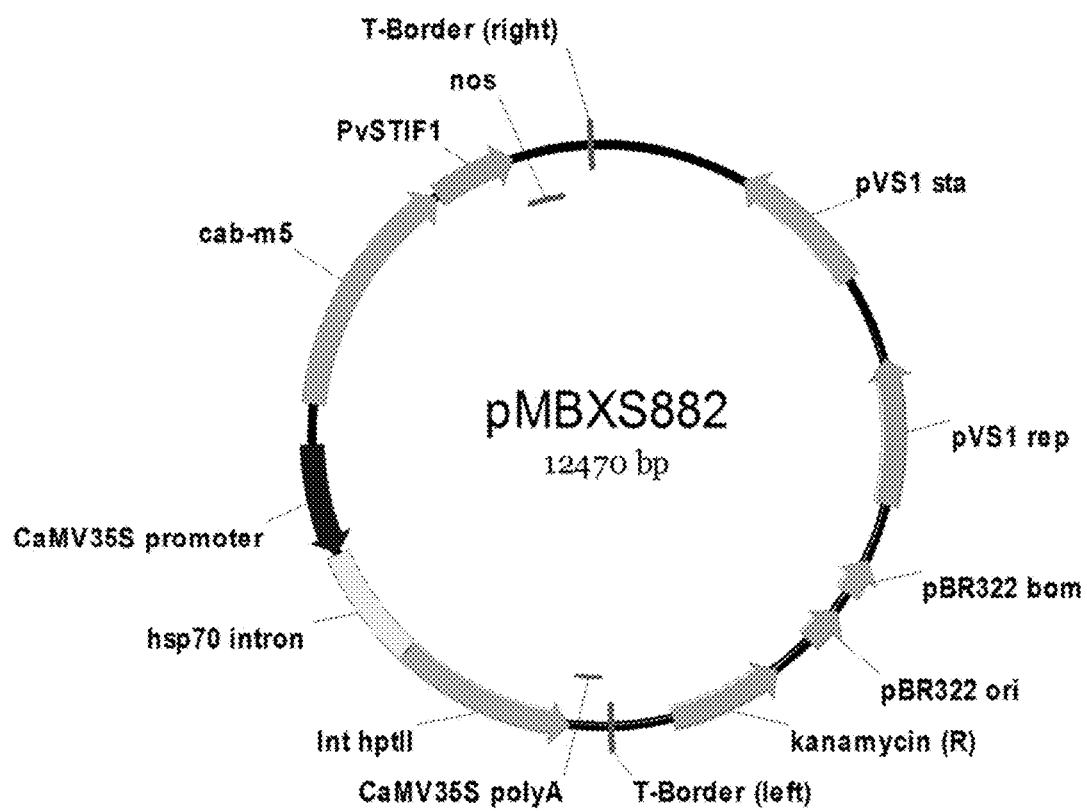
Figure 7C:
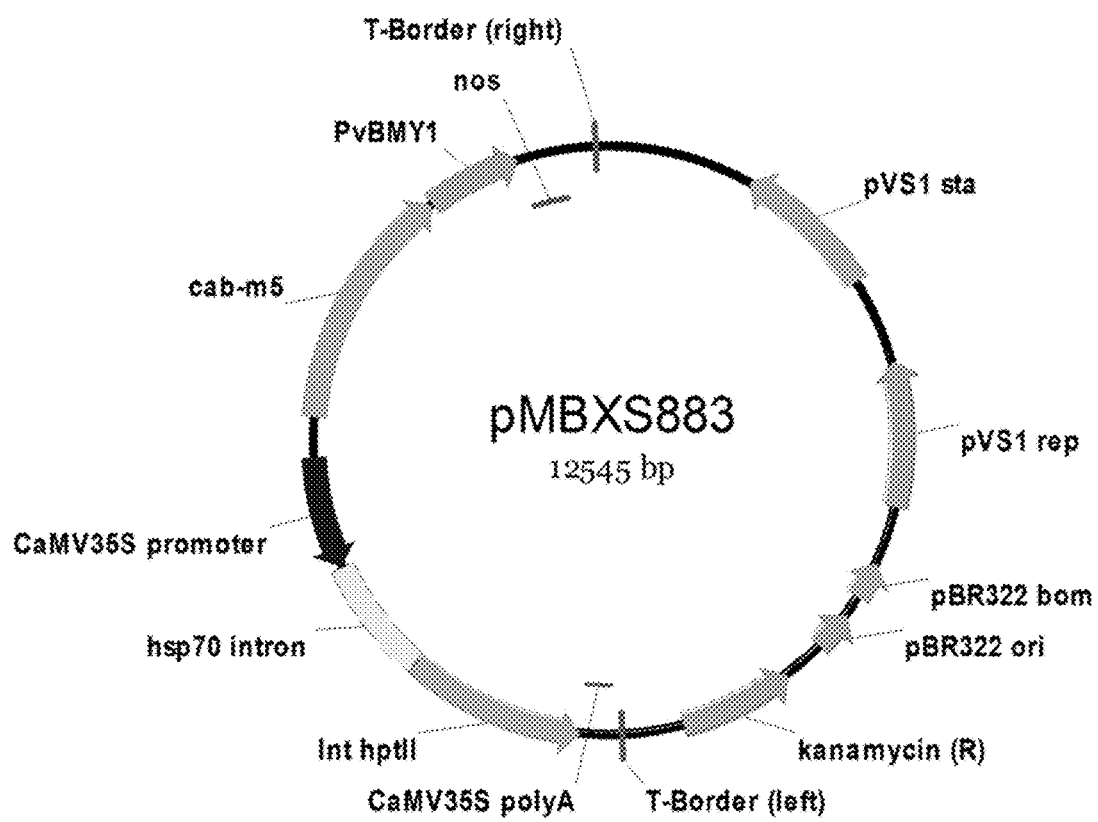

Two sets of gene constructs, one set containing the bar gene (conferring resistance to bialaphos) as a selectable marker and another one with the hptII gene (conferring resistance to hygromycin), were created for overexpression of the transcription factor genes of the invention in switchgrass (Table 2, FIGS. 6 and 7).

TABLE 2

Summary of plant transformation vectors for expression of transcription factors and PHB biosynthesis genes.

| Vector | Locus Name | Gene of interest[1] | Marker gene[2] |
| --- | --- | --- | --- |
| pMBXS809 | Pavirv00046166m | PvSTR1 | bar |
| pMBXS810 | Pavirv00013751m | PvSTIF1 | bar |
| pMBXS855 | Pavirv00029298m | PvBMY1 | bar |
| pMBXS881 | Pavirv00046166m | PvSTR1 | hptII |
| pMBXS882 | Pavirv00013751m | PvSTIF1 | hptII |
| pMBXS883 | Pavirv00029298m | PvBMY1 | hptII |

[1]Driven by the maize cab-m5 promoter fused to the maize hsp70 intron;
[2]Driven by the 35S promoter.

The vectors pMBXS809, pMBXS810, and pMBXS855 (FIG. 6) were used for *Agrobacterium*-mediated transformation of switchgrass for generation of transgenic lines for functional analyses of the novel transcription factors (see Example 3). In each vector, the transcription factor gene is under the control of the cab-m5 light-inducible promoter of the chlorophyll a/b-binding protein in maize (Sullivan et al., 1989, *Mol. Gen. Genet.* 215: 431-440; Becker et al., 1992, *Plant Mol. Biol.* 20: 49-60) fused to the heat shock protein 70 (hsp70) intron (U.S. Pat. No. 5,593,874), while the marker genes are driven by the 35S promoter (Table 2).

The annotation of the genes and genetic elements assembled in the vectors pMBXS809, pMBXS810, and pMBXS855 are presented in Table 3 (see also FIGS. 6 and 7).

TABLE 3

Plant transformation vectors for overexpression of the transcription factor genes PvSTR1, PvSTIF1 and PvBMY1 in switchgrass.

| Vector ID* | TF gene/ marker | Annotation | SEQ ID | Coordinates (bp) |
|---|---|---|---|---|
| pMBXS809 | PvSTR1/bar | Agrobacterium T-DNA right border | 19 | 1 to 26 |
| | | Cab-m5 promoter with hsp70 intron to drive PvSTR1 gene | | 8951 to 10645 |
| | | PvSTR1 coding region | | 10646 to 11636 |
| | | nos terminator | | 11637 to 11891 |
| | | CaMV35S promoter to drive bar gene | | 7911 to 8680 |
| | | bar coding region | | 6543 to 7094 |
| | | CaMV35S polyA terminator | | 6335 to 6537 |
| | | Agrobacterium T-DNA left border | | 6260 to 6285 |
| pMBXS810 | PvSTIF1/bar | Agrobacterium T-DNA right border | 20 | 1 to 26 |
| | | Cab-m5 promoter with hsp70 intron to drive PvSTIF1 gene | | 8951 to 10645 |
| | | PvSTIF1 coding region | | 10646 to 11240 |
| | | nos terminator | | 11241 to 11495 |
| | | CaMV35S promoter to drive bar gene | | 7911 to 8680 |
| | | bar coding region | | 6543 to 7094 |
| | | CaMV35S polyA terminator | | 6335 to 6537 |
| | | Agrobacterium T-DNA left border | | 6260 to 6285 |
| pMBXS855 | PvBMY1/bar | Agrobacterium T-DNA right border | 21 | 1 to 26 |
| | | Cab-m5 promoter with hsp70 intron to drive PvBMY1 gene | | 8951 to 10645 |
| | | PvBMY1 coding region | | 10646 to 11961 |
| | | nos terminator | | 11978 to 12232 |
| | | CaMV35S promoter to drive bar gene | | 7911 to 8680 |
| | | bar coding region | | 6543 to 7094 |
| | | CaMV35S polyA terminator | | 6335 to 6537 |
| | | Agrobacterium T-DNA left border | | 6260 to 6285 |

*All vectors are based on the transformation vector pCambia3300 found at world wide web at cambia.org; the bar gene (conferring resistance to bialaphos) is used as a marker for selection of transformed callus cultures and plants.

Example 3. Transformation of Switchgrass

Highly embryogenic callus cultures initiated from different explants were used for introduction of the gene constructs described in Example 2.

Culture Initiation and Plant Regeneration:

Callus cultures were initiated from mature caryopses of cv. Alamo following a previously published procedure (Denchev & Conger, 1994, Crop Sci., 34: 1623-1627). Their embryogenic potential and plant regeneration ability were evaluated as described previously (U.S. Pat. No. 8,487,159 to Somleva et al.).

Switchgrass plants from Alamo genotype 56 (Somleva et al., 2008, Plant Biotechol. J. 6: 663-678; U.S. Pat. No. 8,487,159 to Somleva et al.) grown under greenhouse conditions were used for initiation of immature inflorescence-derived callus cultures. The top culm nodes of elongating tillers with 3-4 visible nodes were used for development of inflorescences in tissue culture following a previously published procedure (Alexandrova et al., 1996, Crop Sci. 36: 175-178). Callus cultures were initiated from individual spikelets from in vitro developed panicles and propagated by transferring on to a fresh medium for callus growth (Denchev and Conger, 1994, Crop Sci. 34: 1623-1627) every four weeks.

Callus cultures were grown at 27° C., in the dark and maintained by monthly subcultures on a fresh medium for callus growth (Somleva et al., 2002, Crop Sci. 42: 2080-2087). For plant regeneration, calluses were plated on MS basal medium supplemented with 1.4 µM gibberellic acid and incubated at 27° C. with a 16-h photoperiod (cool white fluorescent bulbs, 80 µmol/m²/s).

Transformation of Mature Caryopses- and Immature Inflorescence-derived Cultures:

Highly embryogenic callus cultures were transformed with Agrobacterium tumefaciens following previously published protocols (Somleva et al., 2002, Crop Sci. 42: 2080-2087; Somleva, 2006, Agrobacterium Protocols, Wang K., ed., pp 65-74: Humana Press). Transformed cultures and plants regenerated from them were selected with 200 mg/L hygromycin (WO 2010/102220 A1 and US 2010/0229256 A1 to Somleva & Ali) or 10 mg/L bialaphos (Somleva et al., 2002, Crop Sci. 42: 2080-2087; Somleva, 2006, Agrobacterium Protocols, Wang K., ed., pp 65-74: Humana Press). Transgenic plants overexpressing the transcription factor genes PvSTR1, PvSTIF1, and PvBMY1 were obtained from cultures transformed with the vectors pMBXS809, pMBXS810, and pMBXS855 (Table 2). The presence of the transcription factor and marker genes in putative transformants was confirmed by PCR using primers specific for the coding regions of the transgenes and the amplification conditions described previously (Somleva et al., Plant Biotechol. J. 6: 663-678). More than 200 To plants representing 58 independent transformation events were identified (Table 4). Plants regenerated from untransformed callus cultures and grown under the same conditions were used as controls (non-transgenic plants; wild-type plants) in expression and functional analyses of transgenic lines.

TABLE 4

Transformations for overexpression of transcription factors in switchgrass.

| Vector | Gene of interest | Alamo genotype 56[1] | | Alamo genotype 16[2] | |
|---|---|---|---|---|---|
| | | # events[3] | # plants[4] | # events[3] | # plants[4] |
| pMBXS809 | PvSTR1 | 8 | 60 | 6 | 31 |
| pMBXS810 | PvSTIF1 | 14 | 44 | 12 | 60 |
| pMBXS855 | PvBMY1 | 9 | 27 | 9 | 14 |
| | Total: | 31 | 111 | 27 | 105 |

[1]immature inflorescence-derived callus cultures from this genotype were transformed;
[2]mature caryopsis-derived callus cultures from this genotype were transformed;
[3]number of bialaphos-resistant callus lines producing at least one transgenic plant;
[4]number of primary transformants (as confirmed by PCR).

After transfer to soil, transgenic and wild-type plants obtained from different transformation experiments were grown in a greenhouse at 27° C./24° C. (day/night) with supplemental lighting (16-h photoperiod, sodium halide lamps).

Example 4. Expression Analyses of Transgenic Switchgrass Plants Transformed with the Genes Encoding the Transcription Factors PvSTR1, PvSTIF1, and PvBMY1

Figure 8:
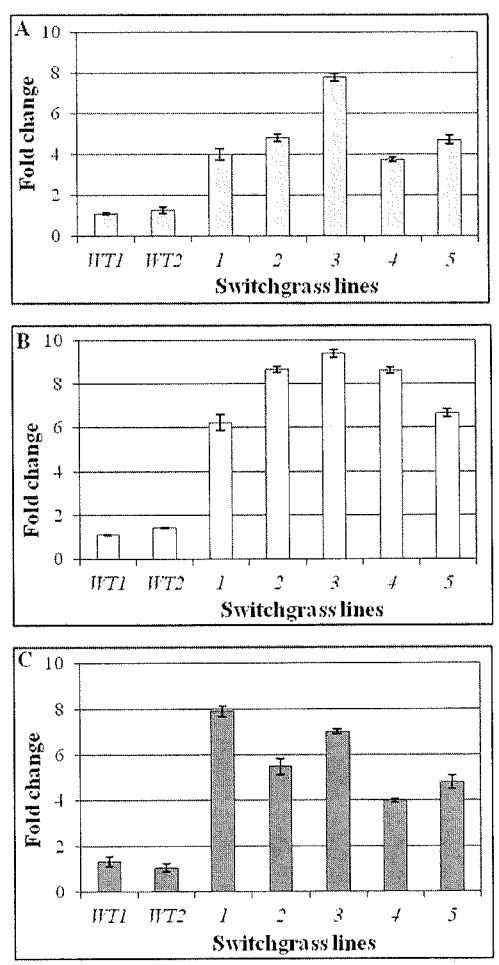
FIG. 8 shows results from qRT-PCR (quantitative reverse transcription polymerase chain reaction or real-time RT-PCR) analysis of the overexpression of the transcription factor genes PvSTR1 (A), PvSTIF1 (B) and PvBMY1 (C) in transgenic switchgrass plants prior to transfer to soil. β-actin amplification was used for transcript normalization. WT1, plants regenerated from non-transformed mature caryopsis-derived callus cultures from genotype 16; WT2, plants regenerated from non-transformed immature inflorescence-derived cultures from genotype 56; 1-5, transgenic lines representing independent transformation events. Data presented as mean values±SE (n=3).

In all experiments, total RNA was isolated from the second youngest leaf of primary transformants and control wild-type plants (3 plants per line) prior to transfer to soil using RNeasy Plant Mini Kit (Qiagen). After DNase treatment and column purification, different amounts of RNA were used for RT-PCR and qRT-PCR (quantitative reverse transcription polymerase chain reaction or real-time RT-PCR). Quantitative analysis of the differences in the expression levels of the TF genes in transgenic and control lines was performed by qRT-PCR using β-actin as a reference. For each sample, 500 ng of total RNA was converted into cDNA using iScript cDNA synthesis kit (Bio-Rad). The cDNA was diluted and subjected to real-time PCR using Fast SYBR® Green Master Mix (Life Technologies) in an Applied Biosystems 7500 Fast Real-Time PCR system. The amplification curves for each line were generated and used to calculate the relative expression ratio (fold change) compared to the wild type control. All of the transgenic lines analyzed showed significantly higher levels of expression of the transcription factor genes in the transgenic lines as compared to the control plants transcript accumulation (from 3 to 9.5 times higher as shown in FIG. 8).

Example 5. Effects of the Overexpression of the Transcription Factors PvSTR1, PvSTIF1 and PvBMY1 on Biomass Production and Photosynthetic Activity in Transgenic Switchgrass Plants For functional characterization of PvSTR1, PvSTIF1 and PvBMY1 transcription factors, biochemical and physiological analyses were performed with transgenic and control wild-type switchgrass plants grown in soil for two months. Both groups of plants were from two Alamo genotypes—56 and 16 (our designation) differing in their morphology.
Measurements of Photosynthetic Activity:

For analyses of the photosynthesis rate in plants overexpressing the TF genes of the invention, various parameters were measured in light adapted leaves using a Dual-PAM-100 Measuring System (Heinz Walz GmbH). All measurements were performed with the leaf attached to the second node from the base of vegetative tillers with the forth emerging leaf The functioning of photosystem I (PSI) and photosystem II (PSII) was studied in terms of photochemical quantum yield (Y) and electron transport rate (ETR). Transgenic lines with improved photosynthetic capacity compared to wild type controls from the corresponding genotypes were identified (results are summarized in Table 5 for PvSTR1, PvSTIF1 and PvBMY1 lines, respectively). In some of the transgenic plants analyzed, the quantum yield of PSI and PSII were significantly increased at photosynthetically active radiation (PAR) of 30-37 µmol m$^{-2}$ s$^{-1}$ (Table 5). The electron transport rates of PSI and PSII in some of the transgenic plants were significantly elevated compared to the wild type control plants at PAR ≥119 µmol m$^{-2}$ s$^{-1}$ (Table 5).

TABLE 5

Effect of the overexpression of transcription factors on photosynthesis.

| | Y(I) | | Y(II) | | ETR(I) | | ETR(II) | |
|---|---|---|---|---|---|---|---|---|
| TF gene | Max value[1] | % to control[2] | Max value[1] | % to control[2] | Max value[1] | % to control[2] | Max value[1] | % to control[2] |
| PvSTR1 | 0.802 | 137 | 0.735 | 112 | 46.8 | 131 | 12.2 | 130 |
| PvSTIF1 | 0.746 | 125 | 0.714 | 108 | 49.7 | 139 | 12.8 | 136 |
| PvBMY1 | 0.887 | 148 | 0.722 | 110 | 48.5 | 136 | 13.2 | 140 |

[1]The maximum value measured in individual transgenic switchgrass plants;
[2]Compared to the average values (5-6 plants, 2-3 measurements per plant) measured in the corresponding wild-type controls in terms of genotype, growth period and sampling date;
Abbreviations:
Y(I), photochemical quantum yield of photosystem I (PSI) - reflects the efficiency of quantum energy absorption by PSI reaction centers;
Y(II), effective quantum yield of photosystem II (PSII) - represents the portion (from 0 to 1) of absorbed quanta that is converted into chemically fixed energy by the PSII reaction centers (the other portion of the quanta is dissipated into heat and fluorescence);
ETR(I), electron transport rate of PSI - represents the rate of the cyclic or non-cyclic transfer of electrons from the excited reaction-center chlorophyll a molecule to the electron acceptor(s);
ETR (II), electron transport rate of PSII - reflects the efficiency of the non-cyclic electron transfer.

Because of the linear correlation between the quantum yield of PSII and $CO_2$ fixation in $C_4$ plants (Leipner et al., 1999, Environ. Exp. Bot. 42: 129-139; Krall & Edwards, 1992, Physiol. Plant. 86: 180-187), the data suggested that the overexpression of the transcription factors resulted in improvement of the overall rate of photosynthesis (Table 5). This suggestion was supported by the significant increase in the electron transport rate (Table 5) based on the linear correlation between photosynthesis rate and ETR due to the lack of photorespiration in $C_4$ species (Kakani et al., 2008, *Photosynthetica* 46: 420-430). In addition, the enhanced ETR of PSI in some of the transgenic lines (Table 5) could indicate increased cyclic electron transport around PSI which provides the additional ATP needed for the $CO_2$ fixation cycle of the $C_4$ photosynthesis (Kiirats et al. 2010, *Photosynth. Res.* 105: 89-99).

After measurements of the photosynthetic activity, the leaf blades were sampled and used for determination of the contents of primary metabolites and photosynthetic pigments as well as for RNA and protein isolation.

97 transgenic plants representing 30 independent lines (10 lines/TF gene). The results are summarized in Table 6.

This initial screening resulted in the identification of transgenic lines (2-5 plants per line) accumulating primary metabolites and pigments at levels significantly higher than the control untransformed plants grown under the same conditions. The data confirmed the predicted function of the tested TF genes as global regulators of the central carbon metabolism (see Example 1) and correlated with the results from the gene expression microarray analysis (see Example 7).

TABLE 6

Summary of the results from screening of transgenic switchgrass lines overexpressing the TF genes PvSTR1, PvSTIF1, and PvBMY1.

| TF gene | Line ID | Metabolites | | | Pigments | | Biomass | |
|---|---|---|---|---|---|---|---|---|
| | | Starch | Soluble sugars | Fatty acids | Chlorophyll | Carotenoids | Dry weight | No. of tillers |
| PvSTR1 | 56-1 | 128 | 101 | 123 | 144 | 133 | 132 | 118 |
| | 56-2 | 125 | 97 | 111 | 137 | 125 | 112 | 111 |
| | 56-3 | 123 | 156 | 107 | 88 | 79 | 102 | 95 |
| | 56-7 | 160 | 138 | 117 | 144 | 141 | 139 | 131 |
| | 56-9 | 159 | 120 | 115 | 116 | 111 | 140 | 128 |
| | 56-13 | 152 | 125 | 107 | 201 | 181 | 143 | 152 |
| | 56-14 | 339 | 244 | 80 | 109 | 100 | 113 | 112 |
| | 16-4 | n.a. | n.a. | 85 | 93 | 80 | 91 | 114 |
| | 16-5 | 113 | 129 | 89 | 104 | 78 | n.a. | n.a. |
| | 16-6 | 168 | 115 | 90 | 119 | 124 | 103 | 111 |
| PvSTIF1 | 56-2 | 180 | 93 | 130 | 142 | 129 | 94 | 68 |
| | 56-3 | 104 | 123 | 128 | 136 | 121 | 105 | 108 |
| | 56-4 | n.a. | 86 | 128 | 158 | 134 | 98 | 107 |
| | 56-8 | 223 | 73 | 122 | 163 | 141 | 107 | 102 |
| | 16-1 | 184 | 119 | 91 | 136 | 142 | 131 | 120 |
| | 16-2 | 222 | 101 | 84 | 135 | 134 | 116 | 112 |
| | 16-3 | 134 | 105 | 89 | 115 | 126 | n.a. | n.a. |
| | 16-4 | 153 | 114 | 88 | 131 | 132 | 137 | 129 |
| | 16-6 | 201 | 88 | 90 | 125 | 139 | 142 | 138 |
| | 16-9 | 186 | 117 | 101 | 125 | 139 | 111 | 126 |
| PvBMY1 | 56-1 | 97 | 96 | 106 | 113 | 113 | 120 | 149 |
| | 56-4 | 174 | 100 | n.a. | 106 | 84 | 115 | 142 |
| | 56-6 | 136 | 137 | 94 | 112 | 98 | 123 | 135 |
| | 56-7 | 123 | 127 | 110 | 117 | 117 | 123 | 156 |
| | 56-8 | 141 | 152 | 99 | 103 | 101 | 133 | 148 |
| | 56-9 | 223 | 192 | 104 | 80 | 73 | 124 | 158 |
| | 16-1 | n.a. | 104 | 71 | 79 | n.a. | n.a. | n.a. |
| | 16-2 | 126 | 99 | 106 | 111 | 111 | 124 | 194 |
| | 16-3 | 270 | 158 | 75 | 92 | 91 | n.a. | 79 |
| | 16-5 | 109 | 71 | 81 | 103 | 122 | 99 | 88 |

Values are average from measurements of 2-5 plants per transgenic line or wild type and are presented as % to the corresponding wild-type control in terms of genotype, growth period and sampling date;
n.a.—not analyzed.

Primary Metabolites:

Leaf tissue was ground in liquid nitrogen and freeze-dried for 3 days. Resultant leaf powder was used for measurements of the levels of primary metabolites using different analytical methods: a quantitative, enzymatic assay for starch (Starch Assay Kit, Sigma) and HPLC for soluble sugars and fatty acids.

The levels of products of the central carbon metabolism (starch, sucrose, glucose, and fatty acids) were measured in more than 80 transgenic plants representing 30 independent lines (10 lines/TF gene). The results are summarized in Table 6.

Photosynthetic Pigments:

Chlorophyll a, chlorophyll b, and carotenoids were determined in freshly harvested leaf tissue following a previously described procedure (Lichtenhaler, 1987, *Methods Enzymol.*, 148: 350-382). The experiments were performed with Individual plants with significantly higher levels of starch (4.2-fold increase), sucrose (4.4-fold increase), glucose (2.7-fold increase), fatty acids (1.5-fold increase), and total chlorophyll (2.5-fold increase) were identified (Table 7).

TABLE 7

Effect of the overexpression of transcription factors on the levels of primary metabolites and photosynthetic pigments in switchgrass leaves.

| TF gene | Metabolite/ Pigment | No. of plants analyzed | Max value measured[1] | % to control[2] |
|---|---|---|---|---|
| PvSTR1 (10 lines; 30 plants in total) | Starch | 26 | 11.659 | 405 |
| | Sucrose | 27 | 5.150 | 331 |
| | Glucose | 27 | 0.575 | 192 |
| | Total fatty acids | 19 | 4.065 | 148 |

TABLE 7-continued

Effect of the overexpression of transcription factors on the levels of primary metabolites and photosynthetic pigments in switchgrass leaves.

| TF gene | Metabolite/ Pigment | No. of plants analyzed | Max value measured[1] | % to control[2] |
|---|---|---|---|---|
| | Chlorophyll a + b | 28 | 2.337 | 203 |
| | Carotenoids | 28 | 0.335 | 187 |
| PvSTIF1 | Starch | 38 | 5.558 | 415 |
| (10 lines; 41 | Sucrose | 38 | 2.681 | 165 |
| plants | Glucose | 38 | 0.735 | 269 |
| in total) | Total fatty acids | 32 | 4.159 | 150 |
| | Chlorophyll a + b | 39 | 2.960 | 252 |
| | Carotenoids | 39 | 0.359 | 199 |
| PvBMY1 | Starch | 29 | 12.272 | 426 |
| (10 lines; 31 | Sucrose | 27 | 6.768 | 435 |
| plants | Glucose | 27 | 0.432 | 132 |
| in total) | Total fatty acids | 23 | 3.916 | 143 |
| | Chlorophyll a + b | 30 | 1.589 | 135 |
| | Carotenoids | 30 | 0.259 | 144 |

[1]Data for starch, sucrose, glucose and fatty acids presented as % DW; data for chlorophyll a + b and carotenoids presented as mg/g FW;
[2]Values compared to the corresponding wild-type control in terms of genotype, growth period and sampling date.

A similar increase in the levels of primary metabolites was also detected in other plant parts. For example, the starch content in the second leaf of a plant from line 56-14 was 405% to the control (Tables 6 and 7). The third and flag leaves from this plant also contained 4 times more starch than the corresponding leaves from wild-type control plants.

Unexpectedly, some of the transgenic switchgrass plants with significantly increased levels of starch and soluble sugars produced the same or slightly higher amounts of biomass compared to the control plants. For example, a plant from the PvBMY1 line 56-8 (Table 6) contained 3.2× more starch and 2.2× more sucrose and glucose than the corresponding control plants but its biomass was only 1% higher than the average biomass of the wild type plants. The total biomass yield of the plant with the highest starch content (415% to control) among the PvSTIF1 plants was similar to the biomass of the control wild-type plants. A 20% increase in biomass production was measured in a plant from the PvSTR1 line 56-14 (Table 6) despite the fact that the content of starch and soluble sugars in the leaves of this plant was 333% to the control.

Figure 9:
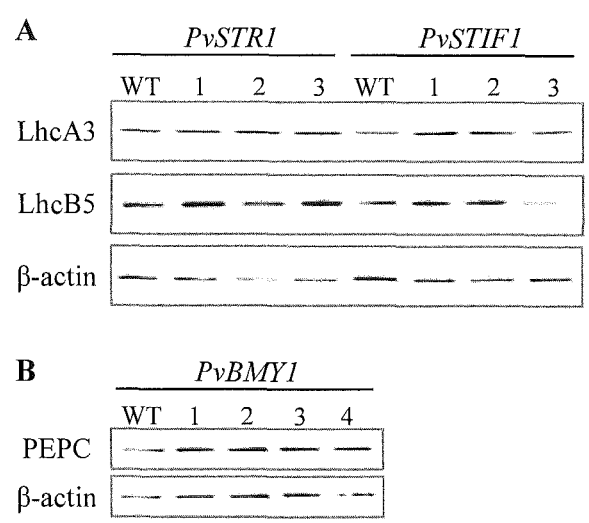
FIG. 9 shows Western blots of total proteins from transgenic and wild-type switchgrass plants. A Protein extracts (6 µg per lane) from PvSTR1 and PvSTIF1 lines incubated with antibodies against the proteins of the light harvesting centers of photosystem I (LhcA3) and photosystem II (LhcB5). β-actin was used as a loading control. B Total protein extracts (6 µg per lane) from PvBMY1 lines incubated with an antibody against phosphoenolpyruvate carboxylase (PEPC). β-actin was used as a loading control. Protein isolation and membrane blotting were performed as described previously (Somleva et al., 2008, *Plant Biotechnol J*, 6: 663-678). Commercially available antibodies (Agrisera) were used for protein detection. An ultra-sensitive chemiluminescent substrate system (Thermo Scientific) was used for signal development. Lanes: WT—a control, wild-type plant; 1 to 4—transgenic switchgrass plants representing different TF lines.

Protein Analyses:

Western blot analysis of total proteins was performed as described previously (Somleva et al., 2008, Plant Biotechol. J. 6: 663-678). An increase in the abundance of the proteins of the light harvesting centers of PSI (LhcA proteins) and PSII (LhcB proteins) was detected in most of the PvSTR1 and PvSTIF1 lines analyzed compared to the corresponding wild-type control (examples for LhcA3 and LhcB5 are shown in FIG. 9A). These findings are in agreement with the enhanced chlorophyll content in these lines (Tables 6 and 7). The accumulation of phosphoenolpyruvate (PEPC) protein in most of the PvBMY1 lines was higher than in the wild-type plants (an example is shown in FIG. 9B).

This is the first report on the effect of any transcription factor on the abundance of Lhc and PEPC proteins.

Biomass Accumulation and Plant Development:

The growth and development of transgenic switchgrass plants overexpressing the transcription factors of the invention were monitored in terms of plant height and number of tillers after transfer to soil. All of the transgenic plants had larger leaf blades and longer internodes compared to the wild type plants from the corresponding genotype.

Total biomass yield was evaluated in plants grown under greenhouse conditions for five months as described in publications, WO 2012/037324 A2 and US 2012/0060413 to Metabolix. All vegetative and reproductive tillers at different developmental stages from each plant were counted and cut below the basal node. Leaves and stem tissues were separated, cut into smaller pieces, air-dried at 27° C. for 12-14 days and dry weight measurements were obtained. The number and ratio of vegetative to reproductive tillers were evaluated to compare the developmental patterns of transgenic and control plants.

The total biomass of 82 transgenic plants representing 29 TF lines and 12 wild type plants was measured. Transgenic lines with increased biomass yield (up to 142% to the control) and number of tillers (up to 194% to the control) were obtained (Table 6).

Most of the transgenic plants—81.5% of the analyzed PvSTR1 plants, 66.7% of the PvSTIF1 plants, and 82.1% of the PvBMY1 plants had higher biomass yield (up to 162%) compared to the control plants (Table 8). TF-overexpressing plants with significantly increased number of tillers (up to 216% to the control) were also identified.

TABLE 8

Effect of the overexpression of transcription factors on switchgrass biomass production.

| TF gene | Biomass | Max value measured [g DW] | % to control[1] |
|---|---|---|---|
| PvSTR1 | Total | 90.6 | 162 |
| (10 lines; | Leaves | 25.9 | 149 |
| 27 plants | Stem | 71.4 | 184 |
| analyzed) | No. of tillers[2] | 45 | 190 |
| PvSTIF1 | Total | 70.9 | 153 |
| (10 lines; | Leaves | 17.5 | 162 |
| 27 plants | Stem | 53.4 | 150 |
| analyzed) | No. of tillers[2] | 25 | 166 |
| PvBMY1 | Total | 79.6 | 142 |
| (9 lines; | Leaves | 25.2 | 145 |
| 28 plants | Stem | 56.8 | 146 |
| analyzed) | No. of tillers[2] | 51 | 216 |

[1]Values compared to the corresponding wild-type control in terms of genotype, growth period and sampling date;
[2]Total number of vegetative and reproductive tillers at different developmental stages (emerging tillers not included).

Similar patterns in the biomass productivity were observed in plants grown in soil for six months after repotting. For example, a plant from line 16-6 whose biomass was 148.8% to the control 4 months after transfer to soil yielded about 300 g DW total biomass after repotting which was 182.3% to the corresponding control.

Example 6. Evaluation of the Stress Response of Switchgrass Lines Overexpressing Transcription Factors To validate the role of the transcription factors of the invention in improvement of plant stress tolerance, a novel method for screening of large populations of transgenic and control plants for their response to drought and salinity has been developed. It utilizes the previously developed tissue culture-based technology for propagation and improvement of polymer production in transgenic switchgrass plants (WO 2010/102220 A1 and US 2010/0229256 A1 to Somleva and Ali).

The stress-inducing conditions were established using non-transformed, wild-type plants. Polyethylene glycol (PEG) and NaCl were chosen for induction of drought and salinity stresses, respectively. Hundreds of plants were regenerated from immature inflorescence-derived callus cultures from Alamo genotype 56. After 3-4 weeks culture on MS medium for plant regeneration, phenotypically uniform plants were transferred to larger tissue culture containers containing the same medium supplemented with different concentrations of PEG and NaCl. Since the first stress-induced changes in plant morphology, such as leaf wilting and yellowing were observed after 3-4 days of treatment in preliminary experiments, this time period was used in the subsequent experiments. The relative water content (RWC), levels of photosynthetic pigments and abundance of the chloroplastic Cu—Zn superoxide dismutase (SOD) protein were used as stress markers. They were measured as follows: RWC according to Smart & Bingham, 1974, *Plant Physiol.* 53: 258-260, pigments as described by Lichtenhaler, 1987, *Methods Enzymol.*, 148: 350-382 and SOD using a Plant SOD ELISA kit (MyBioSource).

Three different concentrations of the stress inducing agents were tested in 3 replicates each (10 plants/replicate). Based on the results from these treatments, 200 mM NaCl and 15% PEG were used in the experiments with the TF plants.

Plants regenerated from immature inflorescence-derived callus cultures initiated from well characterized TF lines along with wild type plants (regenerated from non-transformed cultures) were subjected to stress-inducing treatments under the conditions described above. Non-treated transgenic and wild type plants served as controls. All treatments were conducted in 3-4 replicates (10 plants per replicate).

Figure 10:
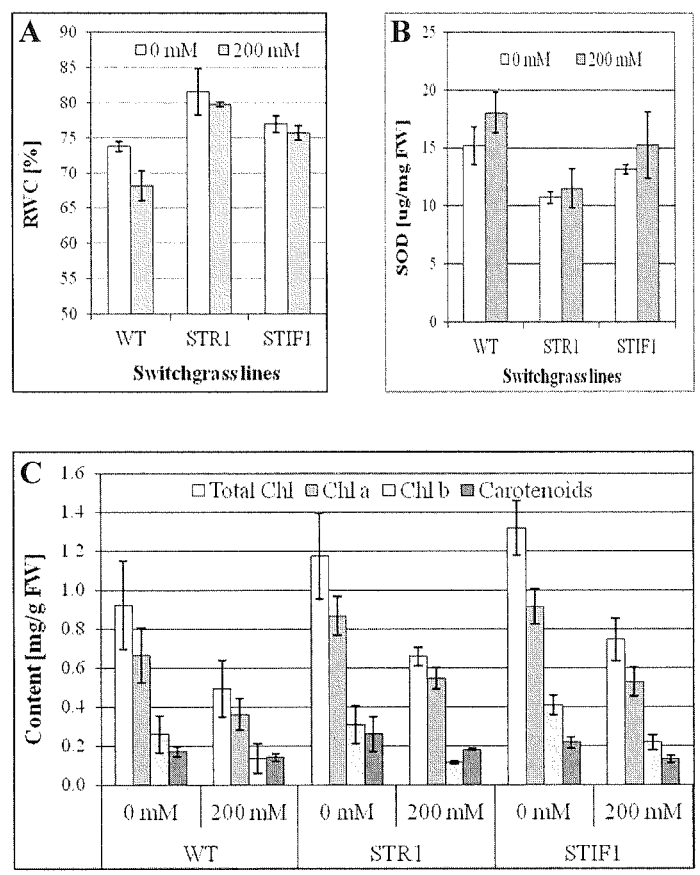
FIG. 10 illustrates the effect of high salinity stress on relative water content (A), the abundance of the chloroplastic Cu-Zn superoxide dismutase (SOD) protein (B) and levels of photosynthetic pigments (C) in switchgrass plants overexpressing the PvSTR1 and PvSTIF1 genes. Bars represent mean±SD values (n=3).

As shown in the example in FIG. 10, treatment with 200 mM NaCl resulted in a slight decrease in RWC in the transgenic plants—2.2% and 1.6% in PvSTR1 and PvSTIF1 plants, respectively, while RWC in the wild-type plants was reduced with 7.6% compared to the non-treated control (FIG. 10A). Interestingly, RWC in the non-stressed TF plants was 4-8% higher than the relative water content in the wild type plants. Non-treated transgenic plants contained significantly lower amounts of the chloroplastic Cu-Zn superoxide dismutase (SOD) protein (as determined by ELISA) compared to non-stressed wild-type plants (FIG. 10B). High salinity stress conditions induced a similar increase in SOD levels in the PvSTIF1 and wild-type plants (16% and 19%, respectively) while the SOD protein content detected in the PvSTR1 plants was with about 7% higher than in the non-treated control (FIG. 10B). The non-treated TF plants also contained higher levels of photosynthetic pigments—27% and 43% higher total chlorophyll content in PvSTR1 and PvSTIF1 plants, respectively, compared to the unstressed wild type plants (FIG. 10C). The salinity stress caused a significant decrease (37-63%) in the chlorophyll content in both transgenic and wild type plants. The content of carotenoids in the stressed wild type plants was reduced with 18.2% compared to the non-treated plants, while in the TF plants it was 30-39% lower than in the corresponding control plants (FIG. 10C). Similar changes in the stress markers were observed when the plants were subjected to PEG-induced drought stress.

This is the first report demonstrating the effect of the overexpression of the transcription factors of the invention on plant stress response and the possibility to test the role of any transcription factors in this process under in vitro conditions.

Example 7. Global Gene Expression Analysis of Switchgrass Transgenic Lines Overexpressing PvSTR1, PvSTIF1 and PvBMY1

To identify the genes whose regulation by the transcription factors of the invention resulted in the observed improved biomass yield and stress tolerance (Examples 5 and 6), gene expression profiling was performed using an Affymetrix switchgrass cDNA GeneChip.

Gene Expression Microarrays, Data Processing and Normalization:

Three of the best performing switchgrass lines overexpressing one of the TF genes (Tables 6, 7, and 8) were selected for the microarray gene expression analysis. Total RNA was isolated from the second leaf of vegetative tillers (3-4 tillers per plant) as described in Example 3. RNA extracts from three plants from each line were pooled and their quality was evaluated using RNA Nano Chip (Agilent Technologies) according to the manufacturer's instructions. The microarray analysis was conducted using an Affymetrix switchgrass GeneChip containing probes to query approximately 43,344 transcripts following the manufacturer's protocol (http://www.affymetrix.com). Raw numeric values representing the signal of each feature were imported into AffylmGUI and the data were background corrected, normalized, and summarized using Robust Multiarray Averaging (RMA). A linear model was used to average data between the replicates and to detect differential expression. Data quality was assessed using box and scatter plots to compare the intensity distributions of all samples and to assess the gene expression variation between the replicates, respectively. Genes with significant probe sets (FDR<0.1) with ≥2.0-fold changes compared to the corresponding wild-type controls were considered differentially expressed.

Identification and Functional Annotations of Differentially Expressed Genes Regulated by PvSTR1, PvSTIF1 and PvBMY1:

Since the genome sequence of switchgrass is not well annotated, a reciprocal BLAST analysis (a common computational method for predicting putative orthologs consisting of two subsequent sets of BLAST analysis) was performed for functional annotation of the differentially expressed genes and their corresponding orthologs. The first BLAST was conducted using the well annotated whole genome sequences of maize, sorghum, rice and *Arabidopsis*. BLASTN or TBLASTX are generally used for analyses of a polynucleotide sequence, while BLASTP or TBLASTN—for a polypeptide sequence. The first set of BLAST results may optionally be filtered. The full-length sequences of either the filtered results or non-filtered results are then BLASTed back (second BLAST) against sequences from the organism from which the query sequence is derived. The results of the first and second BLASTs are then compared. If this returns the switchgrass gene originally used as the highest scorer, then the two genes are considered putative orthologs.

Figure 11:
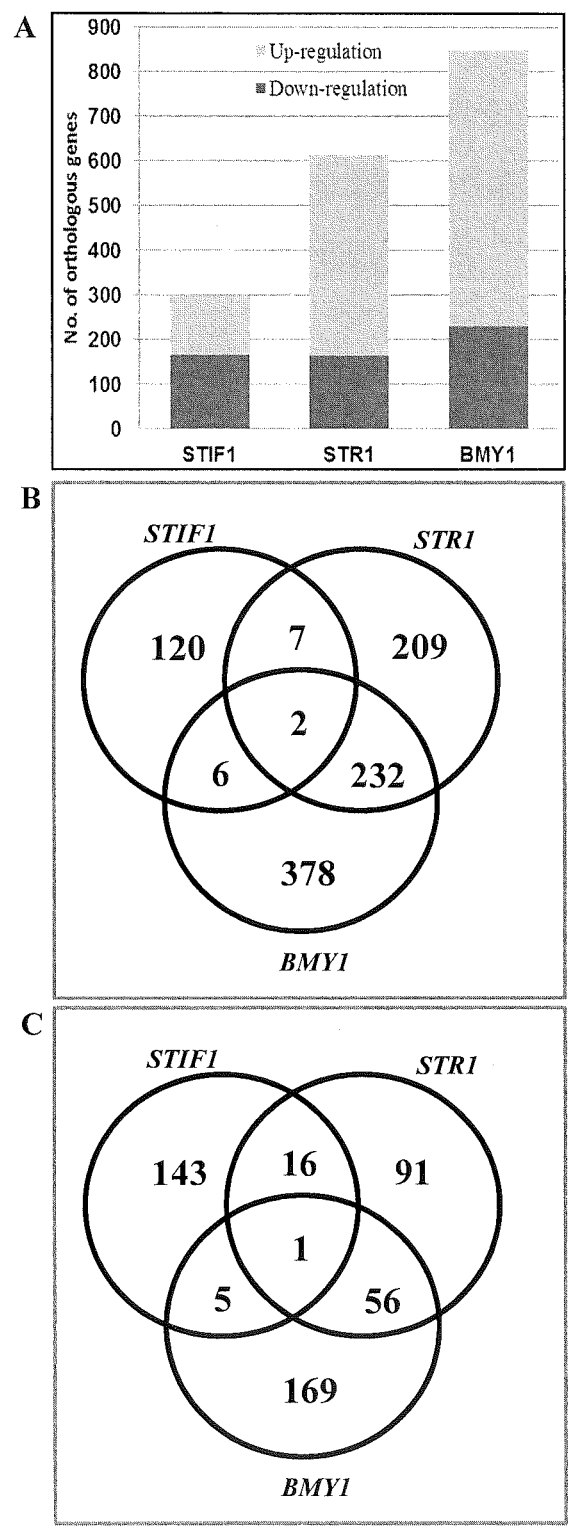
FIG. 11 illustrates the large number of switchgrass genes, including transcription factors whose expression is impacted by over-expression of PvSTR1, PvSTIF1 and PvBMY1. The data is presented as the total number of regulated orthologs (A) as well as the numbers of up-regulated (B) and down-regulated (C) genes common for the three TFs.

The numbers of the annotated genes up- or down-regulated by PvSTR1, PvSTIF1 and PvBMY1 in transgenic switchgrass plants are shown in FIG. 11A. A further analysis of the gene expression data revealed that 450, 135, and 619 genes were up-regulated (FIG. 11B) and 165, 164, and 231 genes were down-regulated (FIG. 11C) by PvSTR1, PvSTIF1 and PvBMY1, respectively. Only 1-2 genes were commonly regulated by all three TFs. A relatively small portion of the differentially expressed genes regulated by PvSTIF1 was also regulated by the other two TFs, while more than 280 genes were regulated by both PvSTR1 and PvBMY1 (FIGS. 11B and C).

These findings indicate that the transcription factors of the invention regulate the expression of genes involved in key processes and pathways by different mechanisms.

Downstream Transcription Factors Regulated by PvSTR1, PvSTIF1 and PvBMY1:

Among the up-regulated genes identified by microarray analysis of transgenic switchgrass lines, 80 were predicted to be transcription factors based on the presence of a DNA-binding domain (Plants TF database v. 3.0). Several of these homologous TF genes have functionally been validated in model and crop plants as regulators of genes involved in economically important agronomic traits, such as biomass production, grain yield and abiotic stress tolerance.

These results confirm that the transcription factors of the current invention appear to function as global transcriptional regulators. The number and variety of the transcription factor genes identified by the microarray analysis indicate that PvSTR1, PvSTIF1 and PvBMY1 regulate key genes in several major pathways and their branches either directly or through downstream transcription factors.

Figure 12A:
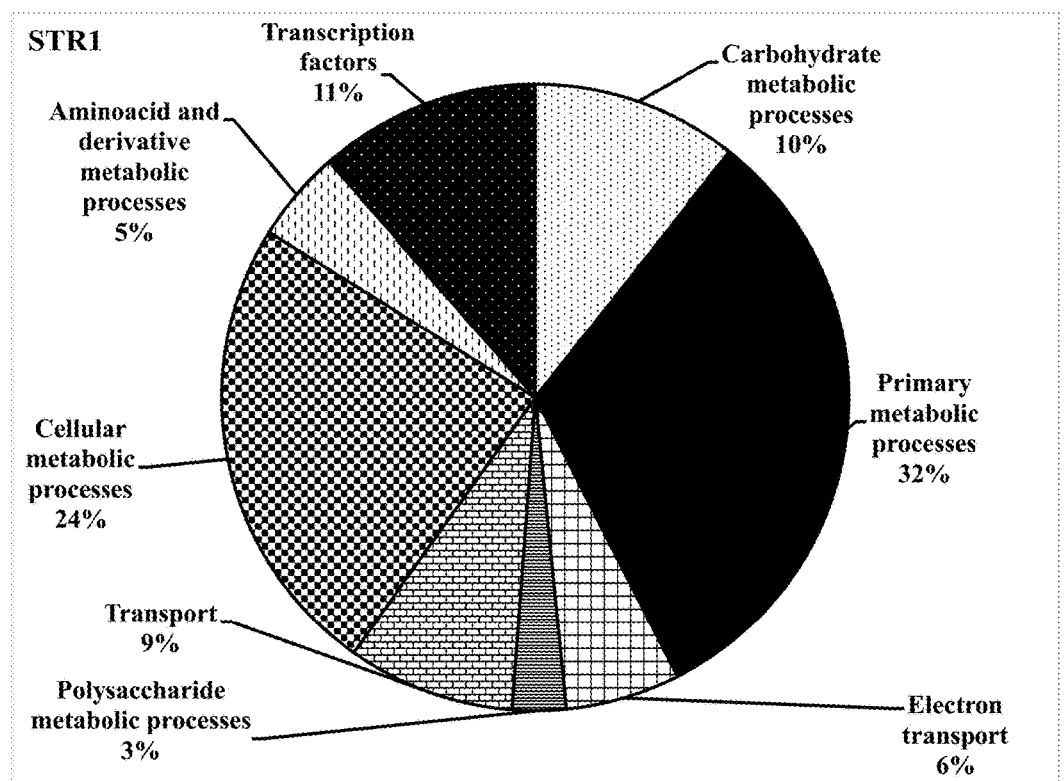
FIG. 12 presents the gene ontology analysis of differentially expressed genes regulated by PvSTR1 (A), PvSTIF1 (B) and PvBMY1 (C) transcription factors. Descriptions of biological functions were assigned on the basis of information retrieved from the world wide web at: bioinfo.cau.edu.cn/agriGO/index.php (P-value calculated by Fisher exact test). Genes that showed more than 2-fold up-regulation and the top enriched pathways are considered for the graphs.
Figure 12B:
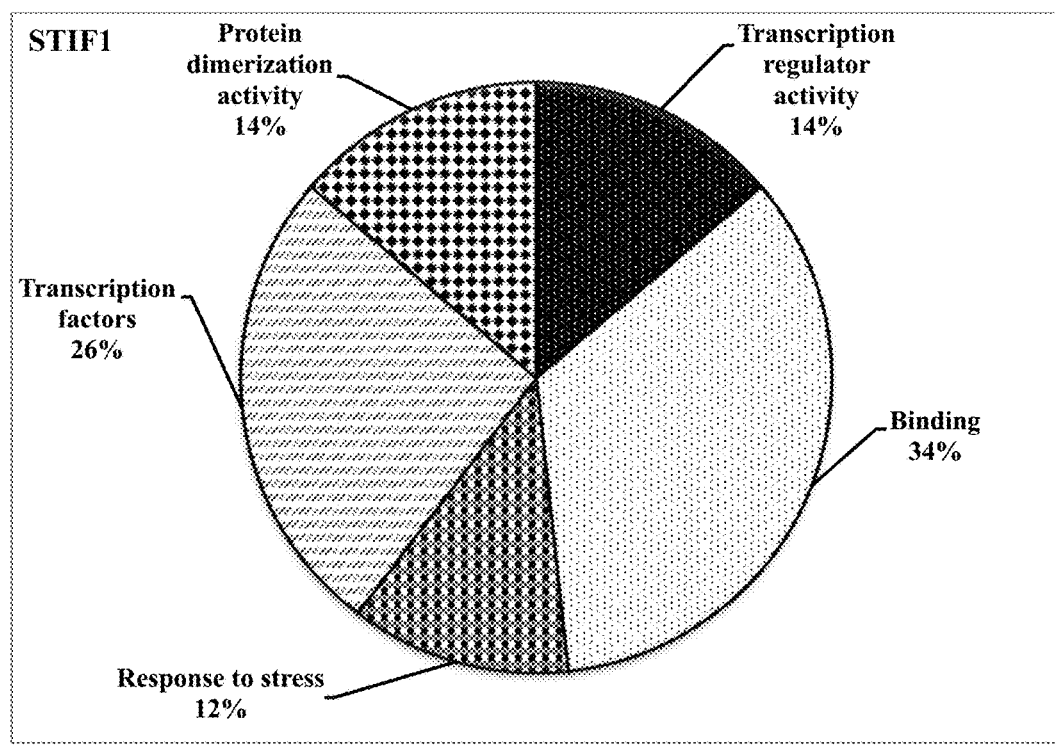
Figure 12C:
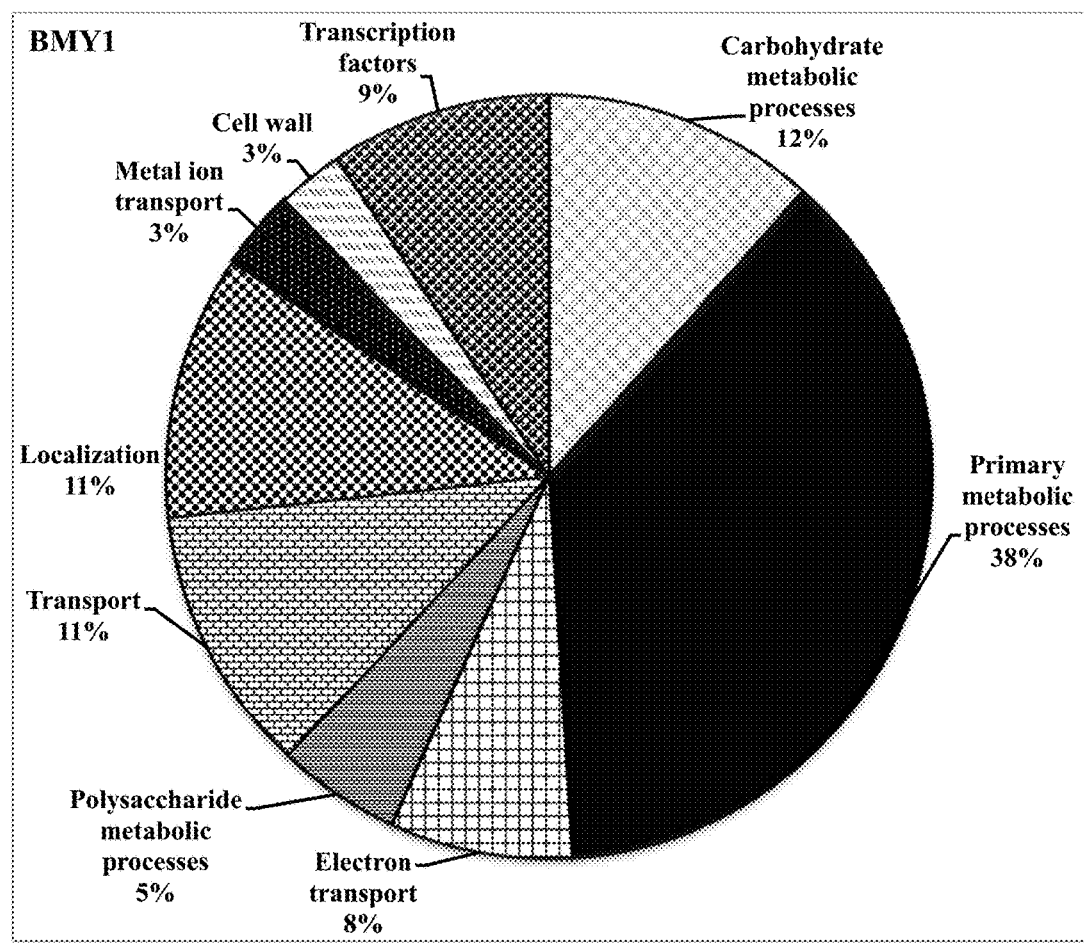

Pathway analysis of differentially expressed genes: For more detailed analysis of the regulatory pattern of the transcription factors of the invention, the differential expression data was used for identification of metabolic and/or signaling pathways or portions of a pathway up-regulated in transgenic switchgrass plants. To investigate the biological functions of differentially expressed genes, gene ontology (GO) analysis was performed to identify the "biological processes category" using a publicly available database (http://bioinfo.cau.edu.cn/agriGO/index.php). The results revealed that PvSTR1 and BMY significantly increased the expression of several genes involved in primary metabolic processes, such as photosynthesis and carbohydrate metabolism, and in amino acid and cell wall biosynthesis related pathways, while most of the genes up-regulated by PvSTIF1 were categorized as transcription factors (FIG. 12).

Taken together, the results presented here and in Example 5 indicate that central carbon metabolism in the transgenic plants in which the transcription factors have been over expressed results in major global impact on central carbon metabolism.

Transcriptional Regulatory Network of the Central Carbon Metabolism in Switchgrass:

Central carbon metabolism (CCM) is crucial for plant growth and development because of its key role in the generation of accessible energy and primary building blocks for other metabolic pathways. The gene expression analysis of switchgrass lines overexpressing PvSTR1, PvSTIF1 and PvBMY1 revealed a distinctive up-regulation of several genes involved in photosynthesis and carbohydrate metabolism as well as in the primary metabolic processes, which are not only necessary for plant growth and development but often confer highly desirable traits.

Example 8. Transcription Factor-mediated Modifications of Economically Valuable Traits The switchgrass transcription factors characterized in this invention (SEQ ID NOs: 1-6) and their homologs (SEQ ID NOs: 7-18) can be introduced into the genome of other plants, including but not limited to the varieties of grain and forage cereals and grasses, oilseeds, biomass crops, legumes, trees, and vegetables. The orthologous genes identified in this invention (see Example 1) can also be used for genetic engineering of economically important crops and model plant systems. It is well known, that transcription factor gene sequences are conserved across different species lines, including plants (Goodrich et al., 1993, Cell 75:519-530; Lin et al., 1991, Nature 353: 569-571). Since the sequences of the switchgrass TFs STR1, STIF1, and BMY 1 are related to sequences in other plant species, one skilled in the art can expect that, when expressed in other plants, the switchgrass TF genes and/or their orthologs can have similar effects on plant metabolism and phenotype to those demonstrated herein. For optimal results, both sequential and phylogenetical analyses of the TF genes need to be performed. Since sorghum (Sorghum bicolor L.) and maize (Zea mays L.) are closely related to switchgrass (FIG. 5), both the switchgrass genes and their corresponding orthologs (FIG. 4) can be expressed to increase the photosynthetic activity, to up-regulate the carbon and nitrogen metabolism as well as to improve the stress tolerance of these crops resulting in higher biomass and/or grain production. In sorghum, for example, PvSTR1, PvSTIF1 and PvBMY1 and their respective orthologs with accession numbers XP002463183, XP002452171 and XP002463163 (identified using the methods described in Example 1) would be expected to have similar effects, while in soybean (Glycine max L.), the orthologous genes (accession numbers NP001238200, XP003522453 and XP003546199) would be preferred due to the distant phylogenetic relation between this crop and switchgrass (FIG. 5). In crops with unknown whole genome sequence, orthologous genes from phylogenetically close species can be used. For example, Arabidopsis orthologs of the transcription factors of the invention can be expressed in camelina to achieve the desired trait modification.

The coding sequences can be cloned in expression cassettes and assembled in single- or multi-gene vectors using the methods provided in the invention. Any of the methods for plant transformation described herein can be used to introduce the TF genes into the target plant. For example, particle bombardment with whole plasmids or minimum cassettes can be used for gene delivery to callus cultures initiated from immature zygotic embryos in wheat (Okubara et al., 2002, Theor. Appl. Genet. 106: 74-83) and barley (Wan & Lemaux, 1994, Plant Physiol. 104: 37-48) and to callus induced from immature leaf rolls from sugarcane (Snyman et al., 2006, Plant Cell Rep. 25: 1016-1023) and energy cane (Fouad et al., 2009, In Vitro Cell. Dev. Biol. 45: S74). The expression of switchgrass transcription factors and their orthologs can be engineered by Agrobacterium-mediated transformation in different crops, such as rice (Sahoo et al., 2011, Plant Methods 7:49-60), other small grain crops (reviewed in Shrawat and Lörz, 2006, Plant Biotech. J. 4: 575-603), industrial crops (cotton, Leelavathi et al., 2004, Plant Cell Rep. 22: 465-470; tobacco, Horsch et al., 1985, Science 227: 1229-1231) as well as crops with $C_4$ photosynthesis, such as maize, sugarcane, sorghum, sweet sorghum, and pearl millet (reviewed in Somleva et al., 2013, Plant Biotech. J. 11: 233-252). The floral dip method can be used for transformation of oilseed crops, such as canola (Li et al., 2010, Int. J. Biol. 2: 127-131) and camelina (Liu et al., 2012, In Vitro Cell. Dev. Biol. 48: 462-468). Both physical and biological transformation methods have been developed for some crops (e.g., soybean, reviewed in Yamada et al., 2012, Breed. Sci. 61: 480-494) and the more efficient method can be used for the purposes of this invention.

Different promoters can be useful for controlling the expression of the TFs of the invention depending on the crop and phenotype of interest. Both constitutive and inducible promoters (responding to environmental, chemical and hormonal signals) can be used. For example, the maize light-inducible cab-m5 promoter is suitable for engineering bioenergy crops, such as switchgrass (Somleva et al., 2008,

*Plant Biotech. J.* 6: 663-678) and sugarcane (Petrasovitch et al., 2012, *Plant Biotech J.* 10: 569-578) because of its high activity in leaf tissue.

Promoters capable of driving the expression of a TF gene in an organ-specific and developmentally-regulated manner are of a particular interest for modifications of economically valuable traits. The engineered spatiotemporal activity of the transcription factors of the invention can be useful, for example, for increased grain yield in maize, rice, wheat, barley and grain varieties of sorghum, for increased oil content in canola and camelina, and for modifications of the biomass composition in bioenergy crops, such as switchgrass, sugarcane, *Miscanthus*, sweet sorghum and energy cane. The transcription factor genes of the invention, their homologs and orthologs can be overexpressed in photosynthetic tissues during different stages of embryo and seed development for improvement of grain yield without increasing the production of vegetative biomass. This approach requires the use of promoters with high activity and tightly controlled specificity. Promising candidates are the promoters of the maize genes cyclin delta 2 (Locus # GRMZM2G476685; SEQ ID NO: 22), phospholipase 2A (Locus # GRMZM2G154523; SEQ ID NO: 23), sucrose transporter (Locus # GRMZM2G081589; SEQ ID NO: 24), and cell wall invertase (Locus # GRMZM2G139300; SEQ ID NO: 25) which have been shown to be expressed in leaves but not in the fertilized ovaries at the onset of seed development (Kakumanu et al., 2012, *Plant Physiol.* 160: 846-847).

Since the genes characterized in the presented invention are global transcriptional regulators, trait modifications can also be achieved through modulating the expression of downstream transcription factors. For example, 10 bZIP transcription factors regulated by the TFs of the invention were identified in transgenic switchgrass by gene expression microarray analysis (see Example 7). Members of the bZIP TF family have been characterized in different plant species and linked to various developmental and physiological processes, such as panicle and seed development, endosperm-specific expression of storage protein genes, vegetative growth and abiotic stress tolerance (reviewed in Nijhawan et al., 2008, *Plant Physiol.* 146: 333-350). In total, 18 MYB transcription factors regulated by PvSTR1, PvSTIF1 and PvBMY1 were also identified in this study (Table 8). Some of these genes are well known for their role in major biological processes—development and cell differentiation, photosynthesis and secondary metabolism, stress tolerance and defense response (reviewed in Ambawat et al., 2013, *Physiol. Mol. Biol. Plants* 19: 307-321) and can be useful in different approaches to crop improvement.

Example 9. Transformation of Other Crop Species

*Agrobacterium*-mediated Transformation of *Miscanthus* Species

*Miscanthus* has been extensively evaluated as a bioenergy crop in Europe since the early 1980s (Lewandowski et al., 2003, *Biomass and Bioenergy,* 25: 335-361) and, more recently, in North America (Heaton et al., 2008, *Global Change Biology,* 14: 2000-2014). The research on biomass productivity and environmental impact has mainly been focused on *M. sacchartflorus* and *Miscanthus* x *giganteus,* a pollen sterile hybrid between *M. sacchartflorus* and *M. sinensis* (Jorgensen & Muhs, 2001, In M. B. Jones and M. Walsh (eds.), *Miscanthus for energy and fibre.* James & James (Science Publishers) Ltd., London, pp. 68-852).

For the development of tissue culture and transformation systems, *Miscanthus* x *giganteus* plants established in soil from rhizomes and grown under greenhouse conditions at 27° C. with a 16-hour photoperiod using supplemental sodium halide lamps (200 mol/m²/s) were used as an explant source. Immature inflorescences, axillary meristems, and basal portions of leaves were harvested and used for culture initiation after surface sterilization. The initial explants and resultant cultures were incubated at 27° C., in the dark. Their response to various concentrations and combinations of plant growth regulators and different nitrate-to-ammonium ratios in the tissue culture medium was tested. After 3-4 weeks of culture, the number of explants forming callus was scored and the callus type was determined according to visual appearance and morphogenetic ability. Callus formation was observed from all types of explants with significant differences in the callus induction frequency and the ratio of the callus types formed. The results revealed that immature inflorescences were the best explants for callus initiation and that MS basal medium supplemented with the synthetic auxin 2,4-D as a sole plant growth regulator was optimal for callus initiation, induction of somatic embryo formation and suppression of precocious plant regeneration in these cultures.

Two approaches to improving the medium for callus initiation and growth were used. The experiments were performed with callus cultures propagated by monthly transfers on to MS medium containing 5 mg/L of 2,4-D and 30 g/L sucrose for 6-9 months. To determine the optimal auxin concentration for callus growth, pre-weighed pieces of embryogenic callus (30 pieces per replication, 2 replications per variant) were plated on MS medium supplemented with 1, 2, 3, 4, and 5 mg/L of 2,4-D. Cultures grown on MS medium without any plant growth regulators served as a control. After 4 weeks, all calluses were weighed and their growth rate was calculated as %=[(callus final fresh weight−callus initial fresh weight)/callus initial fresh weight]×100. Since the highest growth rate was detected in the presence of 2 mg/L of 2,4-D, this concentration was used for callus initiation, propagation and selection in the transformation experiments.

For further optimization of the tissue culture procedure, the effects of several antinecrotic compounds on callus growth and embryogenic response were evaluated. Briefly, pre-weighed embryogenic callus (27-77 mg fresh weight per replication, 2 replications per variant) was plated on MS medium containing 2 mg/L 2,4-D and supplemented with ascorbic acid (15 mg/L), cysteine (40 mg/L), and silver nitrate (5 mg/L) alone or in different combinations. Culture growth and development were monitored on a weekly basis and callus growth rate was calculated as described above after 4 weeks. The results showed that callus growth was promoted by ascorbic acid and cysteine and not affected by silver nitrate. Although the highest growth rate was detected in calluses grown in the presence of all three antinecrotic compounds, some undesired changes in the development of these cultures were also observed. Taken together, the results demonstrated that MS medium supplemented with 2 mg/L of 2,4-D, 15 mg/L of ascorbic acid and 40 mg/L of cysteine was optimal for the growth and development of embryogenic callus cultures.

Since young, developing panicles proved to be an excellent source of explants for callus initiation in *Miscanthus* x *giganteus*, these studies were further extended in order to develop a novel protocol for in vitro production of immature inflorescences and callus initiation from them. The possibility for vegetative propagation by node cultures was also explored. The top culm node and the nodes below the top one of tillers prior to flowering from plants grown under greenhouse conditions were used as explant sources. After surface sterilization, the nodal segments were incubated in a 10% aqueous solution of polyvynilpyrrolidone (PVP40, Sigma), split longitudinally and plated on to MS medium containing 10 mg/L BAP and 30 g/L sucrose. Individual spikelets from panicles formed from the top node were plated on the optimized medium for callus initiation described above. Resultant calluses were propagated by transfers every 3-4 weeks on to a fresh medium and used in transformation experiments. For plant regeneration, calluses initiated from in vitro developed panicles were plated on hormone-free MS medium and incubated at 27° C. with a 16 h photoperiod (cool white fluorescent bulbs, 80 µmol/m$^2$/s) and subcultured every 3-4 weeks. Plantlets with 3-4 leaves were transferred to larger tissue culture containers with the same medium and grown for another 2-3 weeks prior to transfer to soil.

Shoots produced from nodal segments below the top node were also cultured on hormone-free MS medium for 3-4 weeks prior to transfer to soil.

Agrobacterium-mediated transformation of established embryogenic callus cultures initiated from in vitro developed panicles was performed following the previously described procedure for switchgrass transformation (Somleva, 2006, Agrobacterium Protocols Wang K., ed., pp 65-74: Humana Press; Somleva et al., 2002, Crop Sci. 42: 2080-2087) with the following modifications: infected cultures were co-cultivated with Agrobacterium tumefaciens for 5-10 days prior to transfer to a medium supplemented with 3 mg/L bialaphos for callus selection. Using the developed methods, Miscanthus species can be engineered with the transcription factor genes of the invention for increased production of biomass and/or modifications of its composition for bioenergy applications.

Miscanthus sinensis callus cultures were initiated from mature caryopses and their embryogenic potential was evaluated as described previously for switchgrass (U.S. Pat. No. 8,487,159 to Somleva et al.). They were transformed following the procedure for Agrobacterium-mediated transformation of switchgrass (Somleva, 2006, Agrobacterium Protocols Wang K., ed., pp 65-74: Humana Press; Somleva et al., 2002, Crop Sci. 42: 2080-2087).

Agrobacterium-mediated Transformation of Maize

The binary vectors provided in the invention can be used for Agrobacterium-mediated transformation of maize following a previously described procedure (Frame et al., 2006, Agrobacterium Protocols Wang K., ed., Vol. 1, pp 185-199, Humana Press).

Plant material: Plants grown in a greenhouse are used as an explant source. Ears are harvested 9-13 d after pollination and surface sterilized with 80% ethanol.

Explant isolation, infection and co-cultivation: Immature zygotic embryos (1.2-2.0 mm) are aseptically dissected from individual kernels and incubated in A. tumefaciens strain EHA101 culture (grown in 5 ml N6 medium supplemented with 100 µM acetosyringone for stimulation of the bacterial vir genes for 2-5 h prior to transformation) at room temperature for 5 min. The infected embryos are transferred scutellum side up on to a co-cultivation medium (N6 agar-solidified medium containing 300 mg/l cysteine, 5 µM silver nitrate and 100 µM acetosyringone) and incubated at 20° C., in the dark for 3 d. Embryos are transferred to N6 resting medium containing 100 mg/l cefotaxime, 100 mg/l vancomycin and 5 µM silver nitrate and incubated at 28° C., in the dark for 7 d.

Callus selection: All embryos are transferred on to the first selection medium (the resting medium described above supplemented with 1.5 mg/l bialaphos) and incubated at 28° C., in the dark for 2 weeks followed by subculture on a selection medium containing 3 mg/l bialaphos. Proliferating pieces of callus are propagated and maintained by subculture on the same medium every 2 weeks.

Plant regeneration and selection: Bialaphos-resistant embryogenic callus lines are transferred on to regeneration medium I (MS basal medium supplemented with 60 g/l sucrose, 1.5 mg/l bialaphos and 100 mg/l cefotaxime and solidified with 3 g/l Gelrite) and incubated at 25° C., in the dark for 2 to 3 weeks. Mature embryos formed during this period are transferred on to regeneration medium II (the same as regeneration medium I with 3 mg/l bialaphos) for germination in the light (25° C., 80-100 µE/m$^2$/s light intensity, 16/8-h photoperiod). Regenerated plants are ready for transfer to soil within 10-14 days.

Agrobacterium-mediated Transformation of Sorghum

The vectors provided in the invention can be used for sorghum transformation following a previously described procedure (Zhao, 2006, Agrobacterium Protocols Wang K., ed., Vol. 1, pp 233-244, Humana Press).

Plant material: Plants grown under greenhouse, growth chamber or field conditions are used as an explant source. Immature panicles are harvested 9-12 d post pollination and individual kernels are surface sterilized with 50% bleach for 30 min followed by three washes with sterile distilled water.

Explant isolation, infection and co-cultivation: Immature zygotic embryos (1-1.5 mm) are aseptically dissected from individual kernels and incubated in A. tumefaciens strain LBA4404 suspension in PHI-I liquid medium (MS basal medium supplemented with 1 g/l casamino acids, 1.5 mg/l 2,4-D, 68.5 g/l sucrose, 36 g/l glucose and 100 µM acetosyringone) at room temperature for 5 min. The infected embryos are transferred with embryonic axis down on to a co-cultivation PHI-T medium (agar-solidified modified PHI-I medium containing 2.0 mg/l 2,4-D, 20 g/l sucrose, 10 g/l glucose, 0.5 g/l MES, 0.7 g/l proline, 10 mg/l ascorbic acid and 100 µM acetosyringone) and incubated at 25° C., in the dark for 3 d. For resting, embryos are transferred to the same medium (without acetosyringone) supplemented with 100 mg/l carbenicillin and incubated at 28° C., in the dark for 4 d.

Callus selection: Embryos are transferred on to the first selection medium PHI-U (PHI-T medium described above supplemented with 1.5 mg/l 2,4-D, 100 mg/l carbenicillin and 5 mg/l PPT without glucose and acetosyringone) and incubated at 28° C., in the dark for 2 weeks followed by subculture on a selection medium containing 10 mg/l PPT. Proliferating pieces of callus are propagated and maintained by subculture on the same medium every 2 weeks for the remainder of the callus selection process of 10 weeks.

Plant regeneration and selection: Herbicide-resistant callus is transferred on to regeneration medium I (PHI-U medium supplemented with 0.5 mg/l kinetin) and incubated at 28° C., in the dark for 2 to 3 weeks for callus growth and embryo development. Cultures are transferred on to regeneration medium II (MS basal medium with 0.5 mg/l zeatin, 700 mg/l proline, 60 g/l sucrose and 100 mg/l carbenicillin) for shoot formation (28° C., in the dark). After 2-3 weeks, shoots are transferred on to a rooting medium (regeneration II medium supplemented with 20 g/l sucrose, 0.5 mg/l NAA and 0.5 mg/l IBA) and grown at 25° C., 270 µE/m$^2$/s light intensity with a 16/8-h photoperiod. When the regenerated plants are 8-10 cm tall, they can be transferred to soil and grown under greenhouse conditions.

*Agrobacterium*-mediated Transformation of Barley

The vectors provided in the invention can be used for transformation of barley as described by Tingay et al., 1997, *Plant J.* 11: 1369-1376.

Plant material: Plants of the spring cultivar Golden Promise are grown under greenhouse or growth chamber conditions at 18° C. with a 16/8 hours photoperiod. Spikes are harvested when the zygotic embryos are 1.5-2.5 mm in length. Developing caryopses are sterilized with sodium hypochlorite (!5 w/v chlorine) for 10 min and rinsed four times with sterile water.

Explant Isolation, Infection and Co-cultivation:

Immature zygotic embryos are aseptically dissected from individual kernels and after removal of the embryonic axes are placed scutellum side up on a callus induction medium (Gelrite-solidified MS basal medium containing 30 g/l maltose, 1.0 g/l casein hydrolysate, 0.69 g/l proline and 2.5 mg/L dicamba. Embryos are incubated at 24° C. in the dark during subsequent culture. One day after isolation, the embryos are incubated in *A. tumefaciens* strain AGL1 culture (grown from a single colony in MG/L medium) followed by a transfer on to the medium described above.

Callus Selection: After co-cultivation for 2-3 d, embryos are transferred on to the callus induction medium supplemented with 3 mg/l bialaphos and 150 mg/l Timentin. Cultures are selected for about 2 months with transfers to a fresh selection medium every 2 weeks.

Plant Regeneration and Selection:

Bialaphos-resistant embryogenic callus lines are transferred to a Phytagel-solidified regeneration medium containing 1 mg/l BA and 3 mg/l bialaphos for selection of transgenic plants and grown at 24° C. under fluorescent lights with a 16/8 h photoperiod. For root development, regenerated plants are transferred to a hormone-free callus induction medium supplemented with 1 mg/l bialaphos. After development of a root system, plants are transferred to soil and grown in a greenhouse or a growth chamber under the conditions described above.

*Agrobacterium*-mediated Transformation of Rice

The binary vectors provided in the invention can be used for *Agrobacterium*-mediated transformation of rice following a previously described procedure (Herve and Kayano, 2006, *Agrobacterium Protocols* Wang K., ed., Vol. 1, pp 213-222, Humana Press).

Plant material: Mature seeds from *japonica* rice varieties grown in a greenhouse are used as an explant source.

Culture transformation and selection: Dehusked seeds are surface sterilized with 70% ethanol for 1 min and 3% sodium hypochlorite for 30 min followed by six washes with sterile distilled water. Seeds are plated embryo side up on an induction medium (Gelrite-solidified N6 basal medium supplemented with 300 mg/l casamino acids, 2.88 g/l proline, 30 g/l sucrose and 2 mg/l 2,4-D) and incubated at 32° C., under continuous light for 5 d. Germinated seeds with swelling of the scutellum are infected with *A. tumefaciens* strain LBA4404 (culture from 3-d-old plates resuspended in N6 medium supplemented with 100 μM acetosyringone, 68.5 g/l sucrose and 36 g/l glucose) at room temperature for 2 min followed by transfer on to a co-cultivation medium (N6 Gelrite-solidified medium containing 300 mg/l casamino acids, 30 g/l sucrose, 10 g/l glucose, 2 mg/l 2,4-D and 100 μM acetosyringone) and incubation at 25° C., in the dark for 3 d.

For selection of transformed embryogenic tissues, whole seedlings washed with 250 mg/l cephotaxine are transferred on to N6 agar-solidified medium containing 300 mg/l casamino acids, 2.88 g/l proline, 30 g/l sucrose, 2 mg/l 2,4-D, 100 mg/l cefotaxime, 100 mg/l vancomycin and 35 mg/l G418 disulfate). Cultures are incubated at 32° C., under continuous light for 2-3 weeks.

Plant regeneration and selection: Resistant proliferating calluses are transferred on to agar-solidified N6 medium containing 300 mg/l casamino acids, 500 mg/l proline, 30 g/l sucrose, 1 mg/l NAA, 5 mg/l ABA, 2 mg/l kinetin, 100 mg/l cefotaxime, 100 mg/l vancomycin and 20 mg/l G418 disulfate. After one week of growth at 32° C., under continuous light, the surviving calluses are transferred on to MS medium (solidified with 10 g/l agarose) supplemented with 2 g/l casamino acids, 30 g/l sucrose, 30 g/l sorbitol, 0.02 mg/l NAA, 2 mg/l kinetin, 100 mg/l cefotaxime, 100 mg/l vancomycin and 20 mg/l G418 disulfate and incubated under the same conditions for another week followed by a transfer on to the same medium with 7 g/l agarose. After 2 weeks, the emerging shoots are transferred on to Gelrite-solidified MS hormone-free medium containing 30 g/l sucrose and grown under continuous light for 1-2 weeks to promote shoot and root development. When the regenerated plants are 8-10 cm tall, they can be transferred to soil and grown under greenhouse conditions. After about 10-16 weeks, transgenic seeds are harvested.

Indica rice varieties are transformed with *Agrobacterium* following a similar procedure (Datta and Datta, 2006, *Agrobacterium Protocols* Wang K., ed., Vol. 1, pp 201-212, Humana Press).

Microprojectile Bombardment-mediated Transformation of Sugarcane

An expression cassette containing a transcription factor gene can be co-introduced with a cassette of a marker gene (e. g., npt) into sugarcane via biolistics following a previously described protocol (Taparia et al., 2012, *In Vitro Cell. Dev. Biol.* 48: 15-22))

Plant material: Greenhouse-grown plants with 6-8 visible nodes are used as an explant source. Tops are collected and surface sterilized with 70% ethanol. The outermost leaves are removed under aseptic conditions and immature leaf whorl cross sections (about 2 mm) are cutfrom the region 1-10 cm above the apical node.

Culture initiation, transformation and selection: The isolated leaf sections are cultured on MS basal media supplemented with 20 g/l sucrose, 1.86 mg/l p-chlorophenoxyacetic acid (CPA), 1.86 mg/l NAA and 0.09 mg/l BA at 28° C., under 30 μmol/m$^2$/s light intensity and a 16/8-h photoperiod for 7 d. Embryogenic cultures are subcultured to fresh medium and used for transformation.

For microprojectile bombardment, leaf disks are plated on the culture initiation medium supplemented with 0.4 M sorbitol 4 hours before gene transfer. Plasmid DNA (200 ng) containing the expression cassettes of a TF and a marker gene is precipitated onto 1.8 mg gold particles (0.6 μm) following a previously described procedure (Altpeter and Sandhu, 2010, *Genetic transformation—biolistics*, Davey & Anthony eds., pp 217-237, Wiley, Hoboken). The DNA (10 ng per shot) is delivered to the explants by a PDS-1000 Biolistc particle delivery system (Biorad) using 1100-psi rupture disk, 26.5 mmHg chamber vacuum and a shelf distance of 6 cm. pressure). The bombarded expants are transferred to the culture initiation medium described above and incubated for 4 days.

For selection, cultures are transferred on to the initiation medium supplemented with 30 mg/l geneticin and incubated for 10 d followed by another selection cycle under the same conditions.

Plant regeneration and selection: Cultures are transferred on to the selection medium described above without CPA and grown at 28° C., under 100 µmol/m²/s light intensity with a 16/8-h photoperiod. Leaf disks with small shoots (about 0.5 cm) are plated on a hormone-free medium with 30 mg/l geneticin for shoot growth and root development. Prior to transfer to soil, roots of regenerated plants can be dipped into a commercially available root promoting powder.

Transformation of Wheat by Microprojectile Bombardment

The gene constructs provided in the invention can be used for wheat transformation by microprojectile bombardment following a previously described protocol (Weeks et al., 1993, *Plant Physiol.* 102: 1077-1084).

Plant material: Plants from the spring wheat cultivar Bobwhite are grown at 18-20° C. day and 14-16° C. night temperatures under a 16 h photoperiod. Spikes are collected 10-12 weeks after sowing (12-16 days post anthesis). Individual caryopses at the early-medium milk stage are sterilized with 70% ethanol for 5 min and 20% sodium hypochlorite for 15 min followed by three washes with sterile water.

Culture initiation, transformation and selection: Immature zygotic embryos (0.5-1.5 mm) are dissected under aseptic conditions, placed scutellum side up on a culture induction medium (Phytagel-solidified MS medium containing 20 g/l sucrose and 1.5 mg/l 2,4-D) and incubated at 27° C., in the light (43 µmol/m²/s) for 3-5 d.

For microprojectile bombardment, embryo-derived calluses are plated on the culture initiation medium supplemented with 0.4 M sorbitol 4 hours before gene transfer. Plasmid DNA containing the expression cassettes of a TF and the marker gene bar is precipitated onto 0.6-µm gold particles and delivered to the explants as described for sugarcane.

The bombarded expants are transferred to callus selection medium (the culture initiation medium described above containing 1-2 mg/l bialaphos) and subcultured every 2 weeks.

Plant regeneration and selection: After one-two selection cycles, cultures are transferred on to MS regeneration medium supplemented with 0.5 mg/l dicamba and 2 mg/l bialaphos. For root formation, the resulting bialaphos-resistant shoots are transferred to hormone-free half-strength MS medium. Plants with well-developed roots are transferred to soil and acclimated to lower humidity at 21° C. with a 16-h photoperiod (300 µmol/m²/s) for about 2 weeks prior to transfer to a greenhouse.

*Agrobacterium*-mediated Transformation of Camelina

The gene constructs provided in the invention can be used for camelina transformation by floral dip following a previously described protocol (International Patent Application WO 2011034946).

Plant material: Plants grown from seeds under greenhouse conditions (24° C./18° C. day/night temperatures) with unopened flower buds are used for floral dip transformation.

*Agrobacterium* culture preparation and plant inoculation: The constructs of interest are introduced into *Agrobacterium* strain GV3101 by electroporation. A single colony of GV3101 is obtained from a freshly streaked plate and is inoculated into 5 mL LB medium. After overnight growth at 28° C., 2 ml of culture is transferred to a 500-mL flask containing 300 ml of LB and incubated overnight at 28° C. Cells are pelleted by centrifugation (6000 rpm, 20 min) and diluted to an $OD_{600}$ 0.8 with the infiltration medium containing 5% sucrose and 0.05% (v/v) Silwet-L77 (Lehle Seeds, Round Rock, Tex., USA). Camelina plants are transformed as follows. Pots containing plants at the flowering stage are placed in a vacuum desiccator (Bel-Art, Pequannock, N.J., USA) and their inflorescences are immersed into the *Agrobacterium* culture. A vacuum (85 kPa) is applied for 5 min. Plants are removed from the desiccators, covered with plastic bags and kept at room temperature, in the dark for 24 h. Plants are grown in a greenhouse for seed formation.

Identification of transgenic seeds: To identify bialaphos-resistant seeds, seeds from inoculated plants are harvested, sterilized with 70% ethanol and 10% bleach followed by washes with sterile water. Sterilized seeds are placed on germination and selection medium (half-strenght MS basal medium) containing 10 mg/L bialaphos and incubated in a growth chamber at 23/20° C. (day/night) with a 16-h photoperiod (3000 lux). Seedlings with green cotyledons are transferred to soil about six days after initiation of germination.

*Agrobacterium*-mediated Transformation of *Brassica napus*

Plant material: Mature seeds are surface sterilized in 10% commercial bleach for 30 min with gentle shaking and washed three times with sterile distilled water.

Culture initiation and transformation: Seeds are plated on germination medium (MS basal medium supplemented with 30 g/l sucrose) and incubated at 24° C. with a 16-h photoperiod at a light intensity of 60-80 µE/m²/s for 4-5 d. For transformation, cotyledons with ~2 mm of the petiole at the base are excised from the resulting seedlings, immersed in *Agrobacterium tumefacians* strain EHA101 suspension (grown from a single colony in 5 ml of minimal medium supplemented with appropriate antibiotics at 28° C. for 48 h) for 1 s and immediately embedded to a depth of ~2 mm in a co-cultivation medium (MS basal medium with 30 g/l sucrose and 20 µM benzyladenine). The inoculated cotyledons are incubated under the same growth conditions for 48 h.

Plant regeneration and selection: After co-cultivation, cotyledons are transferred on to a regeneration medium comprising MS medium supplemented with 30 g/l sucrose and 20 µM benzyladenine, 300 mg/l timentinin and 20 mg/l kanamycin sulfate. After 2-3 weeks, regenerated shoots are cut and maintained on MS medium for shoot elongation containing 30 g/l sucrose, 300 mg/l timentin, and 20 mg/l kanamycin sulfate. The elongated shoots are transferred to a rooting medium comprising MS basal medium supplemented with 30 g/l sucrose, 2 mg/l indole butyric acid (IBA) and 500 mg/L carbenicillin. After root formation, plants are transferred to soil and grown to seed maturity under growth chamber or greenhouse conditions.

*Agrobacterium*-mediated Transformation of Soybean

The soybean orthologs of the switchgrass transcription factor genes identified in the invention (FIG. 4) are assembled in binary vectors (Table 9) and used for *Agrobacterium*-mediated transformation of soybean following a previously described procedure (Ko et al., 2006, *Agrobacterium Protocols* Wang K., ed., Vol. 1, pp 397-405, Humana Press).

Plant material: Immature seeds from soybean plants grown under greenhouse or field conditions are used as an explant source. Young pods are harvested and surface sterilized with 70% 2-propanol for 30 sec and 25% Clorox for 20 min followed by three washes with sterile distilled water.

Culture transformation and selection: Under aseptic conditions, immature seeds are removed from the pods and the cotyledons are separated from the seed coat followed by incubation in *A. tumefaciens* culture (grown from a single colony at 28° C., overnight) in co-cultivation medium (MS salts and B5 vitamins) supplemented with 30 g/l sucrose, 40 mg/l 2,4-D and 40 mg/l acetosyringone for 60 min. Infected explants are plated abaxial side up on agar-solidified co-cultivation medium and incubated at 25° C., in the dark for 4 d.

For selection of transformed tissues, cotyledons washed with 500 mg/l cephotaxine are placed abaxial side up on a medium for induction of somatic embryo formation (Gelrite-solidified MS medium medium containing 30 g/l sucrose, 40 mg/l 2,4-D, 500 mg/l cefotaxime, and 10 mg/l hygromycin) and incubated at 25° C., under a 23-h photoperiod (10-20 µE/m$^2$/s) for 2 weeks. After another two weeks of growth under the same conditions in the presence of 25 mg/l hygromycin, the antibiotic-resistant somatic embryos are transferred on MS medium for embryo maturation supplemented with 60 g/l maltose, 500 mg/l cefotaxime, and 10 mg/l hygromycin and grown under the same conditions for 8 weeks with 2-week subculture intervals.

Plant regeneration and selection: The resulting cotyledonary stage embryos are desiccated at 25° C., under a 23-h photoperiod (60-80 µE/m$^2$/s) for 5-7 d followed by culture on MS regeneration medium containing 30 g/l sucrose and 500 mg/l cefotaxime for 4-6 weeks for shoot and root development. When the plants are 5-10 cm tall, they are transferred to soil and grown in a greenhouse after acclimatization for 7 d.

TABLE 9

Plant transformation vectors for overexpression of the orthologous transcription factor genes GmSTR1, GmSTIF1 and GmBMY1 in soybean.

| Vector ID* | TF gene/ marker | Annotation | SEQ ID | Coordinates (bp) |
|---|---|---|---|---|
| pMBXS884 | GmSTR1/hpt | Agrobacterium T-DNA right border | 26 | 12780-12805 |
| | | CaMV35S promoter to drive GmSTR1 gene | | 9566-11260 |
| | | GmSTR1 coding region | | 11269-12124 |
| | | nos terminator | | 12258-12532 |
| | | CaMV35S promoter to drive hptII gene | | 7707-9292 |
| | | hptII coding region | | 6456-7692 |
| | | CaMV35S polyA terminator | | 6248-6450 |
| | | Agrobacterium T-DNA left border | | 6173-6198 |
| pMBXS885 | GmSTIF1/hpt | Agrobacterium T-DNA right border | 27 | 12384-12409 |
| | | CaMV35S promoter to drive GmSTIF1 gene | | 9566-11260 |
| | | GmSTIF1 coding region | | 11269-12055 |
| | | nos terminator | | 11862-12136 |
| | | CaMV35S promoter to drive hptII gene | | 7707-9292 |
| | | hptII coding region | | 6456-7692 |
| | | CaMV35S polyA terminator | | 6248-6450 |
| | | Agrobacterium T-DNA left border | | 6173-6198 |
| pMBXS886 | GmBMY1/hpt | Agrobacterium T-DNA right border | 28 | 12459-12484 |
| | | CaMV35S promoter to drive GmBMY1 gene | | 9566-11260 |
| | | GmBMY1 coding region | | 11269-11782 |
| | | nos terminator | | 11937-12211 |
| | | CaMV35S promoter to drive hptII gene | | 7707-9292 |
| | | hptII coding region | | 6456-7692 |
| | | CaMV35S polyA terminator | | 6248-6450 |
| | | Agrobacterium T-DNA left border | | 6173-6198 |

*All vectors are based on the transformation vector pCambia3300 found on the world wide web at cambia.org; the hpt gene (conferring resistance to hygromycin) is used as a marker for selection of transformed explants and plants.

Sequences:

SEQ ID NO: 1 Pvstr1 (STarch Regulator) transcription factor DNA coding sequence

```
  1  ATGTGCGGCG GGGCCATTCT CAGTGATCTC TACTCACCAG TGAGGCGGAC GGTCACTGCC
 61  GGTGACCTAT GGGGAGAGAG TGGCAGCAGC AAGAATGTGA AGAACTGGAA AAGGAGTTCT
121  TGGAAGTTTG ATGAAGGCGA TGAAGACTTT GAAGCTGATT TCAAGGATTT TGAGGATTGC
181  AGTAGCGAGG AGGAGGTAGA TTTTGGACAT GAGGAAAAAG AATTCCAATT GAACAGTTCG
241  AATTTCGTGG AATTCAATGG CCATACTGCC AAAGTCACCA GCAGGAAGCG AAAGATCCAG
301  TACCGAGGGA TCCGGCGGCG GCCTTGGGGC AAATGGGCAG CAGAAATCAG AGACCCACAG
361  AAGGGCGTCC GAGTTTGGCT TGGCACGTTC AGCACTGCCG AGGAAGCTGC AAGGGCATAT
421  GACGTGGAAG CTCTACGCAT ACGTGGCAAG AAAGCCAAGA TGAATTTCCC TACCACCATC
481  ACAGCTGCTG GGAAACACCA CCGGCAGCGT GTGGCTCGAC CGGCAAAGAA GACGTCACAA
541  GAGAGCCTGA AGTCAAGCAA TGCCTCTGGT CATGTCATCT CAGCAGGCAG CAGTACTGAT
601  GGCACCGTTG TCAAGATCGA GTTGTCACAG TCACCAGCTT CTCCACTACC AGTGTCCAGC
661  GCATGGCTTG ATGCTTTTGA GCTGAAGCAG CTTGGTGGAG AAACCCCTGA AGCTGATGGG
```

| | |
|---|---|
| 721 | AGAGAAACCC CTGAAGAAAC TGATCATGAA ACGGGAGTGA CAGCGGATAT GTTTTTTGGC |
| 781 | AATGGCGAAG TGCGGCTTTC AGATGATTTT GCGTCTTACG AGCCTTACCC AAATTTTATG |
| 841 | CAGTTACCTT ATCTAGAAGG TGACTCGTAT GAAACATTG ACACTCTTTT CAACGGTGAA |
| 901 | GCTGCTCAGG ATGGAGTGAA CATCGGAGGT CTTTGGAATT TCGATGATGT GCCAATGGAC |
| 961 | CGTGGTGTTT ACTGA |

SEQ ID NO: 2 PvSTIF1 (Stress Inducible Factor) transcription factor DNA coding sequence

| | |
|---|---|
| 1 | ATGCATATGT ATCCTTTCTA CATACATGCA GGTTACGGGA CGAGAATGCA CTACCGTGGC |
| 61 | GTGCGGCGGC GGCCGTGGGG CAAGTGGGCG GCGGAGATCC GTGACCCCGC CAAGGCGGCG |
| 121 | CGTGTGTGGC TCGGCACCTT CGACACCGCG GAGGCCGCC CCGCAGCGTA CGACGACGCC |
| 181 | GCGCTCCGGT TCAAGGGCGC CAAGGCCAAG CTCAACTTTC CCGAGCGCGT CCGCGGCCGT |
| 241 | ACCGGCCAGG GCGCGTTCCT CGTCAGCCCT GGCGTCCCCC AGCAGCCGCC GCCGTCTTCC |
| 301 | CTGCCAACTG CAGCCGCCGC GCCGACGCCA TTCCCCGGCT TGATGCGGTA CGCGCAACTC |
| 361 | CAGGGTTGGA GCAGCGGGAA CATCGCGGCC AGCAACACCG GTGGTGATCT CGCGCCGCCG |
| 421 | GCACAGGCGT CGTCGTCGGT GCAGATTCTG GACTTCTCGA CGCAGCAACT ACTCCGGGGC |
| 481 | TCACCGACAA CGTTCGGCCC ACCGCCGACG ACGTCGGCAT CGATGTCCAG GACTAGCAGA |
| 541 | GTAGATGAGG CGCACGAGAG TTGCGATGCT CCTGACTGA |

SEQ ID NO: 3 PvBMY1 (Biomass Yield) transcription factor DNA coding sequence

| | |
|---|---|
| 1 | ATGCCGGACT CCGACAACGA GTCCGGCGGG CCGAGCAACG CGGAGTTCTC GTCGCCGCGG |
| 61 | GAGCAGGACC GGTTCCTGCC GATCGCGAAC GTGAGCCGGA TCATGAAGAA GGCGCTCCCG |
| 121 | GCGAACGCCA AGATCTCCAA GGACGCCAAG GAGACGGTGC AGGAGTGCGT CTCCGAGTTC |
| 181 | ATCTCCTTCA TCACCGGCGA GGCCTCCGAC AAGTGCCAGC GCGAGAAGCG CAAGACCATC |
| 241 | AACGGCGACG ACCTCCTCTG GCCATGACC ACGCTCGGCT TCGAGGACTA CATCGAGCCA |
| 301 | CTCAAGCTCT ACCTCCACAA GTTCCGCGAG CTCGAGGGCG AGAAGGTGGC CTCCGGCGCC |
| 361 | GCGGGCTCCT CCGGCTCCGC CTCGCAGCCC CAGAGAGAGA CAACGCCGTC CGCGCACAAT |
| 421 | GGCGCCGCCG GGGCCGTCGG CTACGGCATG TACGGCGCCG CGCCGGGGC CGGCGGAGGC |
| 481 | AGCGGCATGA TCATGATGAT GGGGCAGCCG ATGTACGGCT CCCCACCGGG CGCGTCGGGG |
| 541 | TACCCGCAGC CCCGCACCA CCACATGGTG ATGGGCGCTA AGGTGGCGC CTACGGCCAC |
| 601 | GGCGGCGGCT CGTCGCCATC GCTGTCGGGG CTCGGCAGGC AGGACAGGCT ATGA |

SEQ ID NO: 4 PvSTR1 transcription factor encoded polypeptide sequence

| | |
|---|---|
| 1 | MCGGAILSDL YSPVRRTVTA GDLWGESGSS KNVKNWKRSS WKFDEGDEDF EADFKDFEDC |
| 61 | SSEEEVDFGH EEKEFQLNSS NFVEFNGHTA KVTSRKRKIQ YRGIRRRPWG KWAAEIRDPQ |
| 121 | KGVRVWLGTF STAEEAARAY DVEALRIRGK KAKMNFPTTI TAAGKHHRQR VARPAKKTSQ |
| 181 | ESLKSSNASG HVISAGSSTD GTVVKIELSQ SPASPLPVSS AWLDAFELKQ LGGETPEADG |
| 241 | RETPEETDHE TGVTADMFFG NGEVRLSDDF ASYEPYPNFM QLPYLEGDSY ENIDTLFNGE |
| 301 | AAQDGVNIGG LWNFDDVPMD RGVY |

SEQ ID NO: 5 PvSTIF1 transcription factor encoded polypeptide sequence

| | |
|---|---|
| 1 | MHMYPFYIHA GYGTRMHYRG VRRRPWGKWA AEIRDPAKAA RVWLGTFDTA EAAAAYDDA |
| 61 | ALRFKGAKAK LNFPERVRGR TGQGAFLVSP GVPQQPPPSS LPTAAAAPTP FPGLMRYAQL |
| 121 | QGWSSGNIAA SNTGGDLAPP AQASSSVQIL DFSTQQLLRG SPTTFGPPPT TSASMSRTSR |
| 181 | VDEAHESCDA PD |

| Sequences: |
|---|

SEQ ID NO: 6 PvBMY1 transcription factor encoded polypeptide sequence
```
  1  MPDSDNESGG PSNAEFSSPR EQDRFLPIAN VSRIMKKALP ANAKISKDAK ETVQECVSEF

61  ISFITGEASD KCQREKRKTI NGDDLLWAMT TLGFEDYIEP LKLYLHKFRE LEGEKVASGA

121  AGSSGSASQP QRETTPSAHN GAAGAVGYGM YGAGAGAGGG SGMIMMMGQP MYGSPPGASG

181  YPQPPHHHMV MGAKGGAYGH GGGSSPSLSG LGRQDRL
```

SEQ ID NO: 7 PvSTR homolog 2 Pavirv00061015m
```
  1  ATGTGCGGTG GGGCTATTCT CAGTGATCTC TACTCACCAG TGAGGCGGAC GGTCACTGCC

61  GGTGACCTAT GGGGAGAGAG CGGCAGCACC AAGAATGTGA AGAACTGGAA AAGGAGGAGT

121  TCTTGGAAGT TTGATGAAGA CGATGATGAC TTTGAAGCTG ATTTCGAGGA TTTCAACGAT

181  TGCAGTAGCG AGGAGGAGGT GGATTTTGTA CGTGAGGAAA AAGAATTCCA ATTGAACAGT

241  TCGAATTTTG TGGAACTCAA CGGCCATACC ACCAAAGTCG CCAGCAGGAA GCGAAAGACC

301  CAGTACCGAG GGATCCGACG GCGCCCGTGG GGCAAATGGG CAGCTGAAAT CAGAGACCCA

361  CAGAAGGGCG TCCGAGTTTG GCTTGGCACG TTCAGCACTG CCGAGGAAGC TGCAAAGGCA

421  TATGACGTGG AAGCTCTACG CATACGTGGC AAGAAAGCCA AGGTGAATTT CCCTAACACC

481  ATCACAGCTG CTGGGAAACA CCACCGGCAG CATGTGGCTC GACCAGCAAA GAGGATGTCA

541  CAAGAGAGCC TGAAGTCAAG CGATGCCTCT GGTCATGTCG CTCAGCAGG CAGCAGTACT

601  GATGGCACCG TTGTCAAGAT TGAGTTGATA GAGTCACCAG CTTCTCCACT ACCAGTGTCC

661  AGCGCATGGC TTGATGCTTT TGAGCTGAAC CAACTTGGTG GATTAAGGCA CCTTGAAGCT

721  GATGGGAGAG AAACCACTGA AGAAACTGAT CATGAAACGG GAGTGACAGC AGATATGGTT

781  TTTGGCGATG GCAAAGTGCG GCTTTCAGAT GATTTTGCGT CTTACGAGCC TTACCCAAAT

841  TTTATGCAGT TACCTTACCT GGAAGGTAAC TCGTATGAAA ACATTGACAC TCTTTTCAAC

901  GGTGAAGCCG CTCAGGATGG CGTGAACATC GGAGGTCTCT GGAATTTCGA CGATGTGCCA

961  ATGGACCGTG GTGTTTACTA A
```

SEQ ID NO: 8 PvSTR homolog 3 Pavirv00030328m
```
  1  ATGTGCGGCG GTGCGATCCT CGCCAACCTC ACCAAGCAGC CGGGCCCGCG CCGGCTCACG

61  GAGCGGGACC TCTGGCAGGA GAAGAAGAAG CCCAAGAGGG CGCCGGCGG GGGGAGGCGC

121  TGGTTCCTGG CTGAGGAGGA TGAGGACTTC GAGGCCGACT TCAGGGACTT CCAGGGCGAC

181  TCCGATGAGT CGGATTTGGA ACTCGGGGAG GGGGAGGACG ACGACGTCGT CGAGATCAAG

241  CCCTTCGCCG CCAAGAGGAC TTCCTCCAAA GATGGCTTAA GCACCATGAC TACTGCTGGT

301  TATGATGGCC CTGCAGCAAG GTCAGCCAAA AGGAAGAGAA AGAATCAATA CAGGGGCATC

361  CGCCAGCGCC CTTGGGGTAA GTGGGCTGCT GAGATCAGAG ATCCTCAGAA GGGTGTTCGT

421  GTTTGGCTTG GTACTTTCAA CAGTCCTGAG GAAGCTGCAA GAGCTTATGA TGCTGAAGCA

481  CGCAGGATCC GTGGTAAGAA GGCCAAGGTT AACTTCCCTG ATGCACCAAC AGTTGCTCAG

541  AAGCGCCGTA GTGGGCCAGC TGCTGCTAAA GCACCCAAAT CAAGTGTGGA ACAGAAGCCT

601  ACCGTCAAAC CAGCAGTGAA CAACCTTGCC AACGCAAATG CATCCTACCC ACCTGCTGAC

661  TACACCTCAA GCAAGCCATC TGTTCAGCAT GCCAATATGG CATTTCATCT AGCAATGAAC

721  TCTGCTAGTC CTATTGAGGA TCCAGTTATG AATCTGCACT CTGACCAGGG AAGTAACTCT

781  TTTGATTGCT CAGACTTGAG CTGGGGAGAAT GATACCAAGA CTTCAGACAT AACATCCATT

841  GCTCCCATTT CCACCATAGC TGAAGGTGAC GAGTCTGCAT TTGTCAACAG CAATTTGAAC

901  AACTCACTGG TGCCTTCTGT TATGGAGAAC AATGCAGTTG ATCTCACTGA TGGGCTGACA
```

| Sequences: |
|---|
| 961 GATTTAGAAC CGTACATGAG GTTTCTTCTG GATGATGGTG CAAGTGAGTC AATTGATAAC |
| 1021 CTTCTGAACC TTGATGGATC TGAGGATGTT ATGAGCAACA TGGATCTCTG GAGCTTTGAT |
| 1081 GACATGCCTG CTGCTGGCGA TTTCTATTGA |
| SEQ ID NO: 9 PvSTR homolog 4 Pavirv00035924m |
| 1 ATGTGCGGCG GTGCGATCCT CGCCAACCTC ACCAAGCAGC CGGGCCCGCG CCGGCTCACG |
| 61 GAGCGGGACC TCTGGCAGGA GAAGAAGAAG CCCAAGAGGA GCGCCGGCGG GGGTAGGCGC |
| 121 TGGTTCCTGG CTGAGGAGGA TGAGGACTTC GAGGCCGACT TCGAGGACTT CCAGGGCGAC |
| 181 TCCGACGAGT CAGATTTGGA GCTCGGGGAG GGGGAGGACG ACGACGTCGT CGAGATCAAG |
| 241 CCCTTCGCCG CCAAGAGGAC TTCCTCCAAA GATGGCTTAA GCACCATGAT TACTGCTGGT |
| 301 TATGATGGCC CTGCAGCAAG GTCAGCCAAA AGGAAGAGAA AGAATCAATA CAGGGGCATC |
| 361 CGCCAGCGCC CTTGGGGTAA GTGGGCTGCT GAGATCAGAG ATCCTCAGAA GGGTGTTCGT |
| 421 GTCTGGCTTG GTACTTTCAA CAGTCCTGAG GAAGCTGCAA GAGCTTATGA TGCTGAAGCA |
| 481 CGCAGGATCC GTGGTAAGAA GGCCAAGGTT AACTTCCCTG ATGCACCAAC AGTTTCTCAG |
| 541 AAGCGTCGTA GTGGCCCAGC TGCCGCTAAA GCACCCAAGT TAAGTGTGGA ACAGAAGCCT |
| 601 ACTGTCAAAC CAGCAGTGAA CAACCTTGCC AACGCAAATG CATCTTTCTA CCCACCTGCT |
| 661 GACTACACCT CAAACCAGCA ATTTGTTCAG CATGCCAATA TGCCATTTCA TCCAGCAATG |
| 721 AACTCTGCTA GTCCTACTGA GGATCCAGTT ATGAATCTGC ACTCTGACCA GGGAAGTAAC |
| 781 TCTTTTGATT GCTCAGACTT GAGCTGGGAG AATGATACCA AGACTTCAGA CATAACATCC |
| 841 ATTGCTCCCA TTTCCACCAT AGCTGAAGGT GATGAGTCTG CATTTGTCAA CAGCAATTTG |
| 901 AACAACTCAC TGGTGCCTTC TGTTATGGGG AACAATGCAG TTGATCTCAC TGATGGGCTG |
| 961 ACAGATTTAG AACCCTACAT GAGGTTTCTT CTGGATGATG GTGCAAGTGA GTCAATTGAT |
| 1021 AACCTTCTGA ACCTTGATGG ATCTGAGGAT GTTATGAGCA ACATGGATCT CTGGAGCTTT |
| 1081 GATGACATGC CTGCCACTGG CGATTTCTAT TGA |
| SEQ ID NO: 10 PvSTR homolog 5 Pavirv00053297m |
| 1 ATGTGCGGGG CGCCATTCT CGCGGAACTC ATCCCGTCGC CGCGCCGGGC GGCGTCGAAG |
| 61 CCGGTGACCG CGGGCCACCT CTGGCCGGCG GGCTCCGACA CCAAGAAGGC CGGCAGCGGG |
| 121 AGGAGCAAGA GGCACCAGCT CGCCGACGTC GACGACTTTG AGGCCGCCTT CGAGGACTTC |
| 181 GCCGACGATT TTGACAAGGA GGAGGTCGAG GACCACCATT TCGTGTTCTC GTCCAAATCC |
| 241 GCATTCTCCC CAGCCCACGG CGTGCGCGCG GCGACCCAGA AGAGGCGCGG CCGCCGCCAC |
| 301 TTCCGCGGCA TCCGGCAGCG CCCCTGGGGC AAGTGGGCGG CGGAGATCCG CGACCCGCAC |
| 361 AAGGGCACCC GCGTCTGGCT CGGCACCTTC AACACCGCCG AGGACGCCGC CCGGGCCTAC |
| 421 GACGTCGAGG CACGCCGCCT CCGCGGCAGC AAGGCCAAGG TCAACTTCCC CGCGGCCGGC |
| 481 GCGCGCCCAC GCCGCGGCAA CGCGCCGAGA CCGCAGCGCC ACCATGCCGC AGCGCAGCCC |
| 541 GCGTTGCTTG CAGGAGAAA GCGGAAGGAG GAGGAGATCG TCGTGAAGCC TGAAATTGGG |
| 601 GCGTCGTTCG ACTTCGACGT GGGCAGCTTC TTCGACACGG CCTTCCCCGC GGCGCCGCCG |
| 661 GCCATGGAGA ACTCCTTCGC CGGCAGCACC GGGTCGGAGT CCGGTAGCCC CGCAAAGAAG |
| 721 ATGAGATACG ACAACGACTC GTCGTCCGAT GGGATGAGCT CCGGCGGCGG CTCCGCGCTG |
| 781 GAGCTCGCTG ACGAGCTCGC GTTCGATCCG TTCATGCTGC TCCAGATGCC CTACTCGGGC |

-continued

Sequences:

```
841  GGGTACGAGT CCCTCGACGG CCTGTTCGCC GTCGACGCCG CCCAGGACGT GAACAACGAC

901  ATGAACGGCG TCAGCCTGTG GAGCTTCGAC GAGTTCCCCG ACGACAGCGC TGTTTTCTAA
```

SEQ ID NO: 11 PvSTIF homolog 2 Pavirv00058988m
```
  1  AACGTGACGA GAAGCAGGCA CTACCGTGGC GTGCGGCGGC GGCCGTGGGG CAAGTGGGCG

61  GCGGAGATCC GTGACCCCGC CAAGGCGGCG CGCGTGTGGC TCGGCACCTT CGACACCGCG

121  GAGGCCGCCG CTGCAGCGTA CGACGACGCC GCGCTCCGGT TCAAGGGCGC CAAGGCCAAG

181  CTCAACTTCC CCGAGCGCGT CCGAGGCCGC ACCGGCCAGG GCGCGTTCCT CGTCAGCCCT

241  TGCGTCCCCC AGCAGCAGCC GCCGTCGCCG TCTTCCATGC CAACTGCAGC CGCGCCGTTC

301  CCCGGCCTGA TCCGGTATGC ACAGCTGCTC CAGGGTTGGA ACAGCGGGAG CATCGCGGCC

361  AGCAACACCG GTGACCTCGC GCCGCCGGCG GCCTTGCCAA TGCCGCCGGC ACAGGCGTCG

421  TCGTCGGTGC AGATTCTGGA CTTCTCGACG CAGCAGCTCC TCCGGGGCTC GCCGACAACG

481  TTCGGCGGCC CACCGCCGCC GACGTCGGCA TCGATGTCCA GGACTAGCAG AGTAGATGAG

541  GCGCACGAGA GTTGCAATGC TCCTGACTGA
```

SEQ ID NO: 12 PvSTIF homolog 3 Pavirv00031839m
```
  1  GGTCGGAGGC GGCACTACCG AGGGGTGCGG CAGCGGCCGT GGGGGAAGTG GGCGGCAGAG

61  ATCCGGGACC CCAAGAAGGC GGCGCGGGTG TGGCTGGGCA CCTTCGACAC GGCGGAGGAC

121  GCCGCCATCG CCTACGACGA GGCGGCGCTC CGGTTCAAGG GCACCAAGGC CAAGCTCAAC

181  TTCCCGGAGC GCGTCCAGGG CCGCACCGAC CTGGGCTTCC TCGTCACCCG CGGCGTCCCG

241  GACCGGCACC ACCACCAAGG CGCGGCGGCG GCGCAGGCGC AGCTCATGAT GCTGGCCCGC

301  GGCGGCGGCG GCGGCGTCAA CCTGCCGTTC GGAGCGCGCGT CGCCGTTCTC GCCCTCGCCC

361  TCGCCCTCGT CGGCGCCGCA GATCCTGGAC TTCTCCACGC AGCAGCTCAT CCGGCCCGAC

421  CCGCCGTCGC CGGCCGCCGC GATGTCGTCG TCGGGCGCTG CTCCGTCCAC GCCGTCGTCC

481  ACGACCACGG CGTCGTCGCC CGGTGGCGGT GCATGGCCGT ACGGTGGGGA GCACCACAGG

541  AATAAAAAAG ACGCGTGA
```

SEQ ID NO: 13 PvSTIF homolog 4 Pavirv00030284m
```
  1  ATGTGCCACG CCGCGGTGGC GGACTCGGGG GAGCAGCACG GCGGCGGCT TCTCGCCGCC

61  GGCGACGGCG GCGGAGGAGA CCGCCGCCAG CAGCAGCAGC AGCCCCAGCC GCTGGAGCCC

121  GTGGTGATGG AAGCCAACAC GGCGGCGTCG CCGGCGCTGT CGCGGGGCAG GCAGGCCCGG

181  GAGATGTCGG CCATGGTGGC CGCGCTGGCC AGGGTGGTCG CCGGCTCGGC GCCGCCGGCC

241  AAGGCGCCCC CCCAGGCCGT GCAGGATGCC TCCGCGGAGG AGGCGTGGTG GCCGTACGAC

301  GAGCTCGCCG CCGAGCCGTC CCCTGCTTTC GTGCTCGACG GCTACAGCGA GACGCAGCCG

361  CTGCCGGAGC ACTACTGGCC TTCGGCTGCG GCGGCGACAG AGGCGGCGAC TTCCTCGCAG

421  ACGCATTACC GTGCCGCCTC TGCTGCCGCG GCCGAGGAGG AGGTACCTTC GCCGTCGTCC

481  GCCTCCGCCG CCGCCGGGGC GAGCAGCAGC GGCAGCGCGG CGACGCGGAA GCGTTACCGC

541  GGCGTGCGGC AGCGTCCGTG GGGGAAGTGG GCGGCGGAGA TCCGTGACCC GCACAAGGCG

601  GCGCGCGTGT GGCTGGGCAC CTTCGACACC GCCGAGGCCG CCGCCCGGGC CTACGATGGC

661  GCCGCGCTTA GGTTCCGCGG CAGCCGCGCC AGGCTCAACT TCCCCGAGTC CGCCACGCTC

721  CCGTCCCCGC CGCCGCCGGA TCCGGCCTCG CGCGCATTGC CGCCGCCGCC GCCCAGGCCG

781  GACGCGCTTC TGGAGTCGCA GGCTCAGGCG CCCTCCACCG GCGGCGGCAT GGAGCAATAC

841  GCGGAGTACG CCAGGCTCTT GCAGAGCGCC GGCGGCGACC CCGGCGGCTC ATCCGGGACG
```

| | | | | | |
|---|---|---|---|---|---|
| 901 | CCAAGTGGCA | CGTTGCCTCC | CCCTCCTCCT | CCTGCAGCGT | ACAGCTTCGC | CGCCCAGGGC |
| 961 | GTGACACCGT | TCAGCTACCT | GTCGCCGCCG | CAGAGCCGCG | GCGAGCCAGC | AGGCAACCCC |
| 1021 | GCGGCGGCGT | GGGCGGCGAG | CCACTACCAC | GGCTCGTACC | CGCCGTGGCG | GTGGGACCAC |
| 1081 | TCAGGTTGA | | | | | |

SEQ ID NO: 14 PvBMY homolog 2 Pavirv00066236m
| | | | | | |
|---|---|---|---|---|---|
| 1 | ATGCCGGACT | CCGACAAAGA | GTCCGGCTGG | CCGAGCAACG | CGGAGTTCTC | GTCGCCGCGG |
| 61 | GAGCAGGACC | GGTTCCTGCC | GATCGCGAAC | GTCAGCCGGA | TCATGAAGAT | GGCGCTCCCG |
| 121 | GCGAACGCCA | AGATCTCCAA | GGACGCCAAG | GAGACGGTGC | AGGAGTGCGT | CTCCGAGTTC |
| 181 | ATCTCCTTCA | TCACCGGCGA | GGCCTCCGAC | AAGTGCCAGC | GCGAGAAGCG | CAAGACCATC |
| 241 | AACGGCGACG | ACCTCCTCTG | GGCCATGACC | ACGCTCGGCT | TCGAGGACTA | CATCGAGCCG |
| 301 | CTCAAGCTCT | ACCTCCACAA | GTTCCGCGAG | CTCGAGGGCG | AGAAGGTGGC | CTCCGGCGCC |
| 361 | GCGGGCTCCT | CCGGCTCCGG | CTCGCAGCCG | CAGAGGGAGA | CGACGCCGTC | CGCGCACAAT |
| 421 | GGCGCCGGCG | GGGCCGTCGG | CTACGGCATT | TACGGCGCCG | CGCGGGGC | AGGCGGAGGC |
| 481 | AGCGGCATGA | TCATGATGAT | GGGGCAGCCG | ATGTACAACT | CCCCACCGGG | CGCGTCAGGG |
| 541 | TACCCGCAGC | CCCCGCACCA | CCAGATGGTG | ATGGCCGCGA | AGGTGGCGC | CTACGGCCAC |
| 601 | GGCGGCGGCT | CGTCGCCGTC | GCCGCCGGGG | CTCGGCAGGC | AGGACAGGCT | TTGA |

SEQ ID NO: 15 PvBMY homolog 3 Pavirv00042310m
| | | | | | |
|---|---|---|---|---|---|
| 1 | ATGCCGGACT | CGGACAACGA | CTCCGGCGGC | CCGAGCAACG | CCGGCGGCGA | GCTGTCGTCG |
| 61 | CCGCGGGAGC | AGGACAGGTT | CCTCCCCATC | GCGAACGTGA | GCCGGATCAT | GAAGAAGGCG |
| 121 | CTCCCGGCGA | ACGCCAAGAT | CAGCAAGGAC | GCCAAGGAGA | CGGTGCAGGA | GTGCGTCTCC |
| 181 | GAGTTCATCT | CCTTCATCAC | CGGCGAGGCC | TCCGACAAGT | GCCAGCGCGA | GAAGCGCAAG |
| 241 | ACCATCAACG | GCGACGACCT | GCTCTGGGCC | ATGACCACGC | TCGGCTTCGA | GGACTACGTC |
| 301 | GAGCCGCTCA | AGCACTACCT | CCACAAGTTC | CGCGAGATCG | AGGGCGAGAG | GCGGCCGCC |
| 361 | TCCTCGGGCG | CCTCGGGCTC | CGCCGCCGCG | CAGCAGCAGG | GCGACGTGGC | GAGGGGCGCC |
| 421 | ACCAATGCCG | GCGGGTACGC | CGGGTACAGC | GCCGGCGGCA | TGATGATGAT | GGGGCAGCCG |
| 481 | ATGTACGGCT | CGCCGCAGCA | GCAGCACCAA | CAGCATCACA | TGGCAATGGG | AGGCAGAGGC |
| 541 | GGTTACGGCC | ATCAAGGAGG | CGGCGGCTCG | TCGTCGTCGT | CGGGGCTTGG | CCGGCAAGAC |
| 601 | AGGGCGTGA | | | | | |

SEQ ID NO: 16 PvBMY homolog 4 Pavirv00023203m
| | | | | | |
|---|---|---|---|---|---|
| 1 | ATGGCGGACG | CGCCAGCGAG | CCCCGGGGGC | GGCGGCGGGA | GCCACGAGAG | CGGGAGCCCC |
| 61 | AGGGGCGGCG | CCGGGGGCGG | GGGCGGCGGC | GTCAGGGAGC | AGGACAGGTT | CCTGCCCATC |
| 121 | GCCAACATCA | GCCGCATCAT | GAAGAAGGCC | ATCCCGGCCA | ACGGGAAGAT | CGCCAAGGAC |
| 181 | GCCAAGGAGA | CCGTGCAGGA | GTGCGTCTCC | GAGTTCATAT | CCTTCATCAC | CAGCGAGGCG |
| 241 | AGTGACAAGT | GCCAGAGGGA | GAAGAGGAAG | ACCATCAACG | GGACGACCT | ACTGTGGGCC |
| 301 | ATGCCACGT | TGGGGTTCGA | GGACTACATA | GAACCCCTCA | AGGTGTACCT | GCAGAAGTAC |
| 361 | AGAGAGATGG | AGGGTGATAG | CAAGTTAACT | GCAAAAACTG | GCGATGGCTC | TATTAAAAAG |
| 421 | GATGCCCTTG | GCCATGGGGG | AGCAAGTAGC | TCAGCCACAC | AAGGGATGGG | CCAACAAGGA |
| 481 | GCGTACAACC | AAGGAATGGG | TTATATGCAA | CCTCAGTACC | ATAACGGAGA | CATCTCAAAC |
| 541 | TAA | | | | | |

Sequences:

SEQ ID NO: 17 PvBMY homolog 5 Pavirv00061773m
```
   1 ATGGCGGACG ACGGCGGGAG CCACGAGGGC GGCGGCGGCG TCCGGGAGCA GGACCGGTTC
  61 CTGCCCATCG CCAACATCAG CCGCATCATG AAGAAGGCCG TCCCGGCTAA CGGCAAGATC
 121 GCCAAGGATG CCAAGGAGAC CCTGCAGGAG TGCGTCTCCG AGTTCATCTC CTTCGTCACC
 181 AGCGAGGCCA CGACAAGTG CCAGAAGGAA AAGCGCAAGA CCATCAACGG CGATGATCTG
 241 CTCTGGGCGA TGGCTACGCT CGGATTCGAG GAGTACGTCG AGCCCCTCAA GATGTACCTA
 301 CACAAGTACA GAGAGATGGA GGGTGATAGT AAGTTGTCTA CAAAGGCTGG TGAGGGCTCT
 361 GTAAAGAAGG ATGCAATTAG TCCCCATGGT GGCACCAGTA GCTCAAGTAA CCAGTTGGTT
 421 CAACATGGAG TTTACAACCA AGGGATGGGC TATATGCAAC CACAGTACCA TAATGGGGAT
 481 ACCTAA
```

SEQ ID NO: 18 PvBMY homolog 6 Pavirv00024249m
```
   1 ATGGCGGACG CGCCAGCGAG CCCCGGGGGC GGCGGCGGGA GCCACGAGAG TGGGAGCCCC
  61 AAGGGCGGCG GCGGGGGCGG AGGCGGCGGC GTCAGGGAGC AGGACAGGTT CCTGCCCATC
 121 GCCAACATCA GCCGCATCAT GAAGAAGGCC ATCCCGGCCA ACGGGAAGAT CGCCAAGGAC
 181 GCCAAGGAGA CCGTGCAGGA GTGCGTCTCC GAATTCATCT CCTTCATCAC CAGCGAGGCG
 241 AGTGACAAGT GCCAGAGGGA GAAGAGGAAG ACCATCAACG GGACGACCT ACTGTGGGCC
 301 ATGGCCACGC TGGGGTTCGA GGACTACATA GAACCCCTCA AGGTGTACCT GCAGAAGTAC
 361 AGAGAGGTCA CAAAACACTT ATAG
```

SEQ ID NO: 19 pMBXS809
```
   1 GTAAACCTAA GAGAAAAGAG CGTTTATTAG AATAACGGAT ATTTAAAAGG GCGTGAAAAG
  61 GTTTATCCGT TCGTCCATTT GTATGTGCAT GCCAACCACA GGGTTCCCCT CGGGATCAAA
 121 GTACTTTGAT CCAACCCCTC CGCTGCTATA GTGCAGTCGG CTTCTGACGT TCAGTGCAGC
 181 CGTCTTCTGA AAACGACATG TCGCACAAGT CCTAAGTTAC GCGACAGGCT GCCGCCCTGC
 241 CCTTTTCCTG GCGTTTTCTT GTCGCGTGTT TTAGTCGCAT AAAGTAGAAT ACTTGCGACT
 301 AGAACCGGAG ACATTACGCC ATGAACAAGA GCGCCGCCGC TGGCCTGCTG GGCTATGCCC
 361 GCGTCAGCAC CGACGACCAG GACTTGACCA ACCAACGGGC CGAACTGCAC GCGGCCGGCT
 421 GCACCAAGCT GTTTTCCGAG AAGATCACCG GCACCAGGCG CGACCGCCCG GAGCTGGCCA
 481 GGATGCTTGA CCACCTACGC CCTGGCGACG TTGTGACAGT GACCAGGCTA GACCGCCTGG
 541 CCCGCAGCAC CCGCGACCTA CTGGACATTG CCGAGCGCAT CCAGGAGGCC GGCGCGGGCC
 601 TGCGTAGCCT GGCAGAGCCG TGGGCCGACA CCACCACGCC GGCCGGCCGC ATGGTGTTGA
 661 CCGTGTTCGC CGGCATTGCC GAGTTCGAGC GTTCCCTAAT CATCGACCGC ACCCGGAGCG
 721 GGCGCGAGGC CGCCAAGGCC CGAGGCGTGA AGTTTGGCCC CCGCCCTACC CTCACCCCGG
 781 CACAGATCGC GCACGCCCGC GAGCTGATCG ACCAGGAAGG CCGCACCGTG AAAGAGGCGG
 841 CTGCACTGCT TGGCGTGCAT CGCTCGACCC TGTACCGCGC ACTTGAGCGC AGCGAGGAAG
 901 TGACGCCCAC CGAGGCCAGG CGGCGCGGTG CCTTCCGTGA GGACGCATTG ACCGAGGCCG
 961 ACGCCCTGGC GGCCGCCGAG AATGAACGCC AAGAGGAACA AGCATGAAAC CGCACCAGGA
1021 CGGCCAGGAC GAACCGTTTT TCATTACCGA AGAGATCGAG GCGGAGATGA TCGCGGCCGG
1081 GTACGTGTTC GAGCCGCCCG CGCACGTCTC AACCGTGCGG CTGCATGAAA TCCTGGCCGG
1141 TTTGTCTGAT GCCAAGCTGG CGGCCTGGCC GGCCAGCTTG GCCGCTGAAG AAACCGAGCG
1201 CCGCCGTCTA AAAAGGTGAT GTGTATTTGA GTAAAACAGC TTGCGTCATG CGGTCGCTGC
```

-continued

Sequences:

```
1261  GTATATGATG CGATGAGTAA ATAAACAAAT ACGCAAGGGG AACGCATGAA GGTTATCGCT
1321  GTACTTAACC AGAAAGGCGG GTCAGGCAAG ACGACCATCG CAACCCATCT AGCCCGCGCC
1381  CTGCAACTCG CCGGGGCCGA TGTTCTGTTA GTCGATTCCG ATCCCCAGGG CAGTGCCCGC
1441  GATTGGGCGG CCGTGCGGGA AGATCAACCG CTAACCGTTG TCGGCATCGA CCGCCCGACG
1501  ATTGACCGCG ACGTGAAGGC CATCGGCCGG CGCGACTTCG TAGTGATCGA CGGAGCGCCC
1561  CAGGCGGCGG ACTTGGCTGT GTCCGCGATC AAGGCAGCCG ACTTCGTGCT GATTCCGGTG
1621  CAGCCAAGCC CTTACGACAT ATGGGCCACC GCCGACCTGG TGGAGCTGGT TAAGCAGCGC
1681  ATTGAGGTCA CGGATGGAAG GCTACAAGCG GCCTTTGTCG TGTCGCGGGC GATCAAAGGC
1741  ACGCGCATCG GCGGTGAGGT TGCCGAGGCG CTGGCCGGGT ACGAGCTGCC CATTCTTGAG
1801  TCCCGTATCA CGCAGCGCGT GAGCTACCCA GGCACTGCCG CCGCCGGCAC AACCGTTCTT
1861  GAATCAGAAC CCGAGGGCGA CGCTGCCCGC GAGGTCCAGG CGCTGGCCGC TGAAATTAAA
1921  TCAAAACTCA TTTGAGTTAA TGAGGTAAAG AGAAATGAG CAAAAGCACA ACACGCTAA
1981  GTGCCGGCCG TCCGAGCGCA CGCAGCAGCA AGGCTGCAAC GTTGCCAGC CTGGCAGACA
2041  CGCCAGCCAT GAAGCGGGTC AACTTTCAGT TGCCGGCGGA GGATCACACC AAGCTGAAGA
2101  TGTACGCGGT ACGCAAGGC AAGACCATTA CCGAGCTGCT ATCTGAATAC ATCGCGCAGC
2161  TACCAGAGTA AATGAGCAAA TGAATAAATG AGTAGATGAA TTTTAGCGGC TAAAGGAGGC
2221  GGCATGGAAA ATCAAGAACA ACCAGGCACC GACGCCGTGG AATGCCCCAT GTGTGGAGGA
2281  ACGGGCGGTT GGCCAGGCGT AAGCGGCTGG GTTGTCTGCC GGCCCTGCAA TGGCACTGGA
2341  ACCCCCAAGC CCGAGGAATC GGCGTGACGG TCGCAAACCA TCCGGCCCGG TACAAATCGG
2401  CGCGGCGCTG GGTGATGACC TGGTGGAGAA GTTGAAGGCC GCGCAGGCCG CCCAGCGGCA
2461  ACGCATCGAG GCAGAAGCAC GCCCCGGTGA ATCGTGGCAA GCGGCCGCTG ATCGAATCCG
2521  CAAAGAATCC CGGCAACCGC CGGCAGCCGG TGCGCCGTCG ATTAGGAAGC CGCCCAAGGG
2581  CGACGAGCAA CCAGATTTTT TCGTTCCGAT GCTCTATGAC GTGGGCACCC GCGATAGTCG
2641  CAGCATCATG GACGTGGCCG TTTTCCGTCT GTCGAAGCGT GACCGACGAG CTGGCGAGGT
2701  GATCCGCTAC GAGCTTCCAG ACGGGCACGT AGAGGTTTCC GCAGGGCCGC CCGGCATGGC
2761  CAGTGTGTGG GATTACGACC TGGTACTGAT GGCGGTTTCC CATCTAACCG AATCCATGAA
2821  CCGATACCGG GAAGGGAAGG GAGACAAGCC CGGCCGCGTG TTCCGTCCAC ACGTTGCGGA
2881  CGTACTCAAG TTCTGCCGGC GAGCCGATGG CGGAAAGCAG AAAGACGACC TGGTAGAAAC
2941  CTGCATTCGG TTAAACACCA CGCACGTTGC CATGCAGCGT ACGAAGAAGG CCAAGAACGG
3001  CCGCCTGGTG ACGGTATCCG AGGGTGAAGC CTTGATTAGC CGCTACAAGA TCGTAAAGAG
3061  CGAAACCGGG CGGCCGGAGT ACATCGAGAT CGAGCTAGCT GATTGGATGT ACCGCGAGAT
3121  CACAGAAGGC AAGAACCCGG ACGTGCTGAC GGTTCACCCC GATTACTTTT TGATCGATCC
3181  CGGCATCGGC CGTTTTCTCT ACCGCCTGGC ACGCCGCGCC GCAGGCAAGG CAGAAGCCAG
3241  ATGGTTGTTC AAGACGATCT ACGAACGCAG TGGCAGCGCC GGAGAGTTCA AGAAGTTCTG
3301  TTTCACCGTG CGCAAGCTGA TCGGGTCAAA TGACCTGCCG GAGTACGATT TGAAGGAGGA
3361  GGCGGGGCAG CTGGCCCGA TCCTAGTCAT GCGCTACCGC AACCTGATCG AGGGCGAAGC
3421  ATCCGCCGGT TCCTAATGTA CGGAGCAGAT GCTAGGGCAA ATTGCCCTAG CAGGGGAAAA
3481  AGGTCGAAAA GGTCTCTTTC CTGTGGATAG CACGTACATT GGGAACCCAA AGCCGTACAT
```

-continued

| | Sequences: |
|---|---|
| 3541 | TGGGAACCGG AACCCGTACA TTGGGAACCC AAAGCCGTAC ATTGGGAACC GGTCACACAT |
| 3601 | GTAAGTGACT GATATAAAAG AGAAAAAAGG CGATTTTTCC GCCTAAAACT CTTTAAAACT |
| 3661 | TATTAAAACT CTTAAAACCC GCCTGGCCTG TGCATAACTG TCTGGCCAGC GCACAGCCGA |
| 3721 | AGAGCTGCAA AAAGCGCCTA CCCTTCGGTC GCTGCGCTCC CTACGCCCCG CCGCTTCGCG |
| 3781 | TCGGCCTATC GCGGCCGCTG GCCGCTCAAA AATGGCTGGC CTACGGCCAG GCAATCTACC |
| 3841 | AGGGCGCGGA CAAGCCGCGC CGTCGCCACT CGACCGCCGG CGCCCACATC AAGGCACCCT |
| 3901 | GCCTCGCGCG TTTCGGTGAT GACGGTGAAA ACCTCTGACA CATGCAGCTC CCGGAGACGG |
| 3961 | TCACAGCTTG TCTGTAAGCG GATGCCGGGA GCAGACAAGC CCGTCAGGGC GCGTCAGCGG |
| 4021 | GTGTTGGCGG GTGTCGGGGC GCAGCCATGA CCCAGTCACG TAGCGATAGC GGAGTGTATA |
| 4081 | CTGGCTTAAC TATGCGGCAT CAGAGCAGAT TGTACTGAGA GTGCACCATA TGCGGTGTGA |
| 4141 | AATACCGCAC AGATGCGTAA GGAGAAAATA CCGCATCAGG CGCTCTTCCG CTTCCTCGCT |
| 4201 | CACTGACTCG CTGCGCTCGG TCGTTCGGCT GCGGCGAGCG GTATCAGCTC ACTCAAAGGC |
| 4261 | GGTAATACGG TTATCCACAG AATCAGGGGA TAACGCAGGA AAGAACATGT GAGCAAAAGG |
| 4321 | CCAGCAAAAG GCCAGGAACC GTAAAAAGGC CGCGTTGCTG GCGTTTTTCC ATAGGCTCCG |
| 4381 | CCCCCCTGAC GAGCATCACA AAAATCGACG CTCAAGTCAG AGGTGGCGAA ACCCGACAGG |
| 4441 | ACTATAAAGA TACCAGGCGT TTCCCCCTGG AAGCTCCCTC GTGCGCTCTC CTGTTCCGAC |
| 4501 | CCTGCCGCTT ACCGGATACC TGTCCGCCTT TCTCCCTTCG GGAAGCGTGG CGCTTTCTCA |
| 4561 | TAGCTCACGC TGTAGGTATC TCAGTTCGGT GTAGGTCGTT CGCTCCAAGC TGGGCTGTGT |
| 4621 | GCACGAACCC CCCGTTCAGC CCGACCGCTG CGCCTTATCC GGTAACTATC GTCTTGAGTC |
| 4681 | CAACCCGGTA AGACACGACT TATCGCCACT GGCAGCAGCC ACTGGTAACA GGATTAGCAG |
| 4741 | AGCGAGGTAT GTAGGCGGTG CTACAGAGTT CTTGAAGTGG TGGCCTAACT ACGGCTACAC |
| 4801 | TAGAAGGACA GTATTTGGTA TCTGCGCTCT GCTGAAGCCA GTTACCTTCG GAAAAAGAGT |
| 4861 | TGGTAGCTCT TGATCCGGCA ACAAACCAC CGCTGGTAGC GGTGGTTTTT TTGTTTGCAA |
| 4921 | GCAGCAGATT ACGCGCAGAA AAAAAGGATC TCAAGAAGAT CCTTTGATCT TTTCTACGGG |
| 4981 | GTCTGACGCT CAGTGGAACG AAAACTCACG TTAAGGGATT TTGGTCATGC ATTCTAGGTA |
| 5041 | CTAAAACAAT TCATCCAGTA AAATATAATA TTTTATTTTC TCCCAATCAG GCTTGATCCC |
| 5101 | CAGTAAGTCA AAAAATAGCT CGACATACTG TTCTTCCCCG ATATCCTCCC TGATCGACCG |
| 5161 | GACGCAGAAG GCAATGTCAT ACCACTTGTC CGCCCTGCCG CTTCTCCCAA GATCAATAAA |
| 5221 | GCCACTTACT TTGCCATCTT TCACAAAGAT GTTGCTGTCT CCCAGGTCGC CGTGGGAAAA |
| 5281 | GACAAGTTCC TCTTCGGGCT TTTCCGTCTT TAAAAAATCA TACAGCTCGC GCGGATCTTT |
| 5341 | AAATGGAGTG TCTTCTTCCC AGTTTTCGCA ATCCACATCG GCCAGATCGT TATTCAGTAA |
| 5401 | GTAATCCAAT TCGGCTAAGC GGCTGTCTAA GCTATTCGTA TAGGGACAAT CCGATATGTC |
| 5461 | GATGGAGTGA AAGAGCCTGA TGCACTCCGC ATACAGCTCG ATAATCTTTT CAGGGCTTTG |
| 5521 | TTCATCTTCA TACTCTTCCG AGCAAAGGAC GCCATCGGCC TCACTCATGA GCAGATTGCT |
| 5581 | CCAGCCATCA TGCCGTTCAA AGTGCAGGAC CTTTGGAACA GGCAGCTTTC CTTCCAGCCA |
| 5641 | TAGCATCATG TCCTTTTCCC GTTCCACATC ATAGGTGGTC CCTTTATACC GGCTGTCCGT |
| 5701 | CATTTTTAAA TATAGGTTTT CATTTTCTCC CACCAGCTTA TATACCTTAG CAGGAGACAT |
| 5761 | TCCTTCCGTA TCTTTTACGC AGCGGTATTT TTCGATCAGT TTTTTCAATT CCGGTGATAT |
| 5821 | TCTCATTTTA GCCATTTATT ATTTCCTTCC TCTTTTCTAC AGTATTTAAA GATACCCCAA |

-continued

Sequences:

```
5881  GAAGCTAATT ATAACAAGAC GAACTCCAAT TCACTGTTCC TTGCATTCTA AAACCTTAAA

5941  TACCAGAAAA CAGCTTTTTC AAAGTTGTTT TCAAAGTTGG CGTATAACAT AGTATCGACG

6001  GAGCCGATTT TGAAACCGCG GTGATCACAG GCAGCAACGC TCTGTCATCG TTACAATCAA

6061  CATGCTACCC TCCGCGAGAT CATCCGTGTT TCAAACCCGG CAGCTTAGTT GCCGTTCTTC

6121  CGAATAGCAT CGGTAACATG AGCAAAGTCT GCCGCCTTAC AACGGCTCTC CCGCTGACGC

6181  CGTCCCGGAC TGATGGGCTG CCTGTATCGA GTGGTGATTT TGTGCCGAGC TGCCGGTCGG

6241  GGAGCTGTTG GCTGGCTGGT GGCAGGATAT ATTGTGGTGT AAACAAATTG ACGCTTAGAC

6301  AACTTAATAA CACATTGCGG ACGTTTTTAA TGTACTGAAT TAACGCCGAA TTAATTCGGG

6361  GGATCTGGAT TTTAGTACTG GATTTTGGTT TTAGGAATTA GAAATTTTAT TGATAGAAGT

6421  ATTTTACAAA TACAAATACA TACTAAGGGT TTCTTATATG CTCAACACAT GAGCGAAACC

6481  CTATAGGAAC CCTAATTCCC TTATCTGGGA ACTACTCACA CATTATTATG GAGAAACTCG

6541  AGTCAAATCT CGGTGACGGG CAGGACCGGA CGGGGCGGTA CCGGCAGGCT GAAGTCCAGC

6601  TGCCAGAAAC CCACGTCATG CCAGTTCCCG TGCTTGAAGC CGGCCGCCCG CAGCATGCCG

6661  CGGGGGGCAT ATCCGAGCGC CTCGTGCATG CGCACGCTCG GGTCGTTGGG CAGCCCGATG

6721  ACAGCGACCA CGCTCTTGAA GCCCTGTGCC TCCAGGGACT TCAGCAGGTG GGTGTAGAGC

6781  GTGGAGCCCA GTCCCGTCCG CTGGTGGCGG GGGGAGACGT ACACGGTCGA CTCGGCCGTC

6841  CAGTCGTAGG CGTTGCGTGC CTTCCAGGGG CCCGCGTAGG CGATGCCGGC GACCTCGCCG

6901  TCCACCTCGG CGACGAGCCA GGGATAGCGC TCCCGCAGAC GGACGAGGTC GTCCGTCCAC

6961  TCCTGCGGTT CCTGCGGCTC GGTACGGAAG TTGACCGTGC TTGTCTCGAT GTAGTGGTTG

7021  ACGATGGTGC AGACCGCCGG CATGTCCGCC TCGGTGGCAC GGCGGATGTC GGCCGGGCGT

7081  CGTTCTGGGC TCATGGTAGA CCGCTTGGTA TCTGCATTAC AATGAAATGA GCAAAGACTA

7141  TGTGAGTAAC ACTGGTCAAC ACTAGGGAGA AGGCATCGAG CAAGATACGT ATGTAAAGAG

7201  AAGCAATATA GTGTCAGTTG GTAGATACTA GATACCATCA GGAGGTAAGG AGAGCAACAA

7261  AAAGGAAACT CTTTATTTTT AAATTTTGTT ACAACAAACA AGCAGATCAA TGCATCAAAA

7321  TACTGTCAGT ACTTATTTCT TCAGACAACA ATATTTAAAA CAAGTGCATC TGATCTTGAC

7381  TTATGGTCAC AATAAAGGAG CAGAGATAAA CATCAAAATT TCGTCATTTA TATTTATTCC

7441  TTCAGGCGTT AACAATTTAA CAGCACACAA ACAAAAACAG AATAGGAATA TCTAATTTTG

7501  GCAAATAATA AGCTCTGCAG ACGAACAAAT TATTATAGTA TCGCCTATAA TATGAATCCC

7561  TATACTATTG ACCCATGTAG TATGAAGCCT GTGCCTAAAT TAACAGCAAA CTTCTGAATC

7621  CAAGTGCCCT ATAACACCAA CATGTGCTTA ATAAATACC GCTAAGCACC AAATTACACA

7681  TTTCTCGTAT TGCTGTGTAG GTTCTATCTT CGTTTCGTAC TACCATGTCC CTATATTTTG

7741  CTGCTACAAA GGACGGCAAG TAATCAGCAC AGGCAGAACA CGATTTCAGA GTGTAATTCT

7801  AGATCCAGCT AAACCACTCT CAGCAATCAC CACACAAGAG AGCATTCAGA GAAACGTGGC

7861  AGTAACAAAG GCAGAGGGCG GAGTGAGCGC GTACCGAAGA CGGTCTCGAG AGAGATAGAT

7921  TTGTAGAGAG AGACTGGTGA TTTCAGCGTG TCCTCTCCAA ATGAAATGAA CTTCCTTATA

7981  TAGAGGAAGG TCTTGCGAAG GATAGTGGGA TTGTGCGTCA TCCCTTACGT CAGTGGAGAT

8041  ATCACATCAA TCCACTTGCT TTGAAGACGT GGTTGGAACG TCTTCTTTTT CCACGATGCT

8101  CCTCGTGGGT GGGGGTCCAT CTTTGGGACC ACTGTCGGCA GAGGCATCTT GAACGATAGC
```

-continued

| | Sequences: |
|---|---|
| 8161 | CTTTCCTTTA TCGCAATGAT GGCATTTGTA GGTGCCACCT TCCTTTTCTA CTGTCCTTTT |
| 8221 | GATGAAGTGA CAGATAGCTG GGCAATGGAA TCCGAGGAGG TTTCCCGATA TTACCCTTTG |
| 8281 | TTGAAAAGTC TCAATAGCCC TTTGGTCTTC TGAGACTGTA TCTTTGATAT TCTTGGAGTA |
| 8341 | GACGAGAGTG TCGTGCTCCA CCATGTTATC ACATCAATCC ACTTGCTTTG AAGACGTGGT |
| 8401 | TGGAACGTCT TCTTTTTCCA CGATGCTCCT CGTGGGTGGG GGTCCATCTT TGGGACCACT |
| 8461 | GTCGGCAGAG GCATCTTGAA CGATAGCCTT TCCTTTATCG CAATGATGGC ATTTGTAGGT |
| 8521 | GCCACCTTCC TTTTCTACTG TCCTTTTGAT GAAGTGACAG ATAGCTGGGC AATGGAATCC |
| 8581 | GAGGAGGTTT CCCGATATTA CCCTTTGTTG AAAAGTCTCA ATAGCCCTTT GGTCTTCTGA |
| 8641 | GACTGTATCT TTGATATTCT TGGAGTAGAC GAGAGTGTCG TGCTCCACCA TGTTGGCAAG |
| 8701 | CTGCTCTAGC CAATACGCAA ACCGCCTCTC CCCGCGCGTT GGCCGATTCA TTAATGCAGC |
| 8761 | TGGCACGACA GGTTTCCCGA CTGGAAAGCG GGCAGTGAGC GCAACGCAAT TAATGTGAGT |
| 8821 | TAGCTCACTC ATTAGGCACC CCAGGCTTTA CACTTTATGC TTCCGGCTCG TATGTTGTGT |
| 8881 | GGAATTGTGA GCGGATAACA ATTTCACACA GGAAACAGCT ATGACCATGA TTACGAATTG |
| 8941 | GGGTTTAAAC CACGGAAGAT CCAGGTCTCG AGACTAGGAG ACGGATGGGA GGCGCAACGC |
| 9001 | GCGATGGGGA GGGGGCGGC GCTGACCTTT CTGGCGAGGT CGAGGTAGCG ATCGAGCAGC |
| 9061 | TGCAGCGCGG ACACGATGAG GAAGACGAAG ATAGCCGCCA TGGACATGTT CGCCAGCGGC |
| 9121 | GGCGGAGCGA GGCTGAGCCG GTCTCTCCGG CCTCCGGTCG GCGTTAAGTT GGGGATCGTA |
| 9181 | ACGTGACGTG TCTCGTCTCC ACGGATCGAC ACAACCGGCC TACTCGGGTG CACGACGCCG |
| 9241 | CGATAAGGGC GAGATGTCCG TGCACGCAGC CCGTTTGGAG TCCTCGTTGC CCACGAACCG |
| 9301 | ACCCCTTACA GAACAAGGCC TAGCCCAAAA CTATTCTGAG TTGAGCTTTT GAGCCTAGCC |
| 9361 | CACCTAAGCC GAGCGTCATG AACTGATGAA CCCACTACCA CTAGTCAAGG CAAACCACAA |
| 9421 | CCACAAATGG ATCAATTGAT CTAGAACAAT CCGAAGGAGG GGAGGCCACG TCACACTCAC |
| 9481 | ACCAACCGAA ATATCTGCCA GAATCAGATC AACCGGCCAA TAGGACGCCA GCGAGCCCAA |
| 9541 | CACCTGGCGA CGCCGCAAAA TTCACCGCGA GGGGCACCGG GCACGGCAAA AACAAAAGCC |
| 9601 | CGGCGCGGTG AGAATATCTG GCGACTGGCG GAGACCTGGT GGCCAGCGCG CGGCCACATC |
| 9661 | AGCCACCCCA TCCGCCCACC TCACCTCCGG CGAGCCAATG GCAACTCGTC TTAAGATTCC |
| 9721 | ACGAGATAAG GACCCGATCG CCGGCGACGC TATTTAGCCA GGTGCGCCCC CCACGGTACA |
| 9781 | CTCCACCAGC GGCATCTATA GCAACCGGTC CAGCACTTTC ACGCTCAGCT TCAGCAAGAT |
| 9841 | CTACCGTCTT CGGTACGCGC TCACTCCGCC CTCTGCCTTT GTTACTGCCA CGTTTCTCTG |
| 9901 | AATGCTCTCT TGTGTGGTGA TTGCTGAGAG TGGTTTAGCT GGATCTAGAA TTACACTCTG |
| 9961 | AAATCGTGTT CTGCCTGTGC TGATTACTTG CCGTCCTTTG TAGCAGCAAA ATATAGGGAC |
| 10021 | ATGGTAGTAC GAAACGAAGA TAGAACCTAC ACAGCAATAC GAGAAATGTG TAATTTGGTG |
| 10081 | CTTAGCGGTA TTTATTTAAG CACATGTTGG TGTTATAGGG CACTTGGATT CAGAAGTTTG |
| 10141 | CTGTTAATTT AGGCACAGGC TTCATACTAC ATGGGTCAAT AGTATAGGGA TTCATATTAT |
| 10201 | AGGCGATACT ATAATAATTT GTTCGTCTGC AGAGCTTATT ATTTGCCAAA ATTAGATATT |
| 10261 | CCTATTCTGT TTTTGTTTGT GTGCTGTTAA ATTGTTAACG CCTGAAGGAA TAAATATAAA |
| 10321 | TGACGAAATT TTGATGTTTA TCTCTGCTCC TTTATTGTGA CCATAAGTCA AGATCAGATG |
| 10381 | CACTTGTTTT AAATATTGTT GTCTGAAGAA ATAAGTACTG ACAGTATTTT GATGCATTGA |
| 10441 | TCTGCTTGTT TGTTGTAACA AAATTTAAAA ATAAAGAGTT TCCTTTTTGT TGCTCTCCTT |

| Sequences: |
|---|

```
10501  ACCTCCTGAT GGTATCTAGT ATCTACCAAC TGATACTATA TTGCTTCTCT TTACATACGT

10561  ATCTTGCTCG ATGCCTTCTC CTAGTGTTGA CCAGTGTTAC TCACATAGTC TTTGCTCATT

10621  TCATTGTAAT GCAGATACCA AGCGGTTAAT TAAATGTGCG GCGGGGCCAT TCTCAGTGAT

10681  CTCTACTCAC CAGTGAGGCG GACGGTCACT GCCGGTGACC TATGGGGAGA GAGTGGCAGC

10741  AGCAAGAATG TGAAGAACTG GAAAAGGAGT TCTTGGAAGT TTGATGAAGG CGATGAAGAC

10801  TTTGAAGCTG ATTTCAAGGA TTTTGAGGAT TGCAGTAGCG AGGAGGAGGT AGATTTTGGA

10861  CATGAGGAAA AAGAATTCCA ATTGAACAGT TCGAATTTCG TGGAATTCAA TGGCCATACT

10921  GCCAAAGTCA CCAGCAGGAA GCGAAAGATC CAGTACCGAG GGATCCGGCG GCGGCCTTGG

10981  GGCAAATGGG CAGCAGAAAT CAGAGACCCA CAGAAGGGCG TCCGAGTTTG GCTTGGCACG

11041  TTCAGCACTG CCGAGGAAGC TGCAAGGGCA TATGACGTGG AAGCTCTACG CATACGTGGC

11101  AAGAAAGCCA AGATGAATTT CCCTACCACC ATCACAGCTG CTGGGAAACA CCACCGGCAG

11161  CGTGTGGCTC GACCGGCAAA GAAGACGTCA CAAGAGAGCC TGAAGTCAAG CAATGCCTCT

11221  GGTCATGTCA TCTCAGCAGG CAGCAGTACT GATGGCACCG TTGTCAAGAT CGAGTTGTCA

11281  CAGTCACCAG CTTCTCCACT ACCAGTGTCC AGCGCATGGC TTGATGCTTT TGAGCTGAAG

11341  CAGCTTGGTG GAGAAACCCC TGAAGCTGAT GGGAGAGAAA CCCCTGAAGA AACTGATCAT

11401  GAAACGGGAG TGACAGCGGA TATGTTTTTT GGCAATGGCG AAGTGCGGCT TTCAGATGAT

11461  TTTGCGTCTT ACGAGCCTTA CCCAAATTTT ATGCAGTTAC CTTATCTAGA AGGTGACTCG

11521  TATGAAAACA TTGACACTCT TTTCAACGGT GAAGCTGCTC AGGATGGAGT GAACATCGGA

11581  GGTCTTTGGA ATTTCGATGA TGTGCCAATG GACCGTGGTG TTTACTGAGG CGCGCCATCG

11641  TTCAAACATT TGGCAATAAA GTTTCTTAAG ATTGAATCCT GTTGCCGGTC TTGCGATGAT

11701  TATCATATAA TTTCTGTTGA ATTACGTTAA GCATGTAATA ATTAACATGT AATGCATGAC

11761  GTTATTTATG AGATGGGTTT TTATGATTAG AGTCCCGCAA TTATACATTT AATACGCGAT

11821  AGAAAACAAA ATATAGCGCG CAAACTAGGA TAAATTATCG CGCGCGGTGT CATCTATGTT

11881  ACTAGATCCG ATGATAAGCT GTCAAACATG ACCTCAGGAT GAAGCTTGGC ACTGGCCGTC

11941  GTTTTACAAC GTCGTGACTG GGAAAACCCT GGCGTTACCC AACTTAATCG CCTTGCAGCA

12001  CATCCCCCTT TCGCCAGCTG GCGTAATAGC GAAGAGGCCC GCACCGATCG CCCTTCCCAA

12061  CAGTTGCGCA GCCTGAATGG CGAATGCTAG AGCAGCTTGA GCTTGGATCA GATTGTCGTT

12121  TCCCGCCTTC AGTTTAAACT ATCAGTGTTT GACAGGATAT ATTGGCGG
```

SEQ ID NO: 20 pMBXS810

```
   1  GTAAACCTAA GAGAAAAGAG CGTTTATTAG AATAACGGAT ATTTAAAAGG GCGTGAAAAG

61  GTTTATCCGT TCGTCCATTT GTATGTGCAT GCCAACCACA GGGTTCCCCT CGGGATCAAA

121  GTACTTTGAT CCAACCCCTC CGCTGCTATA GTGCAGTCGG CTTCTGACGT TCAGTGCAGC

181  CGTCTTCTGA AAACGACATG TCGCACAAGT CCTAAGTTAC GCGACAGGCT GCCGCCCTGC

241  CCTTTTCCTG GCGTTTTCTT GTCGCGTGTT TTAGTCGCAT AAAGTAGAAT ACTTGCGACT

301  AGAACCGGAG ACATTACGCC ATGAACAAGA GCGCCGCCGC TGGCCTGCTG GGCTATGCCC

361  GCGTCAGCAC CGACGACCAG GACTTGACCA ACCAACGGGC CGAACTGCAC GCGGCCGGCT

421  GCACCAAGCT GTTTTCCGAG AAGATCACCG GCACCAGGCG CGACCGCCCG GAGCTGGCCA

481  GGATGCTTGA CCACCTACGC CCTGGCGACG TTGTGACAGT GACCAGGCTA GACCGCCTGG

541  CCCGCAGCAC CCGCGACCTA CTGGACATTG CCGAGCGCAT CCAGGAGGCC GGCGCGGGCC
```

-continued

| | Sequences: |
|---|---|
| 601 | TGCGTAGCCT GGCAGAGCCG TGGGCCGACA CCACCACGCC GGCCGGCCGC ATGGTGTTGA |
| 661 | CCGTGTTCGC CGGCATTGCC GAGTTCGAGC GTTCCCTAAT CATCGACCGC ACCCGGAGCG |
| 721 | GGCGCGAGGC CGCCAAGGCC CGAGGCGTGA AGTTTGGCCC CCGCCCTACC CTCACCCCGG |
| 781 | CACAGATCGC GCACGCCCGC GAGCTGATCG ACCAGGAAGG CCGCACCGTG AAAGAGGCGG |
| 841 | CTGCACTGCT TGGCGTGCAT CGCTCGACCC TGTACCGCGC ACTTGAGCGC AGCGAGGAAG |
| 901 | TGACGCCCAC CGAGGCCAGG CGGCGCGGTG CCTTCCGTGA GGACGCATTG ACCGAGGCCG |
| 961 | ACGCCCTGGC GGCCGCCGAG AATGAACGCC AAGAGGAACA AGCATGAAAC CGCACCAGGA |
| 1021 | CGGCCAGGAC GAACCGTTTT TCATTACCGA AGAGATCGAG GCGGAGATGA TCGCGGCCGG |
| 1081 | GTACGTGTTC GAGCCGCCCG CGCACGTCTC AACCGTGCGG CTGCATGAAA TCCTGGCCGG |
| 1141 | TTTGTCTGAT GCCAAGCTGG CGGCCTGGCC GGCCAGCTTG GCCGCTGAAG AAACCGAGCG |
| 1201 | CCGCCGTCTA AAAGGTGAT GTGTATTTGA GTAAACAGC TTGCGTCATG CGGTCGCTGC |
| 1261 | GTATATGATG CGATGAGTAA ATAAACAAAT ACGCAAGGGG AACGCATGAA GGTTATCGCT |
| 1321 | GTACTTAACC AGAAAGGCGG GTCAGGCAAG ACGACCATCG CAACCCATCT AGCCCGCGCC |
| 1381 | CTGCAACTCG CCGGGGCCGA TGTTCTGTTA GTCGATTCCG ATCCCCAGGG CAGTGCCCGC |
| 1441 | GATTGGGCGG CCGTGCGGGA AGATCAACCG CTAACCGTTG TCGGCATCGA CCGCCCGACG |
| 1501 | ATTGACCGCG ACGTGAAGGC CATCGGCCGG CGCGACTTCG TAGTGATCGA CGGAGCGCCC |
| 1561 | CAGGCGGCGG ACTTGGCTGT GTCCGCGATC AAGGCAGCCG ACTTCGTGCT GATTCCGGTG |
| 1621 | CAGCCAAGCC CTTACGACAT ATGGGCCACC GCCGACCTGG TGGAGCTGGT TAAGCAGCGC |
| 1681 | ATTGAGGTCA CGGATGGAAG GCTACAAGCG GCCTTTGTCG TGTCGCGGGC GATCAAAGGC |
| 1741 | ACGCGCATCG GCGGTGAGGT TGCCGAGGCG CTGGCCGGGT ACGAGCTGCC CATTCTTGAG |
| 1801 | TCCCGTATCA CGCAGCGCGT GAGCTACCCA GGCACTGCCG CCGCCGGCAC AACCGTTCTT |
| 1861 | GAATCAGAAC CCGAGGGCGA CGCTGCCCGC GAGGTCCAGG CGCTGGCCGC TGAAATTAAA |
| 1921 | TCAAAACTCA TTTGAGTTAA TGAGGTAAAG AGAAAATGAG CAAAAGCACA AACACGCTAA |
| 1981 | GTGCCGGCCG TCCGAGCGCA CGCAGCAGCA AGGCTGCAAC GTTGGCCAGC CTGGCAGACA |
| 2041 | CGCCAGCCAT GAAGCGGGTC AACTTTCAGT TGCCGGCGGA GGATCACACC AAGCTGAAGA |
| 2101 | TGTACGCGGT ACGCCAAGGC AAGACCATTA CCGAGCTGCT ATCTGAATAC ATCGCGCAGC |
| 2161 | TACCAGAGTA AATGAGCAAA TGAATAAATG AGTAGATGAA TTTTAGCGGC TAAAGGAGGC |
| 2221 | GGCATGGAAA ATCAAGAACA ACCAGGCACC GACGCCGTGG AATGCCCCAT GTGTGGAGGA |
| 2281 | ACGGGCGGTT GGCCAGGCGT AAGCGGCTGG GTTGTCTGCC GGCCCTGCAA TGGCACTGGA |
| 2341 | ACCCCCAAGC CCGAGGAATC GGCGTGACGG TCGCAAACCA TCCGGCCCGG TACAAATCGG |
| 2401 | CGCGGCGCTG GGTGATGACC TGGTGGAGAA GTTGAAGGCC GCGCAGGCCG CCCAGCGGCA |
| 2461 | ACGCATCGAG GCAGAAGCAC GCCCCGGTGA ATCGTGGCAA GCGGCCGCTG ATCGAATCCG |
| 2521 | CAAAGAATCC CGGCAACCGC CGGCAGCCGG TGCGCCGTCG ATTAGGAAGC CGCCCAAGGG |
| 2581 | CGACGAGCAA CCAGATTTTT TCGTTCCGAT GCTCTATGAC GTGGGCACCC GCGATAGTCG |
| 2641 | CAGCATCATG GACGTGGCCG TTTTCCGTCT GTCGAAGCGT GACCGACGAG CTGGCGAGGT |
| 2701 | GATCCGCTAC GAGCTTCCAG ACGGGCACGT AGAGGTTTCC GCAGGGCCGG CCGGCATGGC |
| 2761 | CAGTGTGTGG GATTACGACC TGGTACTGAT GGCGGTTTCC CATCTAACCG AATCCATGAA |
| 2821 | CCGATACCGG GAAGGGAAGG GAGACAAGCC CGGCCGCGTG TTCCGTCCAC ACGTTGCGGA |

| | |
|---|---|
| 2881 | CGTACTCAAG TTCTGCCGGC GAGCCGATGG CGGAAAGCAG AAAGACGACC TGGTAGAAAC |
| 2941 | CTGCATTCGG TTAAACACCA CGCACGTTGC CATGCAGCGT ACGAAGAAGG CCAAGAACGG |
| 3001 | CCGCCTGGTG ACGGTATCCG AGGGTGAAGC CTTGATTAGC CGCTACAAGA TCGTAAAGAG |
| 3061 | CGAAACCGGG CGGCCGGAGT ACATCGAGAT CGAGCTAGCT GATTGGATGT ACCGCGAGAT |
| 3121 | CACAGAAGGC AAGAACCCGG ACGTGCTGAC GGTTCACCCC GATTACTTTT TGATCGATCC |
| 3181 | CGGCATCGGC CGTTTTCTCT ACCGCCTGGC ACGCCGCGCC GCAGGCAAGG CAGAAGCCAG |
| 3241 | ATGGTTGTTC AAGACGATCT ACGAACGCAG TGGCAGCGCC GGAGAGTTCA AGAAGTTCTG |
| 3301 | TTTCACCGTG CGCAAGCTGA TCGGGTCAAA TGACCTGCCG GAGTACGATT TGAAGGAGGA |
| 3361 | GGCGGGGCAG GCTGGCCCGA TCCTAGTCAT GCGCTACCGC AACCTGATCG AGGGCGAAGC |
| 3421 | ATCCGCCGGT TCCTAATGTA CGGAGCAGAT GCTAGGGCAA ATTGCCCTAG CAGGGGAAAA |
| 3481 | AGGTCGAAAA GGTCTCTTTC CTGTGGATAG CACGTACATT GGGAACCCAA AGCCGTACAT |
| 3541 | TGGGAACCGG AACCCGTACA TTGGGAACCC AAAGCCGTAC ATTGGGAACC GGTCACACAT |
| 3601 | GTAAGTGACT GATATAAAAG AGAAAAAAGG CGATTTTTCC GCCTAAAACT CTTTAAAACT |
| 3661 | TATTAAAACT CTTAAAACCC GCCTGGCCTG TGCATAACTG TCTGGCCAGC GCACAGCCGA |
| 3721 | AGAGCTGCAA AAAGCGCCTA CCCTTCGGTC GCTGCGCTCC CTACGCCCCG CCGCTTCGCG |
| 3781 | TCGGCCTATC GCGGCCGCTG GCCGCTCAAA AATGGCTGGC CTACGGCCAG GCAATCTACC |
| 3841 | AGGGCGCGGA CAAGCCGCGC CGTCGCCACT CGACCGCCGG CGCCCACATC AAGGCACCCT |
| 3901 | GCCTCGCGCG TTTCGGTGAT GACGGTGAAA ACCTCTGACA CATGCAGCTC CCGGAGACGG |
| 3961 | TCACAGCTTG TCTGTAAGCG GATGCCGGGA GCAGACAAGC CCGTCAGGGC GCGTCAGCGG |
| 4021 | GTGTTGGCGG GTGTCGGGGC GCAGCCATGA CCCAGTCACG TAGCGATAGC GGAGTGTATA |
| 4081 | CTGGCTTAAC TATGCGGCAT CAGAGCAGAT TGTACTGAGA GTGCACCATA TGCGGTGTGA |
| 4141 | AATACCGCAC AGATGCGTAA GGAGAAAATA CCGCATCAGG CGCTCTTCCG CTTCCTCGCT |
| 4201 | CACTGACTCG CTGCGCTCGG TCGTTCGGCT GCGGCGAGCG GTATCAGCTC ACTCAAAGGC |
| 4261 | GGTAATACGG TTATCCACAG AATCAGGGGA TAACGCAGGA AAGAACATGT GAGCAAAAGG |
| 4321 | CCAGCAAAAG GCCAGGAACC GTAAAAAGGC CGCGTTGCTG GCGTTTTTCC ATAGGCTCCG |
| 4381 | CCCCCCTGAC GAGCATCACA AAAATCGACG CTCAAGTCAG AGGTGGCGAA ACCCGACAGG |
| 4441 | ACTATAAAGA TACCAGGCGT TTCCCCCTGG AAGCTCCCTC GTGCGCTCTC CTGTTCCGAC |
| 4501 | CCTGCCGCTT ACCGGATACC TGTCCGCCTT TCTCCCTTCG GGAAGCGTGG CGCTTTCTCA |
| 4561 | TAGCTCACGC TGTAGGTATC TCAGTTCGGT GTAGGTCGTT CGCTCCAAGC TGGGCTGTGT |
| 4621 | GCACGAACCC CCCGTTCAGC CCGACCGCTG CGCCTTATCC GGTAACTATC GTCTTGAGTC |
| 4681 | CAACCCGGTA AGACACGACT TATCGCCACT GGCAGCAGCC ACTGGTAACA GGATTAGCAG |
| 4741 | AGCGAGGTAT GTAGGCGGTG CTACAGAGTT CTTGAAGTGG TGGCCTAACT ACGGCTACAC |
| 4801 | TAGAAGGACA GTATTTGGTA TCTGCGCTCT GCTGAAGCCA GTTACCTTCG GAAAAAGAGT |
| 4861 | TGGTAGCTCT TGATCCGGCA AACAAACCAC CGCTGGTAGC GGTGGTTTTT TTGTTTGCAA |
| 4921 | GCAGCAGATT ACGCGCAGAA AAAAAGGATC TCAAGAAGAT CCTTTGATCT TTTCTACGGG |
| 4981 | GTCTGACGCT CAGTGGAACG AAAACTCACG TTAAGGGATT TTGGTCATGC ATTCTAGGTA |
| 5041 | CTAAAACAAT TCATCCAGTA AAATATAATA TTTTATTTTC TCCCAATCAG GCTTGATCCC |
| 5101 | CAGTAAGTCA AAAAATAGCT CGACATACTG TTCTTCCCCG ATATCCTCCC TGATCGACCG |
| 5161 | GACGCAGAAG GCAATGTCAT ACCACTTGTC CGCCCTGCCG CTTCTCCCAA GATCAATAAA |

-continued

| | Sequences: |
|---|---|
| 5221 | GCCACTTACT TTGCCATCTT TCACAAAGAT GTTGCTGTCT CCCAGGTCGC CGTGGGAAAA |
| 5281 | GACAAGTTCC TCTTCGGGCT TTTCCGTCTT TAAAAAATCA TACAGCTCGC GCGGATCTTT |
| 5341 | AAATGGAGTG TCTTCTTCCC AGTTTTCGCA ATCCACATCG GCCAGATCGT TATTCAGTAA |
| 5401 | GTAATCCAAT TCGGCTAAGC GGCTGTCTAA GCTATTCGTA TAGGGACAAT CCGATATGTC |
| 5461 | GATGGAGTGA AAGAGCCTGA TGCACTCCGC ATACAGCTCG ATAATCTTTT CAGGGCTTTG |
| 5521 | TTCATCTTCA TACTCTTCCG AGCAAAGGAC GCCATCGGCC TCACTCATGA GCAGATTGCT |
| 5581 | CCAGCCATCA TGCCGTTCAA AGTGCAGGAC CTTTGGAACA GGCAGCTTTC CTTCCAGCCA |
| 5641 | TAGCATCATG TCCTTTTCCC GTTCCACATC ATAGGTGGTC CCTTTATACC GGCTGTCCGT |
| 5701 | CATTTTTAAA TATAGGTTTT CATTTTCTCC CACCAGCTTA TATACCTTAG CAGGAGACAT |
| 5761 | TCCTTCCGTA TCTTTTACGC AGCGGTATTT TTCGATCAGT TTTTTCAATT CCGGTGATAT |
| 5821 | TCTCATTTTA GCCATTTATT ATTTCCTTCC TCTTTTCTAC AGTATTTAAA GATACCCCAA |
| 5881 | GAAGCTAATT ATAACAAGAC GAACTCCAAT TCACTGTTCC TTGCATTCTA AAACCTTAAA |
| 5941 | TACCAGAAAA CAGCTTTTTC AAAGTTGTTT TCAAAGTTGG CGTATAACAT AGTATCGACG |
| 6001 | GAGCCGATTT TGAAACCGCG GTGATCACAG GCAGCAACGC TCTGTCATCG TTACAATCAA |
| 6061 | CATGCTACCC TCCGCGAGAT CATCCGTGTT TCAAACCCGG CAGCTTAGTT GCCGTTCTTC |
| 6121 | CGAATAGCAT CGGTAACATG AGCAAAGTCT GCCGCCTTAC AACGGCTCTC CCGCTGACGC |
| 6181 | CGTCCCGGAC TGATGGGCTG CCTGTATCGA GTGGTGATTT TGTGCCGAGC TGCCGGTCGG |
| 6241 | GGAGCTGTTG GCTGGCTGGT GGCAGGATAT ATTGTGGTGT AAACAAATTG ACGCTTAGAC |
| 6301 | AACTTAATAA CACATTGCGG ACGTTTTTAA TGTACTGAAT TAACGCCGAA TTAATTCGGG |
| 6361 | GGATCTGGAT TTTAGTACTG GATTTTGGTT TTAGGAATTA GAAATTTTAT TGATAGAAGT |
| 6421 | ATTTTACAAA TACAAATACA TACTAAGGGT TTCTTATATG CTCAACACAT GAGCGAAACC |
| 6481 | CTATAGGAAC CCTAATTCCC TTATCTGGGA ACTACTCACA CATTATTATG GAGAAACTCG |
| 6541 | AGTCAAATCT CGGTGACGGG CAGGACCGGA CGGGGCGGTA CCGGCAGGCT GAAGTCCAGC |
| 6601 | TGCCAGAAAC CCACGTCATG CCAGTTCCCG TGCTTGAAGC CGGCCGCCCG CAGCATGCCG |
| 6661 | CGGGGGGCAT ATCCGAGCGC CTCGTGCATG CGCACGCTCG GGTCGTTGGG CAGCCCGATG |
| 6721 | ACAGCGACCA CGCTCTTGAA GCCCTGTGCC TCCAGGGACT TCAGCAGGTG GGTGTAGAGC |
| 6781 | GTGGAGCCCA GTCCCGTCCG CTGGTGGCGG GGGGAGACGT ACACGGTCGA CTCGGCCGTC |
| 6841 | CAGTCGTAGG CGTTGCGTGC CTTCCAGGGG CCCGCGTAGG CGATGCCGGC GACCTCGCCG |
| 6901 | TCCACCTCGG CGACGAGCCA GGGATAGCGC TCCCGCAGAC GGACGAGGTC GTCCGTCCAC |
| 6961 | TCCTGCGGTT CCTGCGGCTC GGTACGGAAG TTGACCGTGC TTGTCTCGAT GTAGTGGTTG |
| 7021 | ACGATGGTGC AGACCGCCGG CATGTCCGCC TCGGTGGCAC GGCGGATGTC GGCCGGGCGT |
| 7081 | CGTTCTGGGC TCATGGTAGA CCGCTTGGTA TCTGCATTAC AATGAAATGA GCAAAGACTA |
| 7141 | TGTGAGTAAC ACTGGTCAAC ACTAGGGAGA AGGCATCGAG CAAGATACGT ATGTAAAGAG |
| 7201 | AAGCAATATA GTGTCAGTTG GTAGATACTA GATACCATCA GGAGGTAAGG AGAGCAACAA |
| 7261 | AAAGGAAACT CTTTATTTTT AAATTTGTT ACAACAAACA AGCAGATCAA TGCATCAAAA |
| 7321 | TACTGTCAGT ACTTATTTCT TCAGACAACA ATATTTAAAA CAAGTGCATC TGATCTTGAC |
| 7381 | TTATGGTCAC AATAAAGGAG CAGAGATAAA CATCAAAATT TCGTCATTTA TATTTATTCC |
| 7441 | TTCAGGCGTT AACAATTTAA CAGCACACAA ACAAAAACAG AATAGGAATA TCTAATTTTG |

-continued

| | Sequences: |
|---|---|
| 7501 | GCAAATAATA AGCTCTGCAG ACGAACAAAT TATTATAGTA TCGCCTATAA TATGAATCCC |
| 7561 | TATACTATTG ACCCATGTAG TATGAAGCCT GTGCCTAAAT AACAGCAAA CTTCTGAATC |
| 7621 | CAAGTGCCCT ATAACACCAA CATGTGCTTA AATAAATACC GCTAAGCACC AAATTACACA |
| 7681 | TTTCTCGTAT TGCTGTGTAG GTTCTATCTT CGTTTCGTAC TACCATGTCC CTATATTTTG |
| 7741 | CTGCTACAAA GGACGGCAAG TAATCAGCAC AGGCAGAACA CGATTTCAGA GTGTAATTCT |
| 7801 | AGATCCAGCT AAACCACTCT CAGCAATCAC CACACAAGAG AGCATTCAGA GAAACGTGGC |
| 7861 | AGTAACAAAG GCAGAGGGCG GAGTGAGCGC GTACCGAAGA CGGTCTCGAG AGAGATAGAT |
| 7921 | TTGTAGAGAG AGACTGGTGA TTTCAGCGTG TCCTCTCCAA ATGAAATGAA CTTCCTTATA |
| 7981 | TAGAGGAAGG TCTTGCGAAG GATAGTGGGA TTGTGCGTCA TCCCTTACGT CAGTGGAGAT |
| 8041 | ATCACATCAA TCCACTTGCT TTGAAGACGT GGTTGGAACG TCTTCTTTTT CCACGATGCT |
| 8101 | CCTCGTGGGT GGGGGTCCAT CTTTGGGACC ACTGTCGGCA GAGGCATCTT GAACGATAGC |
| 8161 | CTTTCCTTTA TCGCAATGAT GGCATTTGTA GGTGCCACCT TCCTTTTCTA CTGTCCTTTT |
| 8221 | GATGAAGTGA CAGATAGCTG GGCAATGGAA TCCGAGGAGG TTTCCCGATA TTACCCTTTG |
| 8281 | TTGAAAAGTC TCAATAGCCC TTTGGTCTTC TGAGACTGTA TCTTTGATAT TCTTGGAGTA |
| 8341 | GACGAGAGTG TCGTGCTCCA CCATGTTATC ACATCAATCC ACTTGCTTTG AAGACGTGGT |
| 8401 | TGGAACGTCT TCTTTTTCCA CGATGCTCCT CGTGGGTGGG GGTCCATCTT TGGGACCACT |
| 8461 | GTCGGCAGAG GCATCTTGAA CGATAGCCTT TCCTTTATCG CAATGATGGC ATTTGTAGGT |
| 8521 | GCCACCTTCC TTTTCTACTG TCCTTTTGAT GAAGTGACAG ATAGCTGGGC AATGGAATCC |
| 8581 | GAGGAGGTTT CCCGATATTA CCCTTTGTTG AAAAGTCTCA ATAGCCCTTT GGTCTTCTGA |
| 8641 | GACTGTATCT TTGATATTCT TGGAGTAGAC GAGAGTGTCG TGCTCCACCA TGTTGGCAAG |
| 8701 | CTGCTCTAGC AATACGCAA ACCGCCTCTC CCCGCGCGTT GGCCGATTCA TTAATGCAGC |
| 8761 | TGGCACGACA GGTTTCCCGA CTGGAAAGCG GGCAGTGAGC GCAACGCAAT TAATGTGAGT |
| 8821 | TAGCTCACTC ATTAGGCACC CCAGGCTTTA CACTTTATGC TTCCGGCTCG TATGTTGTGT |
| 8881 | GGAATTGTGA GCGGATAACA ATTTCACACA GGAAACAGCT ATGACCATGA TTACGAATTG |
| 8941 | GGGTTTAAAC CACGGAAGAT CCAGGTCTCG AGACTAGGAG ACGGATGGGA GGCGCAACGC |
| 9001 | GCGATGGGA GGGGGCGGC GCTGACCTTT CTGGCGAGGT CGAGGTAGCG ATCGAGCAGC |
| 9061 | TGCAGCGCGG ACACGATGAG GAAGACGAAG ATAGCCGCCA TGGACATGTT CGCCAGCGGC |
| 9121 | GGCGGAGCGA GGCTGAGCCG GTCTCTCCGG CCTCCGGTCG GCGTTAAGTT GGGGATCGTA |
| 9181 | ACGTGACGTG TCTCGTCTCC ACGGATCGAC ACAACCGGCC TACTCGGGTG CACGACGCCG |
| 9241 | CGATAAGGGC GAGATGTCCG TGCACGCAGC CCGTTTGGAG TCCTCGTTGC CCACGAACCG |
| 9301 | ACCCCTTACA GAACAAGGCC TAGCCCAAAA CTATTCTGAG TTGAGCTTTT GAGCCTAGCC |
| 9361 | CACCTAAGCC GAGCGTCATG AACTGATGAA CCCACTACCA CTAGTCAAGG CAAACCACAA |
| 9421 | CCACAAATGG ATCAATTGAT CTAGAACAAT CCGAAGGAGG GGAGGCCACG TCACACTCAC |
| 9481 | ACCAACCGAA ATATCTGCCA GAATCAGATC AACCGGCCAA TAGGACGCCA GCGAGCCCAA |
| 9541 | CACCTGGCGA CGCCGCAAAA TTCACCGCGA GGGGCACCGG GCACGGCAAA AACAAAAGCC |
| 9601 | CGGCGCGGTG AGAATATCTG GCGACTGGCG GAGACCTGGT GGCCAGCGCG CGGCCACATC |
| 9661 | AGCCACCCCA TCCGCCCACC TCACCTCCGG CGAGCCAATG GCAACTCGTC TTAAGATTCC |
| 9721 | ACGAGATAAG GACCCGATCG CCGGCGACGC TATTTAGCCA GGTGCGCCCC CCACGGTACA |
| 9781 | CTCCACCAGC GGCATCTATA GCAACCGGTC CAGCACTTTC ACGCTCAGCT TCAGCAAGAT |

| Sequences: |
|---|
| 9841 CTACCGTCTT CGGTACGCGC TCACTCCGCC CTCTGCCTTT GTTACTGCCA CGTTTCTCTG |
| 9901 AATGCTCTCT TGTGTGGTGA TTGCTGAGAG TGGTTTAGCT GGATCTAGAA TTACACTCTG |
| 9961 AAATCGTGTT CTGCCTGTGC TGATTACTTG CCGTCCTTTG TAGCAGCAAA ATATAGGGAC |
| 10021 ATGGTAGTAC GAAACGAAGA TAGAACCTAC ACAGCAATAC GAGAAATGTG TAATTTGGTG |
| 10081 CTTAGCGGTA TTTATTTAAG CACATGTTGG TGTTATAGGG CACTTGGATT CAGAAGTTTG |
| 10141 CTGTTAATTT AGGCACAGGC TTCATACTAC ATGGGTCAAT AGTATAGGGA TTCATATTAT |
| 10201 AGGCGATACT ATAATAATTT GTTCGTCTGC AGAGCTTATT ATTTGCCAAA ATTAGATATT |
| 10261 CCTATTCTGT TTTTGTTTGT GTGCTGTTAA ATTGTTAACG CCTGAAGGAA TAAATATAAA |
| 10321 TGACGAAATT TTGATGTTTA TCTCTGCTCC TTTATTGTGA CCATAAGTCA AGATCAGATG |
| 10381 CACTTGTTTT AAATATTGTT GTCTGAAGAA ATAAGTACTG ACAGTATTTT GATGCATTGA |
| 10441 TCTGCTTGTT TGTTGTAACA AAATTTAAAA ATAAAGAGTT TCCTTTTTGT TGCTCTCCTT |
| 10501 ACCTCCTGAT GGTATCTAGT ATCTACCAAC TGATACTATA TTGCTTCTCT TTACATACGT |
| 10561 ATCTTGCTCG ATGCCTTCTC CTAGTGTTGA CCAGTGTTAC TCACATAGTC TTTGCTCATT |
| 10621 TCATTGTAAT GCAGATACCA AGCGGTTAAT TAAATGCATA TGTATCCTTT CTACATACAT |
| 10681 GCAGGTTACG GGACGAGAAT GCACTACCGT GGCGTGCGGC GGCGGCCGTG GGGCAAGTGG |
| 10741 GCGGCGGAGA TCCGTGACCC CGCCAAGGCG GCGCGTGTGT GGCTCGGCAC CTTCGACACC |
| 10801 GCGGAGGCCG CCGCCGCAGC GTACGACGAC GCCGCGCTCC GGTTCAAGGG CGCCAAGGCC |
| 10861 AAGCTCAACT TTCCCGAGCG CGTCCGCGGC CGTACCGGCC AGGGCGCGTT CCTCGTCAGC |
| 10921 CCTGGCGTCC CCCAGCAGCC GCCGCCGTCT TCCCTGCCAA CTGCAGCCGC CGCGCCGACG |
| 10981 CCGTTCCCCG GCTTGATGCG GTACGCGCAA CTCCAGGGTT GGAGCAGCGG GAACATCGCG |
| 11041 GCCAGCAACA CCGGTGGTGA TCTCGCGCCG CCGGCACAGG CGTCGTCGTC GGTGCAGATT |
| 11101 CTGGACTTCT CGACGCAGCA ACTACTCCGG GGCTCACCGA CAACGTTCGG CCCACCGCCG |
| 11161 ACGACGTCGG CATCGATGTC CAGGACTAGC AGAGTAGATG AGGCGCACGA GAGTTGCGAT |
| 11221 GCTCCTGACT GAGGCGCGCC ATCGTTCAAA CATTTGGCAA TAAAGTTTCT TAAGATTGAA |
| 11281 TCCTGTTGCC GGTCTTGCGA TGATTATCAT ATAATTTCTG TTGAATTACG TTAAGCATGT |
| 11341 AATAATTAAC ATGTAATGCA TGACGTTATT TATGAGATGG GTTTTTATGA TTAGAGTCCC |
| 11401 GCAATTATAC ATTTAATACG CGATAGAAAA CAAATATAG CGCGCAAACT AGGATAAATT |
| 11461 ATCGCGCGCG GTGTCATCTA TGTTACTAGA TCCGATGATA AGCTGTCAAA CATGACCTCA |
| 11521 GGATGAAGCT TGGCACTGGC CGTCGTTTTA CAACGTCGTG ACTGGGAAAA CCCTGGCGTT |
| 11581 ACCCAACTTA ATCGCCTTGC AGCACATCCC CCTTTCGCCA GCTGGCGTAA TAGCGAAGAG |
| 11641 GCCCGCACCG ATCGCCCTTC CCAACAGTTG CGCAGCCTGA ATGGCGAATG CTAGAGCAGC |
| 11701 TTGAGCTTGG ATCAGATTGT CGTTTCCCGC CTTCAGTTTA AACTATCAGT GTTTGACAGG |
| 11761 ATATATTGGC GG |
| SEQ ID NO: 21 pMBXS855 |
| 1 GTAAACCTAA GAGAAAAGAG CGTTTATTAG AATAACGGAT ATTTAAAAGG GCGTGAAAAG |
| 61 GTTTATCCGT TCGTCCATTT GTATGTGCAT GCCAACCACA GGGTTCCCCT CGGGATCAAA |
| 121 GTACTTTGAT CCAACCCCTC CGCTGCTATA GTGCAGTCGG CTTCTGACGT TCAGTGCAGC |
| 181 CGTCTTCTGA AAACGACATG TCGCACAAGT CCTAAGTTAC GCGACAGGCT GCCGCCCTGC |
| 241 CCTTTTCCTG GCGTTTTCTT GTCGCGTGTT TTAGTCGCAT AAAGTAGAAT ACTTGCGACT |

-continued

| Sequences: | | | | | |
|---|---|---|---|---|---|
| 301 | AGAACCGGAG | ACATTACGCC | ATGAACAAGA | GCGCCGCCGC | TGGCCTGCTG | GGCTATGCCC |
| 361 | GCGTCAGCAC | CGACGACCAG | GACTTGACCA | ACCAACGGGC | CGAACTGCAC | GCGGCCGGCT |
| 421 | GCACCAAGCT | GTTTTCCGAG | AAGATCACCG | GCACCAGGCG | CGACCGCCCG | GAGCTGGCCA |
| 481 | GGATGCTTGA | CCACCTACGC | CCTGGCGACG | TTGTGACAGT | GACCAGGCTA | GACCGCCTGG |
| 541 | CCCGCAGCAC | CCGCGACCTA | CTGGACATTG | CCGAGCGCAT | CCAGGAGGCC | GGCGCGGGCC |
| 601 | TGCGTAGCCT | GGCAGAGCCG | TGGGCCGACA | CCACCACGCC | GGCCGGCCGC | ATGGTGTTGA |
| 661 | CCGTGTTCGC | CGGCATTGCC | GAGTTCGAGC | GTTCCCTAAT | CATCGACCGC | ACCCGGAGCG |
| 721 | GGCGCGAGGC | CGCCAAGGCC | CGAGGCGTGA | AGTTTGGCCC | CCGCCCTACC | CTCACCCCGG |
| 781 | CACAGATCGC | GCACGCCCGC | GAGCTGATCG | ACCAGGAAGG | CCGCACCGTG | AAAGAGGCGG |
| 841 | CTGCACTGCT | TGGCGTGCAT | CGCTCGACCC | TGTACCGCGC | ACTTGAGCGC | AGCGAGGAAG |
| 901 | TGACGCCCAC | CGAGGCCAGG | CGGCGCGGTG | CCTTCCGTGA | GGACGCATTG | ACCGAGGCCG |
| 961 | ACGCCCTGGC | GGCCGCCGAG | AATGAACGCC | AAGAGGAACA | AGCATGAAAC | CGCACCAGGA |
| 1021 | CGGCCAGGAC | GAACCGTTTT | TCATTACCGA | AGAGATCGAG | GCGGAGATGA | TCGCGGCCGG |
| 1081 | GTACGTGTTC | GAGCCGCCCG | CGCACGTCTC | AACCGTGCGG | CTGCATGAAA | TCCTGGCCGG |
| 1141 | TTTGTCTGAT | GCCAAGCTGG | CGGCCTGGCC | GGCCAGCTTG | CCGCTGAAG | AAACCGAGCG |
| 1201 | CCGCCGTCTA | AAAGGTGAT | GTGTATTTGA | GTAAAACAGC | TTGCGTCATG | CGGTCGCTGC |
| 1261 | GTATATGATG | CGATGAGTAA | ATAAACAAAT | ACGCAAGGGG | AACGCATGAA | GGTTATCGCT |
| 1321 | GTACTTAACC | AGAAAGGCGG | GTCAGGCAAG | ACGACCATCG | CAACCCATCT | AGCCCGCGCC |
| 1381 | CTGCAACTCG | CCGGGGCCGA | TGTTCTGTTA | GTCGATTCCG | ATCCCCAGGG | CAGTGCCCGC |
| 1441 | GATTGGGCGG | CCGTGCGGGA | AGATCAACCG | CTAACCGTTG | TCGGCATCGA | CCGCCCGACG |
| 1501 | ATTGACCGCG | ACGTGAAGGC | CATCGGCCGG | CGCGACTTCG | TAGTGATCGA | CGGAGCGCCC |
| 1561 | CAGGCGGCGG | ACTTGGCTGT | GTCCGCGATC | AAGGCAGCCG | ACTTCGTGCT | GATTCCGGTG |
| 1621 | CAGCCAAGCC | CTTACGACAT | ATGGGCCACC | GCCGACCTGG | TGGAGCTGGT | TAAGCAGCGC |
| 1681 | ATTGAGGTCA | CGGATGGAAG | GCTACAAGCG | GCCTTTGTCG | TGTCGCGGGC | GATCAAAGGC |
| 1741 | ACGCGCATCG | GCGGTGAGGT | TGCCGAGGCG | CTGGCCGGGT | ACGAGCTGCC | CATTCTTGAG |
| 1801 | TCCCGTATCA | CGCAGCGCGT | GAGCTACCCA | GGCACTGCCG | CCGCCGGCAC | AACCGTTCTT |
| 1861 | GAATCAGAAC | CCGAGGGCGA | CGCTGCCCGC | GAGGTCCAGG | CGCTGGCCGC | TGAAATTAAA |
| 1921 | TCAAAACTCA | TTTGAGTTAA | TGAGGTAAAG | AGAAAATGAG | CAAAAGCACA | AACACGCTAA |
| 1981 | GTGCCGGCCG | TCCGAGCGCA | CGCAGCAGCA | AGGCTGCAAC | GTTGGCCAGC | CTGGCAGACA |
| 2041 | CGCCAGCCAT | GAAGCGGGTC | AACTTTCAGT | TGCCGGCGGA | GGATCACACC | AAGCTGAAGA |
| 2101 | TGTACGCGGT | ACGCCAAGGC | AAGACCATTA | CCGAGCTGCT | ATCTGAATAC | ATCGCGCAGC |
| 2161 | TACCAGAGTA | AATGAGCAAA | TGAATAAATG | AGTAGATGAA | TTTTAGCGGC | TAAAGGAGGC |
| 2221 | GGCATGGAAA | ATCAAGAACA | ACCAGGCACC | GACGCCGTGG | AATGCCCCAT | GTGTGGAGGA |
| 2281 | ACGGGCGGTT | GGCCAGGCGT | AAGCGGCTGG | GTTGTCTGCC | GGCCCTGCAA | TGGCACTGGA |
| 2341 | ACCCCCAAGC | CCGAGGAATC | GGCGTGACGG | TCGCAAACCA | TCCGGCCCGG | TACAAATCGG |
| 2401 | CGCGGCGCTG | GGTGATGACC | TGGTGGAGAA | GTTGAAGGCC | GCGCAGGCCG | CCCAGCGGCA |
| 2461 | ACGCATCGAG | GCAGAAGCAC | GCCCCGGTGA | ATCGTGGCAA | GCGGCCGCTG | ATCGAATCCG |
| 2521 | CAAAGAATCC | CGGCAACCGC | CGGCAGCCGG | TGCGCCGTCG | ATTAGGAAGC | CGCCCAAGGG |

| | |
|---|---|
| | -continued |
| | Sequences: |

```
2581  CGACGAGCAA CCAGATTTTT TCGTTCCGAT GCTCTATGAC GTGGGCACCC GCGATAGTCG
2641  CAGCATCATG GACGTGGCCG TTTTCCGTCT GTCGAAGCGT GACCGACGAG CTGGCGAGGT
2701  GATCCGCTAC GAGCTTCCAG ACGGGCACGT AGAGGTTTCC GCAGGGCCGG CCGGCATGGC
2761  CAGTGTGTGG GATTACGACC TGGTACTGAT GGCGGTTTCC CATCTAACCG AATCCATGAA
2821  CCGATACCGG GAAGGGAAGG GAGACAAGCC CGGCCGCGTG TTCCGTCCAC ACGTTGCGGA
2881  CGTACTCAAG TTCTGCCGGC GAGCCGATGG CGGAAAGCAG AAAGACGACC TGGTAGAAAC
2941  CTGCATTCGG TTAAACACCA CGCACGTTGC CATGCAGCGT ACGAAGAAGG CCAAGAACGG
3001  CCGCCTGGTG ACGGTATCCG AGGGTGAAGC CTTGATTAGC CGCTACAAGA TCGTAAAGAG
3061  CGAAACCGGG CGGCCGGAGT ACATCGAGAT CGAGCTAGCT GATTGGATGT ACCGCGAGAT
3121  CACAGAAGGC AAGAACCCGG ACGTGCTGAC GGTTCACCCC GATTACTTTT TGATCGATCC
3181  CGGCATCGGC CGTTTTCTCT ACCGCCTGGC ACGCCGCGCC GCAGGCAAGG CAGAAGCCAG
3241  ATGGTTGTTC AAGACGATCT ACGAACGCAG TGGCAGCGCC GGAGAGTTCA AGAAGTTCTG
3301  TTTCACCGTG CGCAAGCTGA TCGGGTCAAA TGACCTGCCG GAGTACGATT TGAAGGAGGA
3361  GGCGGGGCAG GCTGGCCCGA TCCTAGTCAT GCGCTACCGC AACCTGATCG AGGGCGAAGC
3421  ATCCGCCGGT TCCTAATGTA CGGAGCAGAT GCTAGGGCAA ATTGCCCTAG CAGGGGAAAA
3481  AGGTCGAAAA GGTCTCTTTC CTGTGGATAG CACGTACATT GGGAACCCAA AGCCGTACAT
3541  TGGGAACCGG AACCCGTACA TTGGGAACCC AAAGCCGTAC ATTGGGAACC GGTCACACAT
3601  GTAAGTGACT GATATAAAAG AGAAAAAAGG CGATTTTTCC GCCTAAAACT CTTTAAAACT
3661  TATTAAAACT CTTAAAACCC GCCTGGCCTG TGCATAACTG TCTGGCCAGC GCACAGCCGA
3721  AGAGCTGCAA AAAGCGCCTA CCCTTCGGTC GCTGCGCTCC CTACGCCCCG CCGCTTCGCG
3781  TCGGCCTATC GCGGCCGCTG GCCGCTCAAA AATGGCTGGC CTACGGCCAG GCAATCTACC
3841  AGGGCGCGGA CAAGCCGCGC CGTCGCCACT CGACCGCCGG CGCCCACATC AAGGCACCCT
3901  GCCTCGCGCG TTTCGGTGAT GACGGTGAAA ACCTCTGACA CATGCAGCTC CCGGAGACGG
3961  TCACAGCTTG TCTGTAAGCG GATGCCGGGA GCAGACAAGC CCGTCAGGGC GCGTCAGCGG
4021  GTGTTGGCGG GTGTCGGGGC GCAGCCATGA CCCAGTCACG TAGCGATAGC GGAGTGTATA
4081  CTGGCTTAAC TATGCGGCAT CAGAGCAGAT TGTACTGAGA GTGCACCATA TGCGGTGTGA
4141  AATACCGCAC AGATGCGTAA GGAGAAAATA CCGCATCAGG CGCTCTTCCG CTTCCTCGCT
4201  CACTGACTCG CTGCGCTCGG TCGTTCGGCT GCGGCGAGCG GTATCAGCTC ACTCAAAGGC
4261  GGTAATACGG TTATCCACAG AATCAGGGGA TAACGCAGGA AAGAACATGT GAGCAAAAGG
4321  CCAGCAAAAG GCCAGGAACC GTAAAAAGGC CGCGTTGCTG GCGTTTTTCC ATAGGCTCCG
4381  CCCCCCTGAC GAGCATCACA AAAATCGACG CTCAAGTCAG AGGTGGCGAA ACCCGACAGG
4441  ACTATAAAGA TACCAGGCGT TTCCCCCTGG AAGCTCCCTC GTGCGCTCTC CTGTTCCGAC
4501  CCTGCCGCTT ACCGGATACC TGTCCGCCTT TCTCCCTTCG GGAAGCGTGG CGCTTTCTCA
4561  TAGCTCACGC TGTAGGTATC TCAGTTCGGT GTAGGTCGTT CGCTCCAAGC TGGGCTGTGT
4621  GCACGAACCC CCCGTTCAGC CCGACCGCTG CGCCTTATCC GGTAACTATC GTCTTGAGTC
4681  CAACCCGGTA AGACACGACT TATCGCCACT GGCAGCAGCC ACTGGTAACA GGATTAGCAG
4741  AGCGAGGTAT GTAGGCGGTG CTACAGAGTT CTTGAAGTGG TGGCCTAACT ACGGCTACAC
4801  TAGAAGGACA GTATTTGGTA TCTGCGCTCT GCTGAAGCCA GTTACCTTCG GAAAAAGAGT
4861  TGGTAGCTCT TGATCCGGCA AACAAACCAC CGCTGGTAGC GGTGGTTTTT TTGTTTGCAA
```

-continued

| | Sequences: |
|---|---|
| 4921 | GCAGCAGATT ACGCGCAGAA AAAAAGGATC TCAAGAAGAT CCTTTGATCT TTTCTACGGG |
| 4981 | GTCTGACGCT CAGTGGAACG AAAACTCACG TTAAGGGATT TTGGTCATGC ATTCTAGGTA |
| 5041 | CTAAAACAAT TCATCCAGTA AAATATAATA TTTTATTTTC TCCCAATCAG CTTGATCCC |
| 5101 | CAGTAAGTCA AAAAATAGCT CGACATACTG TTCTTCCCCG ATATCCTCCC TGATCGACCG |
| 5161 | GACGCAGAAG GCAATGTCAT ACCACTTGTC CGCCCTGCCG CTTCTCCCAA GATCAATAAA |
| 5221 | GCCACTTACT TTGCCATCTT TCACAAAGAT GTTGCTGTCT CCCAGGTCGC CGTGGGAAAA |
| 5281 | GACAAGTTCC TCTTCGGGCT TTTCCGTCTT TAAAAAATCA TACAGCTCGC GCGGATCTTT |
| 5341 | AAATGGAGTG TCTTCTTCCC AGTTTTCGCA ATCCACATCG CCAGATCGT TATTCAGTAA |
| 5401 | GTAATCCAAT TCGGCTAAGC GGCTGTCTAA GCTATTCGTA TAGGGACAAT CCGATATGTC |
| 5461 | GATGGAGTGA AAGAGCCTGA TGCACTCCGC ATACAGCTCG ATAATCTTTT CAGGGCTTTG |
| 5521 | TTCATCTTCA TACTCTTCCG AGCAAAGGAC GCCATCGGCC TCACTCATGA GCAGATTGCT |
| 5581 | CCAGCCATCA TGCCGTTCAA AGTGCAGGAC CTTTGGAACA GGCAGCTTTC CTTCCAGCCA |
| 5641 | TAGCATCATG TCCTTTTCCC GTTCCACATC ATAGGTGGTC CCTTTATACC GGCTGTCCGT |
| 5701 | CATTTTTAAA TATAGGTTTT CATTTTCTCC CACCAGCTTA TATACCTTAG CAGGAGACAT |
| 5761 | TCCTTCCGTA TCTTTTACGC AGCGGTATTT TTCGATCAGT TTTTTCAATT CCGGTGATAT |
| 5821 | TCTCATTTTA GCCATTTATT ATTTCCTTCC TCTTTTCTAC AGTATTTAAA GATACCCCAA |
| 5881 | GAAGCTAATT ATAACAAGAC GAACTCCAAT TCACTGTTCC TTGCATTCTA AAACCTTAAA |
| 5941 | TACCAGAAAA CAGCTTTTTC AAAGTTGTTT TCAAAGTTGG CGTATAACAT AGTATCGACG |
| 6001 | GAGCCGATTT TGAAACCGCG GTGATCACAG GCAGCAACGC TCTGTCATCG TTACAATCAA |
| 6061 | CATGCTACCC TCCGCGAGAT CATCCGTGTT TCAAACCCGG CAGCTTAGTT GCCGTTCTTC |
| 6121 | CGAATAGCAT CGGTAACATG AGCAAAGTCT GCCGCCTTAC AACGGCTCTC CCGCTGACGC |
| 6181 | CGTCCCGGAC TGATGGGCTG CCTGTATCGA GTGGTGATTT TGTGCCGAGC TGCCGGTCGG |
| 6241 | GGAGCTGTTG GCTGGCTGGT GGCAGGATAT ATTGTGGTGT AAACAAATTG ACGCTTAGAC |
| 6301 | AACTTAATAA CACATTGCGG ACGTTTTTAA TGTACTGAAT TAACGCCGAA TTAATTCGGG |
| 6361 | GGATCTGGAT TTTAGTACTG GATTTTGGTT TTAGGAATTA GAAATTTAT TGATAGAAGT |
| 6421 | ATTTTACAAA TACAAATACA TACTAAGGGT TTCTTATATG CTCAACACAT GAGCGAAACC |
| 6481 | CTATAGGAAC CCTAATTCCC TTATCTGGGA ACTACTCACA CATTATTATG GAGAAACTCG |
| 6541 | AGTCAAATCT CGGTGACGGG CAGGACCGGA CGGGGCGGTA CCGGCAGGCT GAAGTCCAGC |
| 6601 | TGCCAGAAAC CCACGTCATG CCAGTTCCCG TGCTTGAAGC CGGCCGCCCG CAGCATGCCG |
| 6661 | CGGGGGGCAT ATCCGAGCGC CTCGTGCATG CGCACGCTCG GGTCGTTGGG CAGCCCGATG |
| 6721 | ACAGCGACCA CGCTCTTGAA GCCCTGTGCC TCCAGGGACT TCAGCAGGTG GGTGTAGAGC |
| 6781 | GTGGAGCCCA GTCCCGTCCG CTGGTGGCGG GGGAGACGT ACACGGTCGA CTCGGCCGTC |
| 6841 | CAGTCGTAGG CGTTGCGTGC CTTCCAGGGG CCCGCGTAGG CGATGCCGGC GACCTCGCCG |
| 6901 | TCCACCTCGG CGACGAGCCA GGGATAGCGC TCCCGCAGAC GGACGAGGTC GTCCGTCCAC |
| 6961 | TCCTGCGGTT CCTGCGGCTC GGTACGGAAG TTGACCGTGC TTGTCTCGAT GTAGTGGTTG |
| 7021 | ACGATGGTGC AGACCGCCGG CATGTCCGCC TCGGTGGCAC GGCGGATGTC GGCCGGGCGT |
| 7081 | CGTTCTGGGC TCATGGTAGA CCGCTTGGTA TCTGCATTAC AATGAAATGA GCAAAGACTA |
| 7141 | TGTGAGTAAC ACTGGTCAAC ACTAGGGAGA AGGCATCGAG CAAGATACGT ATGTAAAGAG |

-continued

| | Sequences: |
|---|---|
| 7201 | AAGCAATATA GTGTCAGTTG GTAGATACTA GATACCATCA GGAGGTAAGG AGAGCAACAA |
| 7261 | AAAGGAAACT CTTTATTTTT AAATTTTGTT ACAACAAACA AGCAGATCAA TGCATCAAAA |
| 7321 | TACTGTCAGT ACTTATTTCT TCAGACAACA ATATTTAAAA CAAGTGCATC TGATCTTGAC |
| 7381 | TTATGGTCAC AATAAAGGAG CAGAGATAAA CATCAAAATT TCGTCATTTA TATTTATTCC |
| 7441 | TTCAGGCGTT AACAATTTAA CAGCACACAA ACAAAAACAG AATAGGAATA TCTAATTTTG |
| 7501 | GCAAATAATA AGCTCTGCAG ACGAACAAAT TATTATAGTA TCGCCTATAA TATGAATCCC |
| 7561 | TATACTATTG ACCCATGTAG TATGAAGCCT GTGCCTAAAT TAACAGCAAA CTTCTGAATC |
| 7621 | CAAGTGCCCT ATAACACCAA CATGTGCTTA AATAAATACC GCTAAGCACC AAATTACACA |
| 7681 | TTTCTCGTAT TGCTGTGTAG GTTCTATCTT CGTTTCGTAC TACCATGTCC CTATATTTTG |
| 7741 | CTGCTACAAA GGACGGCAAG TAATCAGCAC AGGCAGAACA CGATTTCAGA GTGTAATTCT |
| 7801 | AGATCCAGCT AAACCACTCT CAGCAATCAC CACACAAGAG AGCATTCAGA GAAACGTGGC |
| 7861 | AGTAACAAAG GCAGAGGGCG GAGTGAGCGC GTACCGAAGA CGGTCTCGAG AGAGATAGAT |
| 7921 | TTGTAGAGAG AGACTGGTGA TTTCAGCGTG TCCTCTCCAA ATGAAATGAA CTTCCTTATA |
| 7981 | TAGAGGAAGG TCTTGCGAAG GATAGTGGGA TTGTGCGTCA TCCCTTACGT CAGTGGAGAT |
| 8041 | ATCACATCAA TCCACTTGCT TTGAAGACGT GGTTGGAACG TCTTCTTTTT CCACGATGCT |
| 8101 | CCTCGTGGGT GGGGGTCCAT CTTTGGGACC ACTGTCGGCA GAGGCATCTT GAACGATAGC |
| 8161 | CTTTCCTTTA TCGCAATGAT GGCATTTGTA GGTGCCACCT TCCTTTTCTA CTGTCCTTTT |
| 8221 | GATGAAGTGA CAGATAGCTG GGCAATGGAA TCCGAGGAGG TTTCCCGATA TTACCCTTTG |
| 8281 | TTGAAAAGTC TCAATAGCCC TTTGGTCTTC TGAGACTGTA TCTTTGATAT TCTTGGAGTA |
| 8341 | GACGAGAGTG TCGTGCTCCA CCATGTTATC ACATCAATCC ACTTGCTTTG AAGACGTGGT |
| 8401 | TGGAACGTCT TCTTTTTCCA CGATGCTCCT CGTGGGTGGG GTCCATCTT TGGGACCACT |
| 8461 | GTCGGCAGAG GCATCTTGAA CGATAGCCTT TCCTTTATCG CAATGATGGC ATTTGTAGGT |
| 8521 | GCCACCTTCC TTTTCTACTG TCCTTTTGAT GAAGTGACAG ATAGCTGGGC AATGGAATCC |
| 8581 | GAGGAGGTTT CCCGATATTA CCCTTTGTTG AAAAGTCTCA ATAGCCCTTT GGTCTTCTGA |
| 8641 | GACTGTATCT TTGATATTCT TGGAGTAGAC GAGAGTGTCG TGCTCCACCA TGTTGGCAAG |
| 8701 | CTGCTCTAGC CAATACGCAA ACCGCCTCTC CCCGCGCGTT GGCCGATTCA TTAATGCAGC |
| 8761 | TGGCACGACA GGTTTCCCGA CTGGAAAGCG GGCAGTGAGC GCAACGCAAT TAATGTGAGT |
| 8821 | TAGCTCACTC ATTAGGCACC CCAGGCTTTA CACTTTATGC TTCCGGCTCG TATGTTGTGT |
| 8881 | GGAATTGTGA GCGGATAACA ATTTCACACA GGAAACAGCT ATGACCATGA TTACGAATTG |
| 8941 | GGGTTTAAAC CACGGAAGAT CCAGGTCTCG AGACTAGGAG ACGGATGGGA GGCGCAACGC |
| 9001 | GCGATGGGGA GGGGGCGGC GCTGACCTTT CTGGCGAGGT CGAGGTAGCG ATCGAGCAGC |
| 9061 | TGCAGCGCGG ACACGATGAG GAAGACGAAG ATAGCCGCCA TGGACATGTT CGCCAGCGGC |
| 9121 | GGCGGAGCGA GGCTGAGCCG GTCTCTCCGG CCTCCGGTCG GCGTTAAGTT GGGGATCGTA |
| 9181 | ACGTGACGTG TCTCGTCTCC ACGGATCGAC ACAACCGGCC TACTCGGGTG CACGACGCCG |
| 9241 | CGATAAGGGC GAGATGTCCG TGCACGCAGC CCGTTTGGAG TCCTCGTTGC CCACGAACCG |
| 9301 | ACCCCTTACA GAACAAGGCC TAGCCCAAAA CTATTCTGAG TTGAGCTTTT GAGCCTAGCC |
| 9361 | CACCTAAGCC GAGCGTCATG AACTGATGAA CCCACTACCA CTAGTCAAGG CAAACCACAA |
| 9421 | CCACAAATGG ATCAATTGAT CTAGAACAAT CCGAAGGAGG GGAGGCCACG TCACACTCAC |
| 9481 | ACCAACCGAA ATATCTGCCA GAATCAGATC AACCGGCCAA TAGGACGCCA GCGAGCCCAA |

-continued

| | Sequences: |
|---|---|
| 9541 | CACCTGGCGA CGCCGCAAAA TTCACCGCGA GGGGCACCGG GCACGGCAAA AACAAAAGCC |
| 9601 | CGGCGCGGTG AGAATATCTG GCGACTGGCG GAGACCTGGT GGCCAGCGCG CGGCCACATC |
| 9661 | AGCCACCCCA TCCGCCCACC TCACCTCCGG CGAGCCAATG GCAACTCGTC TTAAGATTCC |
| 9721 | ACGAGATAAG GACCCGATCG CCGGCGACGC TATTTAGCCA GGTGCGCCCC CCACGGTACA |
| 9781 | CTCCACCAGC GGCATCTATA GCAACCGGTC CAGCACTTTC ACGCTCAGCT TCAGCAAGAT |
| 9841 | CTACCGTCTT CGGTACGCGC TCACTCCGCC CTCTGCCTTT GTTACTGCCA CGTTTCTCTG |
| 9901 | AATGCTCTCT TGTGTGGTGA TTGCTGAGAG TGGTTTAGCT GGATCTAGAA TTACACTCTG |
| 9961 | AAATCGTGTT CTGCCTGTGC TGATTACTTG CCGTCCTTTG TAGCAGCAAA ATATAGGGAC |
| 10021 | ATGGTAGTAC GAAACGAAGA TAGAACCTAC ACAGCAATAC GAGAAATGTG TAATTTGGTG |
| 10081 | CTTAGCGGTA TTTATTTAAG CACATGTTGG TGTTATAGGG CACTTGGATT CAGAAGTTTG |
| 10141 | CTGTTAATTT AGGCACAGGC TTCATACTAC ATGGGTCAAT AGTATAGGGA TTCATATTAT |
| 10201 | AGGCGATACT ATAATAATTT GTTCGTCTGC AGAGCTTATT ATTTGCCAAA ATTAGATATT |
| 10261 | CCTATTCTGT TTTTGTTTGT GTGCTGTTAA ATTGTTAACG CCTGAAGGAA TAAATATAAA |
| 10321 | TGACGAAATT TTGATGTTTA TCTCTGCTCC TTTATTGTGA CCATAAGTCA AGATCAGATG |
| 10381 | CACTTGTTTT AAATATTGTT GTCTGAAGAA ATAAGTACTG ACAGTATTTT GATGCATTGA |
| 10441 | TCTGCTTGTT TGTTGTAACA AAATTTAAAA ATAAAGAGTT TCCTTTTTGT TGCTCTCCTT |
| 10501 | ACCTCCTGAT GGTATCTAGT ATCTACCAAC TGATACTATA TTGCTTCTCT TTACATACGT |
| 10561 | ATCTTGCTCG ATGCCTTCTC CTAGTGTTGA CCAGTGTTAC TCACATAGTC TTTGCTCATT |
| 10621 | TCATTGTAAT GCAGATACCA AGCGGTTAAT TAAATGCCGG ACTCCGACAA CGAGTCCGGC |
| 10681 | GGGCCGAGCA ACGCGGAGTT CTCGTCGCCG CGGGAGCAGG ACCGGTTCCT GCCGATCGCG |
| 10741 | AACGTGAGCC GGATCATGAA GAAGGCGCTC CCGGCGAACG CCAAGATCTC CAAGGACGCC |
| 10801 | AAGGAGACGG TGCAGGAGTG CGTCTCCGAG TTCATCTCCT TCATCACCGG CGAGGCCTCC |
| 10861 | GACAAGTGCC AGCGCGAGAA GCGCAAGACC ATCAACGGCG ACGACCTCCT CTGGGCCATG |
| 10921 | ACCACGCTCG GCTTCGAGGA CTACATCGAG CCACTCAAGC TCTACCTCCA CAAGTTCCGC |
| 10981 | GAGCTCGAGG GCGAGAAGGT GGCCTCCGGC GCCGCGGGCT CCTCCGGCTC CGCCTCGCAG |
| 11041 | CCCCAGAGAG AGACAACGCC GTCCGCGCAC AATGGCGCCG CCGGGGCCGT CGGCTACGGC |
| 11101 | ATGTACGCCG CCGGCGCCGG GGCCGGCGGA GGCAGCGGCA TGATCATGAT GATGGGGCAG |
| 11161 | CCGATGTACG GCTCCCCACC GGGCGCGTCG GGGTACCCGC AGCCCCCGCA CCACCACATG |
| 11221 | GTGATGGGCG CTAAAGGTGG CGCCTACGGC CACGGCGGCG GCTCGTCGCC ATCGCTGTCG |
| 11281 | GGGCTCGGCA GGCAGGACAG GCTATGAATG CCGGACTCCG ACAACGAGTC CGGCGGGCCG |
| 11341 | AGCAACGCGG AGTTCTCGTC GCCGCGGGAG CAGGACCGGT TCCTGCCGAT CGCGAACGTG |
| 11401 | AGCCGGATCA TGAAGAAGGC GCTCCCGGCG AACGCCAAGA TCTCCAAGGA CGCCAAGGAG |
| 11461 | ACGGTGCAGG AGTGCGTCTC CGAGTTCATC TCCTTCATCA CCGGCGAGGC CTCCGACAAG |
| 11521 | TGCCAGCGCG AGAAGCGCAA GACCATCAAC GGCGACGACC TCCTCTGGGC CATGACCACG |
| 11581 | CTCGGCTTCG AGGACTACAT CGAGCCACTC AAGCTCTACC TCCACAAGTT CCGCGAGCTC |
| 11641 | GAGGGCGAGA AGGTGGCCTC CGGCGCCGCG GGCTCCTCCG GCTCCGCCTC GCAGCCCCAG |
| 11701 | AGAGAGACAA CGCCGTCCGC GCACAATGGC GCCGCGGGG CCGTCGGCTA CGGCATGTAC |
| 11761 | GGCGCCGGCG CCGGGGCCGG CGGAGGCAGC GGCATGATCA TGATGATGGG GCAGCCGATG |

| | Sequences: |
|---|---|
| 11821 | TACGGCTCCC CACCGGGCGC GTCGGGGTAC CCGCAGCCCC CGCACCACCA CATGGTGATG |
| 11881 | GGCGCTAAAG GTGGCGCCTA CGGCCACGGC GGCGGCTCGT CGCCATCGCT GTCGGGGCTC |
| 11941 | GGCAGGCAGG ACAGGCTATG AAACTGCAGG GCGCGCCATC GTTCAAACAT TTGGCAATAA |
| 12001 | AGTTTCTTAA GATTGAATCC TGTTGCCGGT CTTGCGATGA TTATCATATA ATTTCTGTTG |
| 12061 | AATTACGTTA AGCATGTAAT AATTAACATG TAATGCATGA CGTTATTTAT GAGATGGGTT |
| 12121 | TTTATGATTA GAGTCCCGCA ATTATACATT TAATACGCGA TAGAAAACAA AATATAGCGC |
| 12181 | GCAAACTAGG ATAAATTATC GCGCGCGGTG TCATCTATGT TACTAGATCC GATGATAAGC |
| 12241 | TGTCAAACAT GACCTCAGGA TGAAGCTTGG CACTGGCCGT CGTTTTACAA CGTCGTGACT |
| 12301 | GGGAAAACCC TGGCGTTACC CAACTTAATC GCCTTGCAGC ACATCCCCCT TTCGCCAGCT |
| 12361 | GGCGTAATAG CGAAGAGGCC CGCACCGATC GCCCTTCCCA ACAGTTGCGC AGCCTGAATG |
| 12421 | GCGAATGCTA GAGCAGCTTG AGCTTGGATC AGATTGTCGT TTCCCGCCTT CAGTTTAAAC |
| 12481 | TATCAGTGTT TGACAGGATA TATTGGCGG |

SEQ ID NO: 22 Cyclin delta 2 promoter from maize
| 1 | CCTTTTTACC ATTTTCTATA TCCTTTGCAT CGGCGCCGTA GATAATTGTT GGCTGAAATT |
|---|---|
| 61 | CATGCCAGCT ATATGCTATG TTTCGACCTA GGATTGGCTG CGCAGAGATG GTGGTAGGGC |
| 121 | ACGCCAATTT ATTTGAGATA CAGGTTCTCC ATACGTTCCT TCACTTCATT GCAATGCAGC |
| 181 | AGAGTCATAT ATATACCTGA ATCCCAATCC CAACAAAGGT ACGGACCTCT GTGTCGTGTC |
| 241 | GTCCTCCTCC TCCGGATACA TTGCGTTTAA TTTCGACCGT ATGGATGGAT GGATGGATGT |
| 301 | GGATGTGGTG GCCGTAATCA TGTACTAGCT TGCTTTGGGG GGTCATACGA TTGATTGATT |
| 361 | GATTGATTGC ACGGGCATAC CAGGCTTCAG TGTATTTGCT GCTCTGTAGA TACTTTACTC |
| 421 | ATGTGAAACC CATAAGGGTC GGAGTGAGCT AGGGCCTGTG CGGCCGGCAC ATAGGGATCG |
| 481 | GACGGATGGA TCGGTGGTGG TATGCTAGTA TATATGCATG GTACTACAGC TACTACCCCT |
| 541 | CCTCCTCCTC CTCCTCCCAT AGTGTATGTG TATGTGTATG AGCAGCAGCA GGCCGTATCG |
| 601 | ACAGGCCCAA CAGACAGACG ATGGATCAGA TCGGATCTCC ACACCTTGCC TGGCTCGAGT |
| 661 | AGATCTTGAC CATCCGTGCT CCAATCATGG CCATGGCCGC CGGACTGCAG AGCACCAGGC |
| 721 | ATGCCATCCG GACCCTACTA CTACTACCAG TCGCTTACAC ACCTCTGCCC CAACCGTGTC |
| 781 | TCATTCTTGG CAGTTTGGGG AGGAAGGAAG CCCAATCTTG TCCCTAAAAA ACGCTGTTCC |
| 841 | ATGTAAGTGA CCAGACGACG ACTATACTAG ATCACTAGCC CCTCGAATCC TCGATGAAAA |
| 901 | GAAAAAATAA AAGTCGCGAG CAGTCACGCT CGCCGAACTC AACGTCCGGC CGGGAAGGAA |
| 961 | ATTAACGGCG ACAGAGGGTC GGTCCCCTTT CGTTCGGAAG TCGGAACTGT CATTGGTCGC |
| 1021 | CGTCGTCGTC GCGTCACTGG CATGTGGGGG CCTCGGTCGG CAAACCATCG AGAGCCGAGA |
| 1081 | GCCGGGAGAG AGAGAGAGAG GATGGCAGGT GCACATGCAT |

SEQ ID NO: 23 Phospholipase 2A promoter from maize
| 1 | CACATCGTGC CAAGTTCGAG GCCCATTGAT GCACTTTGCT TACATATATA CTCGTTTAAA |
|---|---|
| 61 | GCATGAGTTT CGTGTATTGT GTGTCATACA CGAAGCACAT ATATCTAATT TTCTCTCCCA |
| 121 | AGTTTCGTCT AACAACTAGA TAAGATAAGC CTTACCTCTT GCATGAGCAA CCAACCATAC |
| 181 | AACCACCACG AGTGCTTTCT CCTCCCCCTT GTTGATGATG TCGTATATTA ACCTCAACAA |
| 241 | CCTACCATCT CTTTCCTCGT CTGCTTCTTC CTCACCCAAA TTCTTCTGTA CCACCATAGA |
| 301 | TGACATCGAG TAGGCCATCC TGCTGGTCTC CGACTCGCTA ACCGCAGCGC CCCACCGCGA |
| 361 | CACCGTCTTT ACCTTCCCCC GTCGACAAGC GCTTCGGAGA GACAATAAGG CAAGAACAAC |

```
421  CGAGTGAGAG GAGGAGACGC TCCGGATCTC GAGTTTAGTT TTATGTTAGT TGTTGACAAA
481  GAAATTGTGA TATATTATGG TCGATAATAA TATATATATA TTGCTGGGTA TCGAATGTTT
541  ATGTGTCGTC GTAACATGCG GATATGTACT AGTATATATA TTATTTGTCA TCTCAAGTGA
601  GGGACCTAAC CATCCATCAC CCGTAGCCAA TGACGCAGTC GGATCAACGA GACACAGGTG
661  GTTGACTCGG TCGGATGCGT TCGATCATGT CTTAGCGATA GATTACTGGT TTATCAGCCT
721  TCGATAAATG TGTTGTTTTG AGTATTATTC TGAGTGCAGG CTTTTGTAGG CTTGTAACAA
781  GTGGGCAGTG ACAAGATTAT TAATGGTTGT TAACAAGTTA GTTTCATGGT GGGAGAGTGC
841  GTTAGCAGTG TCCTAGATAT AAGCAATATC AACTTCTACT AGTTGTACAG TATTTTATTT
901  TTATAGATTA CAGTGCAACA GTCGACCATG CATCTAGCTT TACTAGCGGT GATCATCGTC
961  GTCCACGACA CAAGCAATCA TATTCTGTGA CACTCTTTCC TCGTCCTTAT CAACCCAATT

SEQ ID NO: 24 Sucrose transporter promoter from maize
  1  ACAAAAGAAG ATTAGACTAA TCCAACAGAA TTAGTAAATT CAGAATTCTG TATGGCGAGT
 61  GAGGTAGACT ATCAAAAAAG AGAATGAATA TGTAGATGAA GATCTACTAA TTTTAAGAGC
121  TATTTACAAA GTCTATTAGA GACATTTTCT TATAATAATA ACCAAATTTA CCTTTACAAA
181  ATAATATGAC TAGTCTTTTG GAGTTGCTCC AATAAACAT ATAAAATGGT ACTAGTATGT
241  GTGTAAACCT TTAACTTCTC GAAAAGGGAC ATATTTTTT AGTGAGACAG AATATCATTA
301  GTGAAAAATT GACTTTTGGA TTGGATCTGA TAAGCTAAAT GGGAAACGTA CATGCGTCGG
361  TCGGTGTCCA TTAGTTACTT GACAGCGTCC AGCTCTGGTC ACGGTTTGAG ATTCTATTCT
421  ACCAGAGTAG TGTTTGAAGA TAAGATAGAA TTTAATCACT ATATATATAT ACAATCAAAC
481  TAAACACAAG TAGAAGTGTA ATATAAGAAG AAGAAAAAAA AATCTAGACA ATGTTTGGTA
541  TGACTTTAGA ACAAAATTCT AAGAAAGAGC TGGCAAGAGC AATAAACACC CTAACTAACA
601  AGTTGTATAC TCTCGCATGT AAAATTGCAA CTCCATTAAA AACAATCCAA TTAATCCAAT
661  TTGTTGATGT TGCCCCTATA TCTTTTTTTT TCTACCAACT ATACTACGTA TCTTGATGAA
721  TCTCCATCAA TGCTTGGCAA AACCCCCCTA CCAAGAAACA GATTAAGGAC GGGAATACGG
781  GATGGATAGC CTTCCCAAAC GGATAAAACC TTCGGCCCGC CGTCTCGCTG CCGGTGGGGC
841  ACACGCCATA AACCACACGC GCCGGCCGCC CCCGCCCGTG GCCTTTAAAA AACCCCCGCT
901  CCCGGCGCTC GCTTTTCGCT SEQ ID NO: 25 Cell wall invertase promoter from maize
  1  AGTATGCCAA CTGAAACGGA TGACACATAC ACTTCGTGAA CCAATCGATA TTTTACTTGC
 61  TTCTATGTTA AATAATGTTA TAATACAATA TTTTATTCAA ATGCTAAAAC TTATTACTAG
121  ATAAAAATAA AATTTAATTA TCTTCAAAAA CTAACCAATA GATATTCCAT CATAACTACA
181  TTTACCAAAC TAATATACTA AAAATATAG GATAATTACT AAATTAATCG TGCAATAATC
241  AGTATTTATG AGATTGATAA TTTTAAATTT TGTGGGCTAC AAACAAAAAT TAAAACTTAC
301  TTTTCAAGTT GGAGATAAGA ACAATGGTAG ACGTAGCTCG GGATGGTATG GCGTCGGTGC
361  AGACGGTTAC CCTTTGTGCG AAGTGGCGCG GGCACGAGGG TGGGGACTTG GTACATGCAT
421  GAGAGAGAGG AAGAACGAAA CAACTTCTCA AATTAAAGCA TATGAAAATC ACCTAATTTT
481  TGTCTGTCGG TGGAAACTAA TAACTAGTTT TTATTATCTT TTTTAATAAG GATCCACGAA
541  AATTATTTTT GACCGATGAA ATCCTGGAT CTTCGTATTA TGTTTCGCCT TTTCCCGACT
601  CTTTGCATGC TAGATTTCCA TGCTTGGACT AAAACGAAGA TAATAAAACC AATCTATCAT
```

| | | | | | |
|---|---|---|---|---|---|
| 661 | TTTCACACGA | TGTATTCATA | CTTGCAATAG | ATAAACCACT | ACTCCGACGG GATTTGCTTT |
| 721 | CTGACCTCTG | AAATCTTGGA | AGGATTATGT | GTCTACACTT | CTCGATCGAG GGGAAAAAGT |
| 781 | CGTAGTACCA | AGTTGTAGTT | AAATTTGTTT | CTTCGATGAC | AAAACAAAGG AGAGGGGCCC |
| 841 | GCGCGGCGCA | GCGCAGCGCA | GTTGGCTGGT | TCCGGAACAC | GAAAACCAAG CACACTCCAC |
| 901 | CAGCTGCCAT | CCACCGGGTT | GGATGGAGAT | TACAATACTC | GAATAGTCAG CCAGCCAGCC |
| 961 | GGCTTGAACG | TGCAGTTTTC | CCCTATAAAA | CG | |

SEQ ID NO: 26 pMBXS884

| | | | | | |
|---|---|---|---|---|---|
| 1 | CATGCCAACC | ACAGGGTTCC | CCTCGGGATC | AAAGTACTTT | GATCCAACCC CTCCGCTGCT |
| 61 | ATAGTGCAGT | CGGCTTCTGA | CGTTCAGTGC | AGCCGTCTTC | TGAAAACGAC ATGTCGCACA |
| 121 | AGTCCTAAGT | TACGCGACAG | GCTGCCGCCC | TGCCCTTTTC | CTGGCGTTTT CTTGTCGCGT |
| 181 | GTTTTAGTCG | CATAAAGTAG | AATACTTGCG | ACTAGAACCG | GAGACATTAC GCCATGAACA |
| 241 | AGAGCGCCGC | CGCTGGCCTG | CTGGGCTATG | CCCGCGTCAG | CACCGACGAC CAGGACTTGA |
| 301 | CCAACCAACG | GGCCGAACTG | CACGCGGCCG | GCTGCACCAA | GCTGTTTTCC GAGAAGATCA |
| 361 | CCGGCACCAG | GCGCGACCGC | CCGGAGCTGG | CCAGGATGCT | TGACCACCTA CGCCCTGGCG |
| 421 | ACGTTGTGAC | AGTGACCAGG | CTAGACCGCC | TGGCCCGCAG | CACCCGCGAC CTACTGGACA |
| 481 | TTGCCGAGCG | CATCCAGGAG | GCCGGCGCGG | GCCTGCGTAG | CCTGGCAGAG CCGTGGGCCG |
| 541 | ACACCACCAC | GCCGGCCGGC | CGCATGGTGT | TGACCGTGTT | CGCCGGCATT GCCGAGTTCG |
| 601 | AGCGTTCCCT | AATCATCGAC | CGCACCCGGA | GCGGGCGCGA | GGCCGCCAAG CCCGAGGCG |
| 661 | TGAAGTTTGG | CCCCCGCCCT | ACCCTCACCC | CGGCACAGAT | CGCGCACGCC CGCGAGCTGA |
| 721 | TCGACCAGGA | AGGCCGCACC | GTGAAAGAGG | CGGCTGCACT | GCTTGGCGTG CATCGCTCGA |
| 781 | CCCTGTACCG | CGCACTTGAG | CGCAGCGAGG | AAGTGACGCC | CACCGAGGCC AGGCGGCGCG |
| 841 | GTGCCTTCCG | TGAGGACGCA | TTGACCGAGG | CCGACGCCCT | GGCGGCCGCC GAGAATGAAC |
| 901 | GCCAAGAGGA | ACAAGCATGA | AACCGCACCA | GGACGGCCAG | GACGAACCGT TTTTCATTAC |
| 961 | CGAAGAGATC | GAGGCGGAGA | TGATCGCGGC | CGGGTACGTG | TTCGAGCCGC CCGCGCACGT |
| 1021 | CTCAACCGTG | CGGCTGCATG | AAATCCTGGC | CGGTTTGTCT | GATGCCAAGC TGGCGGCCTG |
| 1081 | GCCGGCCAGC | TTGGCCGCTG | AAGAAACCGA | GCGCCGCCGT | CTAAAAGGT GATGTGTATT |
| 1141 | TGAGTAAAAC | AGCTTGCGTC | ATGCGGTCGC | TGCGTATATG | ATGCGATGAG TAAATAAACA |
| 1201 | AATACGCAAG | GGGAACGCAT | GAAGGTTATC | GCTGTACTTA | ACCAGAAAGG CGGGTCAGGC |
| 1261 | AAGACGACCA | TCGCAACCCA | TCTAGCCCGC | GCCCTGCAAC | TCGCCGGGGC CGATGTTCTG |
| 1321 | TTAGTCGATT | CCGATCCCCA | GGGCAGTGCC | CGCGATTGGG | CGGCCGTGCG GAAGATCAA |
| 1381 | CCGCTAACCG | TTGTCGGCAT | CGACCGCCCG | ACGATTGACC | GCGACGTGAA GGCCATCGGC |
| 1441 | CGGCGCGACT | TCGTAGTGAT | CGACGGAGCG | CCCCAGGCGG | CGGACTTGGC TGTGTCCGCG |
| 1501 | ATCAAGGCAG | CCGACTTCGT | GCTGATTCCG | GTGCAGCCAA | GCCCTTACGA CATATGGGCC |
| 1561 | ACCGCCGACC | TGGTGGAGCT | GGTTAAGCAG | CGCATTGAGG | TCACGGATGG AAGGCTACAA |
| 1621 | GCGGCCTTTG | TCGTGTCGCG | GGCGATCAAA | GGCACGCGCA | TCGGCGGTGA GGTTGCCGAG |
| 1681 | GCGCTGGCCG | GGTACGAGCT | GCCCATTCTT | GAGTCCCGTA | TCACGCAGCG CGTGAGCTAC |
| 1741 | CCAGGCACTG | CCGCCGCCGG | CACAACCGTT | CTTGAATCAG | AACCCGAGGG CGACGCTGCC |
| 1801 | CGCGAGGTCC | AGGCGCTGGC | CGCTGAAATT | AAATCAAAAC | TCATTTGAGT TAATGAGGTA |
| 1861 | AAGAGAAAAT | GAGCAAAAGC | ACAAACACGC | TAAGTGCCGG | CCGTCCGAGC GCACGCAGCA |

-continued

| | |
|---|---|
| | Sequences: |
| 1921 | GCAAGGCTGC AACGTTGGCC AGCCTGGCAG ACACGCCAGC CATGAAGCGG GTCAACTTTC |
| 1981 | AGTTGCCGGC GGAGGATCAC ACCAAGCTGA AGATGTACGC GGTACGCCAA GGCAAGACCA |
| 2041 | TTACCGAGCT GCTATCTGAA TACATCGCGC AGCTACCAGA GTAAATGAGC AAATGAATAA |
| 2101 | ATGAGTAGAT GAATTTTAGC GGCTAAAGGA GGCGGCATGG AAAATCAAGA CAACCAGGC |
| 2161 | ACCGACGCCG TGGAATGCCC CATGTGTGGA GGAACGGGCG GTTGGCCAGG CGTAAGCGGC |
| 2221 | TGGGTTGTCT GCCGGCCCTG CAATGGCACT GGAACCCCCA AGCCCGAGGA ATCGGCGTGA |
| 2281 | CGGTCGCAAA CCATCCGGCC CGGTACAAAT CGGCGCGCG CTGGGTGATG ACCTGGTGGA |
| 2341 | GAAGTTGAAG GCCGCGCAGG CCGCCCAGCG GCAACGCATC GAGGCAGAAG CACGCCCCGG |
| 2401 | TGAATCGTGG CAAGCGGCCG CTGATCGAAT CCGCAAAGAA TCCCGGCAAC CGCCGGCAGC |
| 2461 | CGGTGCGCCG TCGATTAGGA AGCCGCCCAA GGGCGACGAG CAACCAGATT TTTTCGTTCC |
| 2521 | GATGCTCTAT GACGTGGGCA CCCGCGATAG TCGCAGCATC ATGGACGTGG CCGTTTTCCG |
| 2581 | TCTGTCGAAG CGTGACCGAC GAGCTGGCGA GGTGATCCGC TACGAGCTTC AGACGGGCA |
| 2641 | CGTAGAGGTT TCCGCAGGGC CGGCCGGCAT GGCCAGTGTG TGGGATTACG ACCTGGTACT |
| 2701 | GATGGCGGTT TCCCATCTAA CCGAATCCAT GAACCGATAC CGGGAAGGGA AGGGAGACAA |
| 2761 | GCCCGGCCGC GTGTTCCGTC CACACGTTGC GGACGTACTC AAGTTCTGCC GGCGAGCCGA |
| 2821 | TGGCGGAAAG CAGAAAGACG ACCTGGTAGA AACCTGCATT CGGTTAAACA CCACGCACGT |
| 2881 | TGCCATGCAG CGTACGAAGA AGGCCAAGAA CGGCCGCCTG GTGACGGTAT CCGAGGGTGA |
| 2941 | AGCCTTGATT AGCCGCTACA AGATCGTAAA GAGCGAAACC GGGCGGCCGG AGTACATCGA |
| 3001 | GATCGAGCTA GCTGATTGGA TGTACCGCGA GATCACAGAA GGCAAGAACC CGGACGTGCT |
| 3061 | GACGGTTCAC CCCGATTACT TTTTGATCGA TCCCGGCATC GGCCGTTTTC TCTACCGCCT |
| 3121 | GGCACGCCGC GCCGCAGGCA AGGCAGAAGC CAGATGGTTG TTCAAGACGA TCTACGAACG |
| 3181 | CAGTGGCAGC GCCGGAGAGT TCAAGAAGTT CTGTTTCACC GTGCGCAAGC TGATCGGGTC |
| 3241 | AAATGACCTG CCGGAGTACG ATTTGAAGGA GGAGGCGGGG CAGGCTGGCC CGATCCTAGT |
| 3301 | CATGCGCTAC CGCAACCTGA TCGAGGGCA AGCATCCGCC GGTTCCTAAT GTACGGAGCA |
| 3361 | GATGCTAGGG CAAATTGCCC TAGCAGGGGA AAAAGGTCGA AAAGGTCTCT TTCCTGTGGA |
| 3421 | TAGCACGTAC ATTGGGAACC CAAAGCCGTA CATTGGGAAC CGGAACCCGT ACATTGGGAA |
| 3481 | CCCAAAGCCG TACATTGGGA ACCGGTCACA CATGTAAGTG ACTGATATAA AGAGAAAAA |
| 3541 | AGGCGATTTT TCCGCCTAAA ACTCTTTAAA ACTTATTAAA ACTCTTAAAA CCCGCCTGGC |
| 3601 | CTGTGCATAA CTGTCTGGCC AGCGCACAGC CGAAGAGCTG CAAAAAGCGC CTACCCTTCG |
| 3661 | GTCGCTGCGC TCCCTACGCC CCGCCGCTTC GCGTCGGCCT ATCGCGGCCG CTGGCCGCTC |
| 3721 | AAAAATGGCT GGCCTACGGC CAGGCAATCT ACCAGGGCGC GGACAAGCCG CGCCGTCGCC |
| 3781 | ACTCGACCGC CGGCGCCCAC ATCAAGGCAC CCTGCCTCGC GCGTTTCGGT GATGACGGTG |
| 3841 | AAAACCTCTG ACACATGCAG CTCCCGGAGA CGGTCACAGC TTGTCTGTAA GCGGATGCCG |
| 3901 | GGAGCAGACA AGCCCGTCAG GGCGCGTCAG CGGGTGTTGG CGGGTGTCGG GGCGCAGCCA |
| 3961 | TGACCCAGTC ACGTAGCGAT AGCGGAGTGT ATACTGGCTT AACTATGCGG CATCAGAGCA |
| 4021 | GATTGTACTG AGAGTGCACC ATATGCGGTG TGAAATACCG CACAGATGCG TAAGGAGAAA |
| 4081 | ATACCGCATC AGGCGCTCTT CCGCTTCCTC GCTCACTGAC TCGCTGCGCT CGGTCGTTCG |
| 4141 | GCTGCGGCGA GCGGTATCAG CTCACTCAAA GGCGGTAATA CGGTTATCCA CAGAATCAGG |
| 4201 | GGATAACGCA GGAAAGAACA TGTGAGCAAA AGGCCAGCAA AAGGCCAGGA ACCGTAAAAA |

| | |
|---|---|
| 4261 | GGCCGCGTTG CTGGCGTTTT TCCATAGGCT CCGCCCCCCT GACGAGCATC ACAAAAATCG |
| 4321 | ACGCTCAAGT CAGAGGTGGC GAAACCCGAC AGGACTATAA AGATACCAGG CGTTTCCCCC |
| 4381 | TGGAAGCTCC CTCGTGCGCT CTCCTGTTCC GACCCTGCCG CTTACCGGAT ACCTGTCCGC |
| 4441 | CTTTCTCCCT TCGGGAAGCG TGGCGCTTTC TCATAGCTCA CGCTGTAGGT ATCTCAGTTC |
| 4501 | GGTGTAGGTC GTTCGCTCCA AGCTGGGCTG TGTGCACGAA CCCCCCGTTC AGCCCGACCG |
| 4561 | CTGCGCCTTA TCCGGTAACT ATCGTCTTGA GTCCAACCCG GTAAGACACG ACTTATCGCC |
| 4621 | ACTGGCAGCA GCCACTGGTA ACAGGATTAG CAGAGCGAGG TATGTAGGCG GTGCTACAGA |
| 4681 | GTTCTTGAAG TGGTGGCCTA ACTACGGCTA CACTAGAAGG ACAGTATTTG GTATCTGCGC |
| 4741 | TCTGCTGAAG CCAGTTACCT TCGGAAAAAG AGTTGGTAGC TCTTGATCCG GCAAACAAAC |
| 4801 | CACCGCTGGT AGCGGTGGTT TTTTTGTTTG CAAGCAGCAG ATTACGCGCA GAAAAAAAGG |
| 4861 | ATCTCAAGAA GATCCTTTGA TCTTTTCTAC GGGGTCTGAC GCTCAGTGGA ACGAAAACTC |
| 4921 | ACGTTAAGGG ATTTTGGTCA TGCATTCTAG GTACTAAAAC AATTCATCCA GTAAAATATA |
| 4981 | ATATTTTATT TTCTCCCAAT CAGGCTTGAT CCCCAGTAAG TCAAAAAATA GCTCGACATA |
| 5041 | CTGTTCTTCC CCGATATCCT CCCTGATCGA CCGGACGCAG AAGGCAATGT CATACCACTT |
| 5101 | GTCCGCCCTG CCGCTTCTCC CAAGATCAAT AAAGCCACTT ACTTTGCCAT CTTTCACAAA |
| 5161 | GATGTTGCTG TCTCCCAGGT CGCCGTGGGA AAAGACAAGT TCCTCTTCGG GCTTTTCCGT |
| 5221 | CTTTAAAAAA TCATACAGCT CGCGCGGATC TTTAAATGGA GTGTCTTCTT CCCAGTTTTC |
| 5281 | GCAATCCACA TCGGCCAGAT CGTTATTCAG TAAGTAATCC AATTCGGCTA AGCGGCTGTC |
| 5341 | TAAGCTATTC GTATAGGGAC AATCCGATAT GTCGATGGAG TGAAAGAGCC TGATGCACTC |
| 5401 | CGCATACAGC TCGATAATCT TTTCAGGGCT TTGTTCATCT TCATACTCTT CCGAGCAAAG |
| 5461 | GACGCCATCG GCCTCACTCA TGAGCAGATT GCTCCAGCCA TCATGCCGTT CAAAGTGCAG |
| 5521 | GACCTTTGGA ACAGGCAGCT TTCCTTCCAG CCATAGCATC ATGTCCTTTT CCCGTTCCAC |
| 5581 | ATCATAGGTG GTCCCTTTAT ACCGGCTGTC CGTCATTTTT AAATATAGGT TTTCATTTTC |
| 5641 | TCCCACCAGC TTATATACCT TAGCAGGAGA CATTCCTTCC GTATCTTTTA CGCAGCGGTA |
| 5701 | TTTTTCGATC AGTTTTTTCA ATTCCGGTGA TATTCTCATT TTAGCCATTT ATTATTTCCT |
| 5761 | TCCTCTTTTC TACAGTATTT AAAGATACCC CAAGAAGCTA ATTATAACAA GACGAACTCC |
| 5821 | AATTCACTGT TCCTTGCATT CTAAAACCTT AAATACCAGA AAACAGCTTT TCAAAGTTG |
| 5881 | TTTTCAAAGT TGGCGTATAA CATAGTATCG ACGGAGCCGA TTTTGAAACC GCGGTGATCA |
| 5941 | CAGGCAGCAA CGCTCTGTCA TCGTTACAAT CAACATGCTA CCCTCCGCGA GATCATCCGT |
| 6001 | GTTTCAAACC CGGCAGCTTA GTTGCCGTTC TTCCGAATAG CATCGGTAAC ATGAGCAAAG |
| 6061 | TCTGCCGCCT TACAACGGCT CTCCCGCTGA CGCCGTCCCG GACTGATGGG CTGCCTGTAT |
| 6121 | CGAGTGGTGA TTTTGTGCCG AGCTGCCGGT CGGGGAGCTG TTGGCTGGCT GGTGGCAGGA |
| 6181 | TATATTGTGG TGTAAACAAA TTGACGCTTA GACAACTTAA TAACACATTG CGGACGTTTT |
| 6241 | TAATGTACTG AATTAACGCC GAATTAATTC GGGGGATCTG GATTTTAGTA CTGGATTTTG |
| 6301 | GTTTTAGGAA TTAGAAATTT TATTGATAGA AGTATTTTAC AAATACAAAT ACATACTAAG |
| 6361 | GGTTTCTTAT ATGCTCAACA CATGAGCGAA ACCCTATAGG AACCCTAATT CCCTTATCTG |
| 6421 | GGAACTACTC ACACATTATT ATGGAGAAAC TCGAGGGATC CCGGTCGGCA TCTACTCTAT |
| 6481 | TCCTTTGCCC TCGGACGAGT GCTGGGGCGT CGGTTTCCAC TATCGGCGAG TACTTCTACA |

-continued

| | Sequences: |
|---|---|
| 6541 | CAGCCATCGG TCCAGACGGC CGCGCTTCTG CGGGCGATTT GTGTACGCCC GACAGTCCCG |
| 6601 | GCTCCGGATC GGACGATTGC GTCGCATCGA CCCTGCGCCC AAGCTGCATC ATCGAAATTG |
| 6661 | CCGTCAACCA AGCTCTGATA GAGTTGGTCA AGACCAATGC GGAGCATATA CGCCCGGAGC |
| 6721 | CGCGGCGATC CTGCAAGCTC CGGATGCCTC CGCTCGAAGT AGCGCGTCTG CTGCTCCATA |
| 6781 | CAAGCCAACC ACGGCCTCCA GAAGAAGATG TTGGCGACCT CGTATTGGGA ATCCCCGAAC |
| 6841 | ATCGCCTCGC TCCAGTCAAT GACCGCTGTT ATGCGGCCAT TGTCCGTCAG GACATTGTTG |
| 6901 | GAGCCGAAAT CCGCGTGCAC GAGGTGCCGG ACTTCGGGGC AGTCCTCGGC CCAAAGCATC |
| 6961 | AGCTCATCGA GAGCCTGCGC GACGGACGCA CTGACGGTGT CGTCCATCAC AGTTTGCCAG |
| 7021 | TGATACACAT GGGGATCAGC AATCGCGCAT ATGAAATCAC GCCATGTAGT GTATTGACCG |
| 7081 | ATTCCTTGCG GTCCGAATGG GCCGAACCCG CTCGTCTGGC TAAGATCGGC CGCAGCGATC |
| 7141 | GCATCCATGG CCTCCGCGAC CGGCTGCAGT TATCATCATC ATCATAGACA CACGAAATAA |
| 7201 | AGTAATCAGA TTATCAGTTA AAGCTATGTA ATATTTACAC CATAACCAAT CAATTAAAAA |
| 7261 | ATAGATCAGT TTAAAGAAAG ATCAAAGCTC AAAAAAATAA AAAGAGAAAA GGGTCCTAAC |
| 7321 | CAAGAAAATG AAGGAGAAAA ACTAGAAATT TACCTGCAGA ACAGCGGGCA GTTCGGTTTC |
| 7381 | AGGCAGGTCT TGCAACGTGA CACCCTGTGC ACGGCGGGAG ATGCAATAGG TCAGGCTCTC |
| 7441 | GCTGAATTCC CCAATGTCAA GCACTTCCGG AATCGGGAGC GCGGCCGATG CAAAGTGCCG |
| 7501 | ATAAACATAA CGATCTTTGT AGAAACCATC GGCGCAGCTA TTTACCCGCA GGACATATCC |
| 7561 | ACGCCCTCCT ACATCGAAGC TGAAAGCACG AGATTCTTCG CCCTCCGAGA GCTGCATCAG |
| 7621 | GTCGGAGACG CTGTCGAACT TTTCGATCAG AAACTTCTCG ACAGACGTCG CGGTGAGTTC |
| 7681 | AGGCTTTTTC ATGGTAGAGG AGCTCGCCGC TTGGTATCTG CATTACAATG AAATGAGCAA |
| 7741 | AGACTATGTG AGTAACACTG GTCAACACTA GGGAGAAGGC ATCGAGCAAG ATACGTATGT |
| 7801 | AAAGAGAAGC AATATAGTGT CAGTTGGTAG ATACTAGATA CCATCAGGAG GTAAGGAGAG |
| 7861 | CAACAAAAAG GAAACTCTTT ATTTTTAAAT TTTGTTACAA CAAACAAGCA GATCAATGCA |
| 7921 | TCAAAATACT GTCAGTACTT ATTTCTTCAG ACAACAATAT TTAAAACAAG TGCATCTGAT |
| 7981 | CTTGACTTAT GGTCACAATA AAGGAGCAGA GATAAACATC AAAATTTCGT CATTTATATT |
| 8041 | TATTCCTTCA GGCGTTAACA ATTTAACAGC ACACAAACAA AAACAGAATA GGAATATCTA |
| 8101 | ATTTTGGCAA ATAATAAGCT CTGCAGACGA ACAAATTATT ATAGTATCGC CTATAATATG |
| 8161 | AATCCCTATA CTATTGACCC ATGTAGTATG AAGCCTGTGC CTAAATTAAC AGCAAACTTC |
| 8221 | TGAATCCAAG TGCCCTATAA CACCAACATG TGCTTAAATA AATACCGCTA AGCACCAAAT |
| 8281 | TACACATTTC TCGTATTGCT GTGTAGGTTC TATCTTCGTT TCGTACTACC ATGTCCCTAT |
| 8341 | ATTTTGCTGC TACAAAGGAC GGCAAGTAAT CAGCACAGGC AGAACACGAT TTCAGAGTGT |
| 8401 | AATTCTAGAT CCAGCTAAAC CACTCTCAGC AATCACCACA CAAGAGAGCA TTCAGAGAAA |
| 8461 | CGTGGCAGTA ACAAAGGCAG AGGGCGGAGT GAGCGCGTAC CGAAGACGGT AGATCTCTCG |
| 8521 | AGAGAGATAG ATTTGTAGAG AGAGACTGGT GATTTCAGCG TGTCCTCTCC AAATGAAATG |
| 8581 | AACTTCCTTA TATAGAGGAA GGTCTTGCGA AGGATAGTGG GATTGTGCGT CATCCCTTAC |
| 8641 | GTCAGTGGAG ATATCACATC AATCCACTTG CTTTGAAGAC GTGGTTGGAA CGTCTTCTTT |
| 8701 | TTCCACGATG CTCCTCGTGG GTGGGGGTCC ATCTTTGGGA CCACTGTCGG CAGAGGCATC |
| 8761 | TTGAACGATA GCCTTTCCTT TATCGCAATG ATGGCATTTG TAGGTGCCAC CTTCCTTTTC |
| 8821 | TACTGTCCTT TTGATGAAGT GACAGATAGC TGGGCAATGG AATCCGAGGA GGTTTCCCGA |

-continued

| | | | | | |
|---|---|---|---|---|---|
| 8881 | TATTACCCTT | TGTTGAAAAG | TCTCAATAGC | CCTTTGGTCT | TCTGAGACTG | TATCTTTGAT |
| 8941 | ATTCTTGGAG | TAGACGAGAG | TGTCGTGCTC | CACCATGTTA | TCACATCAAT | CCACTTGCTT |
| 9001 | TGAAGACGTG | GTTGGAACGT | CTTCTTTTTC | CACGATGCTC | CTCGTGGGTG | GGGGTCCATC |
| 9061 | TTTGGGACCA | CTGTCGGCAG | AGGCATCTTG | AACGATAGCC | TTTCCTTTAT | CGCAATGATG |
| 9121 | GCATTTGTAG | GTGCCACCTT | CCTTTTCTAC | TGTCCTTTTG | ATGAAGTGAC | AGATAGCTGG |
| 9181 | GCAATGGAAT | CCGAGGAGGT | TTCCCGATAT | TACCCTTTGT | TGAAAAGTCT | CAATAGCCCT |
| 9241 | TTGGTCTTCT | GAGACTGTAT | CTTTGATATT | CTTGGAGTAG | ACGAGAGTGT | CGTGCTCCAC |
| 9301 | CATGTTGGCA | AGCTGCTCTA | GCCAATACGC | AAACCGCCTC | TCCCCGCGCG | TTGGCCGATT |
| 9361 | CATTAATGCA | GCTGGCACGA | CAGGTTTCCC | GACTGGAAAG | CGGGCAGTGA | GCGCAACGCA |
| 9421 | ATTAATGTGA | GTTAGCTCAC | TCATTAGGCA | CCCCAGGCTT | TACACTTTAT | GCTTCCGGCT |
| 9481 | CGTATGTTGT | GTGGAATTGT | GAGCGGATAA | CAATTTCACA | CAGGAAACAG | CTATGACCAT |
| 9541 | GATTACGAAT | TCGAGCTCGG | TACCCCACGG | AAGATCCAGG | TCTCGAGACT | AGGAGACGGA |
| 9601 | TGGGAGGCGC | AACGCGCGAT | GGGGAGGGGG | GCGGCGCTGA | CCTTTCTGGC | GAGGTCGAGG |
| 9661 | TAGCGATCGA | GCAGCTGCAG | CGCGGACACG | ATGAGGAAGA | CGAAGATAGC | CGCCATGGAC |
| 9721 | ATGTTCGCCA | GCGGCGGCGG | AGCGAGGCTG | AGCCGGTCTC | TCCGGCCTCC | GGTCGGCGTT |
| 9781 | AAGTTGGGGA | TCGTAACGTG | ACGTGTCTCG | TCTCCACGGA | TCGACACAAC | CGGCCTACTC |
| 9841 | GGGTGCACGA | CGCCGCGATA | AGGGCGAGAT | GTCCGTGCAC | GCAGCCCGTT | TGGAGTCCTC |
| 9901 | GTTGCCCACG | AACCGACCCC | TTACAGAACA | AGGCCTAGCC | CAAAACTATT | CTGAGTTGAG |
| 9961 | CTTTTGAGCC | TAGCCCACCT | AAGCCGAGCG | TCATGAACTG | ATGAACCCAC | TACCACTAGT |
| 10021 | CAAGGCAAAC | CACAACCACA | AATGGATCAA | TTGATCTAGA | ACAATCCGAA | GGAGGGGAGG |
| 10081 | CCACGTCACA | CTCACACCAA | CCGAAATATC | TGCCAGAATC | AGATCAACCG | GCCAATAGGA |
| 10141 | CGCCAGCGAG | CCCAACACCT | GGCGACGCCG | CAAAATTCAC | CGCGAGGGGC | ACCGGGCACG |
| 10201 | GCAAAAACAA | AGCCCGGCG | CGGTGAGAAT | ATCTGGCGAC | TGGCGGAGAC | CTGGTGGCCA |
| 10261 | GCGCGCGGCC | ACATCAGCCA | CCCCATCCGC | CCACCTCACC | TCCGGCGAGC | CAATGGCAAC |
| 10321 | TCGTCTTAAG | ATTCCACGAG | ATAAGGACCC | GATCGCCGGC | GACGCTATTT | AGCCAGGTGC |
| 10381 | GCCCCCCACG | GTACACTCCA | CCAGCGGCAT | CTATAGCAAC | CGGTCCAGCA | CTTTCACGCT |
| 10441 | CAGCTTCAGC | AAGATCTACC | GTCTTCGGTA | CGCGCTCACT | CCGCCCTCTG | CCTTTGTTAC |
| 10501 | TGCCACGTTT | CTCTGAATGC | TCTCTTGTGT | GGTGATTGCT | GAGAGTGGTT | TAGCTGGATC |
| 10561 | TAGAATTACA | CTCTGAAATC | GTGTTCTGCC | TGTGCTGATT | ACTTGCCGTC | CTTTGTAGCA |
| 10621 | GCAAAATATA | GGGACATGGT | AGTACGAAAC | GAAGATAGAA | CCTACACAGC | AATACGAGAA |
| 10681 | ATGTGTAATT | TGGTGCTTAG | CGGTATTTAT | TTAAGCACAT | GTTGGTGTTA | TAGGGCACTT |
| 10741 | GGATTCAGAA | GTTTGCTGTT | AATTTAGGCA | CAGGCTTCAT | ACTACATGGG | TCAATAGTAT |
| 10801 | AGGGATTCAT | ATTATAGGCG | ATACTATAAT | AATTTGTTCG | TCTGCAGAGC | TTATTATTTG |
| 10861 | CCAAAATTAG | ATATTCCTAT | TCTGTTTTTG | TTTGTGTGCT | GTTAAATTGT | TAACGCCTGA |
| 10921 | AGGAATAAAT | ATAAATGACG | AAATTTGAT | GTTTATCTCT | GCTCCTTTAT | TGTGACCATA |
| 10981 | AGTCAAGATC | AGATGCACTT | GTTTTAAATA | TTGTTGTCTG | AAGAAATAAG | TACTGACAGT |
| 11041 | ATTTTGATGC | ATTGATCTGC | TTGTTTGTTG | TAACAAAATT | TAAAAATAAA | GAGTTTCCTT |
| 11101 | TTTGTTGCTC | TCCTTACCTC | CTGATGGTAT | CTAGTATCTA | CCAACTGATA | CTATATTGCT |

-continued

| | Sequences: |
|---|---|
| 11161 | TCTCTTTACA NNNNNNTCTT GCTCGATGCC TTCTCCTAGT GTTGACCAGT GTTACTCACA |
| 11221 | TAGTCTTTGC TCATTTCATT GTAATGCAGA TACCAAGCGG TTAATTAACT ATGAGTCTTT |
| 11281 | TCCTTTTACG ATTCCTCCAC TTCTCCAACT ACATCAAAGG GAGTACAACC GCAAAGTCCG |
| 11341 | TAGCCTTCCA GGTGCGCGCT GAGAAATTCG CGAACCGCAA GCGTAAGAAT CAGTATAGAG |
| 11401 | GCATACGCCA GAGACCGTGG GGTAAGTGGG CCGCCGAAAT CCGTGATCCA CGTAAGGGAG |
| 11461 | TGCGAGTCTG GCTTGGCACG TTCAATACTG CAGAAGAAGC GGCGAGGGCG TATGATGCAG |
| 11521 | AGGCAAGGCG TATAAGGGGT AAGAAAGCGA AAGTTAATTT TCCTGAGGAG GCTCCCGGGA |
| 11581 | CCTCTGTCAA ACGTTCCAAA GTGAATCCCC AGGAAAACCT TTCGCACAAA TTCGGCGCCG |
| 11641 | GCAACAATCA CATGGATTTG GTGGAGCAGA AGCCGCTGGT TAATCAGTAC GCAAACATGG |
| 11701 | CGTCATTTCC GGGGAGCGGG AATGGATTAA CCTCTCTACC AAGTAGCGAT GACGTGACAC |
| 11761 | TATACTTCAG TAGCGACCAG GGCTCCAACT CATTTGGGTG GTCCGAGCAG GGGCCGAAAA |
| 11821 | CTCCTGAAAT AAGCAGCATG TTAAGCGCCC CACTCGATTG TGAATCTCAT TTCGTACAAA |
| 11881 | ATGCTAACCA ACAGCCGAAT TCACAGAATG TCGTGTCCAT GGAGGATGAC TCAGCTAAAA |
| 11941 | GGCTGAGCGA AGAACGCGTT GATATTGAGT CGGAGCTAAA ATTCTTCCAA ATGGCGTACT |
| 12001 | TGGAAGGATC ATGGGCGAC ACAAGTCTCG AGTCGCTCCT GTCGGGAGAT ACGACGCAAG |
| 12061 | ACGGCGGGAA TCTAATGAAT CTATGGAGCT TCGATGATAT TCCATCAATG TCTTCTGGCG |
| 12121 | TGTTTATGAG TCTTTTCCTT TTACGATTCC TCCACTTCTC CAACTACATC AAAGGGAGTA |
| 12181 | CAACCGCAAA GTCCGTAGCC TTCCAGGTGC GCGCTGAGAA ATTCGCGAAC CGCAAGCGTA |
| 12241 | AGAATCAGTA TAGAGGCATA CGCCAGAGAC CGTGGGGTAA GTGGGCCGCC GAAATCCGTG |
| 12301 | ATCCACGTAA GGGAGTGCGA GTCTGGCTTG GCACGTTCAA TACTGCAGAA GAAGCGGCGA |
| 12361 | GGGCGTATGA TGCAGAGGCA AGGCGTATAA GGGGTAAGAA AGCGAAAGTT AATTTTCCTG |
| 12421 | AGGAGGCTCC CGGGACCTCT GTCAAACGTT CCAAAGTGAA TCCCCAGGAA AACCTTTCGC |
| 12481 | ACAAATTCGG CGCCGGCAAC AATCACATGG ATTTGGTGGA GCAGAAGCCG CTGGTTAATC |
| 12541 | AGTACGCAAA CATGGCGTCA TTTCCGGGGA GCGGGAATGG ATTAACCTCT CTACCAAGTA |
| 12601 | GCGATGACGT GACACTATAC TTCAGTAGCG ACCAGGGCTC CAACTCATTT GGGTGGTCCG |
| 12661 | AGCAGGGGCC GAAAACTCCT GAAATAAGCA GCATGTTAAG CGCCCCACTC GATTGTGAAT |
| 12721 | CTCATTTCGT ACAAAATGCT AACCAACAGC CGAATTCACA GAATGTCGTG TCCATGGAGG |
| 12781 | ATGACTCAGC TAAAAGGCTG AGCGAAGAAC GCGTTGATAT TGAGTCGGAG CTAAAATTCT |
| 12841 | TCCAAATGGC GTACTTGGAA GGATCATGGG GCGACACAAG TCTCGAGTCG CTCCTGTCGG |
| 12901 | GAGATACGAC GCAAGACGGC GGGAATCTAA TGAATCTATG GAGCTTCGAT GATATTCCAT |
| 12961 | CAATGTCTTC TGGCGTGTTT GCAGGGCGCG CCATCGTTCA AACATTTGGC AATAAAGTTT |
| 13021 | CTTAAGATTG AATCCTGTTG CCGGTCTTGC GATGATTATC ATATAATTTC TGTTGAATTA |
| 13081 | CGTTAAGCAT GTAATAATTA ACATGTAATG CATGACGTTA TTTATGAGAT GGGTTTTTAT |
| 13141 | GATTAGAGTC CCGCAATTAT ACATTTAATA CGCGATAGAA AACAAAATAT AGCGCGCAAA |
| 13201 | CTAGGATAAA TTATCGCGCG CGGTGTCATC TATGTTACTA GATCCGATGA TAAGCTGTCA |
| 13261 | AACATGAAAG CTTGGCACTG GCCGTCGTTT TACAACGTCG TGACTGGGAA ACCCTGGCG |
| 13321 | TTACCCAACT TAATCGCCTT GCAGCACATC CCCCTTTCGC CAGCTGGCGT AATAGCGAAG |
| 13381 | AGGCCCGCAC CGATCGCCCT TCCCAACAGT TGCGCAGCCT GAATGGCGAA TGCTAGAGCA |
| 13441 | GCTTGAGCTT GGATCAGATT GTCGTTTCCC GCCTTCAGTT TAAACTATCA GTGTTTGACA |

-continued

Sequences:

13501 GGATATATTG GCGGGTAAAC CTAAGAGAAA AGAGCGTTTA TTAGAATAAC GGATATTTAA

13561 AAGGGCGTGA AAAGGTTTAT CCGTTCGTCC ATTTGTATGT G

SEQ ID NO: 27 pMBXS885
   1 CATGCCAACC ACAGGGTTCC CCTCGGGATC AAAGTACTTT GATCCAACCC CTCCGCTGCT
  61 ATAGTGCAGT CGGCTTCTGA CGTTCAGTGC AGCCGTCTTC TGAAAACGAC ATGTCGCACA
 121 AGTCCTAAGT TACGCGACAG GCTGCCGCCC TGCCCTTTTC CTGGCGTTTT CTTGTCGCGT
 181 GTTTTAGTCG CATAAAGTAG AATACTTGCG ACTAGAACCG AGACATTAC GCCATGAACA
 241 AGAGCGCCGC CGCTGGCCTG CTGGGCTATG CCCGCGTCAG CACCGACGAC CAGGACTTGA
 301 CCAACCAACG GGCCGAACTG CACGCGGCCG GCTGCACCAA GCTGTTTTCC GAGAAGATCA
 361 CCGGCACCAG GCGCGACCGC CCGGAGCTGG CCAGGATGCT TGACCACCTA CGCCCTGGCG
 421 ACGTTGTGAC AGTGACCAGG CTAGACCGCC TGGCCCGCAG CACCCGCGAC CTACTGGACA
 481 TTGCCGAGCG CATCCAGGAG GCCGGCGCGG GCCTGCGTAG CCTGGCAGAG CCGTGGGCCG
 541 ACACCACCAC GCCGGCCGGC CGCATGGTGT TGACCGTGTT CGCCGGCATT GCCGAGTTCG
 601 AGCGTTCCCT AATCATCGAC CGCACCCGGA GCGGGCGCGA GGCCGCCAAG CCCGAGGCG
 661 TGAAGTTTGG CCCCCGCCCT ACCCTCACCC CGGCACAGAT CGCGCACGCC CGCGAGCTGA
 721 TCGACCAGGA AGGCCGCACC GTGAAAGAGG CGGCTGCACT GCTTGGCGTG CATCGCTCGA
 781 CCCTGTACCG CGCACTTGAG CGCAGCGAGG AAGTGACGCC CACCGAGGCC AGGCGGCGCG
 841 GTGCCTTCCG TGAGGACGCA TTGACCGAGG CCGACGCCCT GGCGGCCGCC GAGAATGAAC
 901 GCCAAGAGGA CAAGCATGA AACCGCACCA GGACGGCCAG GACGAACCGT TTTTCATTAC
 961 CGAAGAGATC GAGGCGGAGA TGATCGCGGC CGGGTACGTG TTCGAGCGCC CCGCGCACGT
1021 CTCAACCGTG CGGCTGCATG AAATCCTGGC CGGTTTGTCT GATGCCAAGC TGGCGGCCTG
1081 GCCGGCCAGC TTGGCCGCTG AAGAAACCGA GCGCCGCCGT CTAAAAAGGT GATGTGTATT
1141 TGAGTAAAAC AGCTTGCGTC ATGCGGTCGC TGCGTATATG ATGCGATGAG TAAATAAACA
1201 AATACGCAAG GGAACGCAT GAAGGTTATC GCTGTACTTA ACCAGAAAGG CGGGTCAGGC
1261 AAGACGACCA TCGCAACCCA TCTAGCCCGC GCCCTGCAAC TCGCCGGGGC CGATGTTCTG
1321 TTAGTCGATT CCGATCCCCA GGGCAGTGCC CGCGATTGGG CGGCCGTGCG GAAGATCAA
1381 CCGCTAACCG TTGTCGGCAT CGACCGCCCG ACGATTGACC GCGACGTGAA GGCCATCGGC
1441 CGGCGCGACT TCGTAGTGAT CGACGGAGCG CCCCAGGCGG CGGACTTGGC TGTGTCCGCG
1501 ATCAAGGCAG CCGACTTCGT GCTGATTCCG GTGCAGCCAA GCCCTTACGA CATATGGGCC
1561 ACCGCCGACC TGGTGGAGCT GGTTAAGCAG CGCATTGAGG TCACGGATGG AAGGCTACAA
1621 GCGGCCTTTG TCGTGTCGCG GGCGATCAAA GGCACGCGCA TCGGCGGTGA GGTTGCCGAG
1681 GCGCTGGCCG GGTACGAGCT GCCCATTCTT GAGTCCCGTA TCACGCAGCG CGTGAGCTAC
1741 CCAGGCACTG CCGCCGCCGG CACAACCGTT CTTGAATCAG AACCCGAGGG CGACGCTGCC
1801 CGCGAGGTCC AGGCGCTGGC CGCTGAAATT AAATCAAAAC TCATTTGAGT TAATGAGGTA
1861 AAGAGAAAAT GAGCAAAAGC ACAAACACGC TAAGTGCCGG CCGTCCGAGC GCACGCAGCA
1921 GCAAGGCTGC AACGTTGGCC AGCCTGGCAG ACACGCCAGC CATGAAGCGG GTCAACTTTC
1981 AGTTGCCGGC GGAGGATCAC ACCAAGCTGA AGATGTACGC GGTACGCCAA GGCAAGACCA
2041 TTACCGAGCT GCTATCTGAA TACATCGCGC AGCTACCAGA GTAAATGAGC AAATGAATAA
2101 ATGAGTAGAT GAATTTTAGC GGCTAAAGGA GGCGGCATGG AAAATCAAGA ACAACCAGGC

| | Sequences: |
|---|---|
| 2161 | ACCGACGCCG TGGAATGCCC CATGTGTGGA GGAACGGGCG GTTGGCCAGG CGTAAGCGGC |
| 2221 | TGGGTTGTCT GCCGGCCCTG CAATGGCACT GGAACCCCCA AGCCCGAGGA ATCGGCGTGA |
| 2281 | CGGTCGCAAA CCATCCGGCC CGGTACAAAT CGGCGCGGCG CTGGGTGATG ACCTGGTGGA |
| 2341 | GAAGTTGAAG GCCGCGCAGG CCGCCCAGCG GCAACGCATC GAGGCAGAAG CACGCCCCGG |
| 2401 | TGAATCGTGG CAAGCGGCCG CTGATCGAAT CCGCAAAGAA TCCCGGCAAC CGCCGGCAGC |
| 2461 | CGGTGCGCCG TCGATTAGGA AGCCGCCCAA GGGCGACGAG CAACCAGATT TTTTCGTTCC |
| 2521 | GATGCTCTAT GACGTGGGCA CCCGCGATAG TCGCAGCATC ATGGACGTGG CCGTTTTCCG |
| 2581 | TCTGTCGAAG CGTGACCGAC GAGCTGGCGA GGTGATCCGC TACGAGCTTC AGACGGGCA |
| 2641 | CGTAGAGGTT TCCGCAGGGC CGGCCGGCAT GGCCAGTGTG TGGGATTACG ACCTGGTACT |
| 2701 | GATGGCGGTT TCCCATCTAA CCGAATCCAT GAACCGATAC CGGGAAGGGA AGGGAGACAA |
| 2761 | GCCCGGCCGC GTGTTCCGTC CACACGTTGC GGACGTACTC AAGTTCTGCC GGCGAGCCGA |
| 2821 | TGGCGGAAAG CAGAAAGACG ACCTGGTAGA AACCTGCATT CGGTTAAACA CCACGCACGT |
| 2881 | TGCCATGCAG CGTACGAAGA AGGCCAAGAA CGGCCGCCTG GTGACGGTAT CCGAGGGTGA |
| 2941 | AGCCTTGATT AGCCGCTACA AGATCGTAAA GAGCGAAACC GGGCGGCCGG AGTACATCGA |
| 3001 | GATCGAGCTA GCTGATTGGA TGTACCGCGA GATCACAGAA GGCAAGAACC CGGACGTGCT |
| 3061 | GACGGTTCAC CCCGATTACT TTTTGATCGA TCCCGGCATC GGCCGTTTTC TCTACCGCCT |
| 3121 | GGCACGCCGC GCCGCAGGCA AGGCAGAAGC CAGATGGTTG TTCAAGACGA TCTACGAACG |
| 3181 | CAGTGGCAGC GCCGGAGAGT TCAAGAAGTT CTGTTTCACC GTGCGCAAGC TGATCGGGTC |
| 3241 | AAATGACCTG CCGGAGTACG ATTTGAAGGA GGAGGCGGGG CAGGCTGGCC CGATCCTAGT |
| 3301 | CATGCGCTAC CGCAACCTGA TCGAGGGCGA AGCATCCGCC GGTTCCTAAT GTACGGAGCA |
| 3361 | GATGCTAGGG CAAATTGCCC TAGCAGGGGA AAAAGGTCGA AAAGGTCTCT TTCCTGTGGA |
| 3421 | TAGCACGTAC ATTGGGAACC CAAAGCCGTA CATTGGGAAC CGGAACCCGT ACATTGGGAA |
| 3481 | CCCAAAGCCG TACATTGGGA ACCGGTCACA CATGTAAGTG ACTGATATAA AAGAGAAAAA |
| 3541 | AGGCGATTTT TCCGCCTAAA ACTCTTTAAA ACTTATTAAA ACTCTTAAAA CCCGCCTGGC |
| 3601 | CTGTGCATAA CTGTCTGGCC AGCGCACAGC CGAAGAGCTG CAAAAAGCGC CTACCCTTCG |
| 3661 | GTCGCTGCGC TCCCTACGCC CCGCCGCTTC GCGTCGGCCT ATCGCGGCCG CTGGCCGCTC |
| 3721 | AAAAATGGCT GGCCTACGGC CAGGCAATCT ACCAGGGCGC GGACAAGCCG CGCCGTCGCC |
| 3781 | ACTCGACCGC CGGCGCCCAC ATCAAGGCAC CCTGCCTCGC GCGTTTCGGT GATGACGGTG |
| 3841 | AAAACCTCTG ACACATGCAG CTCCCGGAGA CGGTCACAGC TTGTCTGTAA GCGGATGCCG |
| 3901 | GGAGCAGACA AGCCCGTCAG GGCGCGTCAG CGGGTGTTGG CGGGTGTCGG GGCGCAGCCA |
| 3961 | TGACCCAGTC ACGTAGCGAT AGCGGAGTGT ATACTGGCTT AACTATGCGG CATCAGAGCA |
| 4021 | GATTGTACTG AGAGTGCACC ATATGCGGTG TGAAATACCG CACAGATGCG TAAGGAGAAA |
| 4081 | ATACCGCATC AGGCGCTCTT CCGCTTCCTC GCTCACTGAC TCGCTGCGCT CGGTCGTTCG |
| 4141 | GCTGCGGCGA GCGGTATCAG CTCACTCAAA GGCGGTAATA CGGTTATCCA CAGAATCAGG |
| 4201 | GGATAACGCA GGAAAGAACA TGTGAGCAAA AGGCCAGCAA AAGGCCAGGA ACCGTAAAAA |
| 4261 | GGCCGCGTTG CTGGCGTTTT TCCATAGGCT CCGCCCCCCT GACGAGCATC ACAAAAATCG |
| 4321 | ACGCTCAAGT CAGAGGTGGC GAAACCCGAC AGGACTATAA AGATACCAGG CGTTTCCCCC |
| 4381 | TGGAAGCTCC CTCGTGCGCT CTCCTGTTCC GACCCTGCCG CTTACCGGAT ACCTGTCCGC |

-continued

| | Sequences: | | | |
|---|---|---|---|---|
| 4441 | CTTTCTCCCT | TCGGGAAGCG | TGGCGCTTTC | TCATAGCTCA | CGCTGTAGGT | ATCTCAGTTC |
| 4501 | GGTGTAGGTC | GTTCGCTCCA | AGCTGGGCTG | TGTGCACGAA | CCCCCCGTTC | AGCCCGACCG |
| 4561 | CTGCGCCTTA | TCCGGTAACT | ATCGTCTTGA | GTCCAACCCG | GTAAGACACG | ACTTATCGCC |
| 4621 | ACTGGCAGCA | GCCACTGGTA | ACAGGATTAG | CAGAGCGAGG | TATGTAGGCG | GTGCTACAGA |
| 4681 | GTTCTTGAAG | TGGTGGCCTA | ACTACGGCTA | CACTAGAAGG | ACAGTATTTG | GTATCTGCGC |
| 4741 | TCTGCTGAAG | CCAGTTACCT | TCGGAAAAAG | AGTTGGTAGC | TCTTGATCCG | GCAAACAAAC |
| 4801 | CACCGCTGGT | AGCGGTGGTT | TTTTTGTTTG | CAAGCAGCAG | ATTACGCGCA | GAAAAAAGG |
| 4861 | ATCTCAAGAA | GATCCTTTGA | TCTTTTCTAC | GGGGTCTGAC | GCTCAGTGGA | ACGAAAACTC |
| 4921 | ACGTTAAGGG | ATTTTGGTCA | TGCATTCTAG | GTACTAAAAC | AATTCATCCA | GTAAAATATA |
| 4981 | ATATTTTATT | TTCTCCCAAT | CAGGCTTGAT | CCCCAGTAAG | TCAAAAAATA | GCTCGACATA |
| 5041 | CTGTTCTTCC | CCGATATCCT | CCCTGATCGA | CCGGACGCAG | AAGGCAATGT | CATACCACTT |
| 5101 | GTCCGCCCTG | CCGCTTCTCC | CAAGATCAAT | AAAGCCACTT | ACTTTGCCAT | CTTTCACAAA |
| 5161 | GATGTTGCTG | TCTCCCAGGT | CGCCGTGGGA | AAAGACAAGT | TCCTCTTCGG | GCTTTTCCGT |
| 5221 | CTTTAAAAAA | TCATACAGCT | CGCGCGGATC | TTTAAATGGA | GTGTCTTCTT | CCCAGTTTTC |
| 5281 | GCAATCCACA | TCGGCCAGAT | CGTTATTCAG | TAAGTAATCC | AATTCGGCTA | AGCGGCTGTC |
| 5341 | TAAGCTATTC | GTATAGGGAC | AATCCGATAT | GTCGATGGAG | TGAAAGAGCC | TGATGCACTC |
| 5401 | CGCATACAGC | TCGATAATCT | TTTCAGGGCT | TGTTCATCT | TCATACTCTT | CCGAGCAAAG |
| 5461 | GACGCCATCG | GCCTCACTCA | TGAGCAGATT | GCTCCAGCCA | TCATGCCGTT | CAAAGTGCAG |
| 5521 | GACCTTTGGA | ACAGGCAGCT | TTCCTTCCAG | CCATAGCATC | ATGTCCTTTT | CCCGTTCCAC |
| 5581 | ATCATAGGTG | GTCCCTTTAT | ACCGGCTGTC | CGTCATTTTT | AAATATAGGT | TTTCATTTTC |
| 5641 | TCCCACCAGC | TTATATACCT | TAGCAGGAGA | CATTCCTTCC | GTATCTTTTA | CGCAGCGGTA |
| 5701 | TTTTTCGATC | AGTTTTTTCA | ATTCCGGTGA | TATTCTCATT | TTAGCCATTT | ATTATTTCCT |
| 5761 | TCCTCTTTTC | TACAGTATTT | AAAGATACCC | CAAGAAGCTA | ATTATAACAA | GACGAACTCC |
| 5821 | AATTCACTGT | TCCTTGCATT | CTAAAACCTT | AAATACCAGA | AAACAGCTTT | TCAAAGTTG |
| 5881 | TTTTCAAAGT | TGGCGTATAA | CATAGTATCG | ACGGAGCCGA | TTTTGAAACC | GCGGTGATCA |
| 5941 | CAGGCAGCAA | CGCTCTGTCA | TCGTTACAAT | CAACATGCTA | CCCTCCGCGA | GATCATCCGT |
| 6001 | GTTTCAAACC | CGGCAGCTTA | GTTGCCGTTC | TTCCGAATAG | CATCGGTAAC | ATGAGCAAAG |
| 6061 | TCTGCCGCCT | TACAACGGCT | CTCCCGCTGA | CGCCGTCCCG | GACTGATGGG | CTGCCTGTAT |
| 6121 | CGAGTGGTGA | TTTTGTGCCG | AGCTGCCGGT | CGGGGAGCTG | TTGGCTGGCT | GGTGGCAGGA |
| 6181 | TATATTGTGG | TGTAAACAAA | TTGACGCTTA | GACAACTTAA | TAACACATTG | CGGACGTTTT |
| 6241 | TAATGTACTG | AATTAACGCC | GAATTAATTC | GGGGGATCTG | GATTTTAGTA | CTGGATTTTG |
| 6301 | GTTTTAGGAA | TTAGAAATTT | TATTGATAGA | AGTATTTTAC | AAATACAAAT | ACATACTAAG |
| 6361 | GGTTTCTTAT | ATGCTCAACA | CATGAGCGAA | ACCCTATAGG | AACCCTAATT | CCCTTATCTG |
| 6421 | GGAACTACTC | ACACATTATT | ATGGAGAAAC | TCGAGGGATC | CCGGTCGGCA | TCTACTCTAT |
| 6481 | TCCTTTGCCC | TCGGACGAGT | GCTGGGCGT | CGGTTCCAC | TATCGGCGAG | TACTTCTACA |
| 6541 | CAGCCATCGG | TCCAGACGGC | CGCGCTTCTG | CGGGCGATTT | GTGTACGCCC | GACAGTCCCG |
| 6601 | GCTCCGGATC | GGACGATTGC | GTCGCATCGA | CCCTGCGCCC | AAGCTGCATC | ATCGAAATTG |
| 6661 | CCGTCAACCA | AGCTCTGATA | GAGTTGGTCA | AGACCAATGC | GGAGCATATA | CGCCCGGAGC |
| 6721 | CGCGGCGATC | CTGCAAGCTC | CGGATGCCTC | CGCTCGAAGT | AGCGCGTCTG | CTGCTCCATA |

-continued

| | Sequences: |
|---|---|
| 6781 | CAAGCCAACC ACGGCCTCCA GAAGAAGATG TTGGCGACCT CGTATTGGGA ATCCCCGAAC |
| 6841 | ATCGCCTCGC TCCAGTCAAT GACCGCTGTT ATGCGGCCAT TGTCCGTCAG GACATTGTTG |
| 6901 | GAGCCGAAAT CCGCGTGCAC GAGGTGCCGG ACTTCGGGGC AGTCCTCGGC CCAAAGCATC |
| 6961 | AGCTCATCGA GAGCCTGCGC GACGGACGCA CTGACGGTGT CGTCCATCAC AGTTTGCCAG |
| 7021 | TGATACACAT GGGGATCAGC AATCGCGCAT ATGAAATCAC GCCATGTAGT GTATTGACCG |
| 7081 | ATTCCTTGCG GTCCGAATGG GCCGAACCCG CTCGTCTGGC TAAGATCGGC CGCAGCGATC |
| 7141 | GCATCCATGG CCTCCGCGAC CGGCTGCAGT TATCATCATC ATCATAGACA CACGAAATAA |
| 7201 | AGTAATCAGA TTATCAGTTA AAGCTATGTA ATATTTACAC CATAACCAAT CAATTAAAAA |
| 7261 | ATAGATCAGT TTAAAGAAAG ATCAAAGCTC AAAAAAATAA AAAGAGAAAA GGGTCCTAAC |
| 7321 | CAAGAAAATG AAGGAGAAAA ACTAGAAATT TACCTGCAGA ACAGCGGGCA GTTCGGTTTC |
| 7381 | AGGCAGGTCT TGCAACGTGA CACCCTGTGC ACGGCGGGAG ATGCAATAGG TCAGGCTCTC |
| 7441 | GCTGAATTCC CCAATGTCAA GCACTTCCGG AATCGGGAGC GCGGCCGATG CAAAGTGCCG |
| 7501 | ATAAACATAA CGATCTTTGT AGAAACCATC GGCGCAGCTA TTTACCCGCA GGACATATCC |
| 7561 | ACGCCCTCCT ACATCGAAGC TGAAAGCACG AGATTCTTCG CCCTCCGAGA GCTGCATCAG |
| 7621 | GTCGGAGACG CTGTCGAACT TTTCGATCAG AAACTTCTCG ACAGACGTCG CGGTGAGTTC |
| 7681 | AGGCTTTTTC ATGGTAGAGG AGCTCGCCGC TTGGTATCTG CATTACAATG AAATGAGCAA |
| 7741 | AGACTATGTG AGTAACACTG GTCAACACTA GGGAGAAGGC ATCGAGCAAG ATACGTATGT |
| 7801 | AAAGAGAAGC AATATAGTGT CAGTTGGTAG ATACTAGATA CCATCAGGAG GTAAGGAGAG |
| 7861 | CAACAAAAAG GAAACTCTTT ATTTTTAAAT TTTGTTACAA CAAACAAGCA GATCAATGCA |
| 7921 | TCAAAATACT GTCAGTACTT ATTTCTTCAG ACAACAATAT TTAAAACAAG TGCATCTGAT |
| 7981 | CTTGACTTAT GGTCACAATA AAGGAGCAGA GATAAACATC AAAATTTCGT CATTTATATT |
| 8041 | TATTCCTTCA GGCGTTAACA ATTTAACAGC ACACAAACAA AAACAGAATA GGAATATCTA |
| 8101 | ATTTTGGCAA ATAATAAGCT CTGCAGACGA ACAAATTATT ATAGTATCGC CTATAATATG |
| 8161 | AATCCCTATA CTATTGACCC ATGTAGTATG AAGCCTGTGC CTAAATTAAC AGCAAACTTC |
| 8221 | TGAATCCAAG TGCCCTATAA CACCAACATG TGCTTAAATA AATACCGCTA AGCACCAAAT |
| 8281 | TACACATTTC TCGTATTGCT GTGTAGGTTC TATCTTCGTT TCGTACTACC ATGTCCCTAT |
| 8341 | ATTTTGCTGC TACAAAGGAC GGCAAGTAAT CAGCACAGGC AGAACACGAT TTCAGAGTGT |
| 8401 | AATTCTAGAT CCAGCTAAAC CACTCTCAGC AATCACCACA CAAGAGAGCA TTCAGAGAAA |
| 8461 | CGTGGCAGTA ACAAAGGCAG AGGGCGGAGT GAGCGCGTAC CGAAGACGGT AGATCTCTCG |
| 8521 | AGAGAGATAG ATTTGTAGAG AGAGACTGGT GATTTCAGCG TGTCCTCTCC AAATGAAATG |
| 8581 | AACTTCCTTA TATAGAGGAA GGTCTTGCGA AGGATAGTGG GATTGTGCGT CATCCCTTAC |
| 8641 | GTCAGTGGAG ATATCACATC AATCCACTTG CTTTGAAGAC GTGGTTGGAA CGTCTTCTTT |
| 8701 | TTCCACGATG CTCCTCGTGG GTGGGGGTCC ATCTTTGGGA CCACTGTCGG CAGAGGCATC |
| 8761 | TTGAACGATA GCCTTTCCTT TATCGCAATG ATGGCATTTG TAGGTGCCAC CTTCCTTTTC |
| 8821 | TACTGTCCTT TTGATGAAGT GACAGATAGC TGGGCAATGG AATCCGAGGA GGTTTCCCGA |
| 8881 | TATTACCCTT TGTTGAAAAG TCTCAATAGC CCTTTGGTCT TCTGAGACTG TATCTTTGAT |
| 8941 | ATTCTTGGAG TAGACGAGAG TGTCGTGCTC CACCATGTTA TCACATCAAT CCACTTGCTT |
| 9001 | TGAAGACGTG GTTGGAACGT CTTCTTTTTC CACGATGCTC CTCGTGGGTG GGGGTCCATC |

-continued

| | Sequences: |
|---|---|
| 9061 | TTTGGGACCA CTGTCGGCAG AGGCATCTTG AACGATAGCC TTTCCTTTAT CGCAATGATG |
| 9121 | GCATTTGTAG GTGCCACCTT CCTTTTCTAC TGTCCTTTTG ATGAAGTGAC AGATAGCTGG |
| 9181 | GCAATGGAAT CCGAGGAGGT TTCCCGATAT TACCCTTTGT TGAAAAGTCT CAATAGCCCT |
| 9241 | TTGGTCTTCT GAGACTGTAT CTTTGATATT CTTGGAGTAG ACGAGAGTGT CGTGCTCCAC |
| 9301 | CATGTTGGCA AGCTGCTCTA GCCAATACGC AAACCGCCTC TCCCCGCGCG TTGGCCGATT |
| 9361 | CATTAATGCA GCTGGCACGA CAGGTTTCCC GACTGGAAAG CGGGCAGTGA GCGCAACGCA |
| 9421 | ATTAATGTGA GTTAGCTCAC TCATTAGGCA CCCCAGGCTT TACACTTTAT GCTTCCGGCT |
| 9481 | CGTATGTTGT GTGGAATTGT GAGCGGATAA CAATTTCACA CAGGAAACAG CTATGACCAT |
| 9541 | GATTACGAAT TCGAGCTCGG TACCCCACGG AAGATCCAGG TCTCGAGACT AGGAGACGGA |
| 9601 | TGGGAGGCGC AACGCGCGAT GGGGAGGGGG GCGGCGCTGA CCTTTCTGGC GAGGTCGAGG |
| 9661 | TAGCGATCGA GCAGCTGCAG CGCGGACACG ATGAGGAAGA CGAAGATAGC CGCCATGGAC |
| 9721 | ATGTTCGCCA GCGGCGGCGG AGCGAGGCTG AGCCGGTCTC TCCGGCCTCC GGTCGGCGTT |
| 9781 | AAGTTGGGGA TCGTAACGTG ACGTGTCTCG TCTCCACGGA TCGACACAAC CGGCCTACTC |
| 9841 | GGGTGCACGA CGCCGCGATA AGGGCGAGAT GTCCGTGCAC GCAGCCCGTT TGGAGTCCTC |
| 9901 | GTTGCCCACG AACCGACCCC TTACAGAACA AGGCCTAGCC CAAAACTATT CTGAGTTGAG |
| 9961 | CTTTTGAGCC TAGCCCACCT AAGCCGAGCG TCATGAACTG ATGAACCCAC TACCACTAGT |
| 10021 | CAAGGCAAAC CACAACCACA AATGGATCAA TTGATCTAGA CAATCCGAA GGAGGGGAGG |
| 10081 | CCACGTCACA CTCACACCAA CCGAAATATC TGCCAGAATC AGATCAACCG GCCAATAGGA |
| 10141 | CGCCAGCGAG CCCAACACCT GGCGACGCCG CAAAATTCAC CGCGAGGGGC ACCGGGCACG |
| 10201 | GCAAAACAA AAGCCCGGCG CGGTGAGAAT ATCTGGCGAC TGGCGGAGAC CTGGTGGCCA |
| 10261 | GCGCGCGGCC ACATCAGCCA CCCCATCCGC CCACCTCACC TCCGGCGAGC CAATGGCAAC |
| 10321 | TCGTCTTAAG ATTCCACGAG ATAAGGACCC GATCGCCGGC GACGCTATTT AGCCAGGTGC |
| 10381 | GCCCCCCACG GTACACTCCA CCAGCGGCAT CTATAGCAAC CGGTCCAGCA CTTTCACGCT |
| 10441 | CAGCTTCAGC AAGATCTACC GTCTTCGGTA CGCGCTCACT CCGCCCTCTG CCTTTGTTAC |
| 10501 | TGCCACGTTT CTCTGAATGC TCTCTTGTGT GGTGATTGCT GAGAGTGGTT TAGCTGGATC |
| 10561 | TAGAATTACA CTCTGAAATC GTGTTCTGCC TGTGCTGATT ACTTGCCGTC CTTTGTAGCA |
| 10621 | GCAAAATATA GGGACATGGT AGTACGAAAC GAAGATAGAA CCTACACAGC AATACGAGAA |
| 10681 | ATGTGTAATT TGGTGCTTAG CGGTATTTAT TTAAGCACAT GTTGGTGTTA TAGGGCACTT |
| 10741 | GGATTCAGAA GTTTGCTGTT AATTTAGGCA CAGGCTTCAT ACTACATGGG TCAATAGTAT |
| 10801 | AGGGATTCAT ATTATAGGCG ATACTATAAT AATTTGTTCG TCTGCAGAGC TTATTATTTG |
| 10861 | CCAAAATTAG ATATTCCTAT TCTGTTTTTG TTTGTGTGCT GTTAAATTGT TAACGCCTGA |
| 10921 | AGGAATAAAT ATAAATGACG AAATTTGAT GTTATCTCT GCTCCTTTAT TGTGACCATA |
| 10981 | AGTCAAGATC AGATGCACTT GTTTTAAATA TTGTTGTCTG AAGAAATAAG TACTGACAGT |
| 11041 | ATTTTGATGC ATTGATCTGC TTGTTTGTTG TAACAAAATT TAAAATAAA GAGTTTCCTT |
| 11101 | TTTGTTGCTC TCCTTACCTC CTGATGGTAT CTAGTATCTA CCAACTGATA CTATATTGCT |
| 11161 | TCTCTTTACA NNNNNNTCTT GCTCGATGCC TTCTCCTAGT GTTGACCAGT GTTACTCACA |
| 11221 | TAGTCTTTGC TCATTTCATT GTAATGCAGA TACCAAGCGG TTAATTAACT ATGTGCGGCG |
| 11281 | GGGCCATTCT CAGTGATCTC TACTCACCAG TGAGGCGGAC GGTCACTGCC GGTGACCTAT |
| 11341 | GGGGAGAGAG TGGCAGCAGC AAGAATGTGA AGAACTGGAA AAGGAGTTCT TGGAAGTTTG |

-continued

Sequences:

```
11401 ATGAAGGCGA TGAAGACTTT GAAGCTGATT TCAAGGATTT TGAGGATTGC AGTAGCGAGG

11461 AGGAGGTAGA TTTTGGACAT GAGGAAAAAG AATTCCAATT GAACAGTTCG AATTTCGTGG

11521 AATTCAATGG CCATACTGCC AAAGTCACCA GCAGGAAGCG AAAGATCCAG TACCGAGGGA

11581 TCCGGCGGCG GCCTTGGGGC AAATGGGCAG CAGAAATCAG AGACCCACAG AAGGGCGTCC

11641 GAGTTTGGCT TGGCACGTTC AGCACTGCCG AGGAAGCTGC AAGGGCATAT GACGTGGAAG

11701 CTCTACGCAT ACGTGGCAAG AAAGCCAAGA TGAATTTCCC TACCACCATC ACAGCTGCTG

11761 GGAAACACCA CCGGCAGCGT GTGGCTCGAC CGGCAAAGAA GACGTCACAA GAGAGCCTGA

11821 AGTCAAGCAA TGCCTCTGGT CATGTCATCT CAGCAGGCAG CAGTACTGAT GGCACCGTTG

11881 TCAAGATCGA GTTGTCACAG TCACCAGCTT CTCCACTACC AGTGTCCAGC GCATGGCTTG

11941 ATGCTTTTGA GCTGAAGCAG CTTGGTGGAG AAACCCCTGA AGCTGATGGG AGAGAAACCC

12001 CTGAAGAAAC TGATCATGAA ACGGGAGTGA CAGCGGATAT GTTTTTTGGC AATGGCGAAG

12061 TGCGGCTTTC AGATGATTTT GCGTCTTACG AGCCTTACCC AAATTTTATG CAGTTACCTT

12121 ATCTAGAAGG TGACTCGTAT GAAAACATTG ACACTCTTTT CAACGGTGAA GCTGCTCAGG

12181 ATGGAGTGAA CATCGGAGGT CTTTGGAATT TCGATGATGT GCCAATGGAC CGTGGTGTTT

12241 ACTGAGCAGG GCGCGCCATC GTTCAAACAT TTGGCAATAA AGTTCTTAA GATTGAATCC

12301 TGTTGCCGGT CTTGCGATGA TTATCATATA ATTTCTGTTG AATTACGTTA AGCATGTAAT

12361 AATTAACATG TAATGCATGA CGTTATTTAT GAGATGGGTT TTTATGATTA GAGTCCCGCA

12421 ATTATACATT TAATACGCGA TAGAAAACAA AATATAGCGC GCAAACTAGG ATAAATTATC

12481 GCGCGCGGTG TCATCTATGT TACTAGATCC GATGATAAGC TGTCAAACAT GAAAGCTTGG

12541 CACTGGCCGT CGTTTTACAA CGTCGTGACT GGGAAAACCC TGGCGTTACC CAACTTAATC

12601 GCCTTGCAGC ACATCCCCCT TTCGCCAGCT GGCGTAATAG CGAAGAGGCC CGCACCGATC

12661 GCCCTTCCCA ACAGTTGCGC AGCCTGAATG GCGAATGCTA GAGCAGCTTG AGCTTGGATC

12721 AGATTGTCGT TTCCCGCCTT CAGTTTAAAC TATCAGTGTT TGACAGGATA TATTGGCGGG

12781 TAAACCTAAG AGAAAGAGC GTTTATTAGA ATAACGGATA TTTAAAGGG CGTGAAAAGG

12841 TTTATCCGTT CGTCCATTTG TATGTG
```

SEQ ID NO: 28 pMBXS886

```
  1 CATGCCAACC ACAGGGTCC CCTCGGGATC AAAGTACTTT GATCCAACCC CTCCGCTGCT

61 ATAGTGCAGT CGGCTTCTGA CGTTCAGTGC AGCCGTCTTC TGAAAACGAC ATGTCGCACA

121 AGTCCTAAGT TACGCGACAG GCTGCCGCCC TGCCCTTTTC CTGGCGTTTT CTTGTCGCGT

181 GTTTTAGTCG CATAAAGTAG AATACTTGCG ACTAGAACCG GAGACATTAC GCCATGAACA

241 AGAGCGCCGC CGCTGGCCTG CTGGGCTATG CCCGCGTCAG CACCGACGAC CAGGACTTGA

301 CCAACCAACG GGCCGAACTG CACGCGGCCG GCTGCACCAA GCTGTTTTCC GAGAAGATCA

361 CCGGCACCAG GCGCGACCGC CCGGAGCTGG CCAGGATGCT TGACCACCTA CGCCCTGGCG

421 ACGTTGTGAC AGTGACCAGG CTAGACCGCC TGGCCCGCAG CACCCGCGAC CTACTGGACA

481 TTGCCGAGCG CATCCAGGAG GCCGGCGCGG GCCTGCGTAG CCTGGCAGAG CCGTGGGCCG

541 ACACCACCAC GCCGGCCGGC CGCATGGTGT TGACCGTGTT CGCCGGCATT GCCGAGTTCG

601 AGCGTTCCCT AATCATCGAC CGCACCCGGA GCGGGCGCGA GGCCGCCAAG GCCCGAGGCG

661 TGAAGTTTGG CCCCCGCCCT ACCCTCACCC CGGCACAGAT CGCGCACGCC CGCGAGCTGA

721 TCGACCAGGA AGGCCGCACC GTGAAGAGG CGGCTGCACT GCTTGGCGTG CATCGCTCGA
```

-continued

| | Sequences: |
|---|---|
| 781 | CCCTGTACCG CGCACTTGAG CGCAGCGAGG AAGTGACGCC CACCGAGGCC AGGCGGCGCG |
| 841 | GTGCCTTCCG TGAGGACGCA TTGACCGAGG CCGACGCCCT GGCGGCCGCC GAGAATGAAC |
| 901 | GCCAAGAGGA ACAAGCATGA AACCGCACCA GGACGCCAG GACGAACCGT TTTTCATTAC |
| 961 | CGAAGAGATC GAGGCGGAGA TGATCGCGGC CGGGTACGTG TTCGAGCCGC CCGCGCACGT |
| 1021 | CTCAACCGTG CGGCTGCATG AAATCCTGGC CGGTTTGTCT GATGCCAAGC TGGCGGCCTG |
| 1081 | GCCGGCCAGC TTGGCCGCTG AAGAAACCGA GCGCCGCCGT CTAAAAGGT GATGTGTATT |
| 1141 | TGAGTAAAAC AGCTTGCGTC ATGCGGTCGC TGCGTATATG ATGCGATGAG TAAATAAACA |
| 1201 | AATACGCAAG GGAACGCAT GAAGGTTATC GCTGTACTTA ACCAGAAAGG CGGGTCAGGC |
| 1261 | AAGACGACCA TCGCAACCCA TCTAGCCCGC GCCCTGCAAC TCGCCGGGGC CGATGTTCTG |
| 1321 | TTAGTCGATT CCGATCCCCA GGGCAGTGCC CGCGATTGGG CGGCCGTGCG GAAGATCAA |
| 1381 | CCGCTAACCG TTGTCGGCAT CGACCGCCCG ACGATTGACC GCGACGTGAA GGCCATCGGC |
| 1441 | CGGCGCGACT TCGTAGTGAT CGACGGAGCG CCCCAGGCGG CGGACTTGGC TGTGTCCGCG |
| 1501 | ATCAAGGCAG CCGACTTCGT GCTGATTCCG GTGCAGCCAA GCCCTTACGA CATATGGGCC |
| 1561 | ACCGCCGACC TGGTGGAGCT GGTTAAGCAG CGCATTGAGG TCACGGATGG AAGGCTACAA |
| 1621 | GCGGCCTTTG TCGTGTCGCG GGCGATCAAA GGCACGCGCA TCGGCGGTGA GGTTGCCGAG |
| 1681 | GCGCTGGCCG GTACGAGCT GCCCATTCTT GAGTCCCGTA TCACGCAGCG CGTGAGCTAC |
| 1741 | CCAGGCACTG CCGCCGCGG CACAACCGTT CTTGAATCAG AACCCGAGGG CGACGCTGCC |
| 1801 | CGCGAGGTCC AGGCGCTGGC CGCTGAAATT AAATCAAAAC TCATTTGAGT TAATGAGGTA |
| 1861 | AAGAGAAAAT GAGCAAAAGC ACAAACACGC TAAGTGCCGG CCGTCCGAGC GCACGCAGCA |
| 1921 | GCAAGGCTGC AACGTTGGCC AGCCTGGCAG ACACGCCAGC CATGAAGCGG GTCAACTTTC |
| 1981 | AGTTGCCGGC GGAGGATCAC ACCAAGCTGA AGATGTACGC GGTACGCCAA GCAAGACCA |
| 2041 | TTACCGAGCT GCTATCTGAA TACATCGCGC AGCTACCAGA GTAAATGAGC AAATGAATAA |
| 2101 | ATGAGTAGAT GAATTTTAGC GGCTAAAGGA GGCGGCATGG AAAATCAAGA ACAACCAGGC |
| 2161 | ACCGACGCCG TGGAATGCCC CATGTGTGGA GGAACGGGCG GTTGGCCAGG CGTAAGCGGC |
| 2221 | TGGGTTGTCT GCCGGCCCTG CAATGGCACT GGAACCCCCA AGCCCGAGGA ATCGGCGTGA |
| 2281 | CGGTCGCAAA CCATCCGGCC CGGTACAAAT CGGCGCGGCG CTGGGTGATG ACCTGGTGGA |
| 2341 | GAAGTTGAAG GCCGCGCAGG CCGCCCAGCG GCAACGCATC GAGGCAGAAG CACGCCCCGG |
| 2401 | TGAATCGTGG CAAGCGGCCG CTGATCGAAT CCGCAAAGAA TCCCGGCAAC CGCCGGCAGC |
| 2461 | CGGTGCGCCG TCGATTAGGA AGCCGCCCAA GGGCGACGAG CAACCAGATT TTTTCGTTCC |
| 2521 | GATGCTCTAT GACGTGGGCA CCCGCGATAG TCGCAGCATC ATGGACGTGG CCGTTTTCCG |
| 2581 | TCTGTCGAAG CGTGACCGAC GAGCTGGCGA GGTGATCCGC TACGAGCTTC AGACGGGCA |
| 2641 | CGTAGAGGTT TCCGCAGGGC CGGCCGGCAT GGCCAGTGTG TGGGATTACG ACCTGGTACT |
| 2701 | GATGGCGGTT TCCCATCTAA CCGAATCCAT GAACCGATAC CGGGAAGGGA AGGGAGACAA |
| 2761 | GCCCGGCCGC GTGTTCCGTC CACACGTTGC GGACGTACTC AAGTTCTGCC GGCGAGCCGA |
| 2821 | TGGCGGAAAG CAGAAAGACG ACCTGGTAGA AACCTGCATT CGGTTAAACA CCACGCACGT |
| 2881 | TGCCATGCAG CGTACGAAGA AGGCCAAGAA CGGCCGCCTG GTGACGGTAT CCGAGGGTGA |
| 2941 | AGCCTTGATT AGCCGCTACA AGATCGTAAA GAGCGAAACC GGGCGGCCGG AGTACATCGA |
| 3001 | GATCGAGCTA GCTGATTGGA TGTACCGCGA GATCACAGAA GGCAAGAACC CGGACGTGCT |

-continued

| | Sequences: |
|---|---|
| 3061 | GACGGTTCAC CCCGATTACT TTTTGATCGA TCCCGGCATC GGCCGTTTTC TCTACCGCCT |
| 3121 | GGCACGCCGC GCCGCAGGCA AGGCAGAAGC CAGATGGTTG TTCAAGACGA TCTACGAACG |
| 3181 | CAGTGGCAGC GCCGGAGAGT TCAAGAAGTT CTGTTTCACC GTGCGCAAGC TGATCGGGTC |
| 3241 | AAATGACCTG CCGGAGTACG ATTTGAAGGA GGAGGCGGGG CAGGCTGGCC CGATCCTAGT |
| 3301 | CATGCGCTAC CGCAACCTGA TCGAGGGCGA AGCATCCGCC GGTTCCTAAT GTACGGAGCA |
| 3361 | GATGCTAGGG CAAATTGCCC TAGCAGGGGA AAAGGTCGA AAGGTCTCT TTCCTGTGGA |
| 3421 | TAGCACGTAC ATTGGGAACC CAAAGCCGTA CATTGGGAAC CGGAACCCGT ACATTGGGAA |
| 3481 | CCCAAAGCCG TACATTGGGA ACCGGTCACA CATGTAAGTG ACTGATATAA AAGAGAAAAA |
| 3541 | AGGCGATTTT TCCGCCTAAA ACTCTTTAAA ACTTATTAAA ACTCTTAAAA CCCGCCTGGC |
| 3601 | CTGTGCATAA CTGTCTGGCC AGCGCACAGC CGAAGAGCTG CAAAAAGCGC CTACCCTTCG |
| 3661 | GTCGCTGCGC TCCCTACGCC CCGCCGCTTC GCGTCGGCCT ATCGCGGCCG CTGGCCGCTC |
| 3721 | AAAAATGGCT GGCCTACGGC CAGGCAATCT ACCAGGGCGC GGACAAGCCG CGCCGTCGCC |
| 3781 | ACTCGACCGC CGGCGCCCAC ATCAAGGCAC CCTGCCTCGC GCGTTTCGGT GATGACGGTG |
| 3841 | AAAACCTCTG ACACATGCAG CTCCCGGAGA CGGTCACAGC TTGTCTGTAA GCGGATGCCG |
| 3901 | GGAGCAGACA AGCCCGTCAG GGCGCGTCAG CGGGTGTTGG CGGGTGTCGG GGCGCAGCCA |
| 3961 | TGACCCAGTC ACGTAGCGAT AGCGGAGTGT ATACTGGCTT AACTATGCGG CATCAGAGCA |
| 4021 | GATTGTACTG AGAGTGCACC ATATGCGGTG TGAAATACCG CACAGATGCG TAAGGAGAAA |
| 4081 | ATACCGCATC AGGCGCTCTT CCGCTTCCTC GCTCACTGAC TCGCTGCGCT CGGTCGTTCG |
| 4141 | GCTGCGGCGA GCGGTATCAG CTCACTCAAA GGCGGTAATA CGGTTATCCA CAGAATCAGG |
| 4201 | GGATAACGCA GGAAAGAACA TGTGAGCAAA AGGCCAGCAA AAGGCCAGGA ACCGTAAAAA |
| 4261 | GGCCGCGTTG CTGGCGTTTT TCCATAGGCT CCGCCCCCCT GACGAGCATC ACAAAAATCG |
| 4321 | ACGCTCAAGT CAGAGGTGGC GAAACCCGAC AGGACTATAA AGATACCAGG CGTTTCCCCC |
| 4381 | TGGAAGCTCC CTCGTGCGCT CTCCTGTTCC GACCCTGCCG CTTACCGGAT ACCTGTCCGC |
| 4441 | CTTTCTCCCT TCGGGAAGCG TGGCGCTTTC TCATAGCTCA CGCTGTAGGT ATCTCAGTTC |
| 4501 | GGTGTAGGTC GTTCGCTCCA AGCTGGGCTG TGTGCACGAA CCCCCCGTTC AGCCCGACCG |
| 4561 | CTGCGCCTTA TCCGGTAACT ATCGTCTTGA GTCCAACCCG GTAAGACACG ACTTATCGCC |
| 4621 | ACTGGCAGCA GCCACTGGTA ACAGGATTAG CAGAGCGAGG TATGTAGGCG GTGCTACAGA |
| 4681 | GTTCTTGAAG TGGTGGCCTA ACTACGGCTA CACTAGAAGG ACAGTATTTG GTATCTGCGC |
| 4741 | TCTGCTGAAG CCAGTTACCT TCGGAAAAAG AGTTGGTAGC TCTTGATCCG GCAAACAAAC |
| 4801 | CACCGCTGGT AGCGGTGGTT TTTTGTTTG CAAGCAGCAG ATTACGCGCA GAAAAAAAGG |
| 4861 | ATCTCAAGAA GATCCTTTGA TCTTTTCTAC GGGGTCTGAC GCTCAGTGGA ACGAAAACTC |
| 4921 | ACGTTAAGGG ATTTTGGTCA TGCATTCTAG GTACTAAAAC AATTCATCCA GTAAAATATA |
| 4981 | ATATTTTATT TTCTCCCAAT CAGGCTTGAT CCCCAGTAAG TCAAAAAATA GCTCGACATA |
| 5041 | CTGTTCTTCC CCGATATCCT CCCTGATCGA CCGGACGCAG AAGGCAATGT CATACCACTT |
| 5101 | GTCCGCCCTG CCGCTTCTCC CAAGATCAAT AAAGCCACTT ACTTTGCCAT CTTTCACAAA |
| 5161 | GATGTTGCTG TCTCCCAGGT CGCCGTGGGA AAAGACAAGT TCCTCTTCGG GCTTTTCCGT |
| 5221 | CTTTAAAAAA TCATACAGCT CGCGCGGATC TTTAAATGGA GTGTCTTCTT CCCAGTTTTC |
| 5281 | GCAATCCACA TCGGCCAGAT CGTTATTCAG TAAGTAATCC AATTCGGCTA AGCGGCTGTC |
| 5341 | TAAGCTATTC GTATAGGGAC AATCCGATAT GTCGATGGAG TGAAAGAGCC TGATGCACTC |

-continued

| | Sequences: |
|---|---|
| 5401 | CGCATACAGC TCGATAATCT TTTCAGGGCT TGTTCATCT TCATACTCTT CCGAGCAAAG |
| 5461 | GACGCCATCG GCCTCACTCA TGAGCAGATT GCTCCAGCCA TCATGCCGTT CAAAGTGCAG |
| 5521 | GACCTTTGGA ACAGGCAGCT TTCCTTCCAG CCATAGCATC ATGTCCTTTT CCCGTTCCAC |
| 5581 | ATCATAGGTG GTCCCTTTAT ACCGGCTGTC CGTCATTTTT AAATATAGGT TTTCATTTTC |
| 5641 | TCCCACCAGC TTATATACCT TAGCAGGAGA CATTCCTTCC GTATCTTTTA CGCAGCGGTA |
| 5701 | TTTTTCGATC AGTTTTTTCA ATTCCGGTGA TATTCTCATT TTAGCCATTT ATTATTTCCT |
| 5761 | TCCTCTTTTC TACAGTATTT AAAGATACCC CAAGAAGCTA ATTATAACAA GACGAACTCC |
| 5821 | AATTCACTGT TCCTTGCATT CTAAAACCTT AAATACCAGA AACAGCTTT TTCAAAGTTG |
| 5881 | TTTTCAAAGT TGGCGTATAA CATAGTATCG ACGGAGCCGA TTTTGAAACC GCGGTGATCA |
| 5941 | CAGGCAGCAA CGCTCTGTCA TCGTTACAAT CAACATGCTA CCCTCCGCGA GATCATCCGT |
| 6001 | GTTTCAAACC CGGCAGCTTA GTTGCCGTTC TTCCGAATAG CATCGGTAAC ATGAGCAAAG |
| 6061 | TCTGCCGCCT TACAACGGCT CTCCCGCTGA CGCCGTCCCG GACTGATGGG CTGCCTGTAT |
| 6121 | CGAGTGGTGA TTTTGTGCCG AGCTGCCGGT CGGGGAGCTG TTGGCTGGCT GGTGGCAGGA |
| 6181 | TATATTGTGG TGTAAACAAA TTGACGCTTA GACAACTTAA TAACACATTG CGGACGTTTT |
| 6241 | TAATGTACTG AATTAACGCC GAATTAATTC GGGGGATCTG GATTTTAGTA CTGGATTTTG |
| 6301 | GTTTTAGGAA TTAGAAATTT TATTGATAGA AGTATTTTAC AAATACAAAT ACATACTAAG |
| 6361 | GGTTTCTTAT ATGCTCAACA CATGAGCGAA ACCCTATAGG AACCCTAATT CCCTTATCTG |
| 6421 | GGAACTACTC ACACATTATT ATGGAGAAAC TCGAGGGATC CCGGTCGGCA TCTACTCTAT |
| 6481 | TCCTTTGCCC TCGGACGAGT GCTGGGGCGT CGGTTCCAC TATCGGCGAG TACTTCTACA |
| 6541 | CAGCCATCGG TCCAGACGGC CGCGCTTCTG CGGGCGATTT GTGTACGCCC GACAGTCCCG |
| 6601 | GCTCCGGATC GGACGATTGC GTCGCATCGA CCCTGCGCCC AAGCTGCATC ATCGAAATTG |
| 6661 | CCGTCAACCA AGCTCTGATA GAGTTGGTCA AGACCAATGC GGAGCATATA CGCCCGGAGC |
| 6721 | CGCGGCGATC CTGCAAGCTC CGGATGCCTC CGCTCGAAGT AGCGCGTCTG CTGCTCCATA |
| 6781 | CAAGCCAACC ACGGCCTCCA GAAGAAGATG TTGGCGACCT CGTATTGGGA ATCCCCGAAC |
| 6841 | ATCGCCTCGC TCCAGTCAAT GACCGCTGTT ATGCGGCCAT TGTCCGTCAG GACATTGTTG |
| 6901 | GAGCCGAAAT CCGCGTGCAC GAGGTGCCGG ACTTCGGGGC AGTCCTCGGC CCAAAGCATC |
| 6961 | AGCTCATCGA GAGCCTGCGC GACGGACGCA CTGACGGTGT CGTCCATCAC AGTTTGCCAG |
| 7021 | TGATACACAT GGGGATCAGC AATCGCGCAT ATGAAATCAC GCCATGTAGT GTATTGACCG |
| 7081 | ATTCCTTGCG GTCCGAATGG GCCGAACCCG CTCGTCTGGC TAAGATCGGC CGCAGCGATC |
| 7141 | GCATCCATGG CCTCCGCGAC CGGCTGCAGT TATCATCATC ATCATAGACA CACGAAATAA |
| 7201 | AGTAATCAGA TTATCAGTTA AAGCTATGTA ATATTTACAC CATAACCAAT CAATTAAAAA |
| 7261 | ATAGATCAGT TTAAAGAAAG ATCAAAGCTC AAAAAAATAA AAAGAGAAAA GGGTCCTAAC |
| 7321 | CAAGAAAATG AAGGAGAAAA ACTAGAAATT TACCTGCAGA ACAGCGGGCA GTTCGGTTTC |
| 7381 | AGGCAGGTCT TGCAACGTGA CACCCTGTGC ACGGCGGGAG ATGCAATAGG TCAGGCTCTC |
| 7441 | GCTGAATTCC CCAATGTCAA GCACTTCCGG AATCGGGAGC GCGGCCGATG CAAAGTGCCG |
| 7501 | ATAAACATAA CGATCTTTGT AGAAACCATC GGCGCAGCTA TTTACCCGCA GGACATATCC |
| 7561 | ACGCCCTCCT ACATCGAAGC TGAAAGCACG AGATTCTTCG CCCTCCGAGA GCTGCATCAG |
| 7621 | GTCGGAGACG CTGTCGAACT TTTCGATCAG AAACTTCTCG ACAGACGTCG CGGTGAGTTC |

| | Sequences: |
|---|---|
| 7681 | AGGCTTTTTC ATGGTAGAGG AGCTCGCCGC TTGGTATCTG CATTACAATG AAATGAGCAA |
| 7741 | AGACTATGTG AGTAACACTG GTCAACACTA GGGAGAAGGC ATCGAGCAAG ATACGTATGT |
| 7801 | AAAGAGAAGC AATATAGTGT CAGTTGGTAG ATACTAGATA CCATCAGGAG GTAAGGAGAG |
| 7861 | CAACAAAAAG GAAACTCTTT ATTTTTAAAT TTTGTTACAA CAAACAAGCA GATCAATGCA |
| 7921 | TCAAAATACT GTCAGTACTT ATTTCTTCAG ACAACAATAT TTAAAACAAG TGCATCTGAT |
| 7981 | CTTGACTTAT GGTCACAATA AAGGAGCAGA GATAAACATC AAAATTTCGT CATTTATATT |
| 8041 | TATTCCTTCA GGCGTTAACA ATTTAACAGC ACACAAACAA AAACAGAATA GGAATATCTA |
| 8101 | ATTTTGGCAA ATAATAAGCT CTGCAGACGA ACAAATTATT ATAGTATCGC CTATAATATG |
| 8161 | AATCCCTATA CTATTGACCC ATGTAGTATG AAGCCTGTGC CTAAATTAAC AGCAAACTTC |
| 8221 | TGAATCCAAG TGCCCTATAA CACCAACATG TGCTTAAATA AATACCGCTA AGCACCAAAT |
| 8281 | TACACATTTC TCGTATTGCT GTGTAGGTTC TATCTTCGTT TCGTACTACC ATGTCCCTAT |
| 8341 | ATTTTGCTGC TACAAAGGAC GGCAAGTAAT CAGCACAGGC AGAACACGAT TTCAGAGTGT |
| 8401 | AATTCTAGAT CCAGCTAAAC CACTCTCAGC AATCACCACA CAAGAGAGCA TTCAGAGAAA |
| 8461 | CGTGGCAGTA ACAAAGGCAG AGGGCGGAGT GAGCGCGTAC CGAAGACGGT AGATCTCTCG |
| 8521 | AGAGAGATAG ATTTGTAGAG AGAGACTGGT GATTTCAGCG TGTCCTCTCC AAATGAAATG |
| 8581 | AACTTCCTTA TATAGAGGAA GGTCTTGCGA AGGATAGTGG GATTGTGCGT CATCCCTTAC |
| 8641 | GTCAGTGGAG ATATCACATC AATCCACTTG CTTTGAAGAC GTGGTTGGAA CGTCTTCTTT |
| 8701 | TTCCACGATG CTCCTCGTGG GTGGGGGTCC ATCTTTGGGA CCACTGTCGG CAGAGGCATC |
| 8761 | TTGAACGATA GCCTTTCCTT TATCGCAATG ATGGCATTTG TAGGTGCCAC CTTCCTTTTC |
| 8821 | TACTGTCCTT TTGATGAAGT GACAGATAGC TGGGCAATGG AATCCGAGGA GGTTTCCCGA |
| 8881 | TATTACCCTT TGTTGAAAAG TCTCAATAGC CCTTTGGTCT TCTGAGACTG TATCTTTGAT |
| 8941 | ATTCTTGGAG TAGACGAGAG TGTCGTGCTC CACCATGTTA TCACATCAAT CCACTTGCTT |
| 9001 | TGAAGACGTG GTTGGAACGT CTTCTTTTTC CACGATGCTC CTCGTGGGTG GGGGTCCATC |
| 9061 | TTTGGGACCA CTGTCGGCAG AGGCATCTTG AACGATAGCC TTTCCTTTAT CGCAATGATG |
| 9121 | GCATTTGTAG GTGCCACCTT CCTTTTCTAC TGTCCTTTTG ATGAAGTGAC AGATAGCTGG |
| 9181 | GCAATGGAAT CCGAGGAGGT TTCCCGATAT TACCCTTTGT TGAAAAGTCT CAATAGCCCT |
| 9241 | TTGGTCTTCT GAGACTGTAT CTTTGATATT CTTGGAGTAG ACGAGAGTGT CGTGCTCCAC |
| 9301 | CATGTTGGCA AGCTGCTCTA GCCAATACGC AAACCGCCTC TCCCCGCGCG TTGGCCGATT |
| 9361 | CATTAATGCA GCTGGCACGA CAGGTTTCCC GACTGGAAAG CGGGCAGTGA GCGCAACGCA |
| 9421 | ATTAATGTGA GTTAGCTCAC TCATTAGGCA CCCCAGGCTT TACACTTTAT GCTTCCGGCT |
| 9481 | CGTATGTTGT GTGGAATTGT GAGCGGATAA CAATTTCACA CAGGAAACAG CTATGACCAT |
| 9541 | GATTACGAAT TCGAGCTCGG TACCCCACGG AAGATCCAGG TCTCGAGACT AGGAGACGGA |
| 9601 | TGGGAGGCGC AACGCGCGAT GGGGAGGGGG GCGGCGCTGA CCTTTCTGGC GAGGTCGAGG |
| 9661 | TAGCGATCGA GCAGCTGCAG CGCGGACACG ATGAGGAAGA CGAAGATAGC CGCCATGGAC |
| 9721 | ATGTTCGCCA GCGGCGGCGG AGCGAGGCTG AGCCGGTCTC TCCGGCCTCC GGTCGGCGTT |
| 9781 | AAGTTGGGGA TCGTAACGTG ACGTGTCTCG TCTCCACGGA TCGACACAAC CGGCCTACTC |
| 9841 | GGGTGCACGA CGCCGCGATA AGGGCGAGAT GTCCGTGCAC GCAGCCCGTT TGGAGTCCTC |
| 9901 | GTTGCCCACG AACCGACCCC TTACAGAACA AGGCCTAGCC CAAAACTATT CTGAGTTGAG |
| 9961 | CTTTTGAGCC TAGCCCACCT AAGCCGAGCG TCATGAACTG ATGAACCCAC TACCACTAGT |

-continued

| | Sequences: |
|---|---|
| 10021 | CAAGGCAAAC CACAACCACA AATGGATCAA TTGATCTAGA ACAATCCGAA GGAGGGGAGG |
| 10081 | CCACGTCACA CTCACACCAA CCGAAATATC TGCCAGAATC AGATCAACCG GCCAATAGGA |
| 10141 | CGCCAGCGAG CCCAACACCT GGCGACGCCG CAAAATTCAC CGCGAGGGGC ACCGGGCACG |
| 10201 | GCAAAAACAA AAGCCCGGCG CGGTGAGAAT ATCTGGCGAC TGGCGGAGAC CTGGTGGCCA |
| 10261 | GCGCGCGGCC ACATCAGCCA CCCCATCCGC CCACCTCACC TCCGGCGAGC CAATGGCAAC |
| 10321 | TCGTCTTAAG ATTCCACGAG ATAAGGACCC GATCGCCGGC GACGCTATTT AGCCAGGTGC |
| 10381 | GCCCCCCACG GTACACTCCA CCAGCGGCAT CTATAGCAAC CGGTCCAGCA CTTTCACGCT |
| 10441 | CAGCTTCAGC AAGATCTACC GTCTTCGGTA CGCGCTCACT CCGCCCTCTG CCTTTGTTAC |
| 10501 | TGCCACGTTT CTCTGAATGC TCTCTTGTGT GGTGATTGCT GAGAGTGGTT TAGCTGGATC |
| 10561 | TAGAATTACA CTCTGAAATC GTGTTCTGCC TGTGCTGATT ACTTGCCGTC CTTTGTAGCA |
| 10621 | GCAAAATATA GGGACATGGT AGTACGAAAC GAAGATAGAA CCTACACAGC AATACGAGAA |
| 10681 | ATGTGTAATT TGGTGCTTAG CGGTATTTAT TTAAGCACAT GTTGGTGTTA TAGGGCACTT |
| 10741 | GGATTCAGAA GTTTGCTGTT AATTTAGGCA CAGGCTTCAT ACTACATGGG TCAATAGTAT |
| 10801 | AGGGATTCAT ATTATAGGCG ATACTATAAT AATTTGTTCG TCTGCAGAGC TTATTATTTG |
| 10861 | CCAAAATTAG ATATTCCTAT TCTGTTTTTG TTTGTGTGCT GTTAAATTGT TAACGCCTGA |
| 10921 | AGGAATAAAT ATAAATGACG AAATTTTGAT GTTTATCTCT GCTCCTTTAT TGTGACCATA |
| 10981 | AGTCAAGATC AGATGCACTT GTTTTAAATA TTGTTGTCTG AAGAAATAAG TACTGACAGT |
| 11041 | ATTTTGATGC ATTGATCTGC TTGTTTGTTG TAACAAAATT TAAAAATAAA GAGTTTCCTT |
| 11101 | TTTGTTGCTC TCCTTACCTC CTGATGGTAT CTAGTATCTA CCAACTGATA CTATATTGCT |
| 11161 | TCTCTTTACA NNNNNNTCTT GCTCGATGCC TTCTCCTAGT GTTGACCAGT GTTACTCACA |
| 11221 | TAGTCTTTGC TCATTTCATT GTAATGCAGA TACCAAGCGG TTAATTAACT ATGTGCGGCG |
| 11281 | GGGCCATTCT CAGTGATCTC TACTCACCAG TGAGGCGGAC GGTCACTGCC GGTGACCTAT |
| 11341 | GGGGAGAGAG TGGCAGCAGC AAGAATGTGA AGAACTGGAA AAGGAGTTCT TGGAAGTTTG |
| 11401 | ATGAAGGCGA TGAAGACTTT GAAGCTGATT TCAAGGATTT TGAGGATTGC AGTAGCGAGG |
| 11461 | AGGAGGTAGA TTTTGGACAT GAGGAAAAAG AATTCCAATT GAACAGTTCA AATTTCGTGG |
| 11521 | AATTCAATGG CCATACTGCC AAAGTCACCA GCAGGAAGCG AAAGATCCAG TACCGAGGGA |
| 11581 | TCCGGCGGCG GCCTTGGGGC AAATGGGCAG CAGAAATCAG AGACCCACAG AAGGGCGTCC |
| 11641 | GAGTTTGGCT TGGCACGTTC AGCACTGCCG AGGAAGCTGC AAGGGCATAT GACGTGGAAG |
| 11701 | CTCTACGCAT ACGTGGCAAG AAAGCCAAGA TGAATTTCCC TACCACCATC ACAGCTGCTG |
| 11761 | GGAAACACCA CCGGCAGCGT GTGGCTCGAC CGGCAAAGAA GACGTCACAA GAGAGCCTGA |
| 11821 | AGTCAAGCAA TGCCTCTGGT CATGTCATCT CAGCAGGCAG CAGTACTGAT GGCACCGTTG |
| 11881 | TCAAGATCGA GTTGTCACAG TCACCAGCTT CTCCACTACC AGTGTCCAGC GCATGGCTTG |
| 11941 | ATGCTTTTGA GCTGAAGCAG CTTGGTGGAG AAACCCCTGA AGCTGATGGG AGAGAAACCC |
| 12001 | CTGAAGAAAC TGATCATGAA ACGGGAGTGA CAGCGGATAT GTTTTTTGGC AATGGCGAAG |
| 12061 | TGCGGCTTTC AGATGATTTT GCGTCTTACG AGCCTTACCC AAATTTTATG CAGTTACCTT |
| 12121 | ATCTAGAAGG TGACTCGTAT GAAAACATTG ACACTCTTTT CAACGGTGAA GCTGCTCAGG |
| 12181 | ATGGAGTGAA CATCGGAGGT CTTTGGAATT TCGATGATGT GCCAATGGAC CGTGGTGTTT |
| 12241 | ACTGAATGTG CGGCGGGGCC ATTCTCAGTG ATCTCTACTC ACCAGTGAGG CGGACGGTCA |

-continued

Sequences:

```
12301   CTGCCGGTGA CCTATGGGGA GAGAGTGGCA GCAGCAAGAA TGTGAAGAAC TGGAAAAGGA

12361   GTTCTTGGAA GTTTGATGAA GGCGATGAAG ACTTTGAAGC TGATTTCAAG GATTTTGAGG

12421   ATTGCAGTAG CGAGGAGGAG GTAGATTTTG GACATGAGGA AAAAGAATTC CAATTGAACA

12481   GTTCGAATTT CGTGGAATTC AATGGCCATA CTGCCAAAGT CACCAGCAGG AAGCGAAAGA

12541   TCCAGTACCG AGGGATCCGG CGGCGGCCTT GGGGCAAATG GGCAGCAGAA ATCAGAGACC

12601   CACAGAAGGG CGTCCGAGTT TGGCTTGGCA CGTTCAGCAC TGCCGAGGAA GCTGCAAGGG

12661   CATATGACGT GGAAGCTCTA CGCATACGTG GCAAGAAAGC CAAGATGAAT TTCCCTACCA

12721   CCATCACAGC TGCTGGGAAA CACCACCGGC AGCGTGTGGC TCGACCGGCA AAGAAGACGT

12781   CACAAGAGAG CCTGAAGTCA AGCAATGCCT CTGGTCATGT CATCTCAGCA GGCAGCAGTA

12841   CTGATGGCAC CGTTGTCAAG ATCGAGTTGT CACAGTCACC AGCTTCTCCA CTACCAGTGT

12901   CCAGCGCATG GCTTGATGCT TTTGAGCTGA AGCAGCTTGG TGGAGAAACC CCTGAAGCTG

12961   ATGGGAGAGA AACCCCTGAA GAAACTGATC ATGAAACGGG AGTGACAGCG GATATGTTTT

13021   TTGGCAATGG CGAAGTGCGG CTTTCAGATG ATTTTGCGTC TTACGAGCCT TACCCAAATT

13081   TTATGCAGTT ACCTTATCTA GAAGGTGACT CGTATGAAAA CATTGACACT CTTTTCAACG

13141   GTGAAGCTGC TCAGGATGGA GTGAACATCG GAGGTCTTTG GAATTTCGAT GATGTGCCAA

13201   TGGACCGTGG TGTTTACTGA GCAGGGCGCG CCATCGTTCA AACATTTGGC AATAAAGTTT

13261   CTTAAGATTG AATCCTGTTG CCGGTCTTGC GATGATTATC ATATAATTTC TGTTGAATTA

13321   CGTTAAGCAT GTAATAATTA ACATGTAATG CATGACGTTA TTTATGAGAT GGGTTTTTAT

13381   GATTAGAGTC CCGCAATTAT ACATTTAATA CGCGATAGAA AACAAAATAT AGCGCGCAAA

13441   CTAGGATAAA TTATCGCGCG CGGTGTCATC TATGTTACTA GATCCGATGA TAAGCTGTCA

13501   AACATGAAAG CTTGGCACTG GCCGTCGTTT TACAACGTCG TGACTGGGAA AACCCTGGCG

13561   TTACCCAACT TAATCGCCTT GCAGCACATC CCCCTTTCGC CAGCTGGCGT AATAGCGAAG

13621   AGGCCCGCAC CGATCGCCCT TCCCAACAGT TGCGCAGCCT GAATGGCGAA TGCTAGAGCA

13681   GCTTGAGCTT GGATCAGATT GTCGTTTCCC GCCTTCAGTT TAAACTATCA GTGTTTGACA

13741   GGATATATTG GCGGGTAAAC CTAAGAGAAA AGAGCGTTTA TTAGAATAAC GGATATTTAA

13801   AAGGGCGTGA AAAGGTTTAT CCGTTCGTCC ATTTGTATGT G
```

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for producing a genetically modified plant or plant cell having an increased carbon flow, the method comprising:
   a) transforming one or more host plants or plant cells with a vector comprising a nucleic acid encoding a polypeptide having at least 95% identity to SEQ ID NO: 6 operably linked to a promoter; and
   (b) selecting one or more transformed plants or plant cells for increased carbon flow by selecting for one or more of increased biomass yield, increased starch yield, increased glucose content, or increased sucrose content as compared to a control plant lacking the vector.

2. The method according to claim 1, the method further comprising collecting seeds comprising said vector from the selected plant.

3. The method according to claim 1, wherein the host plant is *Miscanthus, Medicago*, sweet sorghum, grain sorghum, sugar cane, energy cane, elephant grass, maize, wheat, barley, oat, rice, soybean, oil palm, safflower, sesame, flax, cotton, sunflower, Camelina, *Brassica napus, Brassica carinata, Brassica juncea*, pearl millet, or foxtail millet.

4. The method according to claim 1, the method further comprising regenerating a plant from the selected plant cell and collecting seeds comprising the vector from the regenerated plant.

5. The method of claim 1, wherein the polypeptide has at least 99% sequence identity to SEQ ID NO: 6.

6. The method of claim 1, wherein the polypeptide comprises SEQ ID NO: 6.

7. The method of claim 1, wherein the selected plant further exhibits increased tolerance to one or more abiotic stress factors of excess or deficiency of water and/or light, high or low temperature, or high salinity, as compared to a control plant lacking the vector.

8. The method of claim 1, wherein the plant is a monocotyledonous plant or a dicotyledenous plant.

9. The method of claim 8, wherein the host plant is switchgrass.

10. The method of claim 5, wherein the host plant is *Miscanthus, Medicago*, sweet sorghum, grain sorghum, sugar cane, energy cane, elephant grass, maize, wheat, barley, oat, rice, soybean, oil palm, safflower, sesame, flax, cotton, sunflower, Camelina, *Brassica napus, Brassica carinata, Brassica juncea*, pearl millet, or foxtail millet.

11. The method of claim 1, wherein the promoter is light inducible.

12. The method of claim 1, wherein the promoter comprises positions 8951 to 10645 of SEQ ID NO: 21.

13. The method of claim 8, wherein the host plant is maize.

14. The method of claim 8, wherein the host plant is sugar cane.

* * * * *

SEQUENCE LISTING

<160> NUMBER OF SEQ ID NOS: 77

<210> SEQ ID NO 1
<211> LENGTH: 975
<212> TYPE: DNA
<213> ORGANISM: Panicum virgatum

<400> SEQUENCE: 1

```
atgtgcggcg gggccattct cagtgatctc tactcaccag tgaggcggac ggtcactgcc    60
ggtgacctat ggggagagag tggcagcagc aagaatgtga agaactggaa aaggagttct   120
tggaagtttg atgaaggcga tgaagacttt gaagctgatt tcaaggattt tgaggattgc   180
agtagcgagg aggaggtaga ttttggacat gaggaaaaag aattccaatt gaacagttcg   240
aatttcgtgg aattcaatgg ccatactgcc aaagtcacca gcaggaagcg aaagatccag   300
taccgaggga tccggcggcg gccttggggc aaatgggcag cagaaatcag agacccacag   360
aagggcgtcc gagtttggct tggcacgttc agcactgccg aggaagctgc aagggcatat   420
gacgtggaag ctctacgcat acgtggcaag aaagccaaga tgaatttccc taccaccatc   480
acagctgctg gaaacaccac ccggcagcgt gtggctcgac cggcaaagaa gacgtcacaa   540
gagagcctga agtcaagcaa tgcctctggt catgtcatct cagcaggcag cagtactgat   600
ggcaccgttg tcaagatcga gttgtcacag tcaccagctt ctccactacc agtgtccagc   660
gcatggcttt atgcttttga gctgaagcag cttggtggag aaacccctga agctgatggg   720
agagaaaccc ctgaagaaac tgatcatgaa acgggagtga cagcggatat gttttttggc   780
aatggcgaag tgcggctttc agatgatttt gcgtcttacg agccttaccc aaattttatg   840
cagttacctt atctagaagg tgactcgtat gaaaacattg acactctttt caacggtgaa   900
gctgctcagg atggagtgaa catcggaggt ctttggaatt cgatgatgt gccaatggac   960 cgtggtgttt actga                                                    975

<210> SEQ ID NO 2
<211> LENGTH: 579
<212> TYPE: DNA
<213> ORGANISM: Panicum virgatum

<400> SEQUENCE: 2
atgcatatgt atcctttcta catacatgca ggttacggga cgagaatgca ctaccgtggc    60
gtgcggcggc ggccgtgggg caagtgggcg gcggagatcc gtgaccccgc caaggcggcg   120
cgtgtgtggc tcggcacctt cgacaccgcg gaggccgccg ccgcagcgta cgacgacgcc   180
gcgctccggt tcaagggcgc caaggccaag ctcaactttc ccgagcgcgt ccgcggccgt   240
accggccagg gcgcgttcct cgtcagccct ggcgtccccc agcagccgcc gccgtcttcc   300
ctgccaactg cagccgccgc gccgacgccg ttccccggct tgatgcggta cgcgcaactc   360
cagggttgga gcagcgggaa catcgcggcc agcaacaccg tggtgatct cgcgccgccg   420 gcacaggcgt cgtcgtcggt gcagattctg gacttctcga cgcagcaact actccggggc   480
tcaccgacaa cgttcggccc accgccgacg acgtcggcat cgatgtccag gactagcaga   540
gtagatgagg cgcacgagag ttgcgatgct cctgactga                          579

<210> SEQ ID NO 3
<211> LENGTH: 654
<212> TYPE: DNA
<213> ORGANISM: Panicum virgatum

<400> SEQUENCE: 3
atgccggact ccgacaacga gtccggcggg ccgagcaacg cggagttctc gtcgccgcgg    60
gagcaggacc ggttcctgcc gatcgcgaac gtgagccgga tcatgaagaa ggcgctcccg   120
gcgaacgcca agatctccaa ggacgccaag gagacggtgc aggagtgcgt ctccgagttc   180
atctccttca tcaccggcga ggcctccgac aagtgccagc gcgagaagcg caagaccatc   240
```

```
aacggcgacg acctcctctg ggccatgacc acgctcggct tcgaggacta catcgagcca     300
ctcaagctct acctccacaa gttccgcgag ctcgagggcg agaaggtggc ctccggcgcc     360
gcgggctcct ccggctccgc ctcgcagccc cagagagaga caacgccgtc cgcgcacaat     420
ggcgccgccg gggccgtcgg ctacggcatg tacggcgccg cgccggggc cggcggaggc      480 agcggcatga tcatgatgat ggggcagccg atgtacggct ccccaccggg cgcgtcgggg     540
tacccgcagc ccccgcacca ccacatggtg atgggcgcta aggtggcgc ctacggccac      600 ggcggcggct cgtcgccatc gctgtcgggg ctcggcaggc aggacaggct atga           654
```

<210> SEQ ID NO 4
<211> LENGTH: 324
<212> TYPE: PRT
<213> ORGANISM: Panicum virgatum

<400> SEQUENCE: 4

```
Met Cys Gly Gly Ala Ile Leu Ser Asp Leu Tyr Ser Pro Val Arg Arg
1               5                   10                  15

Thr Val Thr Ala Gly Asp Leu Trp Gly Glu Ser Gly Ser Ser Lys Asn
            20                  25                  30

Val Lys Asn Trp Lys Arg Ser Ser Trp Lys Phe Asp Glu Gly Asp Glu
        35                  40                  45

Asp Phe Glu Ala Asp Phe Lys Asp Phe Glu Asp Cys Ser Ser Glu Glu
    50                  55                  60

Glu Val Asp Phe Gly His Glu Glu Lys Glu Phe Gln Leu Asn Ser Ser
65                  70                  75                  80

Asn Phe Val Glu Phe Asn Gly His Thr Ala Lys Val Thr Ser Arg Lys
                85                  90                  95

Arg Lys Ile Gln Tyr Arg Gly Ile Arg Arg Arg Pro Trp Gly Lys Trp
            100                 105                 110

Ala Ala Glu Ile Arg Asp Pro Gln Lys Gly Val Arg Val Trp Leu Gly
        115                 120                 125

Thr Phe Ser Thr Ala Glu Glu Ala Ala Arg Ala Tyr Asp Val Glu Ala
    130                 135                 140

Leu Arg Ile Arg Gly Lys Lys Ala Lys Met Asn Phe Pro Thr Thr Ile
145                 150                 155                 160

Thr Ala Ala Gly Lys His His Arg Gln Arg Val Ala Arg Pro Ala Lys
                165                 170                 175

Lys Thr Ser Gln Glu Ser Leu Lys Ser Ser Asn Ala Ser Gly His Val
            180                 185                 190

Ile Ser Ala Gly Ser Ser Thr Asp Gly Thr Val Val Lys Ile Glu Leu
        195                 200                 205

Ser Gln Ser Pro Ala Ser Pro Leu Pro Val Ser Ala Trp Leu Asp
    210                 215                 220

Ala Phe Glu Leu Lys Gln Leu Gly Gly Glu Thr Pro Glu Ala Asp Gly
225                 230                 235                 240

Arg Glu Thr Pro Glu Glu Thr Asp His Glu Thr Gly Val Thr Ala Asp
                245                 250                 255

Met Phe Phe Gly Asn Gly Glu Val Arg Leu Ser Asp Asp Phe Ala Ser
            260                 265                 270

Tyr Glu Pro Tyr Pro Asn Phe Met Gln Leu Pro Tyr Leu Glu Gly Asp
        275                 280                 285

Ser Tyr Glu Asn Ile Asp Thr Leu Phe Asn Gly Glu Ala Ala Gln Asp
    290                 295                 300
```

```
Gly Val Asn Ile Gly Gly Leu Trp Asn Phe Asp Asp Val Pro Met Asp
305                 310                 315                 320

Arg Gly Val Tyr

<210> SEQ ID NO 5
<211> LENGTH: 192
<212> TYPE: PRT
<213> ORGANISM: Panicum virgatum

<400> SEQUENCE: 5

Met His Met Tyr Pro Phe Tyr Ile His Ala Gly Tyr Gly Thr Arg Met
1               5                   10                  15

His Tyr Arg Gly Val Arg Arg Pro Trp Gly Lys Trp Ala Ala Glu
            20                  25                  30

Ile Arg Asp Pro Ala Lys Ala Ala Arg Val Trp Leu Gly Thr Phe Asp
        35                  40                  45

Thr Ala Glu Ala Ala Ala Ala Ala Tyr Asp Asp Ala Ala Leu Arg Phe
    50                  55                  60

Lys Gly Ala Lys Ala Lys Leu Asn Phe Pro Glu Arg Val Arg Gly Arg
65                  70                  75                  80

Thr Gly Gln Gly Ala Phe Leu Val Ser Pro Gly Val Pro Gln Gln Pro
                85                  90                  95

Pro Pro Ser Ser Leu Pro Thr Ala Ala Ala Pro Thr Pro Phe Pro
            100                 105                 110

Gly Leu Met Arg Tyr Ala Gln Leu Gln Gly Trp Ser Ser Gly Asn Ile
        115                 120                 125

Ala Ala Ser Asn Thr Gly Gly Asp Leu Ala Pro Pro Ala Gln Ala Ser
    130                 135                 140

Ser Ser Val Gln Ile Leu Asp Phe Ser Thr Gln Gln Leu Leu Arg Gly
145                 150                 155                 160

Ser Pro Thr Thr Phe Gly Pro Pro Thr Thr Ser Ala Ser Met Ser
                165                 170                 175

Arg Thr Ser Arg Val Asp Glu Ala His Glu Ser Cys Asp Ala Pro Asp
            180                 185                 190

<210> SEQ ID NO 6
<211> LENGTH: 217
<212> TYPE: PRT
<213> ORGANISM: Panicum virgatum

<400> SEQUENCE: 6

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys Val Ala Ser Gly Ala Ala Gly Ser Ser Gly Ser Ala Ser
```

|  | 115 |  |  | 120 |  |  |  | 125 |  |  |  |
| --- | --- | --- | --- | --- | --- | --- | --- | --- | --- | --- | --- |

Gln Pro Gln Arg Glu Thr Thr Pro Ser Ala His Asn Gly Ala Ala Gly
130                  135                 140

Ala Val Gly Tyr Gly Met Tyr Gly Ala Gly Gly Ala Gly Gly Gly
145                150                155                160

Ser Gly Met Ile Met Met Gly Gln Pro Met Tyr Gly Ser Pro Pro
                165                170                175

Gly Ala Ser Gly Tyr Pro Gln Pro Pro His His His Met Val Met Gly
           180                  185                190

Ala Lys Gly Gly Ala Tyr Gly His Gly Gly Gly Ser Ser Pro Ser Leu
          195                  200                205

Ser Gly Leu Gly Arg Gln Asp Arg Leu
210                  215

<210> SEQ ID NO 7
<211> LENGTH: 981
<212> TYPE: DNA
<213> ORGANISM: Panicum virgatum

<400> SEQUENCE: 7

```
atgtgcggtg gggctattct cagtgatctc tactcaccag tgaggcggac ggtcactgcc     60
ggtgacctat ggggagagag cggcagcacc aagaatgtga agaactggaa aaggaggagt    120
tcttggaagt ttgatgaaga cgatgatgac tttgaagctg atttcgagga tttcaacgat    180
tgcagtagcg aggaggaggt ggattttgta cgtgaggaaa agaattccaa ttgaacagt    240
tcgaattttg tggaactcaa cggccatacc accaaagtcg ccagcaggaa gcgaaagacc    300
cagtaccgag ggatccgacg gcgcccgtgg ggcaaatggg cagctgaaat cagagaccca    360
cagaagggcg tccgagtttg gcttggcacg ttcagcactg ccgaggaagc tgcaaaggca    420
tatgacgtgg aagctctacg catacgtggc aagaaagcca aggtgaattt ccctaacacc    480
atcacagctg ctgggaaaca ccaccggcag catgtggctc gaccagcaaa gaggatgtca    540
caagagagcc tgaagtcaag cgatgcctct ggtcatgtcg tctcagcagg cagcagtact    600
gatggcaccg ttgtcaagat tgagttgata gagtcaccag cttctccact accagtgtcc    660
agcgcatggc ttgatgcttt tgagctgaac caacttggtg gattaaggca ccttgaagct    720
gatgggagag aaaccactga agaaactgat catgaaacgg gagtgacagc agatatggtt    780
tttggcgatg gcaaagtgcg gctttcagat gattttgcgt cttacgagcc ttacccaaat    840
tttatgcagt taccttacct ggaaggtaac tcgtatgaaa acattgacac tcttttcaac    900
ggtgaagccg ctcaggatgg cgtgaacatc ggaggtctct ggaatttcga cgatgtgcca    960
atggaccgtg gtgtttacta a                                              981
```

<210> SEQ ID NO 8
<211> LENGTH: 1110
<212> TYPE: DNA
<213> ORGANISM: Panicum virgatum

<400> SEQUENCE: 8

```
atgtgcggcg gtgcgatcct cgccaacctc accaagcagc cgggcccgcg ccggctcacg     60
gagcgggacc tctggcagga agaagaagaa cccaagaggg gcgccggcgg ggggaggcgc    120
tggttcctgg ctgaggagga tgaggacttc gaggccgact cgaggacttc caggcgac     180
tccgatgagt cggatttgga actcggggag ggggaggacg acgacgtcgt cgagatcaag    240
cccttcgccg ccaagaggac ttcctccaaa gatggcttaa gcaccatgac tactgctggt    300
```

```
tatgatggcc ctgcagcaag gtcagccaaa aggaagagaa agaatcaata cagggcatc      360 cgccagcgcc cttggggtaa gtgggctgct gagatcagag atcctcagaa gggtgttcgt      420
gtttggcttg gtactttcaa cagtcctgag gaagctgcaa gagcttatga tgctgaagca      480
cgcaggatcc gtggtaagaa ggccaaggtt aacttccctg atgcaccaac agttgctcag      540
aagcgccgta gtgggccagc tgctgctaaa gcacccaaat caagtgtgga acagaagcct      600
accgtcaaac cagcagtgaa caaccttgcc aacgcaaatg catcctaccc acctgctgac      660
tacacctcaa gcaagccatc tgttcagcat gccaatatgg catttcatct agcaatgaac      720
tctgctagtc ctattgagga tccagttatg aatctgcact ctgaccaggg aagtaactct      780
tttgattgct cagacttgag ctgggagaat gataccaaga cttcagacat aacatccatt      840
gctcccattt ccaccatagc tgaaggtgac gagtctgcat tgtcaacag caatttgaac      900 aactcactgg tgccttctgt tatggagaac aatgcagttg atctcactga tgggctgaca      960
gatttagaac cgtacatgag gtttcttctg gatgatggtg caagtgagtc aattgataac     1020
cttctgaacc ttgatggatc tgaggatgtt atgagcaaca tggatctctg gagctttgat     1080
gacatgcctg ctgctggcga tttctattga                                      1110

<210> SEQ ID NO 9
<211> LENGTH: 1113
<212> TYPE: DNA
<213> ORGANISM: Panicum virgatum

<400> SEQUENCE: 9
atgtgcggcg gtgcgatcct cgccaacctc accaagcagc cgggcccgcg ccggctcacg       60
gagcgggacc tctggcagga gaagaagaag cccaagagga gcgccggcgg gggtaggcgc      120
tggttcctgg ctgaggagga tgaggacttc gaggccgact tcgaggactt ccagggcgac      180
tccgacgagt cagatttgga gctcggggag ggggaggacg acgacgtcgt cgagatcaag      240
cccttcgccg ccaagaggac ttcctccaaa gatggcttaa gcaccatgat tactgctggt      300
tatgatggcc ctgcagcaag gtcagccaaa aggaagagaa agaatcaata caggggcatc      360
cgccagcgcc cttggggtaa gtgggctgct gagatcagag atcctcagaa gggtgttcgt      420
gtctggcttg gtactttcaa cagtcctgag gaagctgcaa gagcttatga tgctgaagca      480
cgcaggatcc gtggtaagaa ggccaaggtt aacttccctg atgcaccaac agtttctcag      540
aagcgtcgta gtgggccagc tgccgctaaa gcacccaagt taagtgtgga acagaagcct      600
actgtcaaac cagcagtgaa caaccttgcc aacgcaaatg catctttcta cccacctgct      660
gactacacct caaaccagca atttgttcag catgccaata tgccatttca tccagcaatg      720
aactctgcta gtcctactga ggatccagtt atgaatctgc actctgacca gggaagtaac      780
tcttttgatt gctcagactt gagctgggag aatgatacca agacttcaga cataacatcc      840
attgctccca tttccaccat agctgaaggt gatgagtctg catttgtcaa cagcaatttg      900
aacaactcac tggtgccttc tgttatgggg aacaatgcag ttgatctcac tgatgggctg      960
acagatttag aaccctacat gaggtttctt ctggatgatg gtgcaagtga gtcaattgat     1020
aaccttctga accttgatgg atctgaggat gttatgagca catggatct ctggagcttt     1080 gatgacatgc ctgccactgg cgatttctat tga                                  1113

<210> SEQ ID NO 10
<211> LENGTH: 960
<212> TYPE: DNA
```

<213> ORGANISM: Panicum virgatum

<400> SEQUENCE: 10

| | | | | | |
|---|---|---|---|---|---|
| atgtgcgggg | gcgccattct | cgcggaactc | atcccgtcgc | cgcgccgggc | ggcgtcgaag | 60 |
| ccggtgaccg | cgggccacct | ctggccggcg | ggctccgaca | ccaagaaggc | cggcagcggg | 120 |
| aggagcaaga | ggcaccagct | cgccgacgtc | gacgactttg | aggccgcctt | cgaggacttc | 180 |
| gccgacgatt | ttgacaagga | ggaggtcgag | gaccaccatt | tcgtgttctc | gtccaaatcc | 240 |
| gcattctccc | cagcccacgg | cgtgcgcgcg | gcgacccaga | gaggcgcgg | ccgccgccac | 300 |
| ttccgcggca | tccggcagcg | ccctggggc | aagtgggcgg | cggagatccg | cgacccgcac | 360 |
| aagggcaccc | gcgtctggct | cggcaccttc | aacaccgccg | aggacgccgc | ccgggcctac | 420 |
| gacgtcgagg | cacgccgcct | ccggcagcag | aaggccaagg | tcaacttccc | cgcggccggc | 480 |
| gcgcgcccac | gccgcggcaa | cgcgccgaga | ccgcagcgcc | accatgccgc | agcgcagccc | 540 |
| gcgttgcttg | caggagagaa | gcggaaggag | gaggagatcg | tcgtgaagcc | tgaaattggg | 600 |
| gcgtcgttcg | acttcgacgt | gggcagcttc | ttcgacacgg | ccttcccgc | ggcgccgccg | 660 |
| gccatggaga | actccttcgc | cggcagcacc | gggtcggagt | ccggtagccc | cgcaaagaag | 720 |
| atgagatacg | acaacgactc | gtcgtccgat | gggatgagct | ccggcggcgg | ctccgcgctg | 780 |
| gagctcgctg | acgagctcgc | gttcgatccg | ttcatgctgc | tccagatgcc | ctactcgggc | 840 |
| gggtacgagt | ccctcgacgg | cctgttcgcc | gtcgacgccg | cccaggacgt | gaacaacgac | 900 |
| atgaacggcg | tcagcctgtg | gagcttcgac | gagttccccg | acgacagcgc | tgttttctaa | 960 |

<210> SEQ ID NO 11
<211> LENGTH: 570
<212> TYPE: DNA
<213> ORGANISM: Panicum virgatum

<400> SEQUENCE: 11

| | | | | | |
|---|---|---|---|---|---|
| aacgtgacga | gaagcaggca | ctaccgtggc | gtgcggcggc | ggccgtgggg | caagtgggcg | 60 |
| gcggagatcc | gtgaccccgc | caaggcggcg | cgcgtgtggc | tcggcaccttc | cgacaccgcg | 120 |
| gaggccgccg | ctgcagcgta | cgacgacgcc | gcgctccggt | tcaagggcgc | caaggccaag | 180 |
| ctcaacttcc | ccgagcgcgt | ccgaggccgc | accggccagg | gcgcgttcct | cgtcagccct | 240 |
| tgcgtccccc | agcagcagcc | gccgtcgccg | tcttccatgc | caactgcagc | cgcgccgttc | 300 |
| cccggcctga | tccggtatgc | acagctgctc | cagggttgga | acagcgggag | catcgcggcc | 360 |
| agcaacaccg | gtgacctcgc | gccgccgcg | gccttgccaa | tgccgccggc | acaggcgtcg | 420 |
| tcgtcggtgc | agattctgga | cttctcgacg | cagcagctcc | tccggggctc | gccgacaacg | 480 |
| ttcggcggcc | caccgccgcc | gacgtcggca | tcgatgtcca | ggactagcag | agtagatgag | 540 |
| gcgcacgaga | gttgcaatgc | tcctgactga | | | | 570 |

<210> SEQ ID NO 12
<211> LENGTH: 558
<212> TYPE: DNA
<213> ORGANISM: Panicum virgatum

<400> SEQUENCE: 12

| | | | | | |
|---|---|---|---|---|---|
| ggtcggaggc | ggcactaccg | aggggtgcgg | cagcggccgt | gggggaagtg | ggcggcagag | 60 |
| atccgggacc | ccaagaaggc | ggcgcggggtg | tggctgggca | ccttcgacac | ggcggaggac | 120 |
| gccgccatcg | cctacgacga | ggcggcgctc | cggttcaagg | gcaccaaggc | caagctcaac | 180 |
| ttcccggagc | gcgtccaggg | ccgcaccgac | ctgggcttcc | tcgtcacccg | cggcgtcccg | 240 |

```
gaccggcacc accaccaagg cgcggcggcg gcgcaggcgc agctcatgat gctggcccgc      300
ggcggcggcg gcggcgtcaa cctgccgttc ggagccgcgt cgccgttctc gccctcgccc      360
tcgccctcgt cggcgccgca gatcctggac ttctccacgc agcagctcat ccggcccgac      420
ccgccgtcgc cggccgccgc gatgtcgtcg tcgggcgctg ctccgtccac gccgtcgtcc      480
acgaccacgg cgtcgtcgcc cggtggcggt gcatggccgt acggtgggga gcaccacagg      540
aataaaaaag acgcgtga                                                    558

<210> SEQ ID NO 13
<211> LENGTH: 1089
<212> TYPE: DNA
<213> ORGANISM: Panicum virgatum

<400> SEQUENCE: 13
atgtgccacg ccgcggtggc ggactcgggg gagcagcacg gcggcggct tctcgccgcc       60 ggcgacggcg gcggaggaga ccgccgccag cagcagcagc agcccagcc gctggagccc      120 gtggtgatgg aagccaacac ggcggcgtcg ccggcgctgt cgcggggcag gcaggcccgg      180
gagatgtcgg ccatggtggc cgcgctggcc agggtggtcg ccggctcggc gccgccggcc      240
aaggcgcccc cccaggccgt gcaggatgcc tccgcggagg aggcgtggtg gccgtacgac      300
gagctcgccg ccgagccgtc ccctgctttc gtgctcgacg gctacagcga acgcagccg      360 ctgccggagc actactggcc ttcggctgcg gcggcgacag aggcggcgac ttcctcgcag      420
acgcattacc gtgccgcctc tgctgccgcg gccgaggagg aggtaccttc gccgtcgtcc      480
gcctccgccg ccgccggggc gagcagcagc ggcagcgcgg cgacgcggaa gcgttaccgc      540
ggcgtgcggc agcgtccgtg ggggaagtgg cggcggagga tccgtgaccc gcacaaggcg      600
gcgcgcgtgt ggctgggcac cttcgacacc gccgaggccg ccgcccgggc ctacgatggc      660
gccgcgctta ggttccgcgg cagccgcgcc aggctcaact tccccgagtc cgccacgctc      720
ccgtccccgc cgccgccgga tccggcctcg cgcgcattgc cgccgccgcc gcccaggccg      780
gacgcgcttc tggagtcgca ggctcaggcg ccctccaccg gcggcggcat ggagcaatac      840
gcggagtacg ccaggctctt gcagagcgcc ggcggcgacc ccggcggctc atccgggacg      900
ccaagtggca cgttgcctcc ccctcctcct cctgcagcgt acagcttcgc cgcccagggc      960
gtgacaccgt tcagctacct gtcgccgccg cagagccgcg cgagccagc aggcaacccc     1020 gcggcggcgt gggcggcgag ccactaccac ggctcgtacc cgccgtggcg gtgggaccac     1080
tcaggttga                                                            1089

<210> SEQ ID NO 14
<211> LENGTH: 654
<212> TYPE: DNA
<213> ORGANISM: Panicum virgatum

<400> SEQUENCE: 14
atgccggact ccgacaaaga gtccggctgg ccgagcaacg cggagttctc gtcgccgcgg       60
gagcaggacc ggttcctgcc gatcgcgaac gtcagccgga tcatgaagat ggcgctcccg      120
gcgaacgcca agatctccaa ggacgccaag gagacggtgc aggagtgcgt ctccgagttc      180
atctccttca tcaccggcga ggcctccgac aagtgccagc gcgagaagcg caagaccatc      240 aacgcgacg acctcctctg gccatgacc acgctcggct tcgaggacta catcgagccg      300
ctcaagctct acctccacaa gttccgcgag ctcgagggcg agaaggtggc ctccggcgcc      360
```

| | |
|---|---|
| gcgggctcct ccggctccgg ctcgcagccg cagagggaga cgacgccgtc cgcgcacaat | 420 |
| ggcgccggcg gggccgtcgg ctacggcatt tacggcgccg gcgccggggc aggcggaggc | 480 |
| agcggcatga tcatgatgat ggggcagccg atgtacaact ccccaccggg cgcgtcaggg | 540 |
| tacccgcagc ccccgcacca ccagatggtg atggccgcga aggtggcgc ctacggccac | 600 |
| ggcggcggct cgtcgccgtc gccgccgggg ctcggcaggc aggacaggct ttga | 654 |

<210> SEQ ID NO 15
<211> LENGTH: 609
<212> TYPE: DNA
<213> ORGANISM: Panicum virgatum

<400> SEQUENCE: 15

| | |
|---|---|
| atgccggact cggacaacga ctccggcggc ccgagcaacg ccggcggcga gctgtcgtcg | 60 |
| ccgcgggagc aggacaggtt cctccccatc gcgaacgtga gccggatcat gaagaaggcg | 120 |
| ctcccggcga cgccaagat cagcaaggac gccaaggaga cggtgcagga gtgcgtctcc | 180 |
| gagttcatct ccttcatcac cggcgaggcc tccgacaagt gccagcgcga aagcgcaag | 240 |
| accatcaacg cgacgacct gctctgggcc atgaccacgc tcggcttcga ggactacgtc | 300 |
| gagccgctca gcactacct ccacaagttc gcgagatcg agggcgagag gcggccgcc | 360 |
| tcctcgggcg cctcgggctc cgccgccgcg cagcagcagg gcgacgtggc gaggggcgcc | 420 |
| accaatgccg gcgggtacgc cgggtacagc gccggcggca tgatgatgat ggggcagccg | 480 |
| atgtacggct cgccgcagca gcagcaccaa cagcatcaca tggcaatggg aggcagaggc | 540 |
| ggttacggcc atcaaggagg cggcggctcg tcgtcgtcgt cggggcttgg ccggcaagac | 600 |
| agggcgtga | 609 |

<210> SEQ ID NO 16
<211> LENGTH: 543
<212> TYPE: DNA
<213> ORGANISM: Panicum virgatum

<400> SEQUENCE: 16

| | |
|---|---|
| atggcggacg cgccagcgag ccccggggc ggcggcggga ccacgagag cgggagcccc | 60 |
| aggggcggcg ccggggcgg gggcggcggc gtcagggagc aggacaggtt cctgcccatc | 120 |
| gccaacatca gccgcatcat gaagaaggcc atcccggcca cgggaagat cgccaaggac | 180 |
| gccaaggaga ccgtgcagga gtgcgtctcc gagttcatat ccttcatcac cagcgaggcg | 240 |
| agtgacaagt gccagaggga gaagaggaag accatcaacg gggacgacct actgtgggcc | 300 |
| atggccacgt tggggttcga ggactacata gaacccctca aggtgtacct gcagaagtac | 360 |
| agagagatgg aggtgatag caagttaact gcaaaaactg gcgatggctc tattaaaaag | 420 |
| gatgcccttg gccatggggg agcaagtagc tcagccacac aagggatggg ccaacaagga | 480 |
| gcgtacaacc aaggaatggg ttatatgcaa cctcagtacc ataacggaga catctcaaac | 540 |
| taa | 543 |

<210> SEQ ID NO 17
<211> LENGTH: 486
<212> TYPE: DNA
<213> ORGANISM: Panicum virgatum

<400> SEQUENCE: 17

| | |
|---|---|
| atggcggacg acggcgggag ccacgagggc ggcggcggcg tccgggagca ggaccggttc | 60 |
| ctgcccatcg ccaacatcag ccgcatcatg aagaaggccg tcccggctaa cggcaagatc | 120 |

```
gccaaggatg ccaaggagac cctgcaggag tgcgtctccg agttcatctc cttcgtcacc    180
agcgaggcca gcgacaagtg ccagaaggag aagcgcaaga ccatcaacgg cgatgatctg    240
ctctgggcga tggctacgct cggattcgag gagtacgtcg agcccctcaa gatgtaccta    300
cacaagtaca gagagatgga gggtgatagt aagttgtcta caaaggctgg tgagggctct    360
gtaaagaagg atgcaattag tccccatggt ggcaccagta gctcaagtaa ccagttggtt    420
caacatggag tttacaacca agggatgggc tatatgcaac cacagtacca taatggggat    480
acctaa                                                               486

<210> SEQ ID NO 18
<211> LENGTH: 384
<212> TYPE: DNA
<213> ORGANISM: Panicum virgatum

<400> SEQUENCE: 18
atggcggacg cgccagcgag ccccgggggc ggcggcggga gccacgagag tgggagcccc     60
aagggcggcg gcggggggcgg aggcggcggc gtcagggagc aggacaggtt cctgcccatc    120
gccaacatca gccgcatcat gaagaaggcc atcccggcca cgggaagat  cgccaaggac    180 gccaaggaga ccgtgcagga gtgcgtctcc gaattcatct ccttcatcac cagcgaggcg    240
agtgacaagt gccagaggga aagaggaag accatcaacg gggacgacct actgtgggcc    300
atggccacgc tggggttcga ggactacata gaacccctca aggtgtacct gcagaagtac    360
agagaggtca caaaacactt atag                                           384

<210> SEQ ID NO 19
<211> LENGTH: 12168
<212> TYPE: DNA
<213> ORGANISM: Panicum virgatum

<400> SEQUENCE: 19
gtaaacctaa gagaaaagag cgtttattag aataacggat atttaaaagg gcgtgaaaag     60
gtttatccgt tcgtccattt gtatgtgcat gccaaccaca gggttcccct cgggatcaaa    120
gtactttgat ccaacccctc cgctgctata gtgcagtcgg cttctgacgt tcagtgcagc    180
cgtcttctga aaacgacatg tcgcacaagt cctaagttac gcgacaggct gccgccctgc    240
ccttttcctg gcgttttctt gtcgcgtgtt ttagtcgcat aaagtagaat acttgcgact    300
agaaccggag acattacgcc atgaacaaga gcgccgccgc tggcctgctg gctatgccc    360 gcgtcagcac cgacgaccag gacttgacca accaacgggc cgaactgcac gcggccggct    420
gcaccaagct gttttccgag aagatcaccg gcaccaggcg cgaccgcccg gagctggcca    480
ggatgcttga ccacctacgc cctggcgacg ttgtgacagt gaccaggcta gaccgcctgg    540
cccgcagcac ccgcgaccta ctggacattg ccgagcgcat ccaggaggcc ggcgcgggcc    600
tgcgtagcct ggcagagccg tgggccgaca ccaccacgcc ggccggccgc atggtgttga    660
ccgtgttcgc cggcattgcc gagttcgagc gttccctaat catcgaccgc acccggagcg    720
ggcgcgaggc cgccaaggcc cgaggcgtga agtttggccc ccgccctacc ctcaccccgg    780
cacagatcgc gcacgcccgc gagctgatcg accaggaagg ccgcaccgtg aaagaggcgg    840
ctgcactgct tggcgtgcat cgctcgaccc tgtaccgcgc acttgagcgc agcgaggaag    900
tgacgcccac cgaggccagg cggcgcggtg ccttccgtga ggacgcattg accgaggccg    960
acgccctggc ggccgccgag aatgaacgcc aagaggaaca agcatgaaac cgcaccagga   1020
```

```
cggccaggac gaaccgtttt tcattaccga agagatcgag gcggagatga tcgcggccgg    1080
gtacgtgttc gagccgcccg cgcacgtctc aaccgtgcgg ctgcatgaaa tcctggccgg    1140
tttgtctgat gccaagctgg cggcctggcc ggccagcttg gccgctgaag aaaccgagcg    1200
ccgccgtcta aaaggtgat gtgtatttga gtaaaacagc ttgcgtcatg cggtcgctgc     1260
gtatatgatg cgatgagtaa ataaacaaat acgcaagggg aacgcatgaa ggttatcgct    1320
gtacttaacc agaaaggcgg gtcaggcaag acgaccatcg caacccatct agcccgcgcc    1380
ctgcaactcg ccggggccga tgttctgtta gtcgattccg atccccaggg cagtgcccgc    1440
gattgggcgg ccgtgcggga agatcaaccg ctaaccgttg tcggcatcga ccgcccgacg    1500
attgaccgcg acgtgaaggc catcggccgg cgcgacttcg tagtgatcga cggagcgccc    1560
caggcggcgg acttggctgt gtccgcgatc aaggcagccg acttcgtgct gattccggtg    1620
cagccaagcc cttacgacat atgggccacc gccgacctgg tggagctggt taagcagcgc    1680
attgaggtca cggatggaag gctacaagcg gcctttgtcg tgtcgcgggc gatcaaaggc    1740
acgcgcatcg gcggtgaggt tgccgaggcg ctggccgggt acgagctgcc cattcttgag    1800
tcccgtatca cgcagcgcgt gagctaccca ggcactgccg ccgccggcac aaccgttctt    1860
gaatcagaac ccgagggcga cgctgcccgc gaggtccagg cgctggccgc tgaaattaaa    1920
tcaaaactca tttgagttaa tgaggtaaag agaaaatgag caaaagcaca aacacgctaa    1980
gtgccggccg tccgagcgca cgcagcagca aggctgcaac gttggccagc ctggcagaca    2040
cgccagccat gaagcgggtc aactttcagt tgccggcgga ggatcacacc aagctgaaga    2100
tgtacgcggt acgccaaggc aagaccatta ccgagctgct atctgaatac atcgcgcagc    2160
taccagagta aatgagcaaa tgaataaatg agtagatgaa ttttagcggc taaaggaggc    2220
ggcatggaaa atcaagaaca accaggcacc gacgccgtgg aatgccccat gtgtggagga    2280
acgggcggtt ggccaggcgt aagcggctgg gttgtctgcc ggcctgcaa tggcactgga    2340 acccccaagc ccgaggaatc ggcgtgacgg tcgcaaacca tccggcccgg tacaaatcgg    2400
cgcggcgctg ggtgatgacc tggtggagaa gttgaaggcc gcgcaggccg cccagcggca    2460
acgcatcgag gcagaagcac gccccggtga atcgtggcaa gcggccgctg atcgaatccg    2520
caaagaatcc cggcaaccgc cggcagccgg tgcgccgtcg attaggaagc cgcccaaggg    2580
cgacgagcaa ccagattttt tcgttccgat gctctatgac gtgggcaccc gcgatagtcg    2640
cagcatcatg gacgtggccg ttttccgtct gtcgaagcgt gaccgacgag ctggcgaggt    2700
gatccgctac gagcttccag acgggcacgt agaggtttcc gcaggccgg ccggcatggc    2760 cagtgtgtgg gattacgacc tggtactgat ggcggtttcc catctaaccg aatccatgaa    2820
ccgataccgg gaagggaagg gagacaagcc cggccgcgtg ttccgtccac acgttgcgga    2880
cgtactcaag ttctgccggc gagccgatgg cggaaagcag aaagacgacc tggtagaaac    2940
ctgcattcgg ttaaacacca cgcacgttgc catgcagcgt acgaagaagg ccaagaacgg    3000
ccgcctggtg acggtatccg agggtgaagc cttgattagc cgctacaaga tcgtaaagag    3060
cgaaaccggg cggccggagt acatcgagat cgagctagct gattggatgt accgcgagat    3120
cacagaaggc aagaacccgg acgtgctgac ggttcacccc gattactttt tgatcgatcc    3180
cggcatcggc cgttttctct accgcctggc acgccgcgcc gcaggcaagg cagaagccag    3240
atggttgttc aagacgatct acgaacgcag tggcagcgcc ggagagttca agaagttctg    3300
tttcaccgtg cgcaagctga tcgggtcaaa tgacctgccg gagtacgatt tgaaggagga    3360
ggcggggcag gctggcccga tcctagtcat gcgctaccgc aacctgatcg agggcgaagc    3420
```

-continued

```
atccgccggt tcctaatgta cggagcagat gctagggcaa attgccctag caggggaaaa    3480
aggtcgaaaa ggtctctttc ctgtggatag cacgtacatt gggaacccaa agccgtacat    3540
tgggaaccgg aacccgtaca ttgggaaccc aaagccgtac attgggaacc ggtcacacat    3600
gtaagtgact gatataaaag agaaaaaagg cgatttttcc gcctaaaact ctttaaaact    3660
tattaaaact cttaaaaccc gcctggcctg tgcataactg tctggccagc gcacagccga    3720
agagctgcaa aaagcgccta cccttcggtc gctgcgctcc ctacgccccg ccgcttcgcg    3780
tcggcctatc gcggccgctg ccgctcaaa aatggctggc ctacggccag gcaatctacc     3840
agggcgcgga caagccgcgc cgtcgccact cgaccgccgg cgcccacatc aaggcaccct    3900
gcctcgcgcg tttcggtgat gacggtgaaa acctctgaca catgcagctc ccggagacgg    3960
tcacagcttg tctgtaagcg gatgccggga gcagacaagc ccgtcagggc gcgtcagcgg    4020
gtgttggcgg gtgtcggggc gcagccatga cccagtcacg tagcgatagc ggagtgtata    4080
ctggcttaac tatgcggcat cagagcagat tgtactgaga gtgcaccata tgcggtgtga    4140
aataccgcac agatgcgtaa ggagaaaata ccgcatcagg cgctcttccg cttcctcgct    4200
cactgactcg ctgcgctcgg tcgttcggct gcggcgagcg gtatcagctc actcaaaggc    4260
ggtaatacgg ttatccacag aatcagggga taacgcagga agaacatgt gagcaaaagg     4320
ccagcaaaag gccaggaacc gtaaaaaggc cgcgttgctg gcgttttccc ataggctccg    4380
cccccctgac gagcatcaca aaaatcgacg ctcaagtcag aggtggcgaa acccgacagg    4440
actataaaga taccaggcgt ttccccctgg aagctccctc gtgcgctctc ctgttccgac    4500
cctgccgctt accggatacc tgtccgcctt tctcccttcg ggaagcgtgg cgctttctca    4560
tagctcacgc tgtaggtatc tcagttcggt gtaggtcgtt cgctccaagc tgggctgtgt    4620
gcacgaaccc cccgttcagc ccgaccgctg cgccttatcc ggtaactatc gtcttgagtc    4680
caacccggta agacacgact tatcgccact ggcagcagcc actggtaaca ggattagcag    4740
agcgaggtat gtaggcggtg ctacagagtt cttgaagtgg tggcctaact acggctacac    4800
tagaaggaca gtatttggta tctgcgctct gctgaagcca gttaccttcg gaaaagagt     4860
tggtagctct tgatccggca aacaaaccac cgctggtagc ggtggttttt ttgtttgcaa    4920
gcagcagatt acgcgcagaa aaaaaggatc tcaagaagat cctttgatct tttctacggg    4980
gtctgacgct cagtggaacg aaaactcacg ttaagggatt ttggtcatgc attctaggta    5040
ctaaaacaat tcatccagta aaatataata ttttattttc tcccaatcag gcttgatccc    5100
cagtaagtca aaaaatagct cgacatactg ttcttccccg atatcctccc tgatcgaccg    5160
gacgcagaag gcaatgtcat accacttgtc cgccctgccg cttctcccaa gatcaataaa    5220
gccacttact ttgccatctt tcacaaagat gttgctgtct cccaggtcgc cgtgggaaaa    5280
gacaagttcc tcttcgggct tttccgtctt taaaaaatca tacagctcgc gcggatcttt    5340
aaatggagtg tcttcttccc agttttcgca atccacatcg ccagatcgt tattcagtaa     5400
gtaatccaat tcggctaagc ggctgtctaa gctattcgta tagggacaat ccgatatgtc    5460
gatggagtga aagagcctga tgcactccgc atacagctcg ataatctttt cagggctttg    5520
ttcatcttca tactcttccg agcaaaggac gccatcggcc tcactcatga gcagattgct    5580
ccagccatca tgccgttcaa agtgcaggac ctttggaaca ggcagctttc cttccagcca    5640
tagcatcatg tccttttccc gttccacatc ataggtggtc cctttatacc ggctgtccgt    5700
cattttaaa tataggtttt cattttctcc caccagctta tataccttag caggagacat     5760
```

```
tccttccgta tcttttacgc agcggtattt ttcgatcagt ttttcaatt ccggtgatat    5820
tctcatttta gccatttatt atttccttcc tcttttctac agtatttaaa gatacccaa    5880
gaagctaatt ataacaagac gaactccaat tcactgttcc ttgcattcta aaaccttaaa   5940
taccagaaaa cagcttttc aaagttgttt tcaaagttgg cgtataacat agtatcgacg    6000
gagccgattt tgaaaccgcg gtgatcacag gcagcaacgc tctgtcatcg ttacaatcaa   6060
catgctaccc tccgcgagat catccgtgtt tcaaacccgg cagcttagtt gccgttcttc   6120
cgaatagcat cggtaacatg agcaaagtct gccgccttac aacggctctc ccgctgacgc   6180
cgtcccggac tgatgggctg cctgtatcga gtggtgattt tgtgccgagc tgccggtcgg   6240
ggagctgttg gctggctggt ggcaggatat attgtggtgt aaacaaattg acgcttagac   6300
aacttaataa cacattgcgg acgttttaa tgtactgaat taacgccgaa ttaattcggg    6360
ggatctggat tttagtactg gatttggtt ttaggaatta gaaattttat tgatagaagt    6420
attttacaaa tacaaataca tactaagggt ttcttatatg ctcaacacat gagcgaaacc   6480
ctataggaac cctaattccc ttatctggga actactcaca cattattatg gagaaactcg   6540
agtcaaatct cggtgacggg caggaccgga cggggcggta ccggcaggct gaagtccagc   6600
tgccagaaac ccacgtcatg ccagttcccg tgcttgaagc cggccgcccg cagcatgccg   6660
cgggggggcat atccgagcgc ctcgtgcatg cgcacgctcg ggtcgttggg cagcccgatg   6720
acagcgacca cgctcttgaa gccctgtgcc tccaggggact tcagcaggtg ggtgtagagc   6780
gtggagccca gtcccgtccg ctggtggcgg ggggagacgt acacggtcga ctcggccgtc   6840
cagtcgtagg cgttgcgtgc cttccagggg cccgcgtagg cgatgccggc gacctcgccg   6900
tccacctcgg cgacgagcca gggatagcgc tcccgcagac ggacgaggtc gtccgtccac   6960
tcctgcggtt cctgcggctc ggtacggaag ttgaccgtgc ttgtctcgat gtagtggttg   7020
acgatggtgc agaccgccgg catgtccgcc tcggtggcac ggcggatgtc ggccgggcgt   7080
cgttctgggc tcatggtaga ccgcttggta tctgcattac aatgaaatga gcaaagacta   7140
tgtgagtaac actggtcaac actagggaga aggcatcgag caagatacgt atgtaaagag   7200
aagcaatata gtgtcagttg gtagatacta gataccatca ggaggtaagg agagcaacaa   7260
aaaggaaact ctttatttt aaattttgtt acaacaaaca agcagatcaa tgcatcaaaa    7320
tactgtcagt acttatttct tcagacaaca atatttaaaa caagtgcatc tgatcttgac   7380
ttatggtcac aataaaggag cagagataaa catcaaaatt tcgtcattta tatttattcc   7440
ttcaggcgtt aacaatttaa cagcacacaa acaaaaacag aataggaata tctaattttg   7500
gcaaataata agctctgcag acgaacaaat tattatagta tcgcctataa tatgaatccc   7560
tatactattg acccatgtag tatgaagcct gtgcctaaat taacagcaaa cttctgaatc   7620
caagtgccct ataacaccaa catgtgctta aataaatacc gctaagcacc aaattacaca   7680
tttctcgtat tgctgtgtag gttctatctt cgtttcgtac taccatgtcc ctatattttg   7740
ctgctacaaa ggacggcaag taatcagcac aggcagaaca cgatttcaga gtgtaattct   7800
agatccagct aaaccactct cagcaatcac cacacaagag agcattcaga gaaacgtggc   7860
agtaacaaag gcagagggcg gagtgagcgc gtaccgaaga cggtctcgag agagatagat   7920
ttgtagagag agactggtga tttcagcgtg tcctctccaa atgaaatgaa cttccttata   7980
tagaggaagg tcttgcgaag gatagtggga ttgtgcgtca tcccttacgt cagtggagat   8040
atcacatcaa tccacttgct ttgaagacgt ggttggaacg tcttcttttt ccacgatgct   8100
cctcgtgggt gggggtccat ctttgggacc actgtcggca gaggcatctt gaacgatagc   8160
```

```
ctttcctttta tcgcaatgat ggcatttgta ggtgccacct tccttttcta ctgtcctttt    8220
gatgaagtga cagatagctg ggcaatggaa tccgaggagg tttcccgata ttaccctttg    8280
ttgaaaagtc tcaatagccc tttggtcttc tgagactgta tctttgatat tcttggagta    8340
gacgagagtg tcgtgctcca ccatgttatc acatcaatcc acttgctttg aagacgtggt    8400
tggaacgtct tcttttcca cgatgctcct cgtgggtggg ggtccatctt tgggaccact    8460
gtcggcagag gcatcttgaa cgatagcctt tcctttatcg caatgatggc atttgtaggt    8520
gccaccttcc ttttctactg tccttttgat gaagtgacag atagctgggc aatggaatcc    8580
gaggaggttt cccgatatta ccctttgttg aaaagtctca atagcccttt ggtcttctga    8640
gactgtatct ttgatattct tggagtagac gagagtgtcg tgctccacca tgttggcaag    8700
ctgctctagc caatacgcaa accgcctctc ccgcgcgtt ggccgattca ttaatgcagc     8760
tggcacgaca ggtttcccga ctggaaagcg ggcagtgagc gcaacgcaat taatgtgagt    8820
tagctcactc attaggcacc ccaggcttta cactttatgc ttccggctcg tatgttgtgt    8880
ggaattgtga gcggataaca atttcacaca ggaaacagct atgaccatga ttacgaattg    8940
gggtttaaac cacggaagat ccaggtctcg agactaggag acggatggga ggcgcaacgc    9000
gcgatgggga gggggcggc gctgaccttt ctggcgaggt cgaggtagcg atcgagcagc     9060
tgcagcgcgg acacgatgag gaagacgaag atagccgcca tggacatgtt cgccagcggc    9120
ggcggagcga ggctgagccg gtctctccgg cctccggtcg gcgttaagtt ggggatcgta    9180
acgtgacgtg tctcgtctcc acggatcgac acaaccggcc tactcgggtg cacgacgccg    9240
cgataagggc gagatgtccg tgcacgcagc ccgtttggag tcctcgttgc ccacgaaccg    9300
accccttaca gaacaaggcc tagcccaaaa ctattctgag ttgagctttt gagcctagcc    9360
cacctaagcc gagcgtcatg aactgatgaa cccactacca ctagtcaagg caaaccacaa    9420
ccacaaatgg atcaattgat ctagaacaat ccgaaggagg ggaggccacg tcacactcac    9480
accaaccgaa atatctgcca gaatcagatc aaccggccaa taggacgcca gcgagcccaa    9540
cacctggcga cgccgcaaaa ttcaccgcga ggggcaccgg gcacggcaaa aacaaaagcc    9600
cggcgcggtg agaatatctg gcgactggcg gagacctggt ggccagcgcg cggccacatc    9660 agccaccccca tccgcccacc tcacctccgg cgagccaatg caactcgtc ttaagattcc     9720 acgagataag gacccgatcg ccggcgacgc tatttagcca ggtgcgcccc ccacggtaca    9780
ctccaccagc ggcatctata gcaaccggtc cagcactttc acgctcagct tcagcaagat    9840
ctaccgtctt cggtacgcgc tcactccgcc ctctgccttt gttactgcca cgtttctctg    9900
aatgctctct tgtgtggtga ttgctgagag tggtttagct ggatctagaa ttacactctg    9960
aaatcgtgtt ctgcctgtgc tgattacttg ccgtcctttg tagcagcaaa atatagggac   10020
atggtagtac gaaacgaaga tagaacctac acagcaatac gagaaatgtg taatttggtg   10080
cttagcggta tttatttaag cacatgttgg tgttataggg cacttggatt cagaagtttg   10140
ctgttaattt aggcacaggc ttcatactac atgggtcaat agtatagga ttcatattat     10200 aggcgatact ataataattt gttcgtctgc agagcttatt atttgccaaa attagatatt   10260
cctattctgt ttttgtttgt gtgctgttaa attgttaacg cctgaggaa taaatataaa     10320 tgacgaaatt ttgatgttta tctctgctcc tttattgtga ccataagtca agatcagatg   10380
cacttgtttt aaatattgtt gtctgaagaa ataagtactg acagtatttt gatgcattga   10440
tctgcttgtt tgttgtaaca aaatttaaaa ataaagagtt tccttttgt tgctctcctt     10500
```

```
acctcctgat ggtatctagt atctaccaac tgatactata ttgcttctct ttacatacgt    10560
atcttgctcg atgccttctc ctagtgttga ccagtgttac tcacatagtc tttgctcatt    10620
tcattgtaat gcagatacca agcggttaat taaatgtgcg gcggggccat tctcagtgat    10680
ctctactcac cagtgaggcg gacggtcact gccggtgacc tatggggaga gagtggcagc    10740
agcaagaatg tgaagaactg aaaaggagt tcttggaagt ttgatgaagg cgatgaagac    10800
tttgaagctg atttcaagga ttttgaggat tgcagtagcg aggaggaggt agattttgga    10860
catgaggaaa aagaattcca attgaacagt tcgaatttcg tggaattcaa tggccatact    10920
gccaaagtca ccagcaggaa gcgaaagatc cagtaccgag ggatccggcg gcggccttgg    10980
ggcaaatggg cagcagaaat cagagaccca cagaagggcg tccgagtttg gcttggcacg    11040
ttcagcactg ccgaggaagc tgcaagggca tatgacgtgg aagctctacg catacgtggc    11100
aagaaagcca agatgaattt ccctaccacc atcacagctg ctgggaaaca ccaccggcag    11160
cgtgtggctc gaccggcaaa gaagacgtca caagagagcc tgaagtcaag caatgcctct    11220
ggtcatgtca tctcagcagg cagcagtact gatggcaccg ttgtcaagat cgagttgtca    11280
cagtcaccag cttctccact accagtgtcc agcgcatggc ttgatgcttt tgagctgaag    11340
cagcttggtg gagaaacccc tgaagctgat gggagagaaa ccctgaaga aactgatcat    11400 gaaacgggag tgacagcgga tatgtttttt ggcaatggcg aagtgcggct ttcagatgat    11460
tttgcgtctt acgagcctta cccaaatttt atgcagttac cttatctaga aggtgactcg    11520
tatgaaaaca ttgacactct tttcaacggt gaagctgctc aggatggagt gaacatcgga    11580
ggtctttgga atttcgatga tgtgccaatg gaccgtggtg tttactgagg cgcgccatcg    11640
ttcaaacatt tggcaataaa gtttcttaag attgaatcct gttgccggtc ttgcgatgat    11700
tatcatataa tttctgttga attacgttaa gcatgtaata attaacatgt aatgcatgac    11760
gttatttatg agatgggttt ttatgattag agtcccgcaa ttatacattt aatacgcgat    11820
agaaaacaaa atatagcgcg caaactagga taaattatcg cgcgcggtgt catctatgtt    11880
actagatccg atgataagct gtcaaacatg acctcaggat gaagcttggc actggccgtc    11940
gttttacaac gtcgtgactg gaaaaaccct ggcgttaccc aacttaatcg ccttgcagca    12000
catccccctt tcgccagctg gcgtaatagc gaagaggccc gcaccgatcg cccttcccaa    12060
cagttgcgca gcctgaatgg cgaatgctag agcagcttga gcttggatca gattgtcgtt    12120
tcccgccttc agtttaaact atcagtgttt gacaggatat attggcgg                 12168
```

<210> SEQ ID NO 20
<211> LENGTH: 11772
<212> TYPE: DNA
<213> ORGANISM: Panicum virgatum

<400> SEQUENCE: 20

```
gtaaacctaa gagaaaagag cgtttattag aataacggat atttaaaagg gcgtgaaaag      60
gtttatccgt tcgtccattt gtatgtgcat gccaaccaca gggttcccct cgggatcaaa     120
gtactttgat ccaaccccctc cgctgctata gtgcagtcgg cttctgacgt tcagtgcagc     180
cgtcttctga aaacgacatg tcgcacaagt cctaagttac gcgacaggct gccgccctgc     240 cctttcctg gcgttttctt gtcgcgtgtt ttagtcgcat aaagtagaat acttgcgact     300
agaaccggag acattacgcc atgaacaaga gcgccgccgc tggcctgctg gctatgccc     360 gcgtcagcac cgacgaccag gacttgacca accaacgggc cgaactgcac gcggccggct     420
gcaccaagct gttttccgag aagatcaccg gcaccaggcg cgaccgcccg gagctggcca     480
```

```
ggatgcttga ccacctacgc cctggcgacg ttgtgacagt gaccaggcta gaccgcctgg    540
cccgcagcac ccgcgaccta ctggacattg ccgagcgcat ccaggaggcc ggcgcgggcc    600
tgcgtagcct ggcagagccg tgggccgaca ccaccacgcc ggccggccgc atggtgttga    660
ccgtgttcgc cggcattgcc gagttcgagc gttccctaat catcgaccgc acccggagcg    720
ggcgcgaggc cgccaaggcc cgaggcgtga agtttggccc ccgccctacc ctcaccccgg    780
cacagatcgc gcacgcccgc gagctgatcg accaggaagg ccgcaccgtg aaagaggcgg    840
ctgcactgct tggcgtgcat cgctcgaccc tgtaccgcgc acttgagcgc agcgaggaag    900
tgacgcccac cgaggccagg cggcgcgtg ccttccgtga ggacgcattg accgaggcca    960
acgccctggc ggccgccgag aatgaacgcc aagaggaaca agcatgaaac cgcaccagga   1020
cggccaggac gaaccgtttt tcattaccga agagatcgag gcggagatga tcgcggccgg   1080
gtacgtgttc gagccgcccg cgcacgtctc aaccgtgcgg ctgcatgaaa tcctggccgg   1140
tttgtctgat gccaagctgg cggcctggcc ggccagcttg gccgctgaag aaaccgagcg   1200
ccgccgtcta aaaggtgat gtgtatttga gtaaaacagc ttgcgtcatg cggtcgctgc   1260
gtatatgatg cgatgagtaa ataaacaaat acgcaagggg aacgcatgaa ggttatcgct   1320
gtacttaacc agaaaggcgg gtcaggcaag acgaccatcg caacccatct agcccgcgcc   1380
ctgcaactcg ccggggccga tgttctgtta gtcgattccg atccccaggg cagtgcccgc   1440
gattgggcgg ccgtgcggga agatcaaccg ctaaccgttg tcggcatcga ccgcccgacg   1500
attgaccgcg acgtgaaggc catcggccgg cgcgacttcg tagtgatcga cggagcgccc   1560
caggcggcgg acttggctgt gtccgcgatc aaggcagccg acttcgtgct gattccggtg   1620
cagccaagcc cttacgacat atgggccacc gccgacctgg tggagctggt taagcagcgc   1680
attgaggtca cggatggaag gctacaagcg gcctttgtcg tgtcgcgggc gatcaaaggc   1740
acgcgcatcg gcggtgaggt tgccgaggcg ctggccgggt acgagctgcc cattcttgag   1800
tcccgtatca cgcagcgcgt gagctaccca ggcactgccg ccgccggcac aaccgttctt   1860
gaatcagaac ccgagggcga cgctgcccgc gaggtccagg cgctggccgc tgaaattaaa   1920
tcaaaactca tttgagttaa tgaggtaaag agaaaatgag caaaagcaca aacacgctaa   1980
gtgccggccg tccgagcgca cgcagcagca aggctgcaac gttggccagc ctggcagaca   2040
cgccagccat gaagcgggtc aactttcagt tgccggcgga ggatcacacc aagctgaaga   2100
tgtacgcggt acgccaaggc aagaccatta ccgagctgct atctgaatac atcgcgcagc   2160
taccagagta aatgagcaaa tgaataaatg agtagatgaa ttttagcggc taaaggaggc   2220
ggcatggaaa atcaagaaca accaggcacc gacgccgtgg aatgccccat gtgtggagga   2280
acgggcggtt ggccaggcgt aagcggctgg gttgtctgcc ggcctgcaa tggcactgga   2340 accccaagc ccgaggaatc ggcgtgacgg tcgcaaacca tccggcccgg tacaaatcgg   2400
cgcggcgctg ggtgatgacc tggtggagaa gttgaaggcc gcgcaggccg cccagcggca   2460
acgcatcgag gcagaagcac gccccggtga atcgtggcaa gcggccgctg atcgaatccg   2520
caaagaatcc cggcaaccgc cggcagccgg tgcgccgtcg attaggaagc cgcccaaggg   2580
cgacgagcaa ccagatttt tcgttccgat gctctatgac gtgggcaccc gcgatagtcg   2640
cagcatcatg gacgtggccg tttcccgtct gtcgaagcgt gaccgacgag ctggcgaggt   2700
gatccgctac gagcttccag acgggcacgt agaggtttcc gcaggccgg ccggcatggc   2760 cagtgtgtgg gattacgacc tggtactgat ggcggtttcc catctaaccg aatccatgaa   2820
```

```
ccgataccgg gaagggaagg gagacaagcc cggccgcgtg ttccgtccac acgttgcgga    2880
cgtactcaag ttctgccggc gagccgatgg cggaaagcag aaagacgacc tggtagaaac    2940
ctgcattcgg ttaaacacca cgcacgttgc catgcagcgt acgaagaagg ccaagaacgg    3000
ccgcctggtg acggtatccg agggtgaagc cttgattagc cgctacaaga tcgtaaagag    3060
cgaaaccggg cggccggagt acatcgagat cgagctagct gattggatgt accgcgagat    3120
cacagaaggc aagaacccgg acgtgctgac ggttcacccc gattactttt tgatcgatcc    3180
cggcatcggc cgtttctct accgcctggc acgccgcgcc gcaggcaagg cagaagccag    3240
atggttgttc aagacgatct acgaacgcag tggcagcgcc ggagagttca agaagttctg    3300
tttcaccgtg cgcaagctga tcgggtcaaa tgacctgccg gagtacgatt tgaaggagga    3360
ggcggggcag gctggcccga tcctagtcat gcgctaccgc aacctgatcg agggcgaagc    3420
atccgccggt tcctaatgta cggagcagat gctagggcaa attgccctag cagggggaaaa    3480 aggtcgaaaa ggtctctttc ctgtggatag cacgtacatt gggaacccaa agccgtacat    3540
tgggaaccgg aacccgtaca ttgggaaccc aaagccgtac attgggaacc ggtcacacat    3600
gtaagtgact gatataaaag agaaaaaagg cgattttttcc gcctaaaact ctttaaaact    3660
tattaaaact cttaaaaccc gcctggcctg tgcataactg tctggccagc gcacagccga    3720
agagctgcaa aaagcgccta cccttcggtc gctgcgctcc ctacgccccg ccgcttcgcg    3780
tcggcctatc gcgccgctg gccgctcaaa atggctggc ctacgccag gcaatctacc    3840 agggcgcgga caagccgcgc cgtcgccact cgaccgccgg cgcccacatc aaggcaccct    3900
gcctcgcgcg tttcggtgat gacggtgaaa acctctgaca catgcagctc ccggagacgg    3960
tcacagcttg tctgtaagcg gatgccggga gcagacaagc ccgtcagggc gcgtcagcgg    4020
gtgttggcgg gtgtcgggc gcagccatga cccagtcacg tagcgatagc ggagtgtata    4080
ctggcttaac tatgcggcat cagagcagat tgtactgaga gtgcaccata tgcggtgtga    4140
aataccgcac agatgcgtaa ggagaaaata ccgcatcagg cgctcttccg cttcctcgct    4200
cactgactcg ctgcgctcgg tcgttcggct gcggcgagcg gtatcagctc actcaaaggc    4260
ggtaatacgg ttatccacag aatcaggga taacgcagga agaacatgt gagcaaaagg    4320 ccagcaaaag gccaggaacc gtaaaaaggc cgcgttgctg gcgttttttcc ataggctccg    4380 ccccctgac gagcatcaca aaaatcgacg ctcaagtcag aggtggcgaa acccgacagg    4440
actataaaga taccaggcgt ttccccctgg aagctccctc gtgcgctctc ctgttccgac    4500
cctgccgctt accggatacc tgtccgcctt tctcccttcg ggaagcgtgg cgctttctca    4560
tagctcacgc tgtaggtatc tcagttcggt gtaggtcgtt cgctccaagc tgggctgtgt    4620
gcacgaaccc cccgttcagc ccgaccgctg cgccttatcc ggtaactatc gtcttgagtc    4680
caacccggta agacacgact tatcgccact ggcagcagcc actggtaaca ggattagcag    4740
agcgaggtat gtaggcggtg ctacagagtt cttgaagtgg tggcctaact acggctacac    4800
tagaaggaca gtatttggta tctgcgctct gctgaagcca gttaccttcg gaaaaagagt    4860
tggtagctct tgatccggca acaaaccac cgctggtagc ggtggttttt ttgtttgcaa    4920
gcagcagatt acgcgcagaa aaaaaggatc tcaagaagat cctttgatct tttctacggg    4980
gtctgacgct cagtggaacg aaaactcacg ttaagggatt ttggtcatgc attctaggta    5040
ctaaaacaat tcatccagta aaatataata ttttattttc tcccaatcag gcttgatccc    5100
cagtaagtca aaaaatagct cgacatactg ttcttccccg atatcctccc tgatcgaccc    5160
gacgcagaag gcaatgtcat accacttgtc cgccctgccg cttctcccaa gatcaataaa    5220
```

```
gccacttact ttgccatctt tcacaaagat gttgctgtct cccaggtcgc cgtgggaaaa   5280
gacaagttcc tcttcgggct tttccgtctt taaaaaatca tacagctcgc gcggatcttt   5340
aaatggagtg tcttcttccc agttttcgca atccacatcg gccagatcgt tattcagtaa   5400
gtaatccaat tcggctaagc ggctgtctaa gctattcgta tagggacaat ccgatatgtc   5460
gatggagtga aagagcctga tgcactccgc atacagctcg ataatctttt cagggctttg   5520
ttcatcttca tactcttccg agcaaaggac gccatcggcc tcactcatga gcagattgct   5580
ccagccatca tgccgttcaa agtgcaggac ctttggaaca ggcagctttc cttccagcca   5640
tagcatcatg tccttttccc gttccacatc ataggtggtc cctttatacc ggctgtccgt   5700 cattttaaa tataggtttt cattttctcc caccagctta tataccttag caggagacat    5760
tccttccgta tcttttacgc agcggtattt ttcgatcagt tttttcaatt ccggtgatat   5820
tctcatttta gccatttatt atttccttcc tcttttctac agtatttaaa gatacccaa    5880 gaagctaatt ataacaagac gaactccaat tcactgttcc ttgcattcta aaaccttaaa   5940
taccagaaaa cagcttttc aaagttgttt tcaaagttgg cgtataacat agtatcgacg    6000
gagccgattt tgaaaccgcg gtgatcacag gcagcaacgc tctgtcatcg ttacaatcaa   6060
catgctaccc tccgcgagat catccgtgtt tcaaacccgg cagcttagtt gccgttcttc   6120
cgaatagcat cggtaacatg agcaaagtct gccgccttac aacggctctc ccgctgacgc   6180
cgtcccggac tgatgggctg cctgtatcga gtggtgattt tgtgccgagc tgccggtcgg   6240
ggagctgttg gctggctggt ggcaggatat attgtggtgt aaacaaattg acgcttagac   6300
aacttaataa cacattgcgg acgttttaa tgtactgaat taacgccgaa ttaattcggg    6360
ggatctggat tttagtactg gattttggtt ttaggaatta gaaattttat tgatagaagt   6420
attttacaaa tacaaataca tactaagggt ttcttatatg ctcaacacat gagcgaaacc   6480
ctataggaac cctaattccc ttatctggga actactcaca cattattatg gagaaactcg   6540
agtcaaatct cggtgacggg caggaccgga cggggcggta ccggcaggct gaagtccagc   6600
tgccagaaac ccacgtcatg ccagttcccg tgcttgaagc cggccgcccg cagcatgccg   6660
cggggggcat atccgagcgc ctcgtgcatg cgcacgctcg ggtcgttggg cagcccgatg   6720
acagcgacca cgctcttgaa gccctgtgcc tccagggact tcagcaggtg ggtgtagagc   6780
gtggagccca gtcccgtccg ctggtggcgg ggggagacgt acacggtcga ctcggccgtc   6840
cagtcgtagg cgttgcgtgc cttccagggg cccgcgtagg cgatgccggc gacctcgccg   6900
tccacctcgg cgacgagcca gggatagcgc tcccgcagac ggacgaggtc gtccgtccac   6960
tcctgcggtt cctgcggctc ggtacggaag ttgaccgtgc ttgtctcgat gtagtggttg   7020
acgatggtgc agaccgccgg catgtccgcc tcggtggcac ggcggatgtc ggccgggcgt   7080
cgttctgggc tcatggtaga ccgcttggta tctgcattac aatgaaatga gcaaagacta   7140
tgtgagtaac actggtcaac actagggaga aggcatcgag caagatacgt atgtaaagag   7200
aagcaatata gtgtcagttg gtagatacta gataccatca ggaggtaagg agagcaacaa   7260
aaaggaaact ctttattttt aaattttgtt acaacaaaca agcagatcaa tgcatcaaaa   7320
tactgtcagt acttatttct tcagacaaca atatttaaaa caagtgcatc tgatcttgac   7380
ttatggtcac aataaaggag cagagataaa catcaaaatt tcgtcattta tatttattcc   7440
ttcaggcgtt aacaatttaa cagcacacaa acaaaaacag aataggaata tctaattttg   7500
gcaaataata agctctgcag acgaacaaat tattatagta tcgcctataa tatgaatccc   7560
```

```
tatactattg acccatgtag tatgaagcct gtgcctaaat aacagcaaa cttctgaatc   7620
caagtgccct ataacaccaa catgtgctta aataaatacc gctaagcacc aaattacaca   7680
tttctcgtat tgctgtgtag gttctatctt cgtttcgtac taccatgtcc ctatattttg   7740
ctgctacaaa ggacggcaag taatcagcac aggcagaaca cgatttcaga gtgtaattct   7800
agatccagct aaaccactct cagcaatcac cacacaagag agcattcaga gaaacgtggc   7860
agtaacaaag gcagagggcg gagtgagcgc gtaccgaaga cggtctcgag agagatagat   7920
ttgtagagag agactggtga tttcagcgtg tcctctccaa atgaaatgaa cttccttata   7980
tagaggaagg tcttgcgaag gatagtggga ttgtgcgtca tcccttacgt cagtggagat   8040
atcacatcaa tccacttgct ttgaagacgt ggttggaacg tcttcttttt ccacgatgct   8100
cctcgtgggt gggggtccat ctttgggacc actgtcggca gaggcatctt gaacgatagc   8160
cttccttta tcgcaatgat ggcatttgta ggtgccacct ccttttcta ctgtcctttt   8220
gatgaagtga cagatagctg ggcaatgaa tccgaggagg tttcccgata ttaccctttg   8280
ttgaaaagtc tcaatagccc tttggtcttc tgagactgta tctttgatat tcttggagta   8340
gacgagagtg tcgtgctcca ccatgttatc acatcaatcc acttgctttg aagacgtggt   8400
tggaacgtct tcttttcca cgatgctcct cgtgggtggg ggtccatctt tgggaccact   8460
gtcggcagag gcatcttgaa cgatagcctt tcctttatcg caatgatggc atttgtaggt   8520
gccaccttcc ttttctactg tccttttgat gaagtgacag atagctgggc aatggaatcc   8580
gaggaggttt cccgatatta cccttttgttg aaaagtctca atagcccttt ggtcttctga   8640
gactgtatct ttgatattct tggagtagac gagagtgtcg tgctccacca tgttggcaag   8700
ctgctctagc caatacgcaa accgcctctc cccgcgcgtt ggccgattca ttaatgcagc   8760
tggcacgaca ggtttcccga ctggaaagcg ggcagtgagc gcaacgcaat taatgtgagt   8820
tagctcactc attaggcacc ccaggcttta cactttatgc ttccggctcg tatgttgtgt   8880
ggaattgtga gcggataaca atttcacaca ggaaacagct atgaccatga ttacgaattg   8940
gggtttaaac cacggaagat ccaggtctcg agactaggag acggatggga ggcgcaacgc   9000
gcgatgggga gggggggcggc gctgaccttt ctggcgaggt cgaggtagcg atcgagcagc   9060
tgcagcgcgg acacgatgag gaagacgaag atagccgcca tggacatgtt cgccagcggc   9120
ggcggagcga ggctgagccg gtctctccgg cctccggtcg gcgttaagtt ggggatcgta   9180
acgtgacgtg tctcgtctcc acggatcgac acaaccggcc tactcgggtg cacgacgccg   9240
cgataagggc gagatgtccg tgcacgcagc ccgtttggag tcctcgttgc ccacgaaccg   9300
acccccttaca gaacaaggcc tagcccaaaa ctattctgag ttgagctttt gagcctagcc   9360
cacctaagcc gagcgtcatg aactgatgaa cccactacca ctagtcaagg caaaccacaa   9420
ccacaaatgg atcaattgat ctagaacaat ccgaaggagg ggaggccacg tcacactcac   9480
accaaccgaa atatctgcca gaatcagatc aaccggccaa taggacgcca gcgagcccaa   9540
cacctggcga cgccgcaaaa ttcaccgcga ggggcaccgg gcacggcaaa aacaaaagcc   9600
cggcgcggtg agaatatctg gcgactggcg gagacctggt ggccagcgcg cggccacatc   9660
agccaccca tccgcccacc tcacctccgg cgagccaatg gcaactcgtc ttaagattcc   9720
acgagataag gacccgatcg ccggcgacgc tatttagcca ggtgcgcccc ccacggtaca   9780
ctccaccagc ggcatctata gcaaccggtc cagcactttc acgctcagct tcagcaagat   9840
ctaccgtctt cggtacgcgc tcactccgcc ctctgccttt gttactgcca cgtttctctg   9900
aatgctctct tgtgtggtga ttgctgagag tggtttagct ggatctagaa ttacactctg   9960
```

-continued

```
aaatcgtgtt ctgcctgtgc tgattacttg ccgtcctttg tagcagcaaa atatagggac    10020
atggtagtac gaaacgaaga tagaacctac acagcaatac gagaaatgtg taatttggtg    10080
cttagcggta tttatttaag cacatgttgg tgttataggg cacttggatt cagaagtttg    10140
ctgttaattt aggcacaggc ttcatactac atgggtcaat agtataggga ttcatattat    10200
aggcgatact ataataattt gttcgtctgc agagcttatt atttgccaaa attagatatt    10260
cctattctgt ttttgtttgt gtgctgttaa attgttaacg cctgaaggaa taaatataaa    10320
tgacgaaatt ttgatgttta tctctgctcc tttattgtga ccataagtca agatcagatg    10380
cacttgtttt aaatattgtt gtctgaagaa ataagtactg acagtatttt gatgcattga    10440
tctgcttgtt tgttgtaaca aaatttaaaa ataaagagtt tccttttgt tgctctcctt     10500 acctcctgat ggtatctagt atctaccaac tgatactata ttgcttctct ttacatacgt    10560
atcttgctcg atgccttctc ctagtgttga ccagtgttac tcacatagtc tttgctcatt    10620
tcattgtaat gcagatacca agcggttaat taaatgcata tgtatccttt ctacatacat    10680
gcaggttacg ggacgagaat gcactaccgt ggcgtgcggc ggcggccgtg gggcaagtgg    10740
gcggcggaga tccgtgaccc cgccaaggcg gcgcgtgtgt ggctcggcac cttcgacacc    10800
gcggaggccg ccgccgcagc gtacgacgac gccgcgctcc ggttcaaggg cgccaaggcc    10860
aagctcaact ttccgagcg cgtccgcggc cgtaccggcc agggcgcgtt cctcgtcagc     10920
cctggcgtcc cccagcagcc gccgccgtct tccctgccaa ctgcagccgc cgcgccgacg    10980
ccgttccccg gcttgatgcg gtacgcgcaa ctccagggtt ggagcagcgg gaacatcgcg    11040
gccagcaaca ccggtggtga tctcgcgccg ccggcacagg cgtcgtcgtc ggtgcagatt    11100
ctggacttct cgacgcagca actactccgg ggctcaccga caacgttcgg cccaccgccg    11160
acgacgtcgg catcgatgtc caggactagc agagtagatg aggcgcacga gagttgcgat    11220
gctcctgact gaggcgcgcc atcgttcaaa catttggcaa taagtttct taagattgaa      11280 tcctgttgcc ggtcttgcga tgattatcat ataatttctg ttgaattacg ttaagcatgt    11340
aataattaac atgtaatgca tgacgttatt tatgagatgg gttttatga ttagagtccc      11400 gcaattatac atttaatacg cgatagaaaa caaaatatag cgcgcaaact aggataaatt     11460
atcgcgcgcg gtgtcatcta tgttactaga tccgatgata agctgtcaaa catgacctca    11520
ggatgaagct tggcactggc cgtcgttta caacgtcgtg actgggaaaa ccctggcgtt      11580
acccaactta atcgccttgc agcacatccc ctttcgcca gctggcgtaa tagcgaagag      11640
gcccgcaccg atcgcccttc ccaacagttg cgcagcctga atggcgaatg ctagagcagc    11700
ttgagcttgg atcagattgt cgtttccgc cttcagttta aactatcagt gtttgacagg     11760
atatattggc gg                                                          11772
```

<210> SEQ ID NO 21
<211> LENGTH: 12509
<212> TYPE: DNA
<213> ORGANISM: Panicum virgatum

<400> SEQUENCE: 21

```
gtaaacctaa gagaaaagag cgtttattag aataacggat atttaaaagg gcgtgaaaag      60
gtttatccgt tcgtccattt gtatgtgcat gccaaccaca gggttcccct cgggatcaaa    120
gtactttgat ccaaccccctc cgctgctata gtgcagtcgg cttctgacgt tcagtgcagc   180
cgtcttctga aaacgacatg tcgcacaagt cctaagttac gcgacaggct gccgccctgc   240
```

```
ccttttcctg gcgttttctt gtcgcgtgtt ttagtcgcat aaagtagaat acttgcgact      300
agaaccggag acattacgcc atgaacaaga gcgccgccgc tggcctgctg ggctatgccc      360
gcgtcagcac cgacgaccag gacttgacca accaacgggc cgaactgcac gcggccggct      420
gcaccaagct gttttccgag aagatcaccg gcaccaggcg cgaccgcccg gagctggcca      480
ggatgcttga ccacctacgc cctggcgacg ttgtgacagt gaccaggcta gaccgcctgg      540
cccgcagcac ccgcgaccta ctggacattg ccgagcgcat ccaggaggcc ggcgcgggcc      600
tgcgtagcct ggcagagccg tgggccgaca ccaccacgcc ggccggccgc atggtgttga      660
ccgtgttcgc cggcattgcc gagttcgagc gttccctaat catcgaccgc acccggagcg      720
ggcgcgaggc cgccaaggcc cgaggcgtga agtttggccc ccgccctacc ctcaccccgg      780
cacagatcgc gcacgcccgc gagctgatcg accaggaagg ccgcaccgtg aaagaggcgg      840
ctgcactgct tggcgtgcat cgctcgaccc tgtaccgcgc acttgagcgc agcgaggaag      900
tgacgcccac cgaggccagg cggcgcggtg ccttccgtga ggacgcattg accgaggccg      960
acgccctggc ggccgccgag aatgaacgcc aagaggaaca agcatgaaac cgcaccagga     1020
cggccaggac gaaccgtttt tcattaccga agagatcgag gcggagatga tcgcggccgg     1080
gtacgtgttc gagccgcccg cgcacgtctc aaccgtgcgg ctgcatgaaa tcctggccgg     1140
tttgtctgat gccaagctgg cggcctggcc ggccagcttg gccgctgaag aaaccgagcg     1200
ccgccgtcta aaaggtgat gtgtatttga gtaaaacagc ttgcgtcatg cggtcgctgc      1260
gtatatgatg cgatgagtaa ataaacaaat acgcaagggg aacgcatgaa ggttatcgct     1320
gtacttaacc agaaaggcgg gtcaggcaag acgaccatcg caacccatct agcccgcgcc     1380
ctgcaactcg ccggggccga tgttctgtta gtcgattccg atccccaggg cagtgcccgc     1440
gattgggcgg ccgtgcggga agatcaaccg ctaaccgttg tcggcatcga ccgcccgacg     1500
attgaccgcg acgtgaaggc catcggccgg cgcgacttcg tagtgatcga cggagcgccc     1560
caggcggcgg acttggctgt gtccgcgatc aaggcagccg acttcgtgct gattccggtg     1620
cagccaagcc cttacgacat atgggccacc gccgacctgg tggagctggt taagcagcgc     1680
attgaggtca cggatggaag gctacaagcg gcctttgtcg tgtcgcgggc gatcaaaggc     1740
acgcgcatcg gcggtgaggt tgccgaggcg ctggccgggt acgagctgcc cattcttgag     1800
tcccgtatca cgcagcgcgt gagctaccca ggcactgccg ccgccggcac aaccgttctt     1860
gaatcagaac ccgagggcga cgctgcccgc gaggtccagg cgctggccgc tgaaattaaa     1920
tcaaaactca tttgagttaa tgaggtaaag agaaaatgag caaaagcaca aacacgctaa     1980
gtgccggccg tccgagcgca cgcagcagca aggctgcaac gttggccagc ctggcagaca     2040
cgccagccat gaagcgggtc aactttcagt tgccggcgga ggatcacacc aagctgaaga     2100
tgtacgcggt acgccaaggc aagaccatta ccgagctgct atctgaatac atcgcgcagc     2160
taccagagta aatgagcaaa tgaataaatg agtagatgaa ttttagcggc taaaggaggc     2220
ggcatggaaa atcaagaaca accaggcacc gacgccgtgg aatgccccat gtgtggagga     2280
acgggcggtt ggccaggcgt aagcggctgg gttgtctgcc ggcctgcaa tggcactgga     2340
accccaagc cgaggaatc ggcgtgacgg tcgcaaacca tccggcccgg tacaaatcgg      2400
cgcggcgctg ggtgatgacc tggtggagaa gttgaaggcc gcgcaggccg cccagcggca     2460
acgcatcgag gcagaagcac gccccggtga atcgtggcaa gcggccgctg atcgaatccg     2520
caaagaatcc cggcaaccgc cggcagccgg tgcgccgtcg attaggaagc cgcccaaggg     2580
cgacgagcaa ccagatttttt tcgttccgat gctctatgac gtgggcaccc gcgatagtcg     2640
```

```
cagcatcatg gacgtggccg ttttccgtct gtcgaagcgt gaccgacgag ctggcgaggt    2700
gatccgctac gagcttccag acgggcacgt agaggtttcc gcagggccgg ccggcatggc    2760
cagtgtgtgg gattacgacc tggtactgat ggcggtttcc catctaaccg aatccatgaa    2820
ccgataccgg gaagggaagg gagacaagcc cggccgcgtg ttccgtccac acgttgcgga    2880
cgtactcaag ttctgccggc gagccgatgg cggaaagcag aaagacgacc tggtagaaac    2940
ctgcattcgg ttaaacacca cgcacgttgc catgcagcgt acgaagaagg ccaagaacgg    3000
ccgcctggtg acggtatccg agggtgaagc cttgattagc cgctacaaga tcgtaaagag    3060
cgaaaccggc cggccggagt acatcgagat cgagctagct gattggatgt accgcgagat    3120
cacagaaggc aagaacccgg acgtgctgac ggttcacccc gattactttt tgatcgatcc    3180
cggcatcggc cgttttctct accgcctggc acgccgcgcc gcaggcaagg cagaagccag    3240
atggttgttc aagacgatct acgaacgcag tggcagcgcc ggagagttca agaagttctg    3300
tttcaccgtg cgcaagctga tcgggtcaaa tgacctgccg gagtacgatt tgaaggagga    3360
ggcggggcag gctggcccga tcctagtcat gcgctaccgc aacctgatcg agggcgaagc    3420
atccgccggt tcctaatgta cggagcagat gctagggcaa attgccctag caggggaaaa    3480
aggtcgaaaa ggtctctttc ctgtggatag cacgtacatt gggaacccaa agccgtacat    3540
tgggaaccgg aacccgtaca ttgggaaccc aaagccgtac attgggaacc ggtcacacat    3600
gtaagtgact gatataaaag agaaaaaagg cgattttttcc gcctaaaact ctttaaaact    3660
tattaaaact cttaaaaccc gcctggcctg tgcataactg tctggccagc gcacagccga    3720
agagctgcaa aaagcgccta cccttcggtc gctgcgctcc ctacgccccg ccgcttcgcg    3780
tcggcctatc gcggccgctg gccgctcaaa aatggctggc ctacggccag gcaatctacc    3840
agggcgcgga caagccgcgc cgtcgccact cgaccgccgg cgcccacatc aaggcaccct    3900
gcctcgcgcg tttcggtgat gacggtgaaa acctctgaca catgcagctc ccggagacgg    3960
tcacagcttg tctgtaagcg gatgccggga gcagacaagc ccgtcagggc gcgtcagcgg    4020
gtgttggcgg gtgtcgggc gcagccatga cccagtcacg tagcgatagc ggagtgtata    4080
ctggcttaac tatgcggcat cagagcagat tgtactgaga gtgcaccata tgcggtgtga    4140
aataccgcac agatgcgtaa ggagaaaata ccgcatcagg cgctcttccg cttcctcgct    4200
cactgactcg ctgcgctcgg tcgttcggct gcggcgagcg gtatcagctc actcaaaggc    4260
ggtaatacgg ttatccacag aatcagggga taacgcagga agaacatgt gagcaaaagg    4320 ccagcaaaag gccaggaacc gtaaaaaggc cgcgttgctg gcgttttcc ataggctccg    4380 cccccctgac gagcatcaca aaaatcgacg ctcaagtcag aggtggcgaa acccgacagg    4440
actataaaga taccaggcgt ttccccctgg aagctccctc gtgcgctctc ctgttccgac    4500
cctgccgctt accggatacc tgtccgcctt tctcccttcg ggaagcgtgg cgctttctca    4560
tagctcacgc tgtaggtatc tcagttcggt gtaggtcgtt cgctccaagc tgggctgtgt    4620
gcacgaaccc cccgttcagc ccgaccgctg cgccttatcc ggtaactatc gtcttgagtc    4680
caacccggta agacacgact tatcgccact ggcagcagcc actggtaaca ggattagcag    4740
agcgaggtat gtaggcggtg ctacagagtt cttgaagtgg tggcctaact acggctacac    4800
tagaaggaca gtatttggta tctgcgctct gctgaagcca gttaccttcg gaaaaagagt    4860
tggtagctct tgatccggca acaaaccac cgctggtagc ggtggttttt ttgtttgcaa    4920
gcagcagatt acgcgcagaa aaaaaggatc tcaagaagat cctttgatct tttctacggg    4980
```

```
gtctgacgct cagtggaacg aaaactcacg ttaagggatt ttggtcatgc attctaggta    5040
ctaaaacaat tcatccagta aaatataata ttttattttc tcccaatcag gcttgatccc    5100
cagtaagtca aaaaatagct cgacatactg ttcttcccg atatcctccc tgatcgaccg     5160
gacgcagaag gcaatgtcat accacttgtc cgccctgccg cttctcccaa gatcaataaa    5220
gccacttact ttgccatctt tcacaaagat gttgctgtct cccaggtcgc cgtgggaaaa    5280
gacaagttcc tcttcgggct tttccgtctt taaaaaatca tacagctcgc gcggatcttt    5340
aaatggagtg tcttcttccc agttttcgca atccacatcg gccagatcgt tattcagtaa    5400
gtaatccaat tcggctaagc ggctgtctaa gctattcgta tagggacaat ccgatatgtc    5460
gatggagtga aagagcctga tgcactccgc atacagctcg ataatctttt cagggctttg    5520
ttcatcttca tactcttccg agcaaaggac gccatcggcc tcactcatga gcagattgct    5580
ccagccatca tgccgttcaa agtgcaggac ctttggaaca ggcagctttc cttccagcca    5640
tagcatcatg tccttttccc gttccacatc ataggtggtc cctttatacc ggctgtccgt    5700 cattttaaa tataggtttt cattttctcc caccagctta tataccttag caggagacat     5760
tccttccgta tcttttacgc agcggtattt ttcgatcagt tttttcaatt ccggtgatat    5820
tctcatttta gccatttatt atttccttcc tcttttctac agtatttaaa gataccccaa    5880
gaagctaatt ataacaagac gaactccaat tcactgttcc ttgcattcta aaaccttaaa    5940
taccagaaaa cagcttttc aaagttgttt tcaaagttgg cgtataacat agtatcgacg     6000
gagccgattt tgaaaccgcg gtgatcacag gcagcaacgc tctgtcatcg ttacaatcaa    6060
catgctaccc tccgcgagat catccgtgtt tcaaacccgg cagcttagtt gccgttcttc    6120
cgaatagcat cggtaacatg agcaaagtct gccgccttac aacggctctc ccgctgacgc    6180
cgtcccggac tgatgggctg cctgtatcga gtggtgattt tgtgccgagc tgccggtcgg    6240
ggagctgttg gctggctggt ggcaggatat attgtggtgt aaacaaattg acgcttagac    6300
aacttaataa cacattgcgg acgttttaa tgtactgaat taacgccgaa ttaattcggg     6360
ggatctggat tttagtactg gattttggtt ttaggaatta gaaattttat tgatagaagt    6420
attttacaaa tacaaataca tactaagggt ttcttatatg ctcaacacat gagcgaaacc    6480
ctataggaac cctaattccc ttatctggga actactcaca cattattatg gagaaactcg    6540
agtcaaatct cggtgacggg caggaccgga cggggcggta ccgcaggct gaagtccagc     6600 tgccagaaac ccacgtcatg ccagttcccg tgcttgaagc cggccgcccg cagcatgccg    6660 cgggggggcat atccgagcgc ctcgtgcatg cgcacgctcg ggtcgttggg cagcccgatg    6720
acagcgacca cgctcttgaa gccctgtgcc tccagggact tcagcaggtg ggtgtagagc    6780
gtggagccca gtcccgtccg ctggtggcgg ggggagacgt acacggtcga ctcggccgtc    6840
cagtcgtagg cgttgcgtgc cttccagggg cccgcgtagg cgatgccggc gacctcgccg    6900
tccacctcgg cgacgagcca gggatagcgc tcccgcagac ggacgaggtc gtccgtccac    6960
tcctgcggtt cctgcggctc ggtacggaag ttgaccgtgc ttgtctcgat gtagtggttg    7020
acgatggtgc agaccgccgg catgtccgcc tcggtggcac ggcggatgtc ggccgggcgt    7080
cgttctgggc tcatgtaga ccgcttggta tctgcattac aatgaaatga gcaaagacta     7140
tgtgagtaac actggtcaac actagggaga aggcatcgag caagatacgt atgtaaagag    7200
aagcaatata gtgtcagttg gtagatacta gataccatca ggaggtaagg agagcaacaa    7260
aaaggaaact ctttattttt aaattttgtt acaacaaaca agcagatcaa tgcatcaaaa    7320
tactgtcagt acttatttct tcagacaaca atatttaaaa caagtgcatc tgatcttgac    7380
```

```
ttatggtcac aataaaggag cagagataaa catcaaaatt tcgtcattta tatttattcc   7440
ttcaggcgtt aacaatttaa cagcacacaa acaaaaacag aataggaata tctaattttg   7500
gcaaataata agctctgcag acgaacaaat tattatagta tcgcctataa tatgaatccc   7560
tatactattg acccatgtag tatgaagcct gtgcctaaat taacagcaaa cttctgaatc   7620
caagtgccct ataacaccaa catgtgctta aataaatacc gctaagcacc aaattacaca   7680
tttctcgtat tgctgtgtag gttctatctt cgtttcgtac taccatgtcc ctatattttg   7740
ctgctacaaa ggacggcaag taatcagcac aggcagaaca cgatttcaga gtgtaattct   7800
agatccagct aaaccactct cagcaatcac cacacaagag agcattcaga gaaacgtggc   7860
agtaacaaag gcagagggcg gagtgagcgc gtaccgaaga cggtctcgag agagatagat   7920
ttgtagagag agactggtga tttcagcgtg tcctctccaa atgaaatgaa cttccttata   7980
tagaggaagg tcttgcgaag gatagtggga ttgtgcgtca tcccttacgt cagtggagat   8040
atcacatcaa tccacttgct ttgaagacgt ggttggaacg tcttcttttt ccacgatgct   8100
cctcgtgggt gggggtccat ctttgggacc actgtcggca gaggcatctt gaacgatagc   8160
cttttccttta tcgcaatgat ggcatttgta ggtgccacct tcctttttcta ctgtcctttt   8220
gatgaagtga cagatagctg gcaatggaaa tccgaggagg tttcccgata ttaccctttg   8280
ttgaaaagtc tcaatagccc tttggtcttc tgagactgta tctttgatat tcttggagta   8340
gacgagagtg tcgtgctcca ccatgttatc acatcaatcc acttgctttg aagacgtggt   8400
tggaacgtct tcttttttcca cgatgctcct cgtgggtggg ggtccatctt tgggaccact   8460
gtcggcagag gcatcttgaa cgatagcctt tcctttatcg caatgatggc atttgtaggt   8520
gccaccttcc ttttctactg tccttttgat gaagtgacag atagctgggc aatggaatcc   8580
gaggaggttt cccgatatta ccctttgttg aaaagtctca atagcccttt ggtcttctga   8640
gactgtatct ttgatattct tggagtagac gagagtgtcg tgctccacca tgttggcaag   8700
ctgctctagc caatacgcaa accgcctctc cccgcgcgtt ggccgattca ttaatgcagc   8760
tggcacgaca ggtttcccga ctggaaagcg ggcagtgagc gcaacgcaat taatgtgagt   8820
tagctcactc attaggcacc ccaggcttta cactttatgc ttccggctcg tatgttgtgt   8880
ggaattgtga gcggataaca atttcacaca ggaaacagct atgaccatga ttacgaattg   8940
gggtttaaac cacggaagat ccaggtctcg agactaggag acggatggga ggcgcaacgc   9000
gcgatgggga gggggcggc gctgaccttt ctggcgaggt cgaggtagcg atcgagcagc   9060
tgcagcgcg acacgatgag gaagacgaag atagccgcca tggacatgtt cgccagcggc   9120
ggcggagcga ggctgagccg gtctctccgg cctccggtcg gcgttaagtt ggggatcgta   9180
acgtgacgtg tctcgtctcc acggatcgac acaaccggcc tactcgggtg cacgacgccg   9240
cgataagggc gagatgtccg tgcacgcagc ccgtttggag tcctcgttgc ccacgaaccg   9300
acccccttaca gaacaaggcc tagcccaaaa ctattctgag ttgagctttt gagcctagcc   9360
cacctaagcc gagcgtcatg aactgatgaa cccactacca ctagtcaagg caaaccacaa   9420
ccacaaatgg atcaattgat ctagaacaat ccgaaggagg ggaggccacg tcacactcac   9480
accaaccgaa atatctgcca gaatcagatc aaccggccaa taggacgcca gcgagcccaa   9540
cacctggcga cgccgcaaaa ttcaccgcga ggggcaccgg gcacggcaaa aacaaaagcc   9600
cggcgcggtg agaatatctg gcgactggcg gagacctggt ggccagcgcg cggccacatc   9660
agccacccca tccgcccacc tcacctccgg cgagccaatg gcaactcgtc ttaagattcc   9720
```

```
acgagataag gacccgatcg ccggcgacgc tatttagcca ggtgcgcccc ccacggtaca    9780
ctccaccagc ggcatctata gcaaccggtc cagcactttc acgctcagct tcagcaagat    9840
ctaccgtctt cggtacgcgc tcactccgcc ctctgccttt gttactgcca cgtttctctg    9900
aatgctctct tgtgtggtga ttgctgagag tggtttagct ggatctagaa ttacactctg    9960
aaatcgtgtt ctgcctgtgc tgattacttg ccgtcctttg tagcagcaaa atatagggac   10020
atggtagtac gaaacgaaga tagaacctac acagcaatac gagaaatgtg taatttggtg   10080
cttagcggta tttatttaag cacatgttgg tgttataggg cacttggatt cagaagtttg   10140
ctgttaattt aggcacaggc ttcatactac atgggtcaat agtataggga ttcatattat   10200
aggcgatact ataataattt gttcgtctgc agagcttatt atttgccaaa attagatatt   10260
cctattctgt ttttgtttgt gtgctgttaa attgttaacg cctgaaggaa taaatataaa   10320
tgacgaaatt ttgatgttta tctctgctcc tttattgtga ccataagtca agatcagatg   10380
cacttgtttt aaatattgtt gtctgaagaa ataagtactg acagtatttt gatgcattga   10440
tctgcttgtt tgttgtaaca aaatttaaaa ataaagagtt tccttttgt tgctctcctt    10500 acctcctgat ggtatctagt atctaccaac tgatactata ttgcttctct ttacatacgt   10560
atcttgctcg atgcctcttc ctagtgttga ccagtgttac tcacatagtc tttgctcatt   10620
tcattgtaat gcagatacca agcggttaat taaatgccgg actccgacaa cgagtccggc   10680
gggccgagca acgcggagtt ctcgtcgccg cgggagcagg accggttcct gccgatcgcg   10740
aacgtgagcc ggatcatgaa gaaggcgctc ccggcgaacg ccaagatctc caaggacgcc   10800
aaggagacgg tgcaggagtg cgtctccgag ttcatctcct tcatcaccgg cgaggcctcc   10860
gacaagtgcc agcgcgagaa gcgcaagacc atcaacggcg acgacctcct ctgggccatg   10920
accacgctcg gcttcgagga ctacatcgag ccactcaagc tctacctcca caagttccgc   10980
gagctcgagg gcgagaaggt ggcctccggc gccgcgggct cctccggctc cgcctcgcag   11040
ccccagagag agacaacgcc gtccgcgcac aatggcgccg ccggggccgt cggctacggc   11100
atgtacggcg ccggcgccgg ggccggcgga ggcagcggca tgatcatgat gatggggcag   11160
ccgatgtacg gctccccacc gggcgcgtcg gggtacccgc agcccccgca ccaccacatg   11220
gtgatgggcg ctaaaggtgg cgcctacggc cacggcggcg gctcgtcgcc atcgctgtcg   11280
gggctcggca ggcaggacag gctatgaatg ccggactccg acaacgagtc cggcgggccg   11340
agcaacgcgg agttctcgtc gccgcgggag caggaccggt tcctgccgat cgcgaacgtg   11400
agccggatca tgaagaaggc gctcccggcg aacgccaaga tctccaagga cgccaaggag   11460
acggtgcagg agtgcgtctc cgagttcatc tccttcatca ccggcgaggc ctccgacaag   11520
tgccagcgcg agaagcgcaa gaccatcaac ggcgacgacc tcctctgggc catgaccacg   11580
ctcggcttcg aggactacat cgagccactc aagctctacc tccacaagtt ccgcgagctc   11640
gagggcgaga aggtggcctc cggcgccgcg ggctcctccg gctccgcctc gcagccccag   11700
agagagacaa cgccgtccgc gcacaatggc cgccggggg ccgtcggcta cggcatgtac   11760
ggcgccggcg ccggggccgg cggaggcagc ggcatgatca tgatgatggg gcagccgatg   11820
tacggctccc caccgggcgc gtcggggtac ccgcagcccc cgcaccacca catggtgatg   11880
ggcgctaaag gtggcgccta cggccacggc ggcggctcgt cgccatcgct gtcggggctc   11940
ggcaggcagg acaggctatg aaactgcagg gcgcgccatc gttcaaacat ttggcaataa   12000
agtttcttaa gattgaatcc tgttgccggt cttgcgatga ttatcatata atttctgttg   12060
aattacgtta agcatgtaat aattaacatg taatgcatga cgttatttat gagatgggtt   12120
```

| | | | | |
|---|---|---|---|---|
| tttatgatta | gagtcccgca | attatacatt | taatacgcga | tagaaaacaa aatatagcgc | 12180 |
| gcaaactagg | ataaattatc | gcgcgcggtg | tcatctatgt | tactagatcc gatgataagc | 12240 |
| tgtcaaacat | gacctcagga | tgaagcttgg | cactggccgt | cgttttacaa cgtcgtgact | 12300 |
| gggaaaaccc | tggcgttacc | caacttaatc | gccttgcagc | acatccccct ttcgccagct | 12360 |
| ggcgtaatag | cgaagaggcc | cgcaccgatc | gcccttccca | acagttgcgc agcctgaatg | 12420 |
| gcgaatgcta | gagcagcttg | agcttggatc | agattgtcgt | ttcccgcctt cagttaaac | 12480 |
| tatcagtgtt | tgacaggata | tattggcgg | | | 12509 |

<210> SEQ ID NO 22
<211> LENGTH: 1120
<212> TYPE: DNA
<213> ORGANISM: Panicum virgatum

<400> SEQUENCE: 22

| | | | | | |
|---|---|---|---|---|---|
| cctttttacc | attttctata | tcctttgcat | cggcgccgta | gataattgtt ggctgaaatt | 60 |
| catgccagct | atatgctatg | tttcgaccta | ggattggctg | cgcagagatg gtggtagggc | 120 |
| acgccaattt | atttgagata | caggttctcc | atacgttcct | tcacttcatt gcaatgcagc | 180 |
| agagtcatat | atatacctga | atcccaatcc | caacaaaggt | acggacctct gtgtcgtgtc | 240 |
| gtcctcctcc | tccggataca | ttgcgtttaa | tttcgaccgt | atggatggat ggatggatgt | 300 |
| ggatgtggtg | gccgtaatca | tgtactagct | tgctttgggg | ggtcatacga ttgattgatt | 360 |
| gattgattgc | acgggcatac | caggcttcag | tgtatttgct | gctctgtaga tactttactc | 420 |
| atgtgaaacc | cataagggtc | ggagtgagct | agggcctgtg | cggccggcac atagggatcg | 480 |
| gacggatgga | tcggtggtgg | tatgctagta | tatatgcatg | gtactacagc tactacccct | 540 |
| cctcctcctc | ctcctcccat | agtgtatgtg | tatgtgtatg | agcagcagca ggccgtatcg | 600 |
| acaggcccaa | cagacagacg | atggatcaga | tcggatctcc | acaccttgcc tggctcgagt | 660 |
| agatcttgac | catccgtgct | ccaatcatgg | ccatggccgc | cggactgcag agcaccaggc | 720 |
| atgccatccg | gacccctacta | ctactaccag | tcgcttacac | acctctgccc caaccgtgtc | 780 |
| tcattcttgg | cagtttgggg | aggaaggaag | cccaatcttg | tccctaaaaa acgctgttcc | 840 |
| atgtaagtga | ccagacgacg | actatactag | atcactagcc | cctcgaatcc tcgatgaaaa | 900 |
| gaaaaaataa | aagtcgcgag | cagtcacgct | cgccgaactc | aacgtccggc cgggaaggaa | 960 |
| attaacggcg | acagagggtc | ggtccccttt | cgttcggaag | tcggaactgt cattggtcgc | 1020 |
| cgtcgtcgtc | gcgtcactgg | catgtggggg | cctcggtcgg | caaaccatcg agagccgaga | 1080 |
| gccgggagag | agagagagag | gatggcaggt | gcacatgcat | | 1120 |

<210> SEQ ID NO 23
<211> LENGTH: 1020
<212> TYPE: DNA
<213> ORGANISM: Panicum virgatum

<400> SEQUENCE: 23

| | | | | | |
|---|---|---|---|---|---|
| cacatcgtgc | caagttcgag | gcccattgat | gcactttgct | tacatatata ctcgtttaaa | 60 |
| gcatgagttt | cgtgtattgt | gtgtcataca | cgaagcacat | atatctaatt ttctctccca | 120 |
| agtttcgtct | aacaactaga | taagataagc | cttacctctt | gcatgagcaa ccaaccatac | 180 |
| aaccaccacg | agtgctttct | cctccccctt | gttgatgatg | tcgtatatta acctcaacaa | 240 |
| cctaccatct | ctttcctcgt | ctgcttcttc | ctcacccaaa | ttcttctgta ccaccataga | 300 |

```
tgacatcgag taggccatcc tgctggtctc cgactcgcta accgcagcgc cccaccgcga    360
caccgtcttt accttccccc gtcgacaagc gcttcggaga acaataagg caagaacaac     420 cgagtgagag gaggagacgc tccggatctc gagtttagtt ttatgttagt tgttgacaaa    480
gaaattgtga tatattatgg tcgataataa tatatatata ttgctgggta tcgaatgttt    540
atgtgtcgtc gtaacatgcg gatatgtact agtatatata ttatttgtca tctcaagtga    600
gggacctaac catccatcac ccgtagccaa tgacgcagtc ggatcaacga gacacaggtg    660
gttgactcgg tcggatgcgt tcgatcatgt cttagcgata gattactggt ttatcagcct    720
tcgataaatg tgttgttttg agtattattc tgagtgcagg cttttgtagg cttgtaacaa    780
gtgggcagtg acaagattat taatggttgt taacaagtta gtttcatggt gggagagtgc    840
gttagcagtg tcctagatat aagcaatatc aacttctact agttgtacag tattttattt    900
ttatagatta cagtgcaaca gtcgaccatg catctagctt tactagcggt gatcatcgtc    960
gtccacgaca caagcaatca tattctgtga cactctttcc tcgtccttat caacccaatt   1020

<210> SEQ ID NO 24
<211> LENGTH: 920
<212> TYPE: DNA
<213> ORGANISM: Panicum virgatum

<400> SEQUENCE: 24 acaaagaag attagactaa tccaacagaa ttagtaaatt cagaattctg tatggcgagt      60
gaggtagact atcaaaaaag agaatgaata tgtagatgaa gatctactaa ttttaagagc    120
tatttacaaa gtctattaga gacatttttct tataataata accaaattta cctttacaaa   180
ataatatgac tagtcttttg gagttgctcc aataaaacat ataaaatggt actagtatgt    240
gtgtaaacct ttaacttctc gaaaagggac atattttttt agtgagacag aatatcatta    300
gtgaaaaatt gacttttgga ttggatctga taagctaaat gggaaacgta catgcgtcgg    360
tcggtgtcca ttagttactt gacagcgtcc agctctggtc acggtttgag attctattct    420
accagagtag tgtttgaaga taagatagaa tttaatcact atatatatat acaatcaaac    480
taaacacaag tagaagtgta atataagaag aagaaaaaaa aatctagaca atgtttggta    540
tgactttaga acaaaattct aagaaagagc tggcaagagc aataaacacc ctaactaaca    600
agttgtatac tctcgcatgt aaaattgcaa ctccattaaa aacaatccaa ttaatccaat    660
ttgttgatgt tgcccctata tctttttttt tctaccaact atactacgta tcttgatgaa    720
tctccatcaa tgcttggcaa aaccccccta ccaagaaaca gattaaggac gggaatacgg    780
gatggatagc cttcccaaac ggataaaacc ttcggcccgc cgtctcgctg ccggtggggc    840
acacgccata aaccacacgc gccggccgcc cccgcccgtg gcctttaaaa accccccgct    900
cccggcgctc gcttttcgct                                                920

<210> SEQ ID NO 25
<211> LENGTH: 992
<212> TYPE: DNA
<213> ORGANISM: Panicum virgatum

<400> SEQUENCE: 25
agtatgccaa ctgaaacgga tgacacatac acttcgtgaa ccaatcgata ttttacttgc      60
ttctatgtta aataatgtta taatacaata ttttattcaa atgctaaaac ttattactag     120
ataaaaataa aatttaatta tcttcaaaaa ctaaccaata gatattccat cataactaca     180
tttaccaaac taatatacta aaaaatatag gataattact aaattaatcg tgcaataatc     240
```

```
agtatttatg agattgataa ttttaaattt tgtgggctac aaacaaaaat taaaacttac      300
ttttcaagtt ggagataaga acaatggtag acgtagctcg ggatggtatg gcgtcggtgc      360
agacggttac cctttgtgcg aagtggcgcg ggcacgaggg tggggacttg gtacatgcat      420
gagagagagg aagaacgaaa caacttctca aattaaagca tatgaaaatc acctaatttt      480
tgtctgtcgg tggaaactaa taactagttt ttattatctt ttttaataag gatccacgaa      540
aattattttt gaccgatgaa aatcctggat cttcgtatta tgtttcgcct tttcccgact      600
ctttgcatgc tagatttcca tgcttggact aaaacgaaga taataaaacc aatctatcat      660
tttcacacga tgtattcata cttgcaatag ataaaccact actccgacgg gatttgcttt      720
ctgacctctg aaatcttgga aggattatgt gtctacactt ctcgatcgag gggaaaaagt      780
cgtagtacca agttgtagtt aaatttgttt cttcgatgac aaaacaaagg agaggggccc      840
gcgcggcgca gcgcagcgca gttggctggt tccggaacac gaaaaccaag cacactccac      900
cagctgccat ccaccgggtt ggatggagat tacaatactc gaatagtcag ccagccagcc      960
ggcttgaacg tgcagttttc ccctataaaa cg                                    992

<210> SEQ ID NO 26
<211> LENGTH: 13601
<212> TYPE: DNA
<213> ORGANISM: Panicum virgatum
<220> FEATURE:
<221> NAME/KEY: modified_base
<222> LOCATION: (11171)..(11176)
<223> OTHER INFORMATION: A, T, C or G

<400> SEQUENCE: 26
catgccaacc acagggttcc cctcgggatc aaagtacttt gatccaaccc ctccgctgct       60
atagtgcagt cggcttctga cgttcagtgc agccgtcttc tgaaaacgac atgtcgcaca      120
agtcctaagt tacgcgacag gctgccgccc tgcccttttc ctggcgtttt cttgtcgcgt      180
gttttagtcg cataaagtag aatacttgcg actagaaccg gagacattac gccatgaaca      240
agagcgccgc cgctggcctg ctgggctatg cccgcgtcag caccgacgac caggacttga      300
ccaaccaacg ggccgaactg cacgcggccg gctgcaccaa gctgttttcc gagaagatca      360
ccggcaccag gcgcgaccgc ccggagctgg ccaggatgct tgaccaccta cgccctggcg      420
acgttgtgac agtgaccagg ctagaccgcc tggcccgcag cacccgcgac ctactggaca      480
ttgccgagcg catccaggag gccggcgcgg gcctgcgtag cctggcagag ccgtgggccg      540
acaccaccac gccggccggc cgcatggtgt tgaccgtgtt cgccggcatt gccgagttcg      600
agcgttccct aatcatcgac cgcacccgga gcgggcgcga ggccgccaag gcccgaggcg      660
tgaagtttgg ccccccgccct accctcaccc cggcacagat cgcgcacgcc cgcgagctga      720
tcgaccagga aggccgcacc gtgaaagagg cggctgcact gcttggcgtg catcgctcga      780
ccctgtaccg cgcacttgag cgcagcgagg aagtgacgcc caccgaggcc aggcggcgcg      840
gtgccttccg tgaggacgca ttgaccgagg ccgacgccct ggcggccgcc gagaatgaac      900
gccaagagga acaagcatga aaccgcacca ggacggccag gacgaaccgt ttttcattac      960
cgaagagatc gaggcggaga tgatcgcggc cgggtacgtg ttcgagccgc ccgcgcacgt     1020
ctcaaccgtg cggctgcatg aaatcctggc cggtttgtct gatgccaagc tggcggcctg     1080 gccgccagc ttgccgctg aagaaaccga gcgccgccgt ctaaaaggt gatgtgtatt     1140 tgagtaaaac agcttgcgtc atgcggtcgc tgcgtatatg atgcgatgag taaataaaca     1200
```

```
aatacgcaag gggaacgcat gaaggttatc gctgtactta accagaaagg cgggtcaggc      1260
aagacgacca tcgcaaccca tctagcccgc gccctgcaac tcgccggggc cgatgttctg      1320
ttagtcgatt ccgatcccca gggcagtgcc cgcgattggg cggccgtgcg ggaagatcaa      1380
ccgctaaccg ttgtcggcat cgaccgcccg acgattgacc gcgacgtgaa ggccatcggc      1440
cggcgcgact tcgtagtgat cgacggagcg ccccaggcgg cggacttggc tgtgtccgcg      1500
atcaaggcag ccgacttcgt gctgattccg gtgcagccaa gcccttacga catatgggcc      1560
accgccgacc tggtggagct ggttaagcag cgcattgagg tcacggatgg aaggctacaa      1620
gcggcctttg tcgtgtcgcg ggcgatcaaa ggcacgcgca tcggcggtga ggttgccgag      1680
gcgctggccg ggtacgagct gcccattctt gagtcccgta tcacgcagcg cgtgagctac      1740
ccaggcactg ccgccgccgg cacaaccgtt cttgaatcag aacccgaggg cgacgctgcc      1800
cgcgaggtcc aggcgctggc cgctgaaatt aaatcaaaac tcatttgagt taatgaggta      1860
aagagaaaat gagcaaaagc acaaacacgc taagtgccgg ccgtccgagc gcacgcagca      1920
gcaaggctgc aacgttggcc agcctggcag acacgccagc catgaagcgg gtcaactttc      1980
agttgccggc ggaggatcac accaagctga agatgtacgc ggtacgccaa ggcaagacca      2040
ttaccgagct gctatctgaa tacatcgcgc agctaccaga gtaaatgagc aaatgaataa      2100
atgagtagat gaattttagc ggctaaagga ggcggcatgg aaaatcaaga caaccaggc       2160 accgacgccg tggaatgccc catgtgtgga ggaacgggcg gttggccagg cgtaagcggc      2220
tgggttgtct gccggccctg caatggcact ggaaccccca gcccgagga atcggcgtga       2280 cggtcgcaaa ccatccggcc cggtacaaat cggcgcggcg ctgggtgatg acctggtgga      2340
gaagttgaag gccgcgcagg ccgcccagcg gcaacgcatc gaggcagaag cacgccccgg      2400
tgaatcgtgg caagcggccg ctgatcgaat ccgcaaagaa tcccggcaac cgccggcagc      2460
cggtgcgccg tcgattagga agccgcccaa gggcgacgag caaccagatt ttttcgttcc      2520
gatgctctat gacgtgggca cccgcgatag tcgcagcatc atggacgtgg ccgttttccg      2580
tctgtcgaag cgtgaccgac gagctggcga ggtgatccgc tacgagcttc cagacgggca      2640
cgtagaggtt tccgcagggc cggccggcat ggccagtgtg tgggattacg acctggtact      2700
gatggcggtt tccatctaa ccgaatccat gaaccgatac cgggaaggga agggagacaa       2760
gcccggccgc gtgttccgtc cacacgttgc ggacgtactc aagttctgcc ggcgagccga      2820
tggcggaaag cagaaagacg acctggtaga aacctgcatt cggttaaaca ccacgcacgt      2880
tgccatgcag cgtacgaaga aggccaagaa cggccgcctg gtgacggtat ccagggtga      2940 agccttgatt agccgctaca agatcgtaaa gagcgaaacc gggcggccgg agtacatcga      3000
gatcgagcta gctgattgga tgtaccgcga gatcacagaa gcaagaacc cggacgtgct      3060 gacggttcac cccgattact ttttgatcga tcccggcatc ggccgttttc tctaccgcct      3120
ggcacgccgc gccgcaggca aggcagaagc cagatggttg ttcaagacga tctacgaacg      3180
cagtggcagc gccggagagt tcaagaagtt ctgtttcacc gtgcgcaagc tgatcgggtc      3240
aaatgacctg ccggagtacg atttgaagga ggaggcgggg caggctggcc cgatcctagt      3300
catgcgctac cgcaacctga tcgagggcga agcatccgcc ggttcctaat gtacggagca      3360
gatgctaggg caaattgccc tagcagggga aaaggtcga aaaggtctct ttcctgtgga       3420
tagcacgtac attgggaacc caaagccgta cattgggaac cggaacccgt acattgggaa      3480
cccaaagccg tacattggga accggtcaca catgtaagtg actgatataa aagagaaaaa      3540
aggcgatttt tccgcctaaa actctttaaa acttattaaa actcttaaaa cccgcctggc      3600
```

```
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accagggcgc ggacaagccg cgccgtcgcc    3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt ttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980 atatttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat ctttcacaaa    5160
gatgttgctg tctcccaggt cgccgtggga aaagacaagt tcctcttcgg cttttccgt    5220 ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtcctttt cccgttccac    5580
atcataggtg gtcccttat accggctgtc cgtcattttt aaatataggt ttcattttc    5640 tcccaccagc ttatatacct tagcaggaga cattccttcc gtatctttta cgcagcggta    5700 ttttcgatc agttttttca attccggtga tattctcatt ttagccattt attatttcct    5760
tcctcttttc tacagtattt aaagataccc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
```

```
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtggcagga    6180
tatattgtgg tgtaaacaaa ttgacgctta gacaacttaa taacacattg cggacgtttt    6240
taatgtactg aattaacgcc gaattaattc ggggatctg gattttagta ctggattttg    6300
gttttaggaa ttagaaattt tattgataga agtatttac aaatacaaat acatactaag    6360
ggtttcttat atgctcaaca catgagcgaa accctatagg aaccctaatt cccttatctg    6420
ggaactactc acacattatt atggagaaac tcgagggatc ccggtcggca tctactctat    6480
tcctttgccc tcggacgagt gctggggcgt cggtttccac tatcggcgag tacttctaca    6540
cagccatcgg tccagacggc cgcgcttctg cgggcgattt gtgtacgccc gacagtcccg    6600
gctccggatc ggacgattgc gtcgcatcga ccctgcgccc aagctgcatc atcgaaattg    6660
ccgtcaacca agctctgata gagttggtca agaccaatgc ggagcatata cgcccggagc    6720
cgcggcgatc ctgcaagctc cggatgcctc cgctcgaagt agcgcgtctg ctgctccata    6780
caagccaacc acgcctcca gaagaagatg ttggcgacct cgtattggga atccccgaac    6840
atcgcctcgc tccagtcaat gaccgctgtt atgcggccat tgtccgtcag gacattgttg    6900
gagccgaaat ccgcgtgcac gaggtgccgg acttcggggc agtcctcggc ccaaagcatc    6960
agctcatcga gagcctgcgc gacggacgca ctgacggtgt cgtccatcac agtttgccag    7020
tgatacacat ggggatcagc aatcgcgcat atgaaatcac gccatgtagt gtattgaccg    7080
attccttgcg gtccgaatgg gccgaacccg ctcgtctggc taagatcggc cgcagcgatc    7140
gcatccatgg cctccgcgac cggctgcagt tatcatcatc atcatagaca cacgaaataa    7200
agtaatcaga ttatcagtta aagctatgta atatttacac cataaccaat caattaaaaa    7260
atagatcagt ttaaagaaag atcaaagctc aaaaaaataa aaagagaaaa gggtcctaac    7320
caagaaaatg aaggagaaaa actagaaatt tacctgcaga acagcgggca gttcggtttc    7380
aggcaggtct tgcaacgtga caccctgtgc acggcgggag atgcaatagg tcaggctctc    7440
gctgaattcc ccaatgtcaa gcacttccgg aatcgggagc gcggccgatg caaagtgccg    7500
ataaacataa cgatctttgt agaaaccatc ggcgcagcta tttacccgca ggacatatcc    7560
acgccctcct acatcgaagc tgaaagcacg agattcttcg ccctccgaga gctgcatcag    7620
gtcggagacg ctgtcgaact tttcgatcag aaacttctcg acagacgtcg cggtgagttc    7680
aggcttttc atggtagagg agctcgccgc ttggtatctg cattacaatg aaatgagcaa    7740
agactatgtg agtaacactg gtcaacacta gggagaaggc atcgagcaag atacgtatgt    7800
aaagagaagc aatatagtgt cagttggtag atactagata ccatcaggag gtaaggagag    7860
caacaaaaag gaaactcttt attttaaat tttgttacaa caaacaagca gatcaatgca    7920
tcaaaatact gtcagtactt atttcttcag acaacaatat ttaaacaag tgcatctgat    7980
cttgacttat ggtcacaata aaggagcaga gataaacatc aaaatttcgt catttatatt    8040
tattccttca ggcgttaaca atttaacagc acacaaacaa aaacagaata ggaatatcta    8100
attttggcaa ataataagct ctgcagacga acaaattatt atagtatcgc ctataatatg    8160
aatccctata ctattgaccc atgtagtatg aagcctgtgc ctaaattaac agcaaacttc    8220
tgaatccaag tgccctataa caccaacatg tgcttaaata aataccgcta agcaccaaat    8280
tacacatttc tcgtattgct gtgtaggttc tatcttcgtt tcgtactacc atgtccctat    8340
```

```
atttttgctgc tacaaaggac ggcaagtaat cagcacaggc agaacacgat ttcagagtgt   8400
aattctagat ccagctaaac cactctcagc aatcaccaca caagagagca ttcagagaaa   8460
cgtggcagta acaaaggcag agggcggagt gagcgcgtac cgaagacggt agatctctcg   8520
agagagatag atttgtagag agagactggt gatttcagcg tgtcctctcc aaatgaaatg   8580
aacttcctta tatagaggaa ggtcttgcga aggatagtgg gattgtgcgt catcccttac   8640
gtcagtggag atatcacatc aatccacttg ctttgaagac gtggttggaa cgtcttcttt   8700
ttccacgatg ctcctcgtgg gtggggtcc  atctttggga ccactgtcgg cagaggcatc   8760
ttgaacgata gccttttcctt tatcgcaatg atggcatttg taggtgccac cttccttttc   8820
tactgtcctt ttgatgaagt gacagatagc tgggcaatgg aatccgagga ggtttcccga   8880
tattacccctt tgttgaaaag tctcaatagc cctttggtct tctgagactg tatctttgat   8940
attcttggag tagacgagag tgtcgtgctc caccatgtta tcacatcaat ccacttgctt   9000
tgaagacgtg gttggaacgt cttcttttttc cacgatgctc ctcgtgggtg ggggtccatc   9060
tttgggacca ctgtcggcag aggcatcttg aacgatagcc tttcctttat cgcaatgatg   9120
gcatttgtag gtgccacctt ccttttctac tgtccttttg atgaagtgac agatagctgg   9180
gcaatggaat ccgaggaggt ttcccgatat tacccctttgt tgaaaagtct caatagccct   9240
ttggtcttct gagactgtat ctttgatatt cttggagtag acgagagtgt cgtgctccac   9300
catgttggca agctgctcta gccaatacgc aaaccgcctc tccccgcgcg ttggccgatt   9360
cattaatgca gctggcacga caggtttccc gactggaaag cgggcagtga gcgcaacgca   9420
attaatgtga gttagctcac tcattaggca ccccaggctt tacactttat gcttccggct   9480
cgtatgttgt gtggaattgt gagcggataa caatttcaca caggaaacag ctatgaccat   9540
gattacgaat tcgagctcgg tacccccacgg aagatccagg tctcgagact aggagacgga   9600
tgggaggcgc aacgcgcgat ggggaggggg gcggcgctga cctttctggc gaggtcgagg   9660
tagcgatcga gcagctgcag cgcggacacg atgaggaaga cgaagatagc cgccatggac   9720
atgttcgcca gcggcggcgg agcgaggctg agccggtctc tccggcctcc ggtcggcgtt   9780
aagttgggga tcgtaacgtg acgtgtctcg tctccacgga tcgacacaac cggcctactc   9840
gggtgcacga cgccgcgata agggcgagat gtccgtgcac gcagcccgtt tggagtcctc   9900
gttgcccacg aaccgacccc ttacagaaca aggcctagcc caaaactatt ctgagttgag   9960
cttttgagcc tagcccacct aagccgagcg tcatgaactg atgaacccac taccactagt  10020
caaggcaaac cacaaccaca aatggatcaa ttgatctaga acaatccgaa ggaggggagg  10080
ccacgtcaca ctcacaccaa ccgaaatatc tgccagaatc agatcaaccg gccaatagga  10140
cgccagcgag cccaacacct ggcgacgccg caaaattcac cgcgagggc  accgggcacg  10200
gcaaaaacaa agcccggcg  cggtgagaat atctggcgac tggcggagac ctggtggcca  10260
gcgcgcggcc acatcagcca ccccatccgc ccacctcacc tccggcgagc caatggcaac  10320
tcgtcttaag attccacgag ataaggaccc gatcgccggc gacgctattt agccaggtgc  10380
gccccccacg gtacactcca ccagcggcat ctatagcaac cggtccagca ctttcacgct  10440
cagcttcagc aagatctacc gtcttcggta cgcgctcact ccgccctctg cctttgttac  10500
tgccacgttt ctctgaatgc tctcttgtgt ggtgattgct gagagtggtt tagctggatc  10560
tagaattaca ctctgaaatc gtgttctgcc tgtgctgatt acttgccgtc ctttgtagca  10620
gcaaaatata gggacatggt agtacgaaac gaagatagaa cctacacagc aatacgagaa  10680
```

```
atgtgtaatt tggtgcttag cggtatttat ttaagcacat gttggtgtta tagggcactt    10740
ggattcagaa gtttgctgtt aatttaggca caggcttcat actacatggg tcaatagtat    10800
agggattcat attataggcg atactataat aatttgttcg tctgcagagc ttattatttg    10860
ccaaaattag atattcctat tctgttttg tttgtgtgct gttaaattgt taacgcctga     10920
aggaataaat ataaatgacg aaattttgat gtttatctct gctcctttat tgtgaccata    10980
agtcaagatc agatgcactt gttttaaata ttgttgtctg aagaaataag tactgacagt    11040
attttgatgc attgatctgc ttgtttgttg taacaaaatt taaaaataaa gagtttcctt    11100
tttgttgctc tccttacctc ctgatggtat ctagtatcta ccaactgata ctatattgct    11160
tctctttaca nnnnnntctt gctcgatgcc ttctcctagt gttgaccagt gttactcaca    11220
tagtctttgc tcatttcatt gtaatgcaga taccaagcgg ttaattaact atgagtcttt    11280
tcctttacg attcctccac ttctccaact acatcaaagg gagtacaacc gcaaagtccg     11340
tagccttcca ggtgcgcgct gagaaattcg cgaaccgcaa gcgtaagaat cagtatagag    11400
gcatacgcca gagaccgtgg ggtaagtggg ccgccgaaat ccgtgatcca cgtaagggag    11460
tgcgagtctg gcttggcacg ttcaatactg cagaagaagc ggcgagggcg tatgatgcag    11520
aggcaaggcg tataagggt aagaaagcga aagttaattt tcctgaggag gctcccggga     11580
cctctgtcaa acgttccaaa gtgaatcccc aggaaaacct ttcgcacaaa ttcggcgccg    11640
gcaacaatca catggatttg gtggagcaga agccgctggt taatcagtac gcaaacatgg    11700
cgtcatttcc ggggagcggg aatggattaa cctctctacc aagtagcgat gacgtgacac    11760
tatacttcag tagcgaccag ggctccaact catttgggtg gtccgagcag gggccgaaaa    11820
ctcctgaaat aagcagcatg ttaagcgccc cactcgattg tgaatctcat ttcgtacaaa    11880
atgctaacca acagccgaat tcacagaatg tcgtgtccat ggaggatgac tcagctaaaa    11940
ggctgagcga agaacgcgtt gatattgagt cggagctaaa attcttccaa atggcgtact    12000
tggaaggatc atggggcgac acaagtctcg agtcgtcct gtcgggagat acgacgcaag     12060
acggcgggaa tctaatgaat ctatggagct tcgatgatat tccatcaatg tcttctggcg    12120
tgtttatgag tcttttcctt ttacgattcc tccacttctc caactacatc aaagggagta    12180
caaccgcaaa gtccgtagcc ttccaggtgc gcgctgagaa attcgcgaac cgcaagcgta    12240
agaatcagta tagaggcata cgccagagac cgtgggggtaa gtgggccgcc gaaatccgtg    12300
atccacgtaa gggagtgcga gtctggcttg gcacgttcaa tactgcagaa gaagcggcga    12360
gggcgtatga tgcagaggca aggcgtataa ggggtaagaa agcgaaagtt aattttcctg    12420
aggaggctcc cgggacctct gtcaaacgtt ccaaagtgaa tccccaggaa aacctttcgc    12480
acaaattcgg cgccgcaac aatcacatgg atttggtgga gcagaagccg ctggttaatc     12540
agtacgcaaa catggcgtca tttccgggga gcgggaatgg attaacctct ctaccaagta    12600
gcgatgacgt gacactatac ttcagtagcg accagggctc caactcattt gggtggtccg    12660
agcagggggcc gaaaactcct gaaataagca gcatgttaag cgccccactc gattgtgaat    12720
ctcatttcgt acaaaatgct aaccaacagc cgaattcaca gaatgtcgtg tccatggagg    12780
atgactcagc taaaaggctg agcgaagaac gcgttgatat tgagtcggag ctaaaattct    12840
tccaaatggc gtacttggaa ggatcatggg gcgacacaag tctcgagtcg ctcctgtcgg    12900
gagatacgac gcaagacggc gggaatctaa tgaatctatg gagcttcgat gatattccat    12960
caatgtcttc tggcgtgttt gcagggcgcg ccatcgttca aacatttggc aataaagttt    13020
cttaagattg aatcctgttg ccggtcttgc gatgattatc atataatttc tgttgaatta    13080
```

```
cgttaagcat gtaataatta acatgtaatg catgacgtta tttatgagat gggtttttat    13140
gattagagtc ccgcaattat acatttaata cgcgatagaa acaaaatat  agcgcgcaaa    13200 ctaggataaa ttatcgcgcg cggtgtcatc tatgttacta gatccgatga taagctgtca    13260
aacatgaaag cttggcactg gccgtcgttt tacaacgtcg tgactgggaa acccctggcg    13320
ttacccaact taatcgcctt gcagcacatc cccctttcgc cagctggcgt aatagcgaag    13380
aggcccgcac cgatcgccct tcccaacagt tgcgcagcct gaatggcgaa tgctagagca    13440
gcttgagctt ggatcagatt gtcgtttccc gccttcagtt taaactatca gtgtttgaca    13500
ggatatattg gcgggtaaac ctaagagaaa agagcgttta ttagaataac ggatatttaa    13560
aagggcgtga aaaggtttat ccgttcgtcc atttgtatgt g                       13601
```

<210> SEQ ID NO 27
<211> LENGTH: 12866
<212> TYPE: DNA
<213> ORGANISM: Panicum virgatum
<220> FEATURE:
<221> NAME/KEY: modified_base
<222> LOCATION: (11171)..(11176)
<223> OTHER INFORMATION: A, T, C or G

<400> SEQUENCE: 27

```
catgccaacc acagggttcc cctcgggatc aaagtacttt gatccaaccc ctccgctgct      60
atagtgcagt cggcttctga cgttcagtgc agccgtcttc tgaaaacgac atgtcgcaca     120
agtcctaagt tacgcgacag gctgccgccc tgccttttc ctggcgtttt cttgtcgcgt     180
gttttagtcg cataaagtag aatacttgcg actagaaccg gagacattac gccatgaaca     240
agagcgccgc cgctggcctg ctgggctatg cccgcgtcag caccgacgac caggacttga     300
ccaaccaacg ggccgaactg cacgcggccg gctgcaccaa gctgttttcc gagaagatca     360
ccggcaccag gcgcgaccgc ccggagctgg ccaggatgct tgaccaccta cgccctggcg     420
acgttgtgac agtgaccagg ctagaccgcc tggcccgcag caccccgcgac ctactggaca     480 ttgccgagcg catccaggag gccggcgcgg gcctgcgtag cctggcagag ccgtgggccg     540
acaccaccac gccggccggc cgcatggtgt tgaccgtgtt cgccggcatt gccgagttcg     600
agcgttccct aatcatcgac cgcacccgga gcgggcgcga ggccgccaag gcccgaggcg     660
tgaagtttgg cccccgccct accctcaccc cggcacagat cgcgcacgcc cgcgagctga     720
tcgaccagga aggccgcacc gtgaaagagg cggctgcact gcttggcgtg catcgctcga     780
ccctgtaccg cgcacttgag cgcagcgagg aagtgacgcc caccgaggcc aggcggcgcg     840
gtgccttccg tgaggacgca ttgaccgagg ccgacgccct ggcggccgcc gagaatgaac     900
gccaagagga caagcatga  aaccgcacca ggacggccag gacgaaccgt ttttcattac     960
cgaagagatc gaggcggaga tgatcgcggc cgggtacgtg ttcgagccgc ccgcgcacgt    1020
ctcaaccgtg cggctgcatg aaatcctggc cggtttgtct gatgccaagc tggcggcctg    1080
gccggccagc ttggccgctg aagaaaccga gcgccgccgt ctaaaaaggt gatgtgtatt    1140
tgagtaaaac agcttgcgtc atgcggtcgc tgcgtatatg atgcgatgag taaataaaca    1200
aatacgcaag gggaacgcat gaaggttatc gctgtactta accagaaagg cgggtcaggc    1260
aagacgacca tcgcaaccca tctagcccgc gccctgcaac tcgccggggc cgatgttctg    1320
ttagtcgatt ccgatcccca gggcagtgcc cgcgattggg cggccgtgcg gaagatcaa     1380 ccgctaaccg ttgtcggcat cgaccgcccg acgattgacc gcgacgtgaa ggccatcggc    1440
```

```
cggcgcgact tcgtagtgat cgacggagcg ccccaggcgg cggacttggc tgtgtccgcg      1500
atcaaggcag ccgacttcgt gctgattccg gtgcagccaa gcccttacga catatgggcc      1560
accgccgacc tggtggagct ggttaagcag cgcattgagg tcacggatgg aaggctacaa      1620
gcggcctttg tcgtgtcgcg ggcgatcaaa ggcacgcgca tcggcggtga ggttgccgag      1680
gcgctggccg ggtacgagct gcccattctt gagtcccgta tcacgcagcg cgtgagctac      1740
ccaggcactg ccgccgccgg cacaaccgtt cttgaatcag aacccgaggg cgacgctgcc      1800
cgcgaggtcc aggcgctggc cgctgaaatt aaatcaaaac tcatttgagt taatgaggta      1860
aagagaaaat gagcaaaagc acaaacacgc taagtgccgg ccgtccgagc gcacgcagca      1920
gcaaggctgc aacgttggcc agcctggcag acacgccagc catgaagcgg gtcaactttc      1980
agttgccggc ggaggatcac accaagctga agatgtacgc ggtacgccaa ggcaagacca      2040
ttaccgagct gctatctgaa tacatcgcgc agctaccaga gtaaatgagc aaatgaataa      2100
atgagtagat gaattttagc ggctaaagga ggcggcatgg aaaatcaaga caaccaggc       2160 accgacgccg tggaatgccc catgtgtgga ggaacgggcg gttggccagg cgtaagcggc      2220
tgggttgtct gccggccctg caatggcact ggaaccccca gcccgagga atcggcgtga       2280 cggtcgcaaa ccatccggcc cggtacaaat cggcgcggcg ctgggtgatg acctggtgga     2340
gaagttgaag gccgcgcagg ccgcccagcg gcaacgcatc gaggcagaag cacgccccgg     2400
tgaatcgtgg caagcggccg ctgatcgaat ccgcaaagaa tcccggcaac cgccggcagc      2460
cggtgcgccg tcgattagga agccgcccaa gggcgacgag caaccagatt ttttcgttcc     2520
gatgctctat gacgtgggca cccgcgatag tcgcagcatc atggacgtgg ccgttttccg     2580
tctgtcgaag cgtgaccgac gagctggcga ggtgatccgc tacgagcttc cagacgggca     2640
cgtagaggtt tccgcagggc cggccggcat ggccagtgtg tgggattacg acctggtact    2700
gatggcggtt tcccatctaa ccgaatccat gaaccgatac cgggaaggga agggagacaa    2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccagggtga     2940 agccttgatt agccgctaca agatcgtaaa gagcgaaacc gggcggccgg agtacatcga    3000
gatcgagcta gctgattgga tgtaccgcga gatcacagaa ggcaagaacc cggacgtgct     3060
gacggttcac cccgattact ttttgatcga tccccggcatc ggccgttttc tctaccgcct     3120
ggcacgccgc gccgcaggca aggcagaagc cagatggttg ttcaagacga tctacgaacg     3180
cagtggcagc gccggagagt tcaagaagtt ctgtttcacc gtgcgcaagc tgatcgggtc     3240
aaatgacctg ccggagtacg atttgaagga ggaggcgggg caggctggcc cgatcctagt     3300
catgcgctac cgcaacctga tcgagggcga agcatccgcc ggttcctaat gtacggagca    3360
gatgctaggg caaattgccc tagcagggga aaaaggtcga aaaggtctct ttcctgtgga     3420
tagcacgtac attgggaacc caaagccgta cattgggaac cggaacccgt acattgggaa     3480
cccaaagccg tacattggga accggtcaca catgtaagtg actgatataa aagagaaaaa     3540
aggcgatttt ccgcctaaa  actctttaaa acttattaaa actcttaaaa cccgcctggc     3600
ctgtgcataa ctgtctggcc agcgcacagc cgaagagctg caaaaagcgc ctacccttcg     3660
gtcgctgcgc tccctacgcc ccgccgcttc gcgtcggcct atcgcggccg ctggccgctc    3720
aaaaatggct ggcctacggc caggcaatct accaggcgcg gacaagccg cgccgtcgcc      3780 actcgaccgc cggcgcccac atcaaggcac cctgcctcgc gcgtttcggt gatgacggtg    3840
```

```
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
caccgctggt agcggtggtt tttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980 atatttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat cttttcacaaa    5160 gatgttgctg tctcccaggt cgccgtggga aaagacaagt tcctcttcgg gcttttccgt    5220
ctttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct ttgttcatct tcatactctt ccgagcaaag    5460
gacgccatcg gcctcactca tgagcagatt gctccagcca tcatgccgtt caaagtgcag    5520
gacctttgga acaggcagct ttccttccag ccatagcatc atgtcctttt cccgttccac    5580
atcataggtg gtccctttat accggctgtc cgtcattttt aaatataggt tttcattttc    5640
tcccaccagc ttatatacct tagcaggaga cattccttcc gtatctttta cgcagcggta    5700 ttttcgatc agttttttca attcggtga tattctcatt ttagccattt attatttcct    5760
tcctcttttc tacagtattt aaagataccc aagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga tttttgtgccg agctgccggt cggggagctg ttggctggct ggtggcagga    6180
```

```
tatattgtgg tgtaaacaaa ttgacgctta gacaacttaa taacacattg cggacgtttt    6240
taatgtactg aattaacgcc gaattaattc gggggatctg gattttagta ctggattttg    6300
gttttaggaa ttagaaattt tattgataga agtattttac aaatacaaat acatactaag    6360
ggtttcttat atgctcaaca catgagcgaa accctatagg aaccctaatt cccttatctg    6420
ggaactactc acacattatt atggagaaac tcgagggatc ccggtcggca tctactctat    6480
tcctttgccc tcggacgagt gctggggcgt cggtttccac tatcggcgag tacttctaca    6540
cagccatcgg tccagacggc cgcgcttctg cgggcgattt gtgtacgccc gacagtcccg    6600
gctccggatc ggacgattgc gtcgcatcga ccctgcgccc aagctgcatc atcgaaattg    6660
ccgtcaacca agctctgata gagttggtca agaccaatgc ggagcatata cgcccggagc    6720
cgcggcgatc ctgcaagctc cggatgcctc cgctcgaagt agcgcgtctg ctgctccata    6780
caagccaacc acggcctcca agaagaagatg ttggcgacct cgtattggga atccccgaac    6840
atcgcctcgc tccagtcaat gaccgctgtt atgcggccat tgtccgtcag gacattgttg    6900
gagccgaaat ccgcgtgcac gaggtgccgg acttcggggc agtcctcggc ccaaagcatc    6960
agctcatcga gagcctgcgc gacggacgca ctgacggtgt cgtccatcac agtttgccag    7020
tgatacacat ggggatcagc aatcgcgcat atgaaatcac gccatgtagt gtattgaccg    7080
attccttgcg gtccgaatgg gccgaacccg ctcgtctggc taagatcggc cgcagcgatc    7140
gcatccatgg cctccgcgac cggctgcagt tatcatcatc atcatagaca cacgaaataa    7200
agtaatcaga ttatcagtta aagctatgta atatttacac cataaccaat caattaaaaa    7260
atagatcagt ttaagaaaag atcaaagctc aaaaaaataa aaagagaaaa gggtcctaac    7320
caagaaaatg aaggagaaaa actagaaatt tacctgcaga acagcgggca gttcggtttc    7380
aggcaggtct tgcaacgtga caccctgtgc acggcgggag atgcaatagg tcaggctctc    7440
gctgaattcc ccaatgtcaa gcacttccgg aatcgggagc gcggccgatg caaagtgccg    7500
ataaacataa cgatctttgt agaaaccatc ggcgcagcta tttacccgca ggacatatcc    7560
acgccctcct acatcgaagc tgaaagcacg agattcttcg ccctccgaga gctgcatcag    7620
gtcggagacg ctgtcgaact tttcgatcag aaacttctcg acagacgtcg cggtgagttc    7680 aggcttttc atggtagagg agctcgccgc ttggtatctg cattacaatg aaatgagcaa    7740
agactatgtg agtaacactg gtcaacacta gggagaaggc atcgagcaag atacgtatgt    7800
aaagagaagc aatatagtgt cagttggtag atactagata ccatcaggag gtaaggagag    7860
caacaaaaag gaaactcttt attttaaat tttgttacaa caaacaagca gatcaatgca    7920
tcaaaatact gtcagtactt atttcttcag acaacaatat ttaaacaag tgcatctgat    7980 cttgacttat ggtcacaata aaggagcaga gataaacatc aaaatttcgt catttatatt    8040
tattccttca ggcgttaaca atttaacagc acacaaacaa aaacagaata ggaatatcta    8100
attttggcaa ataataagct ctgcagacga acaaattatt atagtatcgc ctataatatg    8160
aatccctata ctattgaccc atgtagtatg aagcctgtgc ctaaattaac agcaaacttc    8220
tgaatccaag tgccctataa caccaacatg tgcttaaata aataccgcta agcaccaaat    8280
tacacatttc tcgtattgct gtgtaggttc tatcttcgtt tcgtactacc atgtccctat    8340
attttgctgc tacaaaggac ggcaagtaat cagcacaggc agaacacgat ttcagagtgt    8400
aattctagat ccagctaaac cactctcagc aatcaccaca caagagagca ttcagagaaa    8460
cgtggcagta acaaaggcag agggcggagt gagcgcgtac cgaagacggt agatctctcg    8520
agagagatag atttgtagag agagactggt gatttcagcg tgtcctctcc aaatgaaatg    8580
```

```
aacttcctta tatagaggaa ggtcttgcga aggatagtgg gattgtgcgt catcccttac   8640
gtcagtggag atatcacatc aatccacttg ctttgaagac gtggttggaa cgtcttcttt   8700
ttccacgatg ctcctcgtgg gtggggtcc atctttggga ccactgtcgg cagaggcatc    8760
ttgaacgata gcctttcctt tatcgcaatg atggcatttg taggtgccac cttccttttc   8820
tactgtcctt ttgatgaagt gacagatagc tgggcaatgg aatccgagga ggtttcccga   8880
tattacccct tgttgaaaag tctcaatagc cctttggtct tctgagactg tatctttgat   8940
attcttggag tagacgagag tgtcgtgctc caccatgtta tcacatcaat ccacttgctt   9000
tgaagacgtg gttggaacgt cttcttttc cacgatgctc ctcgtgggtg ggggtccatc    9060
tttgggacca ctgtcggcag aggcatcttg aacgatagcc tttcctttat cgcaatgatg   9120
gcatttgtag gtgccacctt ccttttctac tgtccttttg atgaagtgac agatagctgg   9180
gcaatggaat ccgaggaggt ttcccgatat tacccttgt tgaaaagtct caatagccct    9240
ttggtcttct gagactgtat ctttgatatt cttggagtag acgagagtgt cgtgctccac   9300
catgttggca agctgctcta gccaatacgc aaaccgcctc tccccgcgcg ttggccgatt   9360
cattaatgca gctggcacga caggtttccc gactggaaag cgggcagtga gcgcaacgca   9420
attaatgtga gttagctcac tcattaggca ccccaggctt tacactttat gcttccggct   9480
cgtatgttgt gtggaattgt gagcggataa caatttcaca caggaaacag ctatgaccat   9540
gattacgaat tcgagctcgg taccccacgg aagatccagg tctcgagact aggagacgga   9600
tgggaggcgc aacgcgcgat ggggagggg gcggcgctga cctttctggc gaggtcgagg    9660
tagcgatcga gcagctgcag cgcggacacg atgaggaaga cgaagatagc cgccatggac   9720
atgttcgcca gcggcggcgg agcgaggctg agccggtctc tccggcctcc ggtcggcgtt   9780
aagttgggga tcgtaacgtg acgtgtctcg tctccacgga tcgacacaac cggcctactc   9840
gggtgcacga cgccgcgata agggcgagat gtccgtgcac gcagcccgtt tggagtcctc   9900
gttgcccacg aaccgacccc ttacagaaca aggcctagcc caaaactatt ctgagttgag   9960
cttttgagcc tagcccacct aagccgagcg tcatgaactg atgaacccac taccactagt   10020
caaggcaaac cacaaccaca aatggatcaa ttgatctaga acaatccgaa ggaggggagg   10080
ccacgtcaca ctcacaccaa ccgaaatatc tgccagaatc agatcaaccg gccaatagga   10140
cgccagcgag cccaacacct ggcgacgccg caaaattcac cgcgagggc accgggcacg    10200
gcaaaaacaa agcccggcg cggtgagaat atctggcgac tggcggagac ctggtggcca    10260
gcgcgcggcc acatcagcca ccccatccgc ccacctcacc tccggcgagc caatggcaac   10320
tcgtcttaag attccacgag ataaggaccc gatcgccggc gacgctattt agccaggtgc   10380
gccccccacg gtacactcca ccagcggcat ctatagcaac cggtccagca ctttcacgct   10440
cagcttcagc aagatctacc gtcttcggta cgcgctcact ccgccctctg cctttgttac   10500
tgccacgttt ctctgaatgc tctccttgtgt ggtgattgct gagagtggtt tagctggatc  10560
tagaattaca ctctgaaatc gtgttctgcc tgtgctgatt acttgccgtc ctttgtagca   10620
gcaaaatata gggacatggt agtacgaaac gaagatagaa cctacacagc aatacgagaa   10680
atgtgtaatt tggtgcttag cggtatttat ttaagcacat gttggtgtta tagggcactt   10740
ggattcagaa gtttgctgtt aatttaggca caggcttcat actacatggg tcaatagtat   10800
agggattcat attataggcg atactataat aatttgttcg tctgcagagc ttattatttg   10860
ccaaaattag atattcctat tctgtttttg tttgtgtgct gttaaattgt taacgcctga   10920
```

```
aggaataaat ataaatgacg aaattttgat gtttatctct gctcctttat tgtgaccata    10980
agtcaagatc agatgcactt gttttaaata ttgttgtctg aagaaataag tactgacagt    11040
attttgatgc attgatctgc ttgtttgttg taacaaaatt taaaaataaa gagtttcctt    11100
tttgttgctc tccttacctc ctgatggtat ctagtatcta ccaactgata ctatattgct    11160
tctctttaca nnnnnntctt gctcgatgcc ttctcctagt gttgaccagt gttactcaca    11220
tagtctttgc tcatttcatt gtaatgcaga taccaagcgg ttaattaact atgtgcggcg    11280
gggccattct cagtgatctc tactcaccag tgaggcggac ggtcactgcc ggtgacctat    11340
ggggagagag tggcagcagc aagaatgtga agaactggaa aaggagttct tggaagtttg    11400
atgaaggcga tgaagacttt gaagctgatt tcaaggattt tgaggattgc agtagcgagg    11460
aggaggtaga ttttggacat gaggaaaaag aattccaatt gaacagttcg aatttcgtgg    11520
aattcaatgg ccatactgcc aaagtcacca gcaggaagcg aaagatccag taccgaggga    11580
tccggcggcg gccttggggc aaatgggcag cagaaatcag agacccacag aagggcgtcc    11640
gagtttggct tggcacgttc agcactgccg aggaagctgc aagggcatat gacgtggaag    11700
ctctacgcat acgtggcaag aaagccaaga tgaatttccc taccaccatc acagctgctg    11760
ggaaacacca ccggcagcgt gtggctcgac cggcaaagaa gacgtcacaa gagagcctga    11820
agtcaagcaa tgcctctggt catgtcatct cagcaggcag cagtactgat ggcaccgttg    11880
tcaagatcga gttgtcacag tcaccagctt ctccactacc agtgtccagc gcatggcttg    11940
atgcttttga gctgaagcag cttggtggag aaacccctga agctgatggg agagaaaccc    12000
ctgaagaaac tgatcatgaa acgggagtga cagcggatat gttttttggc aatggcgaag    12060
tgcggctttc agatgatttt gcgtcttacg agccttaccc aaatttttatg cagttaccttt   12120
```

-continued

```
atagtgcagt cggcttctga cgttcagtgc agccgtcttc tgaaaacgac atgtcgcaca    120
agtcctaagt tacgcgacag gctgccgccc tgccctttc ctggcgtttt cttgtcgcgt    180
gttttagtcg cataaagtag aatacttgcg actagaaccg agacattac gccatgaaca    240
agagcgccgc cgctggcctg ctgggctatg cccgcgtcag caccgacgac caggacttga    300
ccaaccaacg ggccgaactg cacgcggccg gctgcaccaa gctgttttcc gagaagatca    360
ccggcaccag gcgcgaccgc ccggagctgg ccaggatgct tgaccaccta cgccctggcg    420
acgttgtgac agtgaccagg ctagaccgcc tggcccgcag caccgcgac ctactggaca    480
ttgccgagcg catccaggag gccggcgcgg gcctgcgtag cctggcagag ccgtgggccg    540
acaccaccac gccggccggc cgcatggtgt tgaccgtgtt cgccggcatt gccgagttcg    600
agcgttccct aatcatcgac cgcacccgga gcgggcgcga ggccgccaag gcccgaggcg    660
tgaagtttgg ccccgccct accctcaccc cggcacagat cgcgcacgcc cgcgagctga    720
tcgaccagga aggccgcacc gtgaaagagg cggctgcact gcttggcgtg catcgctcga    780
ccctgtaccg cgcacttgag cgcagcgagg aagtgacgcc caccgaggcc aggcggcgcg    840
gtgccttccg tgaggacgca ttgaccgagg ccgacgccct ggcggccgcc gagaatgaac    900
gccaagagga acaagcatga aaccgcacca ggacggccag gacgaaccgt ttttcattac    960
cgaagagatc gaggcggaga tgatcgcggc cgggtacgtg ttcgagccgc ccgcgcacgt    1020
ctcaaccgtg cggctgcatg aaatcctggc cggtttgtct gatgccaagc tggcggcctg    1080
gccggccagc ttggccgctg aagaaaccga gcgccgccgt ctaaaaaggt gatgtgtatt    1140
tgagtaaaac agcttgcgtc atgcggtcgc tgcgtatatg atgcgatgag taaataaaca    1200
aatacgcaag gggaacgcat gaaggttatc gctgtactta accagaaagg cgggtcaggc    1260
aagacgacca tcgcaaccca tctagcccgc gccctgcaac tcgccggggc cgatgttctg    1320
ttagtcgatt ccgatcccca gggcagtgcc cgcgattggg cggccgtgcg gaagatcaa    1380
ccgctaaccg ttgtcggcat cgaccgcccg acgattgacc gcgacgtgaa ggccatcggc    1440
cggcgcgact tcgtagtgat cgacggagcc ccccaggcgg cggacttggc tgtgtccgcg    1500
atcaaggcag ccgacttcgt gctgattccg gtgcagccaa gccttacga catatgggcc    1560
accgccgacc tggtggagct ggttaagcag cgcattgagg tcacggatgg aaggctacaa    1620
gcggcctttg tcgtgtcgcg gcgatcaaa ggcacgcgca tcggcggtga ggttgccgag    1680
gcgctggccg ggtacgagct gcccattctt gagtcccgta tcacgcagcg cgtgagctac    1740
ccaggcactg ccgccgccgg cacaaccgtt cttgaatcag aacccgaggg cgacgctgcc    1800
cgcgaggtcc aggcgctggc cgctgaaatt aaatcaaaac tcatttgagt taatgaggta    1860
aagagaaaat gagcaaaagc acaaacacgc taagtgccgg ccgtccgagc gcacgcagca    1920
gcaaggctgc aacgttggcc agcctggcag acacgccagc catgaagcgg gtcaactttc    1980
agttgccggc ggaggatcac accaagctga agatgtacgc ggtacgccaa gcaagacca    2040
ttaccgagct gctatctgaa tacatcgcgc agctaccaga gtaaatgagc aaatgaataa    2100
atgagtagat gaattttagc ggctaaagga ggcggcatgg aaaatcaaga acaaccaggc    2160
accgacgccg tggaatgccc catgtgtgga ggaacgggcg ttggccagg cgtaagcggc    2220
tgggttgtct gccggccctg caatggcact ggaaccccca gcccgagga atcggcgtga    2280
cggtcgcaaa ccatccggcc cggtacaaat cggcgcggcg ctgggtgatg acctggtgga    2340
gaagttgaag gccgcgcagg ccgcccagcg gcaacgcatc gaggcagaag cacgccccgg    2400
```

```
tgaatcgtgg caagcggccg ctgatcgaat ccgcaaagaa tcccggcaac cgccggcagc    2460
cggtgcgccg tcgattagga agccgcccaa gggcgacgag caaccagatt ttttcgttcc    2520
gatgctctat gacgtgggca cccgcgatag tcgcagcatc atggacgtgg ccgttttccg    2580
tctgtcgaag cgtgaccgac gagctggcga ggtgatccgc tacgagcttc agacgggca    2640 cgtagaggtt tccgcagggc cggccggcat ggccagtgtg tgggattacg acctggtact    2700
gatggcggtt tccatctaa ccgaatccat gaaccgatac cgggaaggga agggagacaa    2760
gcccggccgc gtgttccgtc cacacgttgc ggacgtactc aagttctgcc ggcgagccga    2820
tggcggaaag cagaaagacg acctggtaga aacctgcatt cggttaaaca ccacgcacgt    2880
tgccatgcag cgtacgaaga aggccaagaa cggccgcctg gtgacggtat ccgagggtga    2940
agccttgatt agccgctaca agatcgtaaa gagcgaaacc gggcggccgg agtacatcga    3000
gatcgagcta gctgattgga tgtaccgcga gatcacagaa ggcaagaacc cggacgtgct    3060
gacggttcac cccgattact ttttgatcga tcccggcatc ggccgttttc tctaccgcct    3120
ggcacgccgc gccgcaggca aggcagaagc cagatggttg ttcaagacga tctacgaacg    3180
cagtggcagc gccggagagt tcaagaagtt ctgtttcacc gtgcgcaagc tgatcgggtc    3240
aaatgacctg ccggagtacg atttgaagga ggaggcgggg caggctggcc cgatcctagt    3300
catgcgctac cgcaacctga tcgagggcga agcatccgcc ggttcctaat gtacggagca    3360
gatgctaggg caaattgccc tagcagggga aaaaggtcga aaaggtctct ttcctgtgga    3420
tagcacgtac attgggaacc caaagccgta cattgggaac cggaacccgt acattgggaa    3480
cccaaagccg tacattggga accggtcaca catgtaagtg actgatataa aagagaaaaa    3540
aggcgatttt tccgcctaaa actctttaaa acttattaaa actcttaaaa cccgcctggc    3600
ctgtgcataa ctgtctggcc agcgcacagc cgaagagctg caaaaagcgc ctacccttcg    3660
gtcgctgcgc tccctacgcc ccgccgcttc gcgtcggcct atcgcggccg ctggccgctc    3720
aaaaatggct ggcctacggc caggcaatct accaggcgc ggacaagccg cgccgtcgcc    3780
actcgaccgc cggcgcccac atcaaggcac cctgcctcgc gcgtttcggt gatgacggtg    3840
aaaacctctg acacatgcag ctcccggaga cggtcacagc ttgtctgtaa gcggatgccg    3900
ggagcagaca agcccgtcag ggcgcgtcag cgggtgttgg cgggtgtcgg ggcgcagcca    3960
tgacccagtc acgtagcgat agcggagtgt atactggctt aactatgcgg catcagagca    4020
gattgtactg agagtgcacc atatgcggtg tgaaataccg cacagatgcg taaggagaaa    4080
ataccgcatc aggcgctctt ccgcttcctc gctcactgac tcgctgcgct cggtcgttcg    4140
gctgcggcga gcggtatcag ctcactcaaa ggcggtaata cggttatcca cagaatcagg    4200
ggataacgca ggaaagaaca tgtgagcaaa aggccagcaa aaggccagga accgtaaaaa    4260
ggccgcgttg ctggcgtttt tccataggct ccgcccccct gacgagcatc acaaaaatcg    4320
acgctcaagt cagaggtggc gaaacccgac aggactataa agataccagg cgtttccccc    4380
tggaagctcc ctcgtgcgct ctcctgttcc gaccctgccg cttaccggat acctgtccgc    4440
ctttctccct tcgggaagcg tggcgctttc tcatagctca cgctgtaggt atctcagttc    4500
ggtgtaggtc gttcgctcca agctgggctg tgtgcacgaa ccccccgttc agcccgaccg    4560
ctgcgcctta tccggtaact atcgtcttga gtccaacccg gtaagacacg acttatcgcc    4620
actggcagca gccactggta acaggattag cagagcgagg tatgtaggcg gtgctacaga    4680
gttcttgaag tggtggccta actacggcta cactagaagg acagtatttg gtatctgcgc    4740
tctgctgaag ccagttacct tcggaaaaag agttggtagc tcttgatccg gcaaacaaac    4800
```

```
caccgctggt agcggtggtt tttttgtttg caagcagcag attacgcgca gaaaaaaagg    4860
atctcaagaa gatcctttga tcttttctac ggggtctgac gctcagtgga acgaaaactc    4920
acgttaaggg attttggtca tgcattctag gtactaaaac aattcatcca gtaaaatata    4980
atattttatt ttctcccaat caggcttgat ccccagtaag tcaaaaaata gctcgacata    5040
ctgttcttcc ccgatatcct ccctgatcga ccggacgcag aaggcaatgt cataccactt    5100
gtccgccctg ccgcttctcc caagatcaat aaagccactt actttgccat cttttcacaaa    5160 gatgttgctg tctcccaggt cgccgtggga aaagacaagt tcctcttcgg cttttccgt    5220 cttttaaaaaa tcatacagct cgcgcggatc tttaaatgga gtgtcttctt cccagttttc    5280
gcaatccaca tcggccagat cgttattcag taagtaatcc aattcggcta agcggctgtc    5340
taagctattc gtatagggac aatccgatat gtcgatggag tgaaagagcc tgatgcactc    5400
cgcatacagc tcgataatct tttcagggct tgttcatct tcatactctt ccgagcaaag    5460
gacgccatcg gcctcactca tgagcagatt gctccagcca tcgccgtt caaagtgcag    5520 gacctttgga acaggcagct ttccttccag ccatagcatc atgtcctttt cccgttccac    5580
atcataggtg gtcccttat accggctgtc cgtcattttt aaatataggt tttcattttc    5640
tcccaccagc ttatatacct tagcaggaga cattccttcc gtatctttta cgcagcggta    5700 ttttcgatc agtttttca attccggtga tattctcatt ttagccattt attatttcct    5760
tcctcttttc tacagtattt aaagatacc caagaagcta attataacaa gacgaactcc    5820
aattcactgt tccttgcatt ctaaaacctt aaataccaga aaacagcttt ttcaaagttg    5880
ttttcaaagt tggcgtataa catagtatcg acggagccga ttttgaaacc gcggtgatca    5940
caggcagcaa cgctctgtca tcgttacaat caacatgcta ccctccgcga gatcatccgt    6000
gtttcaaacc cggcagctta gttgccgttc ttccgaatag catcggtaac atgagcaaag    6060
tctgccgcct tacaacggct ctcccgctga cgccgtcccg gactgatggg ctgcctgtat    6120
cgagtggtga ttttgtgccg agctgccggt cggggagctg ttggctggct ggtggcagga    6180
tatattgtgg tgtaaacaaa ttgacgctta gacaacttaa taacacattg cggacgtttt    6240
taatgtactg aattaacgcc gaattaattc gggggatctg gattttagta ctggattttg    6300
gttttaggaa ttagaaattt tattgataga agtattttac aaatacaaat acatactaag    6360
ggtttcttat atgctcaaca catgagcgaa accctatagg aaccctaatt cccttatctg    6420
ggaactactc acacattatt atggagaaac tcgagggatc ccggtcggca tctactctat    6480
tcctttgccc tcggacgagt gctggggcgt cggtttccac tatcggcgag tacttctaca    6540
cagccatcgg tccagacggc cgcgcttctg cgggcgattt tgtgtacgccc gacagtcccg    6600 gctccggatc ggacgattgc gtcgcatcga ccctgcgccc aagctgcatc atcgaaattg    6660
ccgtcaacca agctctgata gagttggtca agaccaatgc ggagcatata cgcccggagc    6720
cgcggcgatc ctgcaagctc cggatgcctc cgctcgaagt agcgcgtctg ctgctccata    6780
caagccaacc acggcctcca gaagaagatg ttggcgacct cgtattggga atccccgaac    6840
atcgcctcgc tccagtcaat gaccgctgtt atgcggccat tgtccgtcag gacattgttg    6900
gagccgaaat ccgcgtgcac gaggtgccgg acttcggggc agtcctcggc ccaaagcatc    6960
agctcatcga gagcctgcgc gacggacgca ctgacggtgt cgtccatcac agtttgccag    7020
tgatacacat ggggatcagc aatcgcgcat atgaaatcac gccatgtagt gtattgaccg    7080
attccttgcg gtccgaatgg gccgaacccg ctcgtctggc taagatcggc cgcagcgatc    7140
```

```
gcatccatgg cctccgcgac cggctgcagt tatcatcatc atcatagaca cacgaaataa    7200
agtaatcaga ttatcagtta aagctatgta atatttacac cataaccaat caattaaaaa    7260
atagatcagt ttaaagaaag atcaaagctc aaaaaaataa aaagagaaaa gggtcctaac    7320
caagaaaatg aaggagaaaa actagaaatt tacctgcaga acagcgggca gttcggtttc    7380
aggcaggtct tgcaacgtga caccctgtgc acggcgggag atgcaatagg tcaggctctc    7440
gctgaattcc ccaatgtcaa gcacttccgg aatcgggagc gcggccgatg caaagtgccg    7500
ataaacataa cgatctttgt agaaaccatc ggcgcagcta tttacccgca ggacatatcc    7560
acgccctcct acatcgaagc tgaaagcacg agattcttcg ccctccgaga gctgcatcag    7620
gtcggagacg ctgtcgaact tttcgatcag aaacttctcg acagacgtcg cggtgagttc    7680
aggctttttc atggtagagg agctcgccgc ttggtatctg cattacaatg aaatgagcaa    7740
agactatgtg agtaacactg gtcaacacta gggagaaggc atcgagcaag atacgtatgt    7800
aaagagaagc aatatagtgt cagttggtag atactagata ccatcaggag gtaaggagag    7860
caacaaaaag gaaactcttt attttttaaat tttgttacaa caaacaagca gatcaatgca    7920
tcaaaatact gtcagtactt atttcttcag acaacaatat ttaaaacaag tgcatctgat    7980
cttgacttat ggtcacaata aaggagcaga gataaacatc aaaatttcgt catttatatt    8040
tattccttca ggcgttaaca atttaacagc acacaaacaa aaacagaata ggaatatcta    8100
attttggcaa ataataagct ctgcagacga acaaattatt atagtatcgc ctataatatg    8160
aatccctata ctattgaccc atgtagtatg aagcctgtgc ctaaattaac agcaaacttc    8220
tgaatccaag tgcccctataa caccaacatg tgcttaaata aataccgcta agcaccaaat    8280
tacacatttc tcgtattgct gtgtaggttc tatcttcgtt tcgtactacc atgtccctat    8340
attttgctgc tacaaaggac ggcaagtaat cagcacaggc agaacacgat ttcagagtgt    8400
aattctagat ccagctaaac cactctcagc aatcaccaca caagagagca ttcagagaaa    8460
cgtggcagta acaaaggcag agggcggagt gagcgcgtac cgaagacggt agatctctcg    8520
agagagatag atttgtagag agagactggt gatttcagcg tgtcctctcc aaatgaaatg    8580
aacttcctta tatagaggaa ggtcttgcga aggatagtgg gattgtgcgt catcccttac    8640
gtcagtggag atatcacatc aatccacttg ctttgaagac gtggttggaa cgtcttcttt    8700
ttccacgatg ctcctcgtgg gtgggggtcc atctttggga ccactgtcgg cagaggcatc    8760
ttgaacgata gccttccctt tatcgcaatg atggcatttg taggtgccac cttccttttc    8820
tactgtcctt ttgatgaagt gacagatagc tgggcaatgg aatccgagga ggtttcccga    8880 tattacccctt tgttgaaaag tctcaatagc cctttggtct tctgagactg tatctttgat    8940
attcttggag tagacgagag tgtcgtgctc caccatgtta tcacatcaat ccacttgctt    9000
tgaagacgtg gttggaacgt cttctttttc cacgatgctc ctcgtgggtg gggtccatc    9060 tttgggacca ctgtcggcag aggcatcttg aacgatagcc tttccttat cgcaatgatg    9120 gcatttgtag gtgccacctt cctttctac tgtccttttg atgaagtgac agatagctgg    9180
gcaatggaat ccgaggaggt ttcccgatat tacccttgt tgaaaagtct caatagccct    9240
ttggtcttct gagactgtat ctttgatatt cttggagtag acgagtgt cgtgctccac    9300 catgttggca agctgctcta gccaatacgc aaaccgcctc tccccgcgcg ttggccgatt    9360
cattaatgca gctggcacga caggtttccc gactggaaag cgggcagtga gcgcaacgca    9420
attaatgtga gttagctcac tcattaggca ccccaggctt tacactttat gcttccggct    9480
cgtatgttgt gtggaattgt gagcggataa caatttcaca caggaaacag ctatgaccat    9540
```

```
gattacgaat tcgagctcgg taccccacgg aagatccagg tctcgagact aggagacgga    9600
tgggaggcgc aacgcgcgat ggggagggg  gcggcgctga cctttctggc gaggtcgagg    9660
tagcgatcga gcagctgcag cgcggacacg atgaggaaga cgaagatagc cgccatggac    9720
atgttcgcca gcggcggcgg agcgaggctg agccggtctc tccggcctcc ggtcggcgtt    9780
aagttgggga tcgtaacgtg acgtgtctcg tctccacgga tcgacacaac cggcctactc    9840
gggtgcacga cgccgcgata agggcgagat gtccgtgcac gcagcccgtt tggagtcctc    9900
gttgcccacg aaccgacccc ttacagaaca aggcctagcc caaaactatt ctgagttgag    9960
cttttgagcc tagcccacct aagccgagcg tcatgaactg atgaacccac taccactagt   10020
caaggcaaac cacaaccaca aatggatcaa ttgatctaga acaatccgaa ggaggggagg   10080
ccacgtcaca ctcacaccaa ccgaaatatc tgccagaatc agatcaaccg gccaatagga   10140
cgccagcgag cccaacacct ggcgacgccg caaaattcac cgcgaggggc accgggcacg   10200
gcaaaaacaa aagcccggcg cggtgagaat atctggcgac tggcggagac ctggtggcca   10260
gcgcgcggcc acatcagcca ccccatccgc ccacctcacc tccggcgagc caatggcaac   10320
tcgtcttaag attccacgag ataaggaccc gatcgccggc gacgctattt agccaggtgc   10380
gcccccacg  gtacactcca ccagcggcat ctatagcaac cggtccagca ctttcacgct   10440
cagcttcagc aagatctacc gtcttcggta cgcgctcact ccgccctctg cctttgttac   10500
tgccacgttt ctctgaatgc tctcttgtgt ggtgattgct gagagtggtt tagctggatc   10560
tagaattaca ctctgaaatc gtgttctgcc tgtgctgatt acttgccgtc ctttgtagca   10620
gcaaaatata gggacatggt agtacgaaac gaagatagaa cctacacagc aatacgagaa   10680
atgtgtaatt tggtgcttag cggtatttat ttaagcacat gttggtgtta tagggcactt   10740
ggattcagaa gtttgctgtt aatttaggca caggcttcat actacatggg tcaatagtat   10800
agggattcat attataggcg atactataat aatttgttcg tctgcagagc ttattatttg   10860
ccaaaattag atattcctat tctgtttttg tttgtgtgct gttaaattgt taacgcctga   10920
aggaataaat ataaatgacg aaattttgat gtttatctct gctcctttat tgtgaccata   10980
agtcaagatc agatgcactt gttttaaata ttgttgtctg aagaaataag tactgacagt   11040
attttgatgc attgatctgc ttgtttgttg taacaaaatt taaaaataaa gagtttcctt   11100
tttgttgctc tccttacctc ctgatggtat ctagtatcta ccaactgata ctatattgct   11160
tctctttaca nnnnnntctt gctcgatgcc ttctcctagt gttgaccagt gttactcaca   11220
tagtctttgc tcatttcatt gtaatgcaga taccaagcgg ttaattaact atgtgcggcg   11280
gggccattct cagtgatctc tactcaccag tgaggcggac ggtcactgcc ggtgacctat   11340
ggggagagag tggcagcagc aagaatgtga agaactggaa aaggagttct tggaagtttg   11400
atgaaggcga tgaagacttt gaagctgatt tcaaggattt tgaggattgc agtagcgagg   11460
aggaggtaga ttttgacat  gaggaaaaag aattccaatt gaacagttcg aatttcgtgg   11520
aattcaatgg ccatactgcc aaagtcacca gcaggaagcg aaagatccag taccgaggga   11580
tccggcggcg gccttgggc  aaatgggcag cagaaatcag agaccacag  aagggcgtcc   11640
gagtttggct tggcacgttc agcactgccg aggaagctgc aagggcatat gacgtggaag   11700
ctctacgcat acgtggcaag aaagccaaga tgaatttccc taccaccatc acagctgctg   11760
ggaaacacca ccggcagcgt gtggctcgac cggcaaagaa gacgtcacaa gagagcctga   11820
agtcaagcaa tgcctctggt catgtcatct cagcaggcag cagtactgat ggcaccgttg   11880
```

-continued

```
tcaagatcga gttgtcacag tcaccagctt ctccactacc agtgtccagc gcatggcttg    11940
atgcttttga gctgaagcag cttggtggag aaaccctga agctgatggg agagaaaccc    12000
ctgaagaaac tgatcatgaa acgggagtga cagcggatat gttttttggc aatggcgaag    12060
tgcggctttc agatgatttt gcgtcttacg agccttaccc aaattttatg cagttacctt    12120
atctagaagg tgactcgtat gaaaacattg acactctttt caacggtgaa gctgctcagg    12180
atggagtgaa catcggaggt ctttggaatt tcgatgatgt gccaatggac cgtggtgttt    12240
actgaatgtg cggcggggcc attctcagtg atctctactc accagtgagg cggacggtca    12300
ctgccggtga cctatgggga gagagtggca gcagcaagaa tgtgaagaac tggaaaagga    12360
gttcttggaa gtttgatgaa ggcgatgaag actttgaagc tgatttcaag gattttgagg    12420
attgcagtag cgaggaggag gtagattttg acatgagga aaaagaattc caattgaaca    12480
gttcgaattt cgtggaattc aatggccata ctgccaaagt caccagcagg aagcgaaaga    12540
tccagtaccg agggatccgg cggcggcctt ggggcaaatg ggcagcagaa atcagagacc    12600
cacagaaggg cgtccgagtt tggcttggca cgttcagcac tgccgaggaa gctgcaaggg    12660
catatgacgt ggaagctcta cgcatacgtg gcaagaaagc caagatgaat ttccctacca    12720
ccatcacagc tgctgggaaa caccaccggc agcgtgtggc tcgaccggca agaagacgt    12780 cacaagagag cctgaagtca agcaatgcct ctggtcatgt catctcagca ggcagcagta    12840
ctgatggcac cgttgtcaag atcgagttgt cacagtcacc agcttctcca ctaccagtgt    12900
ccagcgcatg gcttgatgct tttgagctga agcagcttgg tggagaaacc cctgaagctg    12960
atgggagaga aaccctgaa gaaactgatc atgaaacggg agtgacagcg gatatgtttt    13020
ttggcaatgg cgaagtgcgg ctttcagatg attttgcgtc ttacgagcct acccaaatt    13080 ttatgcagtt accttatcta gaaggtgact cgtatgaaaa cattgacact cttttcaacg    13140
gtgaagctgc tcaggatgga gtgaacatcg gaggtctttg gaatttcgat gatgtgccaa    13200
tggaccgtgg tgtttactga gcagggcgcg ccatcgttca acatttggc aataaagttt    13260 cttaagattg aatcctgttg ccggtcttgc gatgattatc atataatttc tgttgaatta    13320
cgttaagcat gtaataatta acatgtaatg catgacgtta tttatgagat gggtttttat    13380
gattagagtc ccgcaattat acatttaata cgcgatagaa acaaaatat agcgcgcaaa    13440 ctaggataaa ttatcgcgcg cggtgtcatc tatgttacta gatccgatga taagctgtca    13500
aacatgaaag cttggcactg ccgtcgtttt acaacgtcg tgactgggaa accctggcg    13560 ttacccaact taatcgcctt gcagcacatc cccctttcgc cagctggcgt aatagcgaag    13620
aggcccgcac cgatcgccct tcccaacagt tgcgcagcct gaatggcgaa tgctagagca    13680
gcttgagctt ggatcagatt gtcgtttccc gccttcagtt taaactatca gtgtttgaca    13740
ggatatattg gcgggtaaac ctaagagaaa agagcgttta ttagaataac ggatatttaa    13800
aagggcgtga aaggtttat ccgttcgtcc atttgtatgt g    13841
```

<210> SEQ ID NO 29
<211> LENGTH: 87
<212> TYPE: PRT
<213> ORGANISM: Panicum virgatum

<400> SEQUENCE: 29

Val Thr Ser Arg Lys Arg Lys Ile Gln Tyr Arg Gly Ile Arg Arg Arg
1               5                   10                  15

Pro Trp Gly Lys Trp Ala Ala Glu Ile Arg Asp Pro Gln Lys Gly Val
            20                  25                  30

```
Arg Val Trp Leu Gly Thr Phe Ser Thr Ala Glu Glu Ala Ala Arg Ala
            35                  40                  45

Tyr Asp Val Glu Ala Leu Arg Ile Arg Gly Lys Lys Ala Lys Met Asn
 50                  55                  60

Phe Pro Thr Thr Ile Thr Ala Ala Gly Lys His His Arg Gln Arg Val
 65                  70                  75                  80

Ala Arg Pro Ala Lys Lys Thr
                 85

<210> SEQ ID NO 30
<211> LENGTH: 87
<212> TYPE: PRT
<213> ORGANISM: Setaria italica

<400> SEQUENCE: 30

Val Ala Arg Arg Lys Arg Lys Thr Gln Tyr Arg Gly Ile Arg Arg Arg
 1               5                  10                  15

Pro Trp Gly Lys Trp Ala Ala Glu Ile Arg Asp Pro Cys Lys Gly Val
            20                  25                  30

Arg Val Trp Leu Gly Thr Tyr Asn Thr Ala Glu Glu Ala Ala Arg Ala
            35                  40                  45

Tyr Asp Val Ala Ala Arg Arg Ile Arg Gly Lys Lys Ala Lys Val Asn
 50                  55                  60

Phe Pro Asp Thr Ile Thr Ala Ser Ala Lys Arg Leu Pro Gly Arg Val
 65                  70                  75                  80

Pro Arg Pro Ala Lys Lys Val
                 85

<210> SEQ ID NO 31
<211> LENGTH: 87
<212> TYPE: PRT
<213> ORGANISM: Sorghum bicolor

<400> SEQUENCE: 31

Val Ala Ser Arg Lys Arg Arg Thr Gln Tyr Arg Gly Ile Arg Arg Arg
 1               5                  10                  15

Pro Trp Gly Lys Trp Ala Ala Glu Ile Arg Asp Pro Arg Lys Gly Val
            20                  25                  30

Arg Val Trp Leu Gly Thr Tyr Ser Thr Ala Glu Glu Ala Ala Arg Ala
            35                  40                  45

Tyr Asp Thr Ala Ala Trp Arg Ile Arg Gly Lys Lys Ala Lys Val Asn
 50                  55                  60

Phe Pro Ser Ala Ile Thr Asn Pro Glu Lys Arg Arg Arg Gly Arg Val
 65                  70                  75                  80

Ala Arg Pro Arg Lys Lys Ile
                 85

<210> SEQ ID NO 32
<211> LENGTH: 94
<212> TYPE: PRT
<213> ORGANISM: Oryza sativa

<400> SEQUENCE: 32

Gly Gly Ser Arg Lys Arg Lys Thr Arg Tyr Arg Gly Ile Arg Gln Arg
 1               5                  10                  15

Pro Trp Gly Lys Trp Ala Ala Glu Ile Arg Asp Pro Lys Gly Val
            20                  25                  30
```

```
Arg Val Trp Leu Gly Thr Phe Gly Thr Ala Glu Glu Ala Met Ala
        35              40                  45

Tyr Asp Val Glu Ala Arg Arg Ile Arg Gly Lys Lys Ala Lys Val Asn
 50                  55                  60

Phe Pro Asp Ala Ala Ala Ala Pro Lys Arg Pro Arg Arg Ser Ser
 65              70              75                  80

Ala Lys His Ser Pro Gln Gln Gln Lys Ala Arg Ser Ser Ser
                 85              90
```

<210> SEQ ID NO 33
<211> LENGTH: 110
<212> TYPE: PRT
<213> ORGANISM: Jatropha curcas

<400> SEQUENCE: 33

```
Phe Asn Gly Gln Ala Glu Lys Ser Ala Lys Arg Lys Arg Lys Asn Gln
 1               5                  10                  15

Tyr Arg Gly Ile Arg Gln Arg Pro Trp Gly Lys Trp Ala Ala Glu Ile
             20                  25                  30

Arg Asp Pro Arg Lys Gly Val Arg Val Trp Leu Gly Thr Phe Asn Thr
         35                  40                  45

Ala Glu Glu Ala Ala Arg Ala Tyr Asp Ala Glu Ala Arg Arg Ile Arg
     50                  55                  60

Gly Lys Lys Ala Lys Val Asn Phe Pro Glu Glu Ala Pro His Ala Ser
 65                  70                  75                  80

Pro Lys Arg Pro Ser Lys Ala Asn Ser Gln Lys Ser Leu Gly Lys Thr
                 85                  90                  95

Asn Leu Ala Glu Asn Leu Asn Tyr Leu Asp Asn Pro Glu Gln
                100                 105                 110
```

<210> SEQ ID NO 34
<211> LENGTH: 110
<212> TYPE: PRT
<213> ORGANISM: Populus trichocarpa

<400> SEQUENCE: 34

```
Phe Ser Gly Pro Ala Glu Lys Ser Ala Lys Arg Lys Arg Lys Asn Gln
 1               5                  10                  15

Phe Arg Gly Ile Arg Gln Arg Pro Trp Gly Lys Trp Ala Ala Glu Ile
             20                  25                  30

Arg Asp Pro Arg Lys Gly Val Arg Val Trp Leu Gly Thr Phe Asn Thr
         35                  40                  45

Ala Glu Glu Ala Ala Arg Ala Tyr Asp Ser Glu Ala Arg Arg Ile Arg
     50                  55                  60

Gly Lys Lys Ala Lys Val Asn Phe Pro Asp Glu Ala Pro Cys Ala Ser
 65                  70                  75                  80

Ala Arg His Pro Ile Lys Glu Asn Ser Gln Lys Arg Leu Thr Lys Ala
                 85                  90                  95

Asn Leu Ser Gln Asp Phe Ser Tyr Leu Ser Asn Pro Glu Thr
                100                 105                 110
```

<210> SEQ ID NO 35
<211> LENGTH: 117
<212> TYPE: PRT
<213> ORGANISM: Gossypium hirsutum

<400> SEQUENCE: 35

```
Phe Asn Gly Gln Ala Glu Lys Cys Ala Lys Arg Lys Arg Lys Asn Gln
```

```
            1               5                  10                 15
Tyr Arg Gly Ile Arg Gln Arg Pro Trp Gly Lys Trp Ala Ala Glu Ile
                20                 25                 30
Arg Asp Pro Arg Lys Gly Val Arg Val Trp Leu Gly Thr Phe Asn Thr
                35                 40                 45
Ala Glu Glu Ala Ala Arg Ala Tyr Asp Ala Glu Ala Arg Arg Ile Arg
        50                 55                 60
Gly Lys Lys Ala Lys Val Asn Phe Pro Asn Glu Thr Pro Arg Thr Ser
65                 70                 75                 80
Pro Lys His Ala Val Lys Thr Asn Ser Gln Lys Pro Leu Ser Lys Ser
                85                 90                 95
Asn Ser Ser Pro Val Gln Pro Asn Leu Asn Gln Asn Tyr Asn Tyr Leu
                100                105                110
Asn Gln Pro Glu Gln
            115

<210> SEQ ID NO 36
<211> LENGTH: 117
<212> TYPE: PRT
<213> ORGANISM: Theobroma cacao

<400> SEQUENCE: 36

Phe Asn Gly Gln Ala Glu Lys Ser Ala Lys Arg Lys Arg Lys Asn Gln
1               5                  10                 15
Tyr Arg Gly Ile Arg Gln Arg Pro Trp Gly Lys Trp Ala Ala Glu Ile
                20                 25                 30
Arg Asp Pro Arg Lys Gly Val Arg Val Trp Leu Gly Thr Phe Asn Thr
                35                 40                 45
Ala Glu Glu Ala Ala Arg Ala Tyr Asp Ala Glu Ala Arg Arg Ile Arg
        50                 55                 60
Gly Lys Lys Ala Lys Val Asn Phe Pro Asp Ala Pro Arg Thr Ser
65                 70                 75                 80
Pro Lys Arg Ala Val Lys Ala Asn Ser Gln Lys Ser Leu Ser Arg Ser
                85                 90                 95
Asn Leu Ser Pro Val Gln Pro Asn Leu Asp Gln Asn Phe Asn Tyr Leu
                100                105                110
Ser Lys Pro Glu Gln
            115

<210> SEQ ID NO 37
<211> LENGTH: 117
<212> TYPE: PRT
<213> ORGANISM: Malus domestica

<400> SEQUENCE: 37

Phe Asp Gly Gln Ala Glu Lys Ser Ala Lys Arg Lys Arg Lys Asn Gln
1               5                  10                 15
Tyr Arg Gly Ile Arg Gln Arg Pro Trp Gly Lys Trp Ala Ala Glu Ile
                20                 25                 30
Arg Asp Pro Arg Lys Gly Val Arg Val Trp Leu Gly Thr Phe Asn Thr
                35                 40                 45
Ala Glu Glu Ala Ala Arg Ala Tyr Asp Ala Glu Ala Arg Arg Ile Arg
        50                 55                 60
Gly Lys Lys Ala Lys Val Asn Phe Pro Glu Glu Thr Pro Cys Ala Ser
65                 70                 75                 80
Ala Lys Arg Ser Ile Lys Glu Asn Pro Gln Lys Leu Ile Ala Lys Thr
```

```
                    85                  90                  95
Asn Leu Asn Gly Thr Gln Ser Asn Pro Asn Gln Asn Phe Asn Phe Val
                100                 105                 110
Asn Asp Ser Ser Glu
            115

<210> SEQ ID NO 38
<211> LENGTH: 118
<212> TYPE: PRT
<213> ORGANISM: Morus alba

<400> SEQUENCE: 38

Ser Asp Gly Gln Ala Glu Lys Ser Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Asp Glu Thr Pro Arg Ala Leu
65                  70                  75                  80

Pro Lys His Pro Val Lys Glu Ser Pro Lys Arg Ser Leu Pro Lys Glu
                85                  90                  95

Asn Ser Asn Ser Thr Glu Ser Asn Leu Asn Asn Gln Ser Phe Asn Ser
                100                 105                 110

Val Asn Asn Ser Asp Leu
            115

<210> SEQ ID NO 39
<211> LENGTH: 105
<212> TYPE: PRT
<213> ORGANISM: Cucumis sativus

<400> SEQUENCE: 39

Phe Asn Glu Gln Ala Glu Lys Ser Ala Asn Thr Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Ala Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Asn Lys Ala Arg Val Asn Phe Pro Asp Glu Pro Leu Pro Asn Thr
65                  70                  75                  80

Gln Lys Arg Lys Asn Ser Gln Lys Ser Lys Gln His Ile Lys Glu Asn
                85                  90                  95

Val Lys Ala Asn Gln His Pro Asn Gln
            100                 105

<210> SEQ ID NO 40
<211> LENGTH: 113
<212> TYPE: PRT
<213> ORGANISM: Solanum lycopersicum

<400> SEQUENCE: 40

Ser Asn Cys Glu Ala Asp Arg Ser Lys Arg Lys Arg Lys Asn Gln
1               5                   10                  15
```

```
Tyr Arg Gly Ile Arg Gln Arg Pro Trp Gly Lys Trp Ala Ala Glu Ile
            20                  25                  30

Arg Asp Pro Arg Lys Gly Ile Arg Val Trp Leu Gly Thr Phe Asn Ser
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Asp Glu Ala Pro Val Ser Val
65                  70                  75                  80

Ser Arg Arg Ala Ile Lys Gln Asn Pro Gln Lys Ala Leu Arg Glu Glu
                85                  90                  95

Thr Leu Asn Thr Val Gln Pro Asn Met Thr Tyr Ile Ser Asn Leu Asp
            100                 105                 110

Gly

<210> SEQ ID NO 41
<211> LENGTH: 113
<212> TYPE: PRT
<213> ORGANISM: Capsicum annuum

<400> SEQUENCE: 41

Ser Ser Cys Asp Thr Glu Lys Ser Ser Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Ile Arg Val Trp Leu Gly Thr Phe Asn Ser
        35                  40                  45

Ala Glu Glu Ala Ala Arg Ala Tyr Asp Val Glu Ala Arg Arg Ile Arg
    50                  55                  60

Gly Lys Lys Ala Lys Val Asn Phe Pro Asp Gly Ser Pro Ala Ser Ala
65                  70                  75                  80

Ser Arg Arg Ala Val Lys Pro Asn Pro Gln Glu Ala Leu Arg Glu Glu
                85                  90                  95

Ile Leu Asn Thr Val Gln Pro Asn Thr Thr Tyr Ile Asn Asn Leu Asp
            100                 105                 110

Gly

<210> SEQ ID NO 42
<211> LENGTH: 113
<212> TYPE: PRT
<213> ORGANISM: Nicotiana tabacum

<400> SEQUENCE: 42

Ser Asp Lys Asp Ala Asp Arg Ser Ser Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Val Glu Ala Arg Arg Ile Arg
    50                  55                  60

Gly Asn Lys Ala Lys Val Asn Phe Pro Asp Glu Ala Pro Val Pro Ala
65                  70                  75                  80

Ser Arg Arg Thr Val Lys Val Asn Pro Gln Lys Val Leu Pro Lys Glu
                85                  90                  95

Ile Leu Asp Ser Val Gln Pro Asp Ser Thr Ile Ile Asn Asn Met Glu
```

-continued

```
                100                 105                 110
Asp

<210> SEQ ID NO 43
<211> LENGTH: 108
<212> TYPE: PRT
<213> ORGANISM: Glycine max

<400> SEQUENCE: 43

Phe Gln Gly Arg Ala Glu Ile Ser Ala Asn Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Asn Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Glu Ala Pro Gly Thr Ser Ser
65                  70                  75                  80

Val Lys Arg Ser Lys Val Asn Pro Gln Glu Asn Leu Lys Thr Val Gln
                85                  90                  95

Pro Asn Leu Gly His Lys Phe Ser Ala Gly Asn Asn
            100                 105

<210> SEQ ID NO 44
<211> LENGTH: 105
<212> TYPE: PRT
<213> ORGANISM: Arachis hypogaea

<400> SEQUENCE: 44

Val Lys Ala Gln Ser Glu Lys Ser Ala Lys Arg Lys Arg Lys Asn Gln
1               5                   10                  15

Tyr Arg Gly Ile Arg Gln Arg Pro Trp Gly Lys Trp Ala Ala Glu Ile
            20                  25                  30

Arg Asp Pro Arg Lys Gly Val Arg Val Trp Leu Gly Thr Phe Ser Thr
        35                  40                  45

Ala Glu Glu Ala Ala Arg Ala Tyr Asp Ala Glu Ala Arg Arg Ile Arg
    50                  55                  60

Gly Lys Lys Ala Lys Val Asn Phe Pro Glu Glu Ala Pro Arg Thr Pro
65                  70                  75                  80

Pro Lys Arg Ala Arg Pro Asn Leu Asn Ala Val Gln Pro Asn Leu Ser
                85                  90                  95

His Lys Phe Ser Val Gly Asn Asn Met
            100                 105

<210> SEQ ID NO 45
<211> LENGTH: 108
<212> TYPE: PRT
<213> ORGANISM: Medicago truncatula

<400> SEQUENCE: 45

Ser Lys Ser Asn Glu Gln Gly Glu Lys Glu Leu Lys Arg Lys Arg Lys
1               5                   10                  15

Asn Gln Tyr Arg Gly Ile Arg Gln Arg Pro Trp Gly Lys Trp Ala Ala
            20                  25                  30

Glu Ile Arg Asp Pro Arg Lys Gly Val Arg Val Trp Leu Gly Thr Phe
        35                  40                  45
```

-continued

```
Asn Thr Ala Glu Glu Ala Ala Arg Ala Tyr Asp Ala Glu Ala Arg Arg
         50                  55                  60

Ile Arg Gly Lys Lys Ala Lys Val Asn Phe Pro Glu Gly Ala Pro Asn
 65                  70                  75                  80

Ala Ser Ser Lys Arg Leu Lys Thr Asn Ser Glu Thr Gln Leu Leu Asp
                 85                  90                  95

Lys Asn Leu Asn Ser Phe Lys Cys Glu Asn Ile Glu
                100                 105

<210> SEQ ID NO 46
<211> LENGTH: 114
<212> TYPE: PRT
<213> ORGANISM: Zea mays

<400> SEQUENCE: 46

Tyr Asp Ala Pro Ala Ala Arg Leu Ala Lys Arg Lys Arg Lys Asn Gln
 1               5                  10                  15

Tyr Arg Gly Ile Arg Gln Arg Pro Trp Gly Lys Trp Ala Ala Glu Ile
                 20                  25                  30

Arg Asp Pro Gln Lys Gly Val Arg Val Trp Leu Gly Thr Phe Asn Ser
             35                  40                  45

Pro Glu Glu Ala Ala Arg Ala Tyr Asp Ala Glu Ala Arg Arg Ile Arg
 50                  55                  60

Gly Lys Lys Ala Lys Val Asn Phe Pro Asp Ala Pro Val Gly Gln
 65                  70                  75                  80

Lys Cys Arg Ser Ser Ala Ser Ala Lys Ala Leu Lys Ser Cys Val
                 85                  90                  95

Glu Gln Lys Pro Ile Val Lys Thr Asp Met Asn Ile Leu Ala Asn Thr
                100                 105                 110

Asn Ala

<210> SEQ ID NO 47
<211> LENGTH: 114
<212> TYPE: PRT
<213> ORGANISM: Brachypodium distachyon

<400> SEQUENCE: 47

Phe Asp Gly Pro Ala Glu Arg Ser Ala Lys Arg Lys Arg Lys Asn Gln
 1               5                  10                  15

Phe Arg Gly Ile Arg Gln Arg Pro Trp Gly Lys Trp Ala Ala Glu Ile
                 20                  25                  30

Arg Asp Pro Asn Lys Gly Val Arg Val Trp Leu Gly Thr Phe Asn Ser
             35                  40                  45

Ala Glu Glu Ala Ala Arg Ala Tyr Asp Ala Glu Ala Arg Arg Ile Arg
 50                  55                  60

Gly Asn Lys Ala Lys Val Asn Phe Pro Glu Glu Pro Arg Ala Ala Gln
 65                  70                  75                  80

Lys Arg Arg Ala Gly Pro Ala Ala Lys Val Pro Lys Ser Arg Val
                 85                  90                  95

Glu Gln Lys Pro Asn Val Lys Pro Ala Val Asn Asn Leu Ala Asn Thr
                100                 105                 110

Asn Ala

<210> SEQ ID NO 48
<211> LENGTH: 108
<212> TYPE: PRT
<213> ORGANISM: Triticum aestivum
```

<400> SEQUENCE: 48

```
Asp Asp Asp Cys Ala Ser Gly Ser Ala Arg Lys Arg Lys Asn Gln Phe
1               5                   10                  15

Arg Gly Ile Arg Arg Arg Pro Trp Gly Lys Trp Ala Ala Glu Ile Arg
            20                  25                  30

Asp Pro Arg Lys Gly Val Arg Val Trp Leu Gly Thr Tyr Asn Ser Ala
        35                  40                  45

Glu Glu Ala Ala Arg Ala Tyr Asp Val Glu Ala Arg Ile Arg Gly
    50                  55                  60

Lys Lys Ala Glu Val Asn Phe Pro Glu Ala Pro Met Ala Pro Gln
65                  70                  75                  80

Gln Arg Cys Ala Thr Ala Val Lys Val Pro Glu Phe Asn Thr Glu Gln
                85                  90                  95

Lys Pro Val Leu Asn Thr Met Gly Asn Ala Asp Val
                100                 105
```

<210> SEQ ID NO 49
<211> LENGTH: 102
<212> TYPE: PRT
<213> ORGANISM: Hordeum vulgare

<400> SEQUENCE: 49

```
Tyr Asp Gly Gly Arg Ala Ala His Ala Ala Ser Arg Lys Lys Arg Thr
1               5                   10                  15

Gly His Leu His Gly Ile Arg Gln Arg Pro Trp Gly Lys Trp Ala Ala
            20                  25                  30

Glu Ile Arg Asp Pro His Lys Gly Thr Arg Val Trp Leu Gly Thr Phe
        35                  40                  45

Asp Thr Ala Asp Ala Ala Arg Ala Tyr Asp Val Ala Ala Arg Arg
    50                  55                  60

Leu Arg Gly Ser Lys Ala Lys Val Asn Phe Pro Asp Ala Ala Arg Thr
65                  70                  75                  80

Gly Ala Arg Pro Arg Arg Ala Ser Arg Arg Thr Ala Gln Lys Pro Gln
                85                  90                  95

Cys Pro Pro Ala Arg Thr
            100
```

<210> SEQ ID NO 50
<211> LENGTH: 92
<212> TYPE: PRT
<213> ORGANISM: Zea mays

<400> SEQUENCE: 50

```
Thr Leu Thr Thr Thr Met Arg His Tyr Arg Gly Val Arg Arg Arg Pro
1               5                   10                  15

Trp Gly Lys Trp Ala Ala Glu Ile Arg Asp Pro Ala Lys Ala Ala Arg
            20                  25                  30

Val Trp Leu Gly Thr Phe Asp Thr Ala Glu Ala Ala Ala Ala Ala Tyr
        35                  40                  45

Asp Arg Ala Ala Leu Gln Phe Lys Gly Ala Lys Ala Lys Leu Asn Phe
    50                  55                  60

Pro Glu Arg Val Arg Gly Arg Thr Gly Gln Gly Ala Phe Leu Val Ser
65                  70                  75                  80

Pro Gly Ile Pro Gln Pro Pro Val Ser Ala Pro
                85                  90
```

<210> SEQ ID NO 51
<211> LENGTH: 96
<212> TYPE: PRT
<213> ORGANISM: Sorghum bicolor

<400> SEQUENCE: 51

Thr Ser Thr Thr Thr Met Arg His Tyr Arg Gly Val Arg Arg Arg Pro
1               5                   10                  15

Trp Gly Lys Trp Ala Ala Glu Ile Arg Asp Pro Ala Lys Ala Ala Arg
            20                  25                  30

Val Trp Leu Gly Thr Phe Asp Thr Ala Glu Ala Ala Ala Ala Ala Tyr
        35                  40                  45

Asp Asp Ala Ala Leu Arg Phe Lys Gly Ala Lys Ala Lys Leu Asn Phe
    50                  55                  60

Pro Glu Arg Val Arg Gly Arg Thr Gly Gln Gly Ala Phe Leu Val Ser
65                  70                  75                  80

Pro Gly Ile Pro Gln Pro Pro Pro Pro Val Ser Ala Pro Pro Leu
                85                  90                  95

<210> SEQ ID NO 52
<211> LENGTH: 91
<212> TYPE: PRT
<213> ORGANISM: Panicum virgatum

<400> SEQUENCE: 52

Tyr Gly Thr Arg Met His Tyr Arg Gly Val Arg Arg Arg Pro Trp Gly
1               5                   10                  15

Lys Trp Ala Ala Glu Ile Arg Asp Pro Ala Lys Ala Ala Arg Val Trp
            20                  25                  30

Leu Gly Thr Phe Asp Thr Ala Glu Ala Ala Ala Ala Tyr Asp Asp
        35                  40                  45

Ala Ala Leu Arg Phe Lys Gly Ala Lys Ala Lys Leu Asn Phe Pro Glu
    50                  55                  60

Arg Val Arg Gly Arg Thr Gly Gln Gly Ala Phe Leu Val Ser Pro Gly
65                  70                  75                  80

Val Pro Gln Gln Pro Pro Ser Ser Leu Pro
                85                  90

<210> SEQ ID NO 53
<211> LENGTH: 100
<212> TYPE: PRT
<213> ORGANISM: Hordeum vulgare

<400> SEQUENCE: 53

Gly Arg Lys Arg His Tyr Arg Gly Val Arg Gln Arg Pro Trp Gly Lys
1               5                   10                  15

Trp Ala Ala Glu Ile Arg Asp Pro Lys Lys Ala Ala Arg Val Trp Leu
            20                  25                  30

Gly Thr Phe Asp Thr Ala Glu Asp Ala Ala Ile Ala Tyr Asp Glu Ala
        35                  40                  45

Ala Leu Arg Phe Lys Gly Thr Lys Ala Lys Leu Asn Phe Pro Glu Arg
    50                  55                  60

Val Gln Gly Arg Thr Asp Leu Gly Phe Val Val Thr Arg Gly Ile Pro
65                  70                  75                  80

Asp Arg Leu Gln Gln Gln Gln His Tyr Pro Ala Ala Val Gly Ala Pro
                85                  90                  95

Ala Met Arg Pro

<210> SEQ ID NO 54
<211> LENGTH: 99
<212> TYPE: PRT
<213> ORGANISM: Brachypodium distachyon

<400> SEQUENCE: 54

```
Gly Arg Lys Arg His Tyr Arg Gly Val Arg Gln Arg Pro Trp Gly Lys
1               5                   10                  15

Trp Ala Ala Glu Ile Arg Asp Pro Lys Lys Ala Ala Arg Val Trp Leu
            20                  25                  30

Gly Thr Phe Asp Thr Ala Glu Asp Ala Ala Ile Ala Tyr Asp Glu Ala
        35                  40                  45

Ala Leu Arg Phe Lys Gly Thr Lys Ala Lys Leu Asn Phe Pro Glu Arg
    50                  55                  60

Val Gln Gly Arg Thr Asp Leu Gly Phe Val Val Thr Arg Gly Ile Pro
65                  70                  75                  80

Asp Arg Ser Ser Leu His His Gln Gln His Tyr Pro Gly Ser Thr Ala
                85                  90                  95

Met Arg Pro
```

<210> SEQ ID NO 55
<211> LENGTH: 101
<212> TYPE: PRT
<213> ORGANISM: Oryza sativa

<400> SEQUENCE: 55

```
Gly Arg Arg Arg His Tyr Arg Gly Val Arg Gln Arg Pro Trp Gly Lys
1               5                   10                  15

Trp Ala Ala Glu Ile Arg Asp Pro Lys Lys Ala Ala Arg Val Trp Leu
            20                  25                  30

Gly Thr Phe Asp Thr Ala Glu Asp Ala Ala Ile Ala Tyr Asp Glu Ala
        35                  40                  45

Ala Leu Arg Phe Lys Gly Thr Lys Ala Lys Leu Asn Phe Pro Glu Arg
    50                  55                  60

Val Gln Gly Arg Thr Asp Leu Gly Phe Leu Val Thr Arg Gly Ile Pro
65                  70                  75                  80

Pro Ala Ala Thr His Gly Gly Gly Tyr Tyr Pro Ser Ser Ser Pro Ala
                85                  90                  95

Ala Gly Ala Cys Pro
            100
```

<210> SEQ ID NO 56
<211> LENGTH: 105
<212> TYPE: PRT
<213> ORGANISM: Jatropha curcas

<400> SEQUENCE: 56

```
Asn Thr Arg Arg Arg His Tyr Arg Gly Val Arg Gln Arg Pro Trp Gly
1               5                   10                  15

Lys Trp Ala Ala Glu Ile Arg Asp Pro Lys Lys Ala Ala Arg Val Trp
            20                  25                  30

Leu Gly Thr Phe Asp Thr Ala Glu Asp Ala Ala Leu Ala Tyr Asp Lys
        35                  40                  45

Ala Ala Leu Lys Phe Lys Gly Thr Lys Ala Lys Leu Asn Phe Pro Glu
    50                  55                  60
```

```
Arg Val Gln Gly Lys Pro Glu Phe Ser Tyr Phe Met Thr Ser Ser Gly
 65                  70                  75                  80

Asp Ser Ser Ser Ala Leu Ala Pro Glu Gln Asn Pro Met Ala Ala Ala
                 85                  90                  95

Ala Ser Ala Pro Ser Arg His Tyr Leu
            100                 105

<210> SEQ ID NO 57
<211> LENGTH: 101
<212> TYPE: PRT
<213> ORGANISM: Populus trichocarpa

<400> SEQUENCE: 57

Asn Thr Arg Arg Arg His Tyr Arg Gly Val Arg Gln Arg Pro Trp Gly
 1               5                  10                  15

Lys Trp Ala Ala Glu Ile Arg Asp Pro Lys Lys Ala Ala Arg Val Trp
                20                  25                  30

Leu Gly Thr Phe Asp Thr Ala Glu Asp Ala Ala Val Ala Tyr Asp Lys
            35                  40                  45

Ala Ala Leu Lys Phe Lys Gly Thr Lys Ala Lys Leu Asn Phe Pro Glu
         50                 55                  60

Arg Val Gln Gly Arg Thr Glu Phe Gly Tyr Tyr Met Gly Ser Gly Thr
 65                  70                  75                  80

Ser Thr Asn Val Leu Thr Glu Gln Ser Pro Arg Pro Val Ala Pro Pro
                 85                  90                  95

Pro Pro Pro Pro Pro
            100

<210> SEQ ID NO 58
<211> LENGTH: 97
<212> TYPE: PRT
<213> ORGANISM: Theobroma cacao

<400> SEQUENCE: 58

Glu Glu Asn Thr Arg Arg Arg His Tyr Arg Gly Val Arg Gln Arg Pro
 1               5                  10                  15

Trp Gly Lys Trp Ala Ala Glu Ile Arg Asp Pro Lys Lys Ala Ala Arg
                20                  25                  30

Val Trp Leu Gly Thr Phe Asp Thr Ala Glu Asp Ala Ala Leu Ala Tyr
            35                  40                  45

Asp Arg Ala Ala Leu Lys Phe Lys Gly Thr Lys Ala Lys Leu Asn Phe
         50                 55                  60

Pro Glu Arg Val Gln Gly Asn Thr Glu Val Ser Tyr Phe Thr Gly His
 65                  70                  75                  80

Gly Asp Ser Ser Thr Val Arg Pro Asp Gln Asn Pro Thr Pro Ala Ala
                 85                  90                  95

Thr

<210> SEQ ID NO 59
<211> LENGTH: 87
<212> TYPE: PRT
<213> ORGANISM: Medicago truncatula

<400> SEQUENCE: 59

Thr Lys Lys Lys Pro His Tyr Arg Gly Val Arg Gln Arg Pro Trp Gly
 1               5                  10                  15

Lys Trp Ala Ala Glu Ile Arg Asp Pro Lys Lys Ala Ala Arg Val Trp
                20                  25                  30
```

```
Leu Gly Thr Phe Asp Thr Ala Glu Asp Ala Leu Ala Tyr Asp Lys
        35                  40                  45

Ala Ala Leu Lys Phe Lys Gly Thr Lys Ala Lys Leu Asn Phe Pro Glu
 50                  55                  60

Arg Val Val Gln Cys Asn Ser Tyr Ser Ser Thr Ala Asn Asn Ala Ile
 65                  70                  75                  80

Gln Gln Ser Asp Tyr Val Ser
                85
```

<210> SEQ ID NO 60
<211> LENGTH: 110
<212> TYPE: PRT
<213> ORGANISM: Glycine max

<400> SEQUENCE: 60

```
Val Thr Lys Lys Pro His Tyr Arg Gly Val Arg Gln Arg Pro Trp Gly
 1               5                  10                  15

Lys Trp Ala Ala Glu Ile Arg Asp Pro Lys Lys Ala Ala Arg Val Trp
                20                  25                  30

Leu Gly Thr Phe Glu Thr Ala Glu Asp Ala Ala Leu Ala Tyr Asp Lys
        35                  40                  45

Ala Ala Leu Lys Phe Lys Gly Thr Lys Ala Lys Leu Asn Phe Pro Glu
 50                  55                  60

Arg Leu His Gln Asn Val Pro Tyr Met Gln Gln His Gln Gln Gly Ser
 65                  70                  75                  80

Ser Asn Arg Asn Val Phe Pro Phe His Ala Thr Ser Ser Thr Ser Ser
                85                  90                  95

Ser Ala Thr Gly Ser Val Ser Ser Leu Asp Ala Val Ala Pro
            100                 105                 110
```

<210> SEQ ID NO 61
<211> LENGTH: 108
<212> TYPE: PRT
<213> ORGANISM: Malus domestica

<400> SEQUENCE: 61

```
Thr Val Arg Arg Arg His Tyr Arg Gly Val Arg Gln Arg Pro Trp Gly
 1               5                  10                  15

Lys Trp Ala Ala Glu Ile Arg Asp Pro Lys Lys Ala Ala Arg Val Trp
                20                  25                  30

Leu Gly Thr Phe Glu Thr Ala Glu Asp Ala Ala Ile Ala Tyr Asp Asn
        35                  40                  45

Ala Ala Leu Arg Phe Lys Gly Thr Lys Ala Lys Leu Asn Phe Pro Glu
 50                  55                  60

Arg Val Gln Gly Lys Thr Asp Phe Gly Ile Leu Met Gly Ser Ser Gly
 65                  70                  75                  80

Thr Thr Thr Asn Ser Ser Ser Gly Ala Ala Ser Thr Gln Arg Thr Gln
                85                  90                  95

Asn Leu Met Arg Pro Ala Gly Gln Thr Ala Pro Ala
            100                 105
```

<210> SEQ ID NO 62
<211> LENGTH: 92
<212> TYPE: PRT
<213> ORGANISM: Capsicum annuum

<400> SEQUENCE: 62

```
Gly Ser Gly Arg Arg His Tyr Arg Gly Val Arg Gln Arg Pro Trp Gly
1               5                   10                  15

Lys Trp Ala Ala Glu Ile Arg Asn Pro Lys Lys Ala Ala Arg Val Trp
            20                  25                  30

Leu Gly Thr Phe Asp Arg Ala Glu Asp Ala Ala Leu Ala Tyr Asp Glu
            35                  40                  45

Ala Ala Val Arg Phe Lys Gly Ser Lys Ala Lys Leu Asn Phe Pro Glu
        50                  55                  60

Arg Leu Val Gln Gly Gln Pro Gln Leu Leu Ser Gln Asp Thr Ser Pro
65                  70                  75                  80

Gln His Asn Ser His His Phe Glu Glu Phe Asn Thr
                85                  90
```

<210> SEQ ID NO 63
<211> LENGTH: 107
<212> TYPE: PRT
<213> ORGANISM: Brassica juncea

<400> SEQUENCE: 63

```
Ser Gly Asp Gly Pro Gln Arg Arg Tyr Arg Gly Val Arg Gln Arg Pro
1               5                   10                  15

Trp Gly Lys Trp Ala Ala Glu Ile Arg Asp Pro Phe Lys Ala Ala Arg
            20                  25                  30

Val Trp Leu Gly Thr Phe Asp Asn Ala Glu Ser Ala Ala Arg Ala Tyr
            35                  40                  45

Asp Glu Ala Ala Leu Arg Phe Arg Gly Asn Lys Ala Lys Leu Asn Phe
        50                  55                  60

Pro Glu Asn Val Lys Leu Val Arg Pro Ala Ser Thr Thr Pro Thr Leu
65                  70                  75                  80

Ser Val Pro Gln Thr Ala Val Gln Arg Pro Thr Gln Leu Arg Asn Ser
                85                  90                  95

Gly Ser Thr Ser Thr Ile Leu Pro Val Arg His
                100                 105
```

<210> SEQ ID NO 64
<211> LENGTH: 101
<212> TYPE: PRT
<213> ORGANISM: Solanum lycopersicum

<400> SEQUENCE: 64

```
Asn Asn Glu Lys Arg Arg Gln Tyr Arg Gly Val Arg Gln Arg Pro
1               5                   10                  15

Trp Gly Lys Trp Ala Ala Glu Ile Arg Asp Pro Glu Lys Ala Ala Arg
            20                  25                  30

Val Trp Leu Gly Thr Phe His Thr Ala Glu Asp Ala Ala Ile Ala Tyr
            35                  40                  45

Asp Glu Ala Ala Leu Lys Phe Lys Gly Asn Lys Ala Lys Leu Asn Phe
        50                  55                  60

Pro Glu Arg Val Gln Ser Thr Thr Asp Gln Phe Gly Ile Ser Tyr Leu
65                  70                  75                  80

Ile Thr Asn Thr Asn His Gln Gln His Gln Phe Gln Pro Thr Asn Phe
                85                  90                  95

Leu Pro Asn Ser Asp
                100
```

<210> SEQ ID NO 65
<211> LENGTH: 107

```
<212> TYPE: PRT
<213> ORGANISM: Cucumis sativus

<400> SEQUENCE: 65
```

Arg Val Lys Arg Leu Lys Lys Asn Tyr Arg Gly Val Arg Gln Arg Pro
1               5                   10                  15

Trp Gly Lys Trp Ala Ala Glu Ile Arg Asp Pro Ile Arg Ala Ala Arg
            20                  25                  30

Val Trp Leu Gly Thr Phe Asn Thr Ala Glu Asp Ala Ala Arg Ala Tyr
        35                  40                  45

Asp Glu Ala Ala Ile Lys Phe Arg Gly Pro Arg Ala Lys Leu Asn Phe
    50                  55                  60

Pro Phe Pro Asp Tyr Ser Leu Ser Ser Thr Phe His Ser Ser Pro Pro
65                  70                  75                  80

Pro Ala Ser Thr Thr Thr Ser Ala Ser Ala Ser Phe Ser Pro Ala Ala
                85                  90                  95

Pro Pro Pro Pro Pro Leu Leu Pro Thr Ser Thr
                100                 105

```
<210> SEQ ID NO 66
<211> LENGTH: 120
<212> TYPE: PRT
<213> ORGANISM: Populus trichocarpa

<400> SEQUENCE: 66
```

Met Ala Asp Ser Asp Asn Glu Ser Gly Glu Gln Asn Ser Asn Thr
1               5                   10                  15

Asn Tyr Ser Thr Glu Thr Ser Pro Arg Glu Gln Asp Arg Leu Leu Pro
            20                  25                  30

Ile Ala Asn Val Ser Arg Ile Met Lys Lys Ala Leu Pro Ala Asn Ala
        35                  40                  45

Lys Ile Ser Lys Asp Ala Lys Glu Thr Val Gln Glu Cys Val Ser Glu
    50                  55                  60

Phe Ile Ser Phe Ile Thr Gly Glu Ala Ser Asp Lys Cys Gln Arg Glu
65                  70                  75                  80

Lys Arg Lys Thr Ile Asn Gly Asp Asp Leu Leu Trp Ala Met Thr Thr
                85                  90                  95

Leu Gly Phe Glu Asp Tyr Val Glu Pro Leu Lys Ile Tyr Leu Gln Lys
                100                 105                 110

Phe Arg Glu Met Glu Gly Glu Lys
            115                 120

```
<210> SEQ ID NO 67
<211> LENGTH: 116
<212> TYPE: PRT
<213> ORGANISM: Solanum lycopersicum

<400> SEQUENCE: 67
```

Met Ala Asp Ser Asp Asn Glu Ser Gly Gly His Asn Asn Ala Asn Ser
1               5                   10                  15

Glu Gly Ser Thr Arg Glu Gln Asp Arg Phe Leu Pro Ile Ala Asn Val
            20                  25                  30

Ser Arg Ile Met Lys Lys Ala Leu Pro Ala Asn Ala Lys Ile Ser Lys
        35                  40                  45

Asp Ala Lys Glu Thr Val Gln Glu Cys Val Ser Glu Phe Ile Ser Phe
    50                  55                  60

Ile Thr Gly Glu Ala Ser Asp Lys Cys Gln Arg Glu Lys Arg Lys Thr

```
                65                  70                  75                  80
Ile Asn Gly Asp Asp Leu Leu Trp Ala Met Thr Thr Leu Gly Phe Glu
                85                  90                  95

Glu Tyr Val Glu Pro Leu Lys Ile Tyr Leu Ala Lys Tyr Arg Glu Met
            100                 105                 110

Glu Gly Glu Lys
        115

<210> SEQ ID NO 68
<211> LENGTH: 118
<212> TYPE: PRT
<213> ORGANISM: Theobroma cacao

<400> SEQUENCE: 68

Met Ala Asp Ser Asp Asn Asp Ser Gly Gly His Asn Asn Ser Asn Ala
1               5                   10                  15

Asn Asn Glu Leu Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
    50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Glu Pro Leu Lys Val Tyr Leu His Lys Phe Arg
            100                 105                 110

Glu Met Glu Gly Glu Arg
        115

<210> SEQ ID NO 69
<211> LENGTH: 115
<212> TYPE: PRT
<213> ORGANISM: Panicum virgatum

<400> SEQUENCE: 69

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys
        115

<210> SEQ ID NO 70
<211> LENGTH: 115
<212> TYPE: PRT
```

<213> ORGANISM: Setaria italica

<400> SEQUENCE: 70

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys
        115

<210> SEQ ID NO 71
<211> LENGTH: 115
<212> TYPE: PRT
<213> ORGANISM: Sorghum bicolor

<400> SEQUENCE: 71

Met Pro Asp Ser Asp Asn Glu Ser Gly Gly Pro Ser Asn Ala Asp Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Ile Glu Pro Leu Lys Leu Tyr Leu His Lys Phe Arg Glu Leu Glu
            100                 105                 110

Gly Glu Lys
        115

<210> SEQ ID NO 72
<211> LENGTH: 115
<212> TYPE: PRT
<213> ORGANISM: Zea mays

<400> SEQUENCE: 72

Met Pro Asp Ser Asp Asn Glu Ser Gly Gly Pro Ser Asn Ala Glu Phe
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
    50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Glu Pro Leu Lys Leu Tyr Leu His Lys Phe Arg Glu Leu Glu
            100                 105                 110

Gly Glu Lys
        115

<210> SEQ ID NO 73
<211> LENGTH: 115
<212> TYPE: PRT
<213> ORGANISM: Hordeum vulgare

<400> SEQUENCE: 73

Met Pro Asp Ser Asp Asn Asp Ser Gly Gly Pro Ser Asn Ala Asp Phe
1               5                   10                  15

Ser Ser Pro Lys Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Met Glu Pro Leu Lys Leu Tyr Leu His Lys Phe Arg Glu Leu Glu
            100                 105                 110

Gly Glu Lys
        115

<210> SEQ ID NO 74
<211> LENGTH: 118
<212> TYPE: PRT
<213> ORGANISM: Oryza sativa

<400> SEQUENCE: 74

Met Pro Asp Ser Asp Asn Asp Ser Gly Gly Pro Ser Asn Tyr Ala Gly
1               5                   10                  15

Gly Glu Leu Ser Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45

Ser Lys Asp Ala Lys Glu Thr Val Gln Glu Cys Val Ser Glu Phe Ile
50                  55                  60

Ser Phe Ile Thr Gly Glu Ala Ser Asp Lys Cys Gln Arg Glu Lys Arg
65                  70                  75                  80

Lys Thr Ile Asn Gly Asp Asp Leu Leu Trp Ala Met Thr Thr Leu Gly
                85                  90                  95

Phe Glu Asp Tyr Val Asp Pro Leu Lys His Tyr Leu His Lys Phe Arg
            100                 105                 110

Glu Ile Glu Gly Glu Arg
        115

<210> SEQ ID NO 75

```
<211> LENGTH: 117
<212> TYPE: PRT
<213> ORGANISM: Brachypodium distachyon

<400> SEQUENCE: 75

Met Pro Asp Ser Asp Asn Asp Ser Gly Gly Pro Ser Asn Thr Gly Gly
1               5                   10                  15

Glu Leu Ser Ser Pro Arg Glu Gln Asp Arg Phe Leu Pro Ile Ala Asn
            20                  25                  30

Val Ser Arg Ile Met Lys Lys Ala Leu Pro Ala Asn Ala Lys Ile Ser
        35                  40                  45

Lys Asp Ala Lys Glu Thr Val Gln Glu Cys Val Ser Glu Phe Ile Ser
50                  55                  60

Phe Ile Thr Gly Glu Ala Ser Asp Lys Cys Gln Arg Glu Lys Arg Lys
65                  70                  75                  80

Thr Ile Asn Gly Asp Asp Leu Leu Trp Ala Met Thr Thr Leu Gly Phe
                85                  90                  95

Glu Asp Tyr Val Asp Pro Leu Lys His Tyr Leu His Lys Phe Arg Glu
            100                 105                 110

Ile Glu Gly Glu Arg
        115

<210> SEQ ID NO 76
<211> LENGTH: 115
<212> TYPE: PRT
<213> ORGANISM: Triticum aestivum

<400> SEQUENCE: 76

Met Pro Asp Ser Asp Asn Glu Asp Ser Gly Asn Ala Gly Gly Glu Leu
1               5                   10                  15

Ser Ser Pro Arg Glu Gln Asp Arg Phe Leu Pro Ile Ala Asn Val Ser
            20                  25                  30

Arg Ile Met Lys Lys Ala Leu Pro Ala Asn Ala Lys Ile Ser Lys Asp
        35                  40                  45

Ala Lys Glu Thr Val Gln Glu Cys Val Ser Glu Phe Ile Ser Phe Ile
50                  55                  60

Thr Gly Glu Ala Ser Asp Lys Cys Gln Arg Glu Lys Arg Lys Thr Ile
65                  70                  75                  80

Asn Gly Asp Asp Leu Leu Trp Ala Met Thr Thr Leu Gly Phe Glu Asp
                85                  90                  95

Tyr Val Asp Pro Leu Lys His Tyr Leu His Lys Phe Arg Glu Ile Glu
            100                 105                 110

Gly Glu Arg
        115

<210> SEQ ID NO 77
<211> LENGTH: 118
<212> TYPE: PRT
<213> ORGANISM: Glycine max

<400> SEQUENCE: 77

Met Ala Asp Ser Asp Asn Asp Ser Gly Gly Ala His Asn Ala Gly Lys
1               5                   10                  15

Gly Ser Glu Met Ser Pro Arg Glu Gln Asp Arg Phe Leu Pro Ile Ala
            20                  25                  30

Asn Val Ser Arg Ile Met Lys Lys Ala Leu Pro Ala Asn Ala Lys Ile
        35                  40                  45
```

```
Ser Lys Asp Ala Lys Glu Thr Val Gln Glu Cys Val Ser Glu Phe Ile
    50              55              60
Ser Phe Ile Thr Gly Glu Ala Ser Asp Lys Cys Gln Arg Glu Lys Arg
65              70              75              80
Lys Thr Ile Asn Gly Asp Asp Leu Leu Trp Ala Met Thr Thr Leu Gly
                85              90              95
Phe Glu Asp Tyr Val Glu Pro Leu Lys Gly Tyr Leu Gln Arg Phe Arg
            100             105             110
Glu Met Glu Gly Glu Lys
            115
```